US011685921B2

(12) United States Patent
Limphong et al.

(10) Patent No.: US 11,685,921 B2

(45) **Date of Patent: *Jun. 27, 2023**

(54) MOLECULES AND AGENTS FOR TREATING HEPATITIS B VIRUS

(71) Applicant: Arcturus Therapeutics, Inc., San Diego, CA (US)

(72) Inventors: Pattraranee Limphong, San Diego, CA (US); Kiyoshi Tachikawa, San Diego, CA (US); Christine Esau, San Diego, CA (US); Padmanabh Chivukula, San Diego, CA (US)

(73) Assignee: Arcturus Therapeutics, Inc., San Diego, CA (US)

( * ) Notice: Subject to any disclaimer, the term of this patent is extended or adjusted under 35 U.S.C. 154(b) by 656 days.

This patent is subject to a terminal disclaimer.

(21) Appl. No.: 16/724,122

(22) Filed: Dec. 20, 2019

(65) Prior Publication Data

US 2020/0131516 A1 Apr. 30, 2020

Related U.S. Application Data

(63) Continuation of application No. 15/410,984, filed on Jan. 20, 2017, now abandoned, which is a continuation-in-part of application No. 15/212,279, filed on Jul. 17, 2016, now abandoned.

(60) Provisional application No. 62/193,997, filed on Jul. 17, 2015.

(51) Int. Cl.

| | |
|---|---|
| ***C12N 15/11*** | (2006.01) |
| ***C12N 15/113*** | (2010.01) |
| ***A61K 9/127*** | (2006.01) |
| ***A61K 47/69*** | (2017.01) |

(52) U.S. Cl.

CPC ........ *C12N 15/1131* (2013.01); *A61K 9/1271* (2013.01); *A61K 47/6911* (2017.08); *C12N 2310/14* (2013.01); *C12N 2310/315* (2013.01); *C12N 2310/321* (2013.01); *C12N 2310/322* (2013.01); *C12N 2310/323* (2013.01); *C12N 2310/344* (2013.01); *C12N 2310/3515* (2013.01); *C12N 2320/32* (2013.01)

(58) Field of Classification Search

None

See application file for complete search history.

(56) References Cited

U.S. PATENT DOCUMENTS

| | | | |
|---|---|---|---|
| 8,350,021 | B2 | 1/2013 | Pachuk et al. |
| 8,575,327 | B2 | 11/2013 | Pachuk et al. |
| 8,598,334 | B2 | 12/2013 | Hamatake |
| 8,809,293 | B2 | 8/2014 | Chin et al. |
| 9,034,841 | B2 | 5/2015 | Swayze et al. |
| 9,084,808 | B2 | 7/2015 | Han et al. |
| 9,127,278 | B2 | 9/2015 | Freier |
| 9,181,551 | B2 | 11/2015 | McSwiggen et al. |
| 9,200,281 | B2 | 12/2015 | Pachuk et al. |
| 9,200,283 | B2 | 12/2015 | Bazinet et al. |
| 2003/0206887 | A1 | 11/2003 | Morrissey et al. |
| 2007/0027099 | A1 | 2/2007 | Lin et al. |
| 2008/0269148 | A1 | 10/2008 | Han et al. |
| 2009/0226525 | A1 | 9/2009 | de los Rios et al. |
| 2010/0003262 | A1 | 1/2010 | Locarnini et al. |
| 2010/0015708 | A1 | 1/2010 | Quay et al. |
| 2010/0063132 | A1 | 3/2010 | Kim et al. |
| 2010/0209491 | A1 | 8/2010 | Kim et al. |
| 2011/0052496 | A1 | 3/2011 | Cid-Arregui |
| 2011/0313020 | A1 | 12/2011 | Templin et al. |
| 2013/0005793 | A1 | 1/2013 | Chin et al. |
| 2014/0350080 | A1 | 11/2014 | Arbuthnot et al. |
| 2014/0369963 | A1 | 12/2014 | Bazinet et al. |
| 2015/0148402 | A1 | 5/2015 | Han et al. |
| 2015/0376621 | A1 | 12/2015 | Han et al. |
| 2016/0010093 | A1 | 1/2016 | Javanbakh et al. |
| 2016/0021588 | A1 | 1/2016 | Kamdar |
| 2016/0215288 | A1 | 7/2016 | Baryza et al. |

FOREIGN PATENT DOCUMENTS

| | | | |
|---|---|---|---|
| WO | WO-2003094829 | A2 | 11/2003 |
| WO | WO-2005014806 | A2 | 2/2005 |
| WO | WO-2011047312 | A1 | 4/2011 |
| WO | WO-2012024170 | A2 | 2/2012 |
| WO | WO-2013003520 | A1 | 1/2013 |
| WO | WO-2013159109 | A1 | 10/2013 |
| WO | WO-2015050871 | A1 | 4/2015 |
| WO | WO-2015188194 | A1 | 12/2015 |
| WO | WO-2016054421 | A1 | 4/2016 |

OTHER PUBLICATIONS

Kappus, et al., Extrahepatic manifestations of acute hepatitis B virus infection, Gastroenterology and Hematology, 2013, pp. 123-126, vol. 9, Issue 2.

Gish, Chronic hepatitis B: Virology, natural history, current management and a glimpse at future opportunities, Antiviral Research, 2015, pp. 47-58, No. 121.

Kenski, Analysis of acyclic nucleoside modifications in siRNAs finds sensitivity at position 1 that is restored by 5'-terminal phosphorylation both in vitro and in vivo, Nucleic acids research, 2009, pp. 660-671, vol. 38, No. 2.

(Continued)

*Primary Examiner* — Ekaterina Poliakova-Georgantas

(74) *Attorney, Agent, or Firm* — Mintz, Levin, Cohn, Ferris, Glovsky and Popeo, P.C.

(57) ABSTRACT

This invention encompasses compounds and compositions useful in methods for medical therapy, in general, for inhibiting Hepatitis B virus in a subject. The compounds have a first strand and a second strand, each of the strands being 19-29 monomers in length, the monomers comprising UNA monomers and nucleic acid monomers, and the compounds are targeted to a sequence of an HBV genome.

11 Claims, 18 Drawing Sheets

Specification includes a Sequence Listing.

(56) References Cited

OTHER PUBLICATIONS

Laursen, et al., Utilization of unlocked nucleic acid (UNA) to enhance siRNA performance in vitro and in vivo, Molecular BioSystems, 2010, pp. 862-870, vol. 6, No. 5.

Snead, et al., 5' unlocked nucleic acid modification improves siRNA targeting, Molecular Therapy—Nucleic Acids, 2013, 7 pages, vol. 2.

Vaish, et al., Improved specificity of gene silencing by siRNAs containing unlocked nucleobase analogs, Nucleic Acids Research, 2011, pp. 1823-1832, vol. 39, No. 5.

MOLECULES AND AGENTS FOR TREATING HEPATITIS B VIRUS

CROSS REFERENCE TO RELATED APPLICATIONS

This application is a continuation application of U.S. patent application Ser. No. 15/410,984 filed on Jan. 20, 2017, which is a continuation in part of U.S. patent application Ser. No. 15/212,279 filed on Jul. 17, 2016, which claims priority to U.S. Provisional 62/193,997 filed Jul. 17, 2015 which are incorporated herein by reference in their entirety.

SEQUENCE LISTING

This application includes a Sequence Listing submitted electronically as an ASCII file named ARC1444US_SL.txt.

BACKGROUND OF THE INVENTION

Hepatitis B is a liver disease that results from infection with the Hepatitis B virus (HBV). Its severity can be from a mild illness lasting a few weeks, to a serious, lifelong illness. Hepatitis B can be either acute or chronic. Acute Hepatitis B virus infection is a short-term illness that may lead to chronic infection. Chronic Hepatitis B virus infection is a long-term illness that can result in long-term health problems, such as cirrhosis of the liver, liver cancer, and death.

Hepatitis B is usually spread through transfer of a body fluid by sexual contact with an infected person, or through sharing needles for drug-injection. It can also be passed from an infected mother to her baby at birth. In endemic areas, Hepatitis B is most often spread from mother to child at birth, or by exposure to infected blood, especially from an infected child to an uninfected child during the first 5 years of life.

According to the latest WHO estimates, as many as 240 million people are chronically infected with Hepatitis B, defined as Hepatitis B surface antigen positive for at least 6 months. Approximately 780,000 persons die each year from Hepatitis B infection.

There is no specific treatment for acute hepatitis B. Chronic hepatitis B infection can be treated with drugs, including oral antiviral agents. WHO recommends the use of oral treatments such as tenofovir or entecavir. In most people, the treatment suppresses replication of the virus, but does not cure hepatitis B infection. Liver cancer progresses rapidly, and treatment options are limited. Surgery and chemotherapy, or liver transplantation can prolong life for up to a few years.

Laboratory diagnosis of hepatitis B infection can be done by detecting the hepatitis B surface antigen HBsAg. Acute hepatitis B virus infection is characterized by the presence of HBsAg and immunoglobulin M (IgM) antibody to the core antigen, HBcAg. During the initial phase of infection, patients are also seropositive for hepatitis B e-antigen (HBeAg). HBeAg is usually a marker of high levels of replication of the virus. The presence of HBeAg indicates that the blood and body fluids of the infected individual are highly contagious. Chronic infection is characterized by the persistence of HBsAg for at least 6 months, with or without concurrent HBeAg. Persistence of HBsAg is the principal marker of risk for developing chronic liver disease and liver cancer later in life.

HBV is a member of the hepadnavirus family. The virus particles, which can infect liver cells, are 30-42 nm in diameter and have an outer envelope and an icosahedral nucleocapsid core. The nucleocapsid encloses the viral DNA, and a DNA polymerase that can have reverse transcriptase activity. The outer envelope contains proteins that can be involved in viral binding and entry into cells.

In general, HBV has four identified genes, C, P, S, and X. Gene C codes for a core protein, HBcAg. An extracellular protein HBeAg is processed from a pre-core protein. A DNA polymerase is encoded by gene P. Gene S codes for the small surface antigen HBsAg, which is one of three polypeptide surface proteins: large, middle, and small. Gene X may be associated with development of liver cancer.

HBV is a pararetrovirus, which is a non-retrovirus that uses reverse transcription in the replication process. The virus can enter the cell and multiply using RNA made by a host process. The viral genomic DNA can be transferred to the cell nucleus, acted upon by viral polymerase, and provide transcription of four viral mRNAs by host RNA polymerase. A large viral mRNA is used to make the new copies of the genome by reverse transcription, and to make the core protein and the viral DNA polymerase. The viral mRNAs are further processed to form new virus particles.

HBV can be described by four major serotypes based on epitopes presented by envelope proteins: adr, adw, ayr, ayw. HBV has been identified with eight genotypes, A-H, as well as subgenotypes. The genotypes can have distinct geographical distribution, and are used in tracking evolution and transmission of the virus.

What is needed are compositions and methods for treatment of Hepatitis B.

There is an urgent need for new methods and compositions for ameliorating or treating Hepatitis B infection.

BRIEF SUMMARY

This invention relates to the fields of biopharmaceuticals and therapeutics composed of oligomers for gene silencing. More particularly, this invention relates to structures, compositions and methods for therapeutic oligomers directed against Hepatitis B virus.

This invention provides novel molecules to be used as therapeutic agents against Hepatitis B infection. The molecules of this invention can be used as active pharmaceutical ingredients in compositions for ameliorating, preventing or treating Hepatitis B infection.

Molecules of this invention for treating Hepatitis B infection may act against any of the replication, maturation, growth, or transmission modalities of the Hepatitis B virus. By preventing the Hepatitis B virus from carrying out any one or more of its processes, the molecules of this invention can be used for ameliorating or treating Hepatitis B infection.

Embodiments of this invention can provide molecules having one or more properties that advantageously provide enhanced effectiveness against HBV, as well as compositions or formulations for therapeutic agents against Hepatitis B infection, which can provide clinical agents. The properties of the molecules of this invention arise according to their structure, and the molecular structure in its entirety, as a whole, can provide significant benefits and properties.

The active agents of this invention include oligomeric molecules that can inhibit expression of an HBV genome. Oligomers of this invention can provide potent action against HBV infection in a subject by silencing expression of an HBV genome.

In some embodiments, a wide range of novel molecules are provided, which can incorporate one or more linker groups. The linker groups can be attached in a chain in the molecule. Each linker group can also be attached to a nucleobase.

In some aspects, a linker group can be a monomer. Monomers can be attached to form a chain molecule. In a chain molecule of this invention, a linker group monomer can be attached at any point in the chain.

In certain aspects, linker group monomers can be attached in a chain molecule of this invention so that the linker group monomers reside near the ends of the chain. The ends of the chain molecule can be formed by linker group monomers.

In further aspects, the linker groups of a chain molecule can each be attached to a nucleobase. The presence of nucleobases in the chain molecule can provide a sequence of nucleobases.

In certain embodiments, this invention provides oligomer molecules having chain structures that incorporate novel combinations of the linker group monomers, along with certain natural nucleotides, or non-natural nucleotides, or modified nucleotides, or chemically-modified nucleotides.

The oligomer molecules of this invention can display a sequence of nucleobases that is targeted to a component of the HBV genome.

In additional aspects, this invention provides therapeutics for preventing, ameliorating, or treating a disease caused by Hepatitis B infection. An active compound or molecule of this invention may be used in the prevention or treatment of a viral infection caused by Hepatitis B virus.

This invention provides structures, methods and compositions for oligomeric agents that incorporate the linker group monomers. The oligomeric molecules of this invention can be used as active agents in formulations for gene silencing therapeutics targeted to HBV.

Embodiments of this invention include the following:

A compound comprising a first strand and a second strand, each of the strands being 19-29 monomers in length, the monomers comprising UNA monomers and nucleic acid monomers, wherein the compound has a duplex region of from 14 to 29 contiguous monomers in length, wherein the first strand is a passenger strand for RNA interference and the second strand is a guide strand for RNA interference, and wherein the compound comprises a sequence of bases targeted to inhibit expression of an HBV genome. The compound may contain from one to seven UNA monomers.

In some embodiments, the compound may contain a UNA monomer at the 1-end (5' end for non-UNA) of the first strand, a UNA monomer at the 3-end (3' end for non-UNA) of the first strand, and a UNA monomer at the second position from the 5' end of the second strand. A compound can contain a UNA monomer at any one or more of positions 2 to 8 from the 5' end of the second strand.

In certain embodiments, a compound may have a 3' overhang with one or more UNA monomers, natural nucleotides, non-natural nucleotides, modified nucleotides, or chemically-modified nucleotides, or combinations thereof. The 3' overhang can have one or more deoxythymidine nucleotides, 2'-O-methyl nucleotides, inverted abasic monomers, inverted thymidine monomers, L-thymidine monomers, or glyceryl nucleotides.

In some aspects, a compound may have one or more nucleic acid monomers that is a non-natural nucleotide, a modified nucleotide, or a chemically-modified nucleotide. A compound may have one or more monomers connected by a phosphorothioate, a chiral phosphorothioate, or a phosphorodithioate linkage.

In further aspects, a compound may be conjugated to a delivery moiety, such as, for example, a moiety that binds to a glycoprotein receptor, a galactose, a galactosamine, a N-acetylgalactosamine, a GalNAc group, or a cholesterol delivery moiety. A compound may be conjugated to a delivery moiety and have increased uptake in the liver as compared to an unconjugated compound.

This invention includes lipid nanoparticle-oligomer compounds, in which one or more compounds are attached to a lipid nanoparticle.

A composition of this disclosure can include one or more compounds and a pharmaceutically acceptable carrier. The carrier may be lipid nanoparticles or liposomes.

A composition of this disclosure may contain a first compound targeted to a conserved region of HBV transcripts for genes X, C, P and S, a second compound targeted to inhibit HBsAg, a third compound targeted to a conserved region of HBV transcripts for genes X, C and S, and a pharmaceutically acceptable carrier.

Embodiments of this invention include compositions containing one or more compounds having reference positions from any of positions 1525 to 1582, 374 to 414, 1776 to 1782, 244 to 256, and 1818 to 1866. In certain embodiments, a composition may include a compound having a reference position from 1525 to 1582, a compound having a reference position from 374 to 414, and a compound having a reference position from 1776 to 1782.

Embodiments of this invention further contemplate methods for preventing, ameliorating or treating a disease or condition associated with HBV infection in a subject in need, by administering to the subject an effective amount of a composition above. The administration of the composition can reduce HBV viral titer in the subject. A subject may have been diagnosed with a disease associated with Hepatitis B virus infection, for example, a liver disease.

This invention includes methods for inhibiting the replication, maturation, growth, or transmission of a Hepatitis B virus in a subject in need, by administering to the subject an effective amount of a composition above. The composition may reduce serum concentration of HBsAg in the subject. In some embodiments, the administration of the composition may reduce serum concentration of HBsAg in the subject by 2-$\log_{10}$-fold, or by 2-$\log_{10}$-fold for at least 7 days. In certain embodiments, the administration of the composition can reduce HBeAg in the subject, or HBV DNA in the subject.

This invention also contemplates methods for inhibiting expression of a Hepatitis B virus polynucleotide in a subject in need, by administering to the subject a composition above, as well as the use of a composition above for preventing, ameliorating or treating a disease or condition associated with Hepatitis B infection in a subject in need.

In some aspects, this disclosure includes compositions for use in medical therapy, or for use in the treatment of the human or animal body. In certain aspects, this invention includes the use of a composition for preparing or manufacturing a medicament for preventing, ameliorating or treating a disease or condition associated with Hepatitis B infection in a subject in need.

Figure 2:
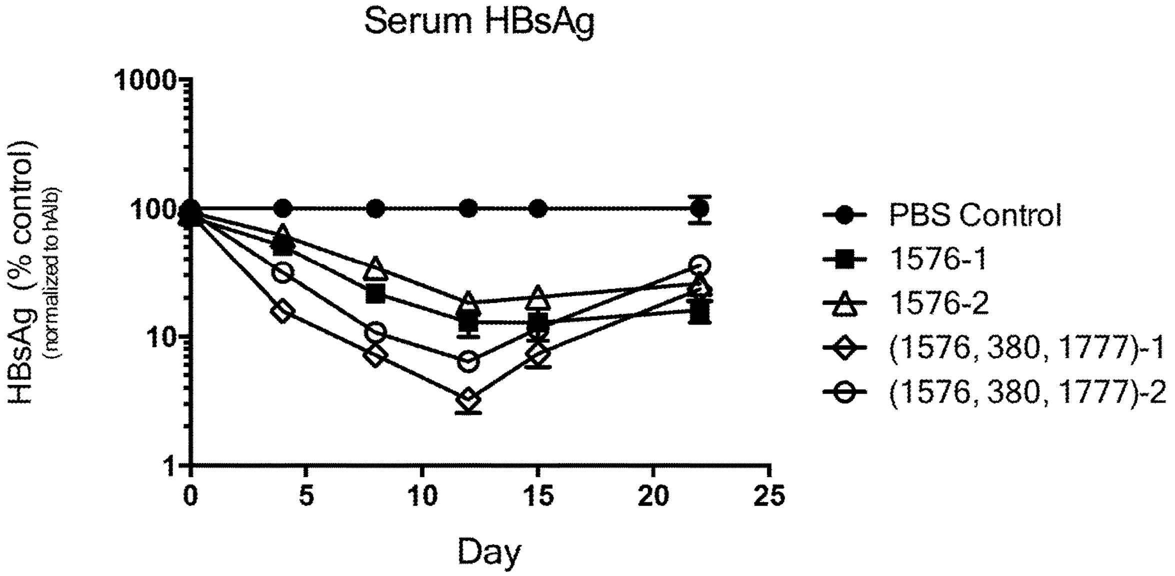

FIG. 2 shows HBV inhibitory effect in vivo for UNA oligomers, observed in a humanized PXB Mouse model of HBV infection. The UNA oligomers of this invention exhibited profound reduction of HBV serum infection parameters in vivo. In this study, the UNA oligomers were contained in lipid nanoparticle formulations, −1 and −2, and an ascending dose was used. The UNA oligomers were formulated in lipid nanoparticles and injected intravenously into HBV-infected Phoenix Bio (PXB) mice containing human hepatocytes (70%). Treatment with both UNA oligomer 1576 and a UNA oligomer triad composition (1576, 380, 177) caused a rapid and sustained reduction in viral endpoint serum HBsAg.

Figure 3:
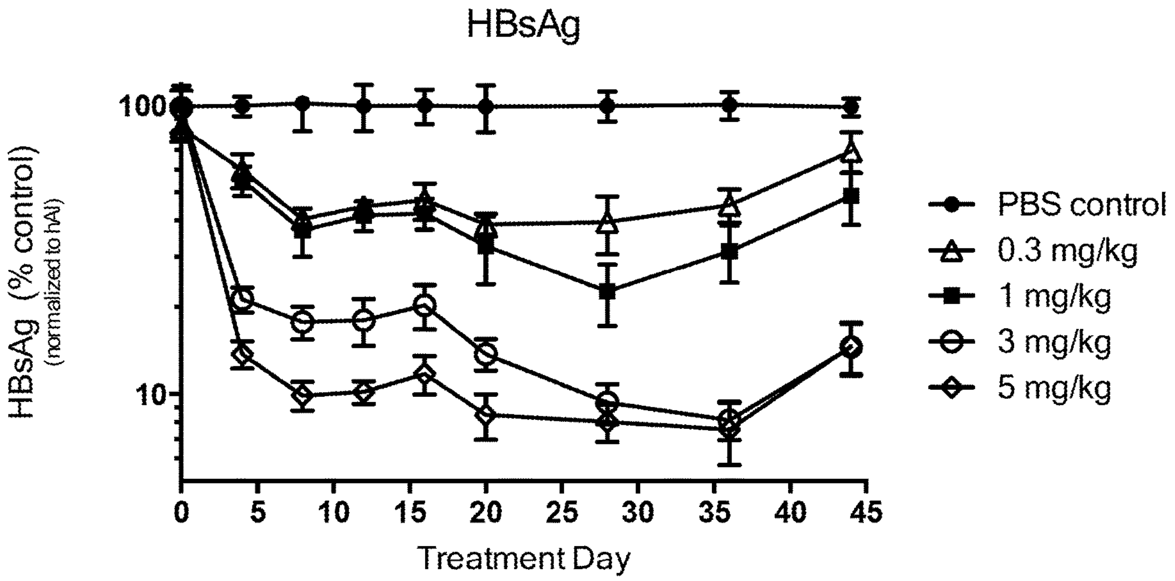

FIG. 3 shows HBV inhibitory effect in vivo for UNA oligomers, observed in a humanized PXB Mouse model of HBV infection. Treatment with UNA oligomer triad (1576, 380, 1777) caused a rapid and sustained reduction in viral endpoint serum HBsAg. The dose-dependent response in vivo shows a pharmacological effect of the UNA oligomer composition. The study used an ascending dose in which mice were administered every 4 days, up to day 40, and viral endpoints were monitored every 4 days through day 44.

Figure 4:
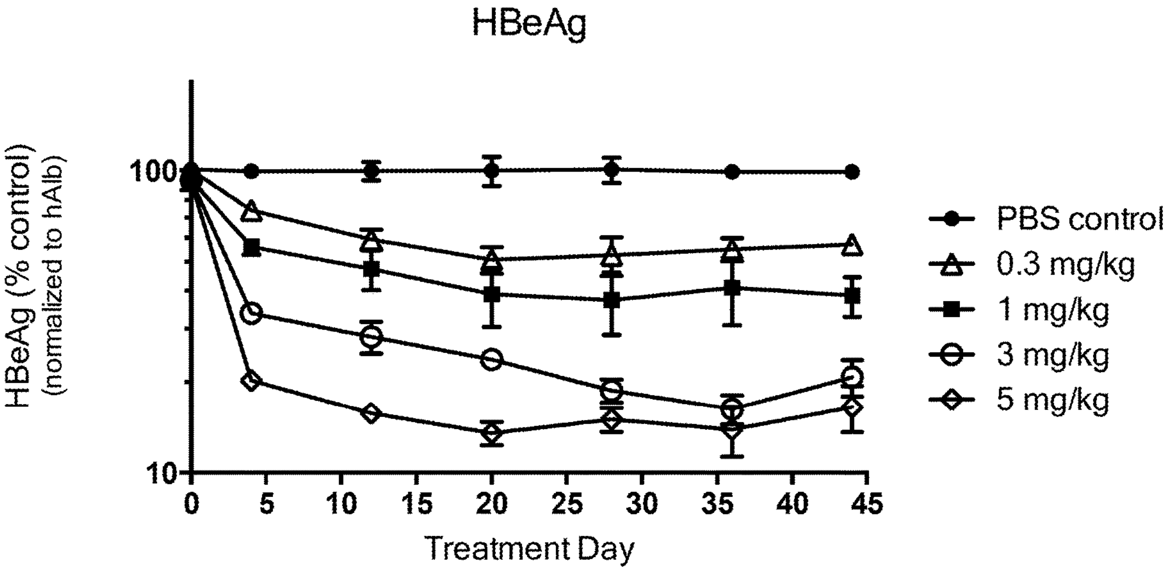

FIG. 4 shows HBV inhibitory effect in vivo for UNA oligomers, observed in a humanized PXB Mouse model of HBV infection. Treatment with UNA oligomer triad (1576, 380, 1777) caused a rapid and sustained reduction in viral endpoint serum HBeAg. The dose-dependent response in vivo shows a pharmacological effect of the UNA oligomer composition. The study used an ascending dose in which mice were administered every 4 days, up to day 40, and viral endpoints were monitored every 4 days through day 44.

Figure 5:
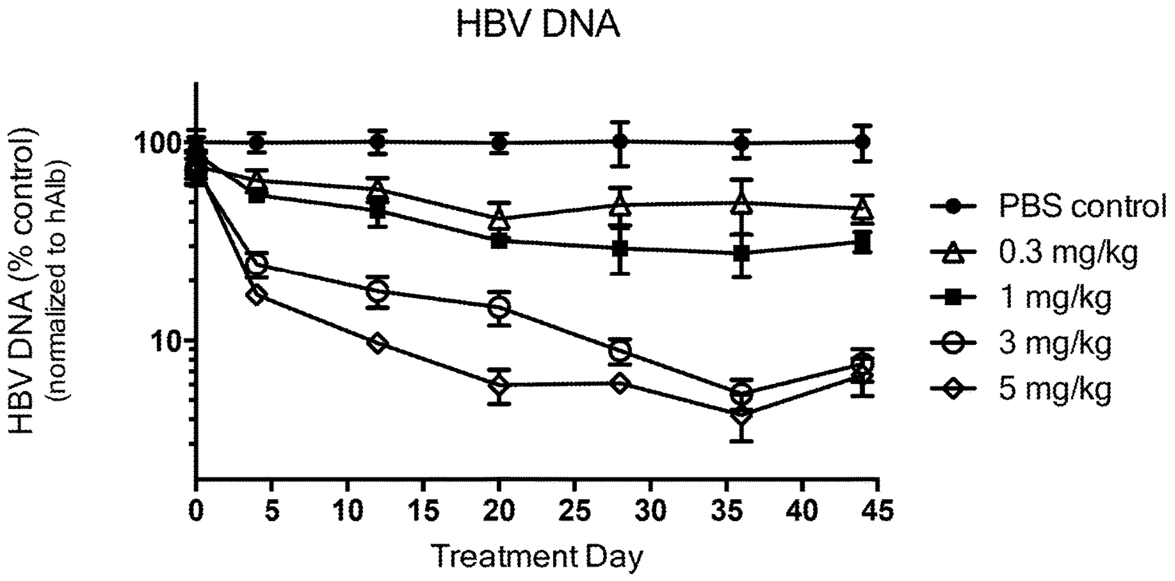

FIG. 5 shows HBV inhibitory effect in vivo for UNA oligomers, observed in a humanized PXB Mouse model of HBV infection. Treatment with UNA oligomer triad (1576, 380, 1777) caused a rapid and sustained reduction in viral endpoint serum HBV DNA. The dose-dependent response in vivo shows a pharmacological effect of the UNA oligomer composition. The study used an ascending dose in which mice were administered every 4 days, up to day 40, and viral endpoints were monitored every 4 days through day 44.

Figure 6:
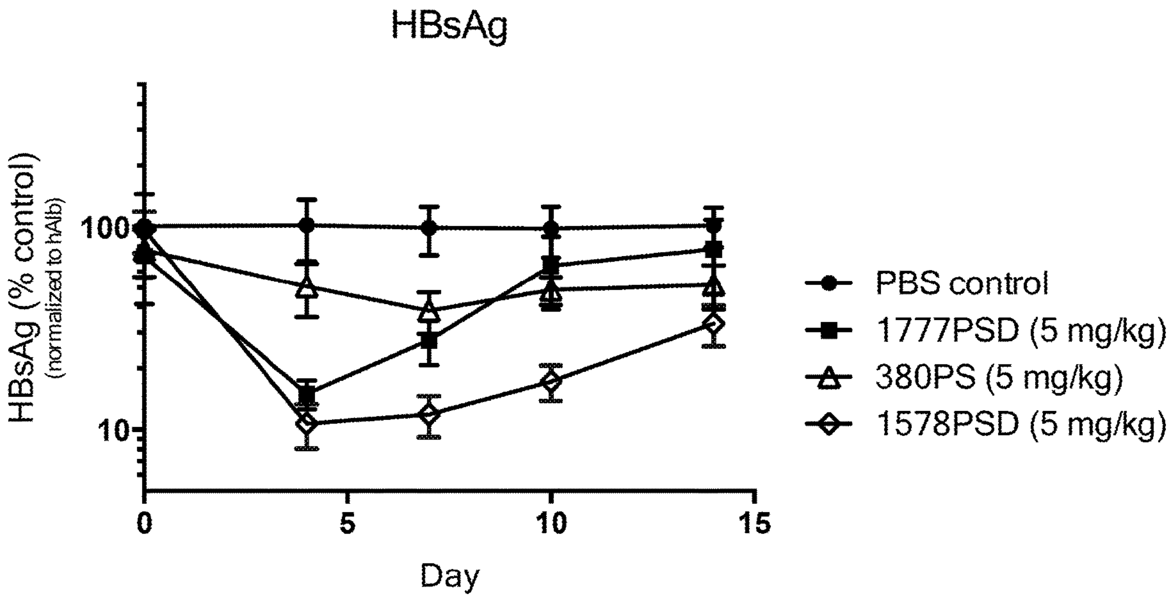

FIG. 6 shows HBV inhibitory effect in vivo for UNA oligomers, observed in a humanized PXB Mouse model of HBV infection. Treatment with UNA oligomers 1777, 380 and 1578 caused a rapid and sustained reduction in viral endpoint serum HBsAg.

Figure 7:
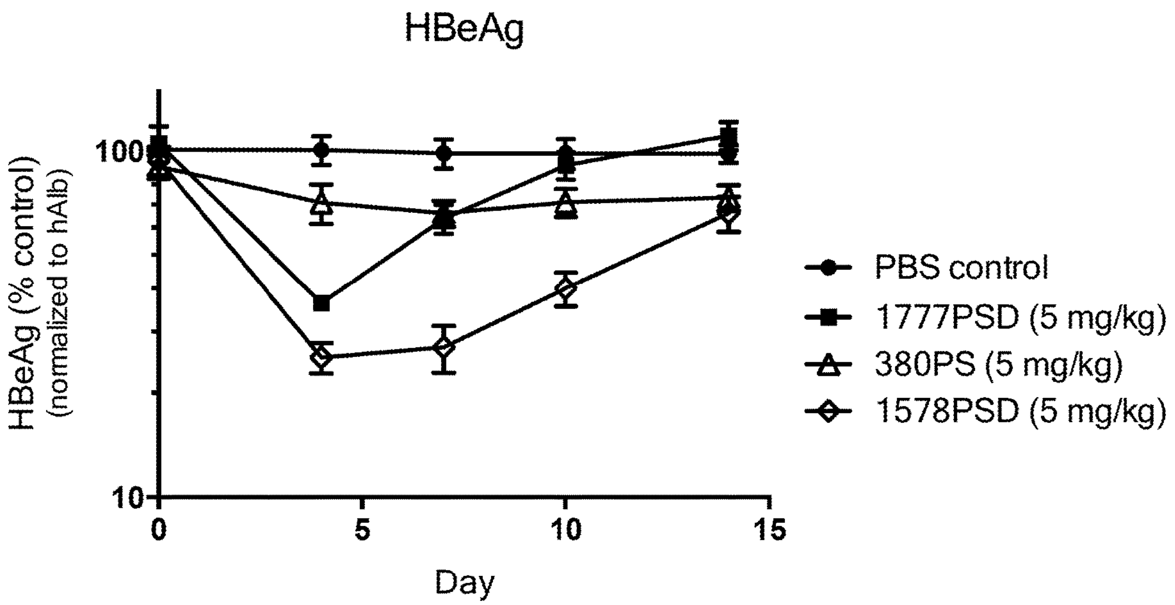

FIG. 7 shows HBV inhibitory effect in vivo for UNA oligomers, observed in a humanized PXB Mouse model of HBV infection. Treatment with UNA oligomers 1777, 380 and 1578 caused a rapid and sustained reduction in viral endpoint serum HBeAg.

Figure 8:
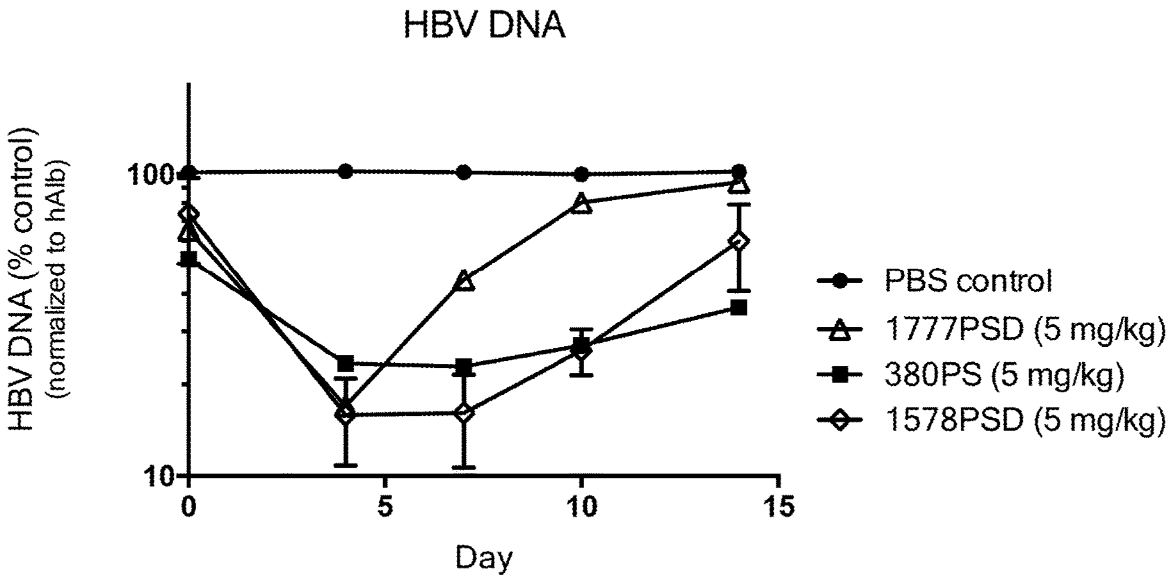

FIG. 8 shows HBV inhibitory effect in vivo for UNA oligomers, observed in a humanized PXB Mouse model of HBV infection. Treatment with UNA oligomers 1777, 380 and 1578 caused a rapid and sustained reduction in viral endpoint serum HBV DNA.

Figure 9:
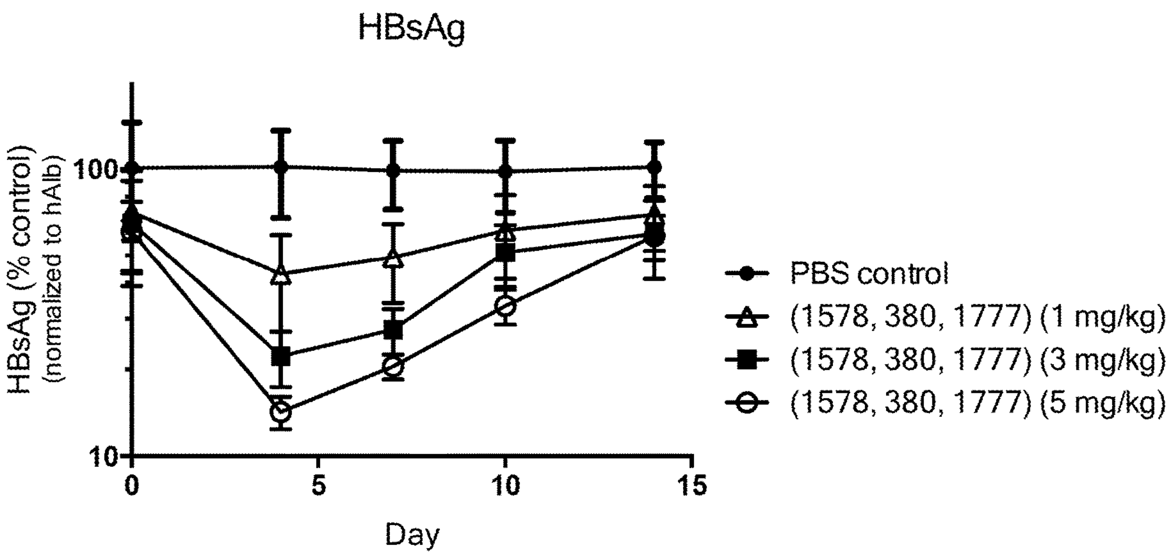

FIG. 9 shows HBV inhibitory effect in vivo for UNA oligomers, observed in a humanized PXB Mouse model of HBV infection. Treatment with a UNA oligomer triad composition (1578, 380, 1777) caused a rapid and sustained reduction in viral endpoint serum HBsAg. The dose-dependent response in vivo shows a pharmacological effect of the UNA oligomer composition.

Figure 10:
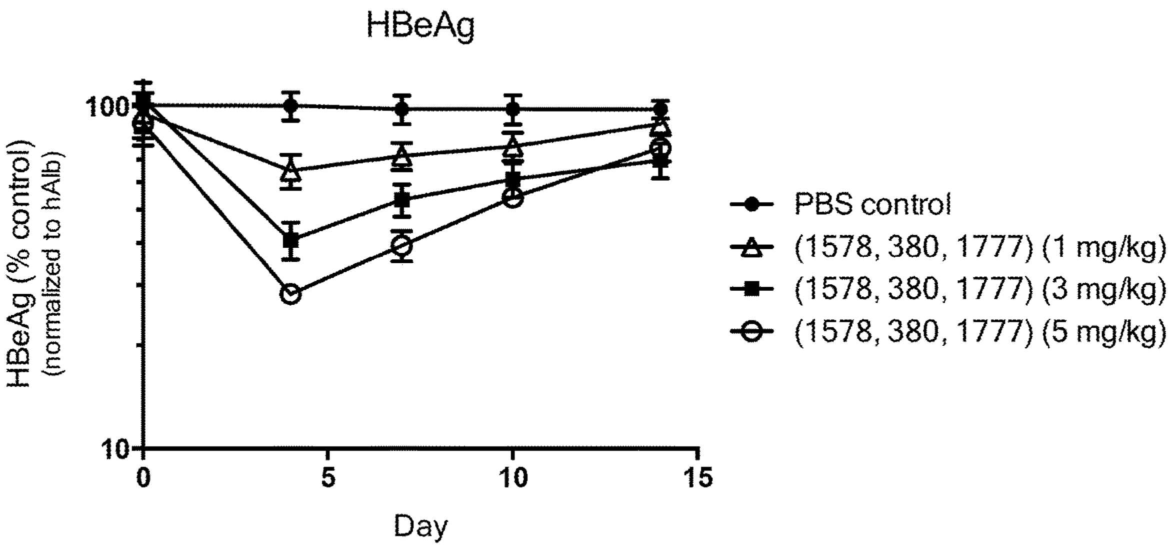

FIG. 10 shows HBV inhibitory effect in vivo for UNA oligomers, observed in a humanized PXB Mouse model of HBV infection. Treatment with a UNA oligomer triad composition (1578, 380, 1777) caused a rapid and sustained reduction in viral endpoint serum HBeAg. The dose-dependent response in vivo shows a pharmacological effect of the UNA oligomer composition.

Figure 11:
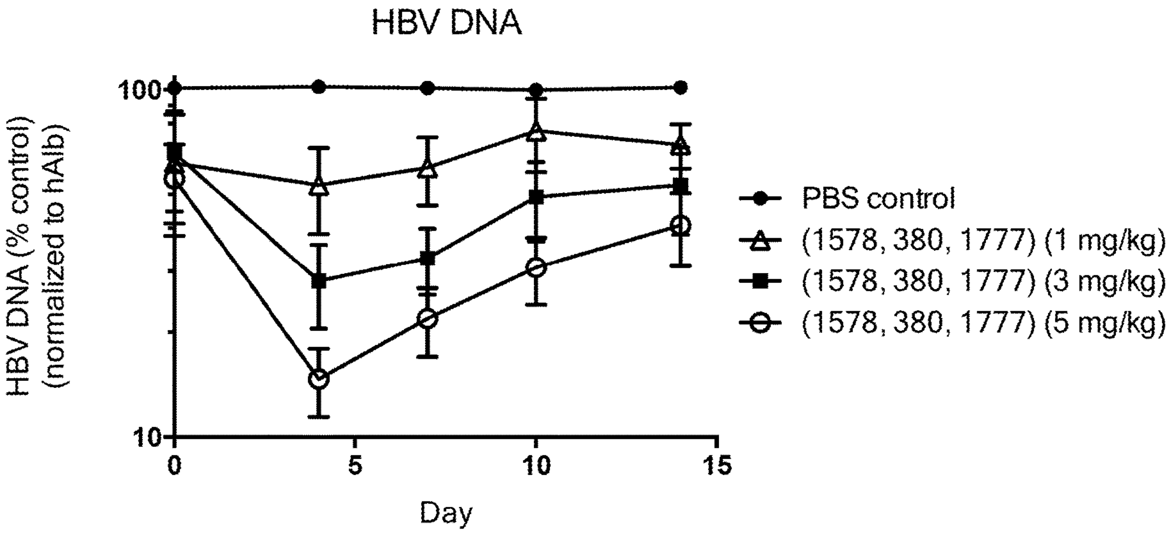

FIG. 11 shows HBV inhibitory effect in vivo for UNA oligomers, observed in a humanized PXB Mouse model of HBV infection. Treatment with a UNA oligomer triad composition (1578, 380, 1777) caused a rapid and sustained reduction in viral endpoint serum HBV DNA. The dose-dependent response in vivo shows a pharmacological effect of the UNA oligomer composition.

Figure 12:
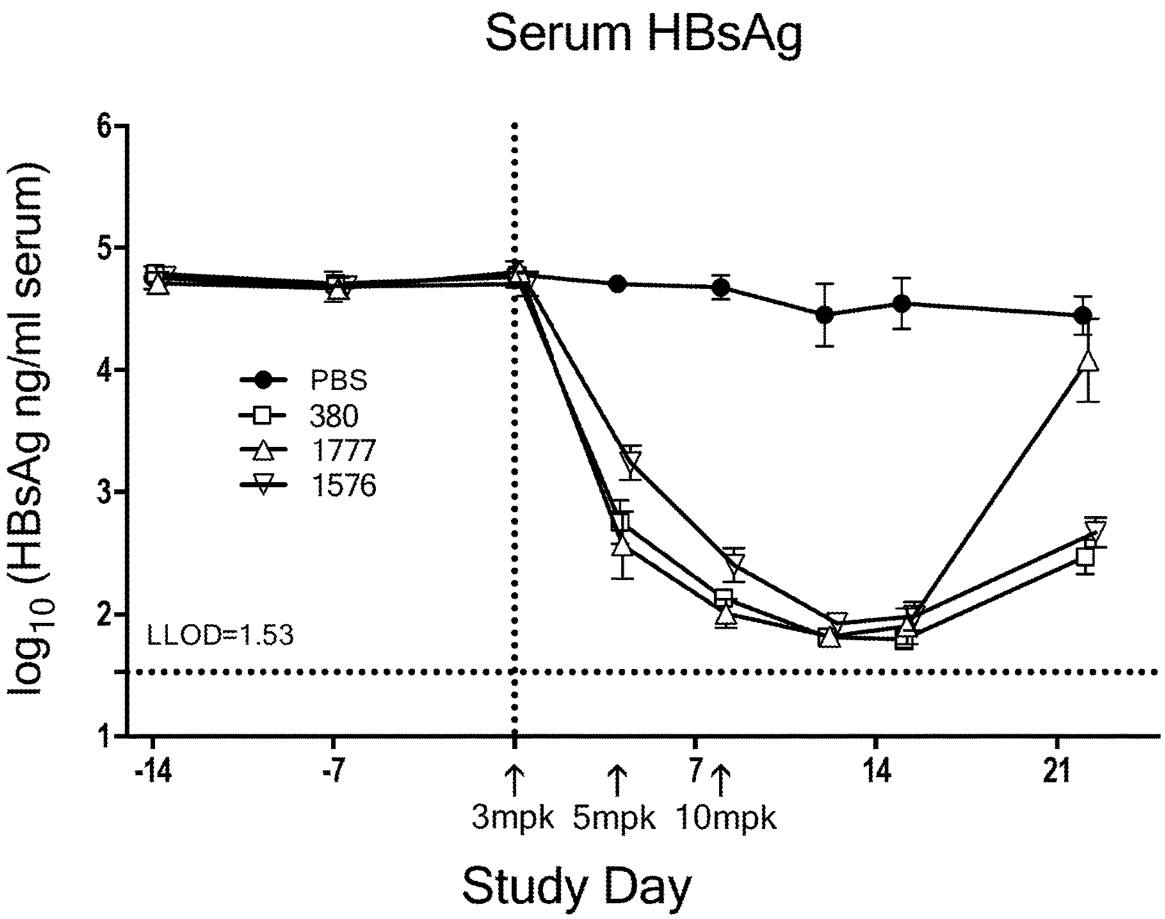

FIG. 12 shows HBV inhibitory effect in vivo for UNA oligomers, observed in an AAV-HBV mouse model of HBV infection. The UNA oligomers of this invention exhibited profound reduction of HBV serum infection parameters in vivo. In general, the AAV-HBV mouse model is a robust model for investigating HBV infection. The UNA oligomers were formulated in lipid nanoparticles and injected intravenously into C57Bl/6 mice with active HBV replication after AAV-mediated delivery of a recombinant HBV genome to the liver. The study used an ascending dose, and serum viral endpoints were monitored 15 days before, and at least 22 days after treatment. Treatment with each of UNA oligomers 380, 1777, and 1576 caused a rapid and sustained reduction in viral endpoint serum HBsAg.

Figure 13:
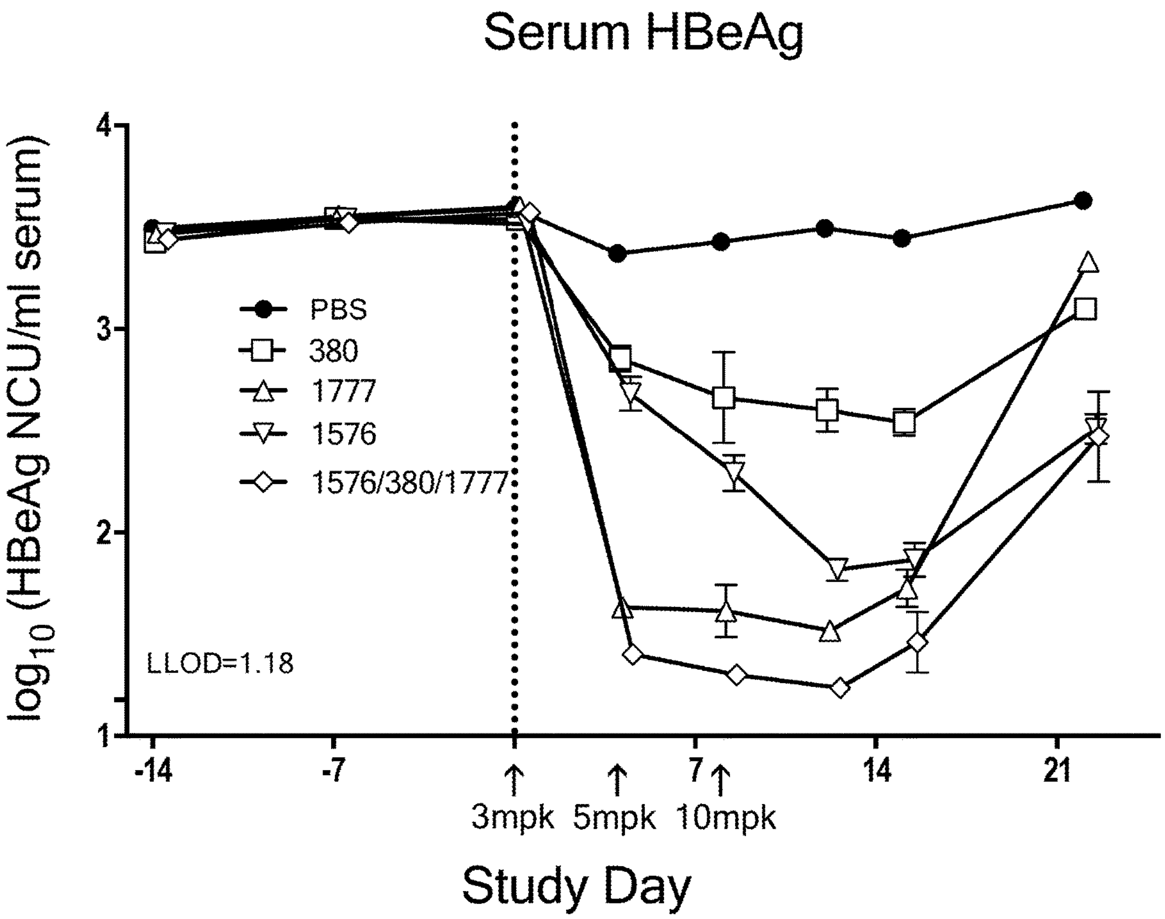

FIG. 13 shows HBV inhibitory effect in vivo for UNA oligomers, observed in an AAV-HBV mouse model of HBV infection. The UNA oligomers were formulated in lipid nanoparticles and injected intravenously into C57Bl/6 mice with active HBV replication after AAV-mediated delivery of a recombinant HBV genome to the liver. Treatment with each of UNA oligomers 380, 1777, and 1576, as well as the UNA oligomer triad composition of the same compounds (1576, 380, 1777) caused a rapid and sustained reduction in viral endpoint serum HBeAg. This head-to-head comparison shows that the triad composition provided surprisingly increased potency throughout the duration of the effect, relative to the individual oligomers.

Figure 14:
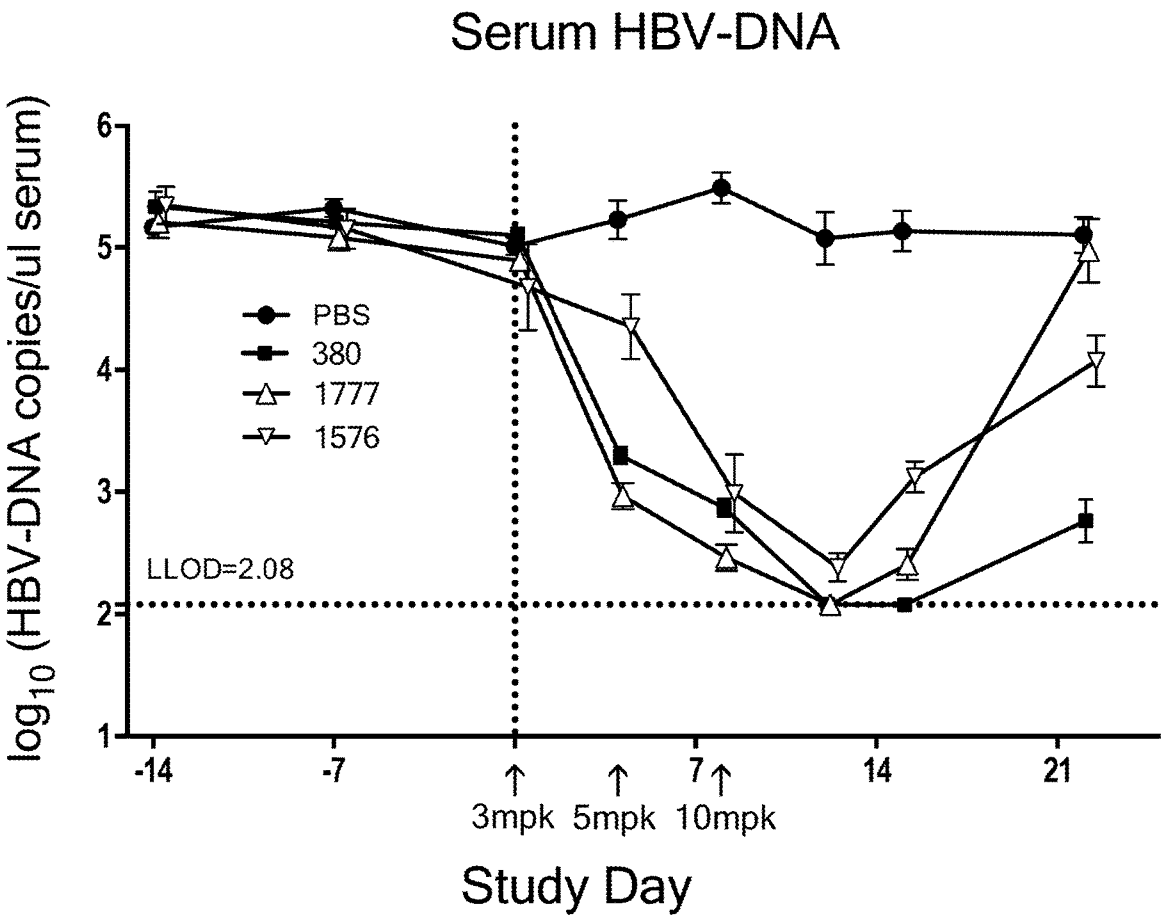

FIG. 14 shows HBV inhibitory effect in vivo for UNA oligomers, observed in an AAV-HBV mouse model of HBV infection. The UNA oligomers were formulated in lipid nanoparticles and injected intravenously into C57Bl/6 mice with active HBV replication after AAV-mediated delivery of a recombinant HBV genome to the liver. Treatment with each of UNA oligomers 380, 1777, and 1576 caused a rapid and sustained reduction in viral endpoint serum HBV DNA.

Figure 15:
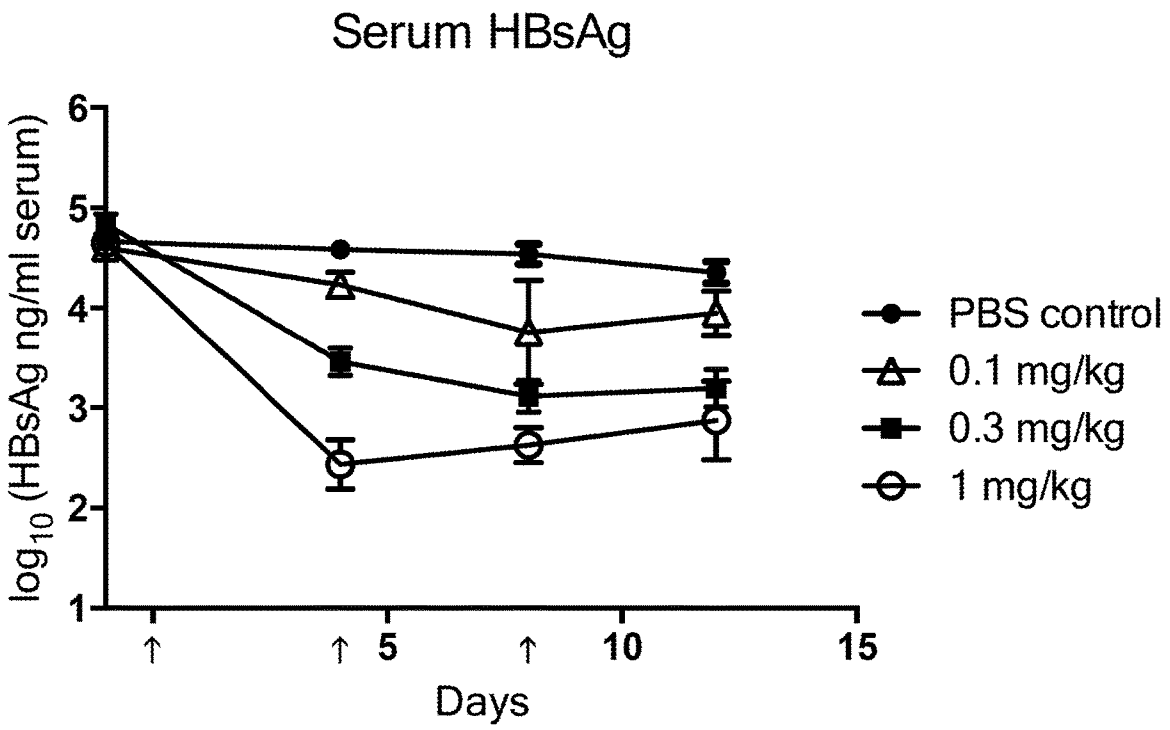

FIG. 15 shows HBV inhibitory effect in vivo for UNA oligomers, observed in an AAV-HBV mouse model of HBV infection. The UNA oligomers were formulated in lipid nanoparticles and injected intravenously into C57Bl/6 mice with active HBV replication after AAV-mediated delivery of a recombinant HBV genome to the liver. The study was an ascending dose design in which mice were treated with 3 mg/kg on day 0, then 5 mg/kg on day 4, then 10 mg/kg on day 8, and serum viral endpoints were monitored up to day 12 after treatment. Treatment with the UNA oligomer triad composition (1777, 380, 1578) caused a rapid and sustained reduction in viral endpoint serum HBsAg. The dose-dependent response in vivo shows a pharmacological effect of the UNA oligomer composition.

Figure 16:
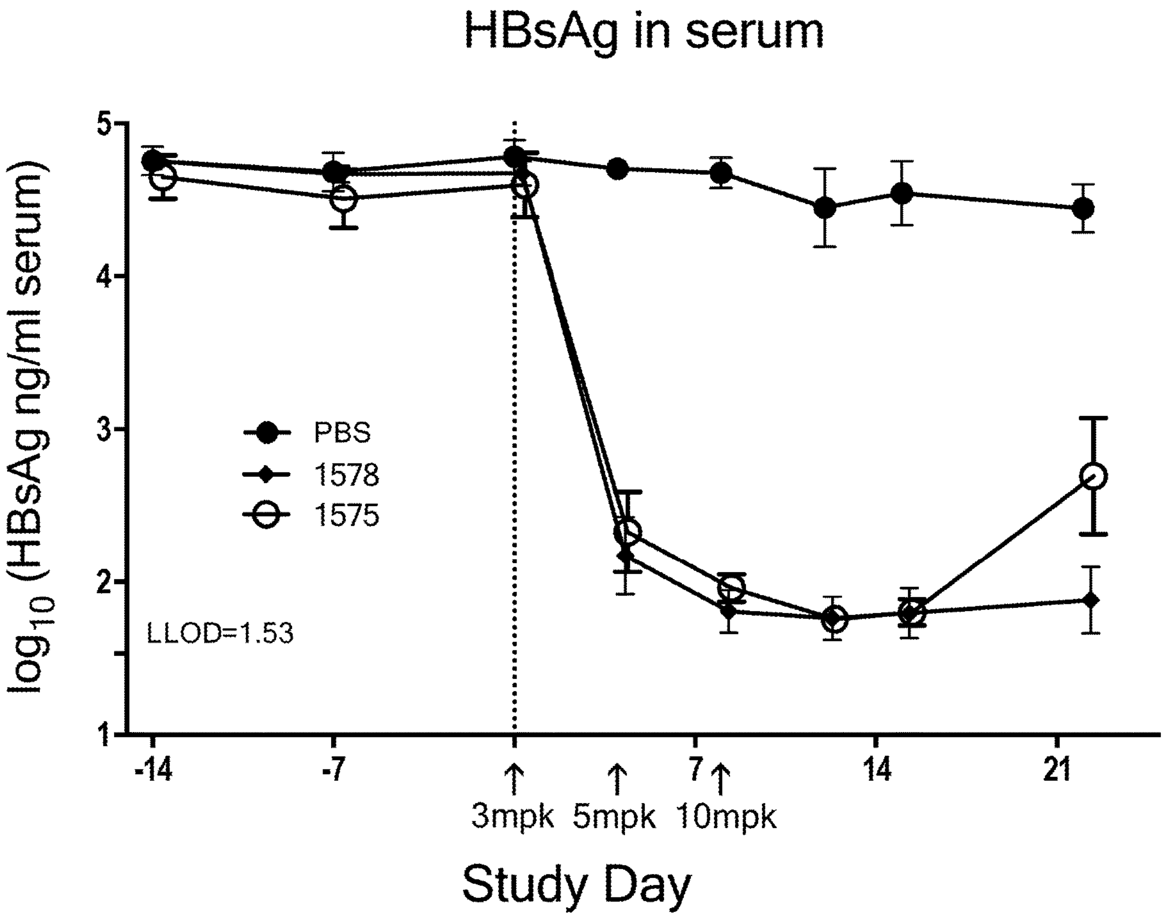

FIG. 16 shows HBV inhibitory effect in vivo for UNA oligomers, observed in an AAV-HBV mouse model of HBV infection. The UNA oligomers were formulated in lipid nanoparticles and injected intravenously into C57Bl/6 mice with active HBV replication after AAV-mediated delivery of a recombinant HBV genome to the liver. Treatment with each of UNA oligomers 1578 and 1575 caused a rapid and sustained reduction in viral endpoint serum HBsAg.

Figure 17:
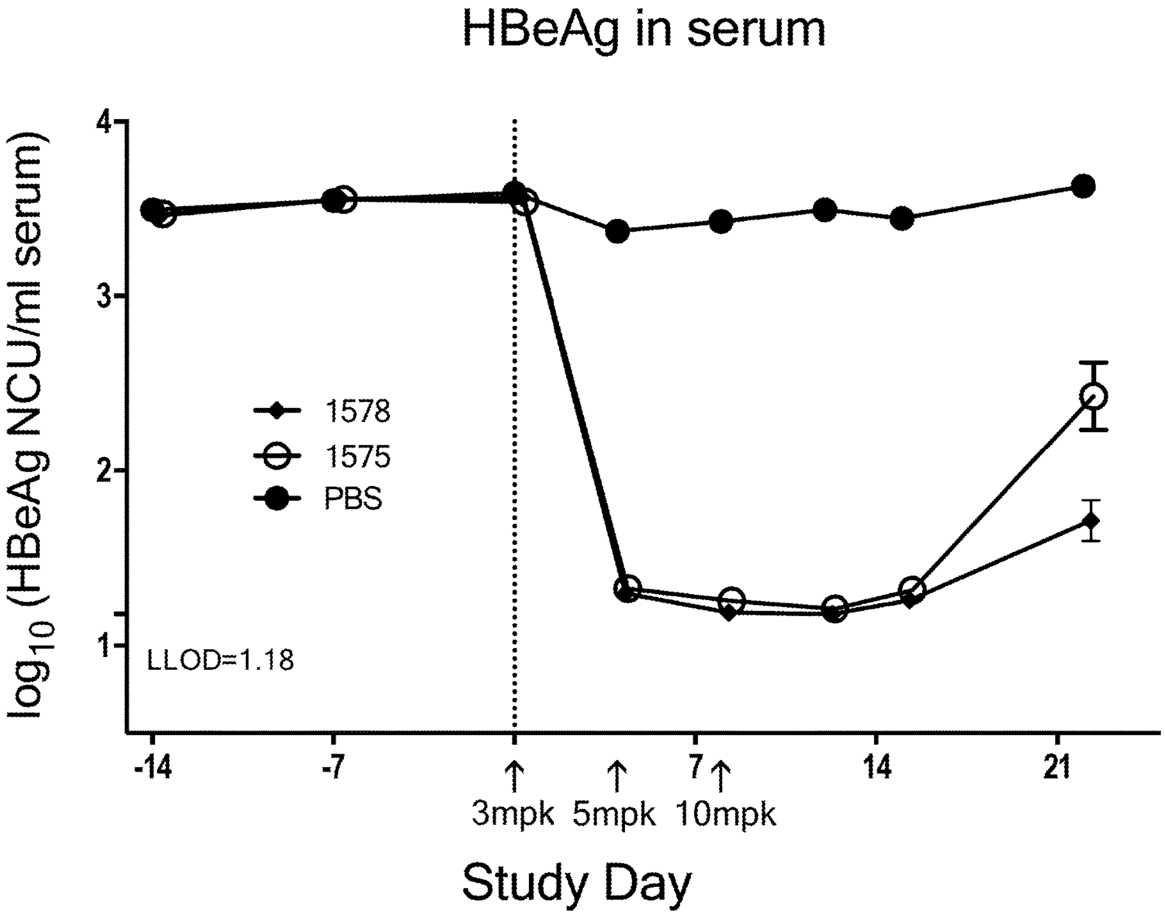

FIG. 17 shows HBV inhibitory effect in vivo for UNA oligomers, observed in an AAV-HBV mouse model of HBV infection. The UNA oligomers were formulated in lipid nanoparticles and injected intravenously into C57Bl/6 mice with active HBV replication after AAV-mediated delivery of a recombinant HBV genome to the liver. Treatment with each of UNA oligomers 1578 and 1575 caused a rapid and sustained reduction in viral endpoint serum HBeAg.

Figure 18:
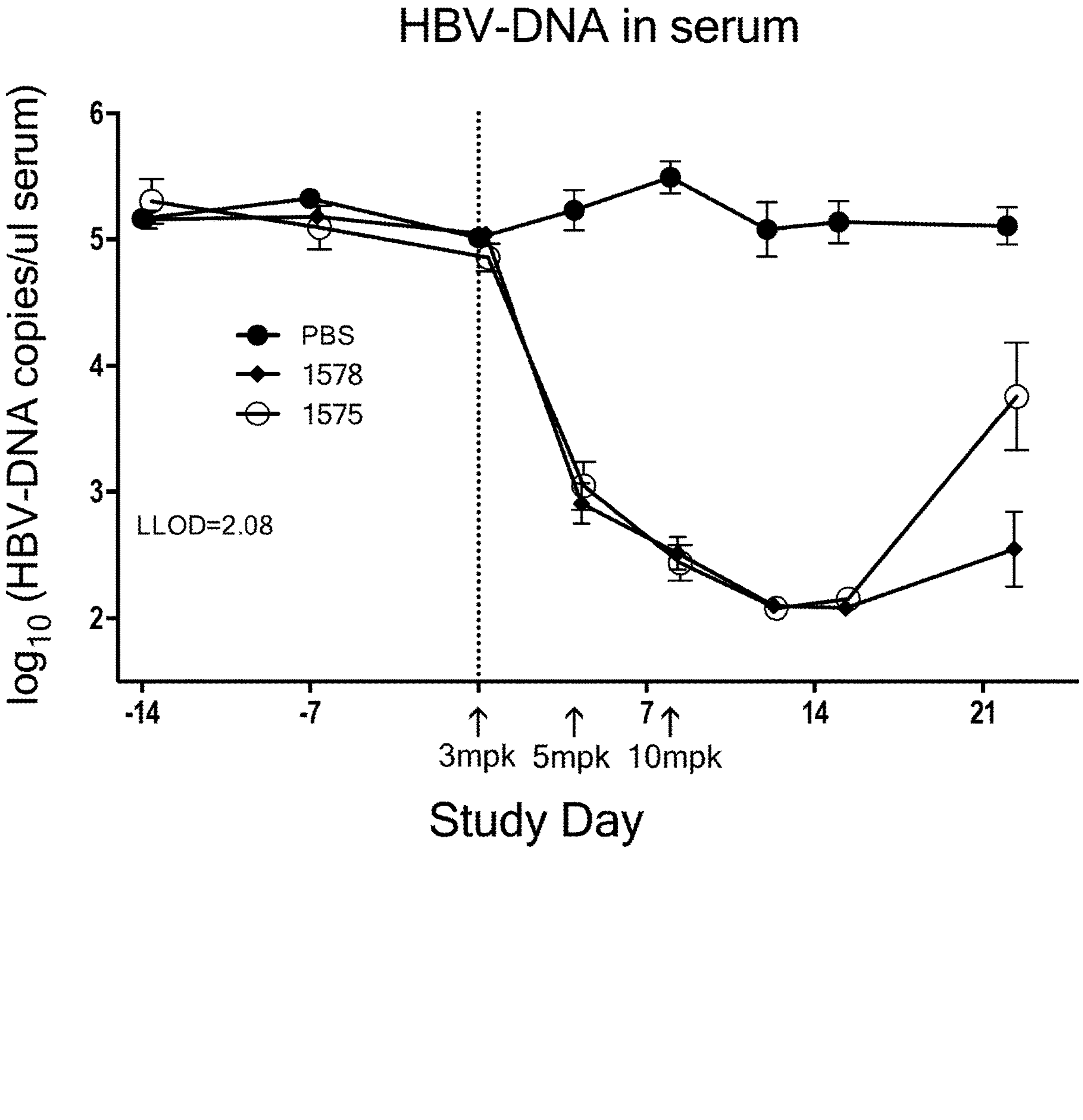

FIG. 18 shows HBV inhibitory effect in vivo for UNA oligomers, observed in an AAV-HBV mouse model of HBV infection. The UNA oligomers were formulated in lipid nanoparticles and injected intravenously into C57Bl/6 mice with active HBV replication after AAV-mediated delivery of a recombinant HBV genome to the liver. Treatment with each of UNA oligomers 1578 and 1575 caused a rapid and sustained reduction in viral endpoint serum HBV DNA.

DETAILED DESCRIPTION OF THE INVENTION

This invention provides a range of novel agents and compositions to be used as therapeutics against Hepatitis B infection. Molecules of this invention can be used as active pharmaceutical ingredients in compositions for ameliorating, preventing or treating Hepatitis B infection.

The galenic molecules of this invention can prevent Hepatitis B virus from carrying out one or more of its processes. Molecules of this invention can be used for ameliorating or treating Hepatitis B infection, and may act against any of the replication, maturation, growth, or transmission modes of the Hepatitis B virus.

Novel agents of this invention include oligomeric molecules that inhibit expression of an HBV genome.

Embodiments of this invention can provide extraordinary and surprisingly enhanced efficacy against HBV infection in a subject by attacking all portions of the HBV genome. More particularly, agents and compositions of this invention can simultaneously inhibit all identified genes of HBV: C, P, S, and X. Thus, the compounds and compositions of this disclosure can inhibit the small surface antigen HBsAg, as well as the extracellular protein HBeAg, in addition to X protein and viral polymerase.

The properties of the compounds of this invention arise according to their molecular structure, and the structure of the molecule in its entirety, as a whole, can provide significant benefits based on those properties. Embodiments of this invention can provide molecules having one or more properties that advantageously provide enhanced effectiveness against HBV, as well as compositions or formulations for therapeutic agents against Hepatitis B infection, which can provide clinical agents.

A wide range of novel molecules are provided, each of which can incorporate specialized linker groups. The linker groups can be attached in a chain in the molecule. Each linker group can also be attached to a nucleobase.

In some aspects, a linker group can be a monomer. Monomers can be attached to form a chain molecule. In a chain molecule of this invention, a linker group monomer can be attached at any point in the chain.

In certain aspects, linker group monomers can be attached in a chain molecule of this invention so that the linker group monomers reside near the ends of the chain. The ends of the chain molecule can be formed by linker group monomers.

As used herein, a chain molecule can also be referred to as an oligomer.

In further aspects, the linker groups of a chain molecule can each be attached to a nucleobase. The presence of nucleobases in the chain molecule can provide a sequence of nucleobases.

In certain embodiments, this invention provides oligomer molecules having chain structures that incorporate novel combinations of the linker group monomers, along with certain natural nucleotides, or non-natural nucleotides, or modified nucleotides, or chemically-modified nucleotides.

The oligomer molecules of this invention can display a sequence of nucleobases that is targeted to a component of an HBV genome. In some embodiments, an oligomer can be targeted to a portion of the HBV genome that is conserved, or highly conserved, among a number of known HBV genomic sequences.

In some aspects, this invention provides active oligomer molecules that correspond to, or are complementary to at least a fragment of an HBV nucleic acid molecule, and that decrease expression of at least such a fragment present in a cell. In some embodiments, the active oligomer molecule can be double-stranded.

Without wishing to be bound by any one particular theory, it is believed that a cellular pathway may use active oligomers of this invention to be sequence-specific regulators in an RNA interference pathway. The active oligomers may bind to the RNA-induced silencing complex (RISC complex), where a sense strand, also referred to as the passenger strand, and an antisense strand, also referred to as the guide strand, can be unwound, and the antisense strand complexed in the RISC complex. The guide strand can bind to a complementary sequence to which it was targeted, for example, a target sequence in an mRNA, which can be subsequently cleaved, resulting in inactivation of the nucleic acid molecule containing the target sequence. As a result, the expression of mRNA containing the target sequence can be reduced.

In some embodiments, an oligomeric molecule may be attached to a delivery moiety. Examples of delivery moieties include glycoprotein receptors, galactoses, galactosamines, N-acetylgalactosamines, GalNAc groups, cholesterols, sterols, phytosterols, steroids, zoosterols, lanosterols, stigmastanols, dihydrolanosterols, zymosterols, zymostenols, desmosterols, and 7-dehydrocholesterol s.

In additional aspects, this invention provides therapeutics for preventing, ameliorating, or treating a disease caused by Hepatitis B infection. An active compound or molecule of this invention may be used in the prevention or treatment of a viral infection caused by Hepatitis B virus.

This invention provides structures, methods and compositions for oligomeric agents that incorporate the linker group monomers. The oligomeric molecules of this invention can be used as active agents in formulations for gene silencing therapeutics targeted to HBV.

This invention provides a range of molecules that are useful for providing therapeutic effects because of their activity in regulating expression of a gene. The molecules of this invention are structured to provide gene regulating or silencing activity in vitro and in vivo.

Embodiments of this invention can provide molecules for use as therapeutic agents against Hepatitis B infection. The molecules can be used as active pharmaceutical ingredients in compositions for ameliorating, preventing or treating Hepatitis B infection.

In certain embodiments, an active molecule can be structured as an oligomer composed of monomers. The oligomeric structures of this invention may contain one or more linker group monomers, along with certain nucleotides.

Modalities of Action

Molecules of this invention for treating Hepatitis B infection may act against any of the replication, maturation, growth, or transmission modalities of the Hepatitis B virus. By preventing the Hepatitis B virus from carrying out any one or more of its normal processes, the molecules of this invention can be used for ameliorating or treating Hepatitis B infection.

This invention can provide unexpectedly advantageous efficacy against HBV infection in a subject by simultaneously modulating all portions of the HBV genome.

In some embodiments, inventive UNA oligomeric agents and compositions of this disclosure can inhibit expression of each of the HBV genes C, P, S, and X.

In some aspects, inventive UNA oligomeric agents and compositions of this disclosure can simultaneously inhibit expression of all genes of HBV, including genes C, P, S, and X.

In particular aspects, inventive UNA oligomeric compositions of this disclosure can simultaneously inhibit expression of multiple genes of HBV, such as genes P and C, or P and S, or P and X.

In further aspects, inventive UNA oligomeric compositions of this disclosure can simultaneously inhibit expression of multiple genes of HBV, such as genes P, S and C, or P, X and S, or P, C and X.

In certain aspects, the compounds of this invention can inhibit the small surface antigen HBsAg in vivo, regardless of the genomic source of HBsAg in the subject.

In further aspects, compounds and compositions of this invention can inhibit the HBV extracellular protein HBeAg, the X protein, and HBV viral polymerase.

In some aspects, a therapeutic molecule of this invention can be active in preventing or inhibiting a step of the replication cycle of hepatitis B virus.

Viral components of HBV can include a nucleocapsid, fully or partially double stranded DNA (relaxed circular, rcDNA), a polymerase, surface antigens, core proteins, a regulatory X-protein, and secreted proteins.

In some embodiments, a therapeutic molecule of this invention can be active in preventing or inhibiting attachment of viral components to cell-associated proteoglycans.

Certain embodiments of this invention provide a therapeutic molecule that can be active in preventing or inhibiting binding of a viral component to a hepatocyte receptor.

In further embodiments, a therapeutic molecule of this invention can be active in preventing or inhibiting entry of a viral component into a cell by endocytosis, or fusion of a viral component to a cell membrane.

A therapeutic molecule of this invention may be active in preventing or inhibiting release of a viral component into the cytoplasm of a cell.

In additional embodiments, a therapeutic molecule of this invention can be active in preventing or inhibiting internal cell transport of an HBV nucleocapsid.

Aspects of this disclosure can provide a therapeutic molecule, which can be active in preventing or inhibiting release of HBV rcDNA in a cell.

In some embodiments, a therapeutic molecule of this invention can be active in preventing or inhibiting operation of the viral polymerase.

Certain embodiments may provide a therapeutic molecule that can be active in preventing or inhibiting development of an HBV genomic DNA in a cell.

In further embodiments, a therapeutic molecule of this invention can be active in preventing or inhibiting production of a viral RNA in a cell.

A therapeutic molecule of this invention may be active in preventing or inhibiting viral replication in a cell.

In additional embodiments, a therapeutic molecule may be active in preventing or inhibiting an HBV regulatory X-protein in a cell.

Further aspects of this disclosure can provide a therapeutic molecule that be active in preventing or inhibiting translation or reverse transcription of a viral RNA in a cell.

In some embodiments, a therapeutic molecule of this invention can be active in preventing or inhibiting maturation of a viral nucleocapsid in a cell.

UNA Monomers

In some embodiments, linker group monomers can be unlocked nucleomonomers (UNA monomers), which are small organic molecules based on a propane-1,2,3-tri-yl-trisoxy structure as shown below:

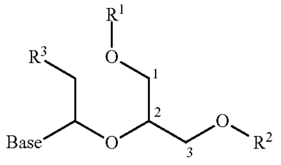

UNA MONOMER where $R^1$ and $R^2$ are H, and $R^1$ and $R^2$ can be phosphodiester linkages, Base can be a nucleobase, and $R^3$ is a functional group described below.

In another view, the UNA monomer main atoms can be drawn in IUPAC notation as follows:

UNA monomer unit

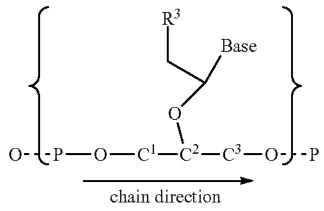

where the direction of progress of the oligomer chain is from the 1-end to the 3-end of the propane residue.

Examples of a nucleobase include uracil, thymine, cytosine, 5-methylcytosine, adenine, guanine, inosine, and natural and non-natural nucleobase analogues.

In general, because the UNA monomers are not nucleotides, they can exhibit at least four forms in an oligomer. First, a UNA monomer can be an internal monomer in an oligomer, where the UNA monomer is flanked by other monomers on both sides. In this form, the UNA monomer can participate in base pairing when the oligomer is a duplex, for example, and there are other monomers with nucleobases in the duplex.

Examples of UNA monomer as internal monomers flanked at both the propane-1-yl position and the propane-3-yl position, where $R^3$ is —OH, are shown below.

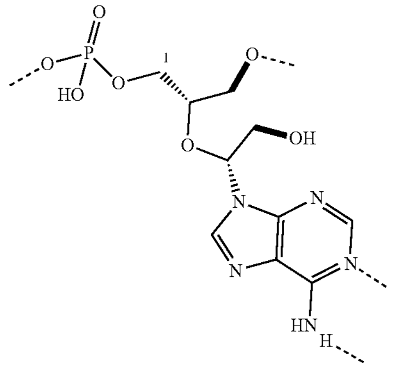

UNA-A

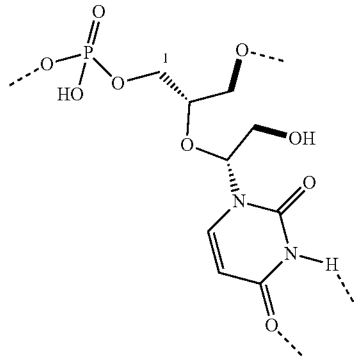

UNA-U

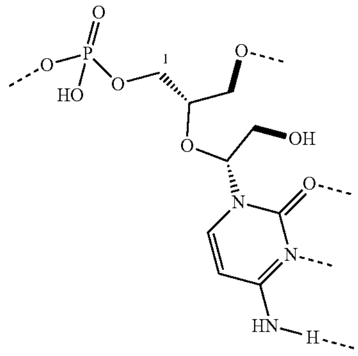

UNA-C

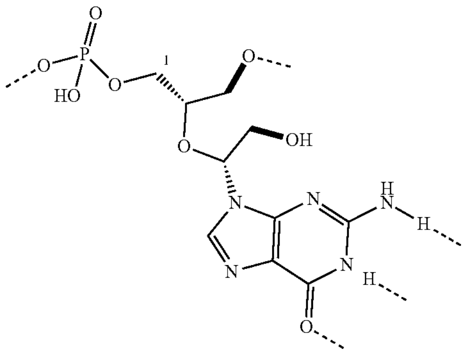

UNA-G

Second, a UNA monomer can be a monomer in an overhang of an oligomer duplex, where the UNA monomer is flanked by other monomers on both sides. In this form, the UNA monomer does not participate in base pairing. Because the UNA monomers are flexible organic structures, unlike nucleotides, the overhang containing a UNA monomer will be a flexible terminator for the oligomer.

A UNA monomer can be a terminal monomer in an overhang of an oligomer, where the UNA monomer is attached to only one monomer at either the propane-1-yl position or the propane-3-yl position. In this form, the UNA monomer does not participate in base pairing. Because the UNA monomers are flexible organic structures, unlike nucleotides, the overhang containing a UNA monomer can be a flexible terminator for the oligomer.

Examples of a UNA monomer as a terminal monomer attached at the propane-3-yl position are shown below.

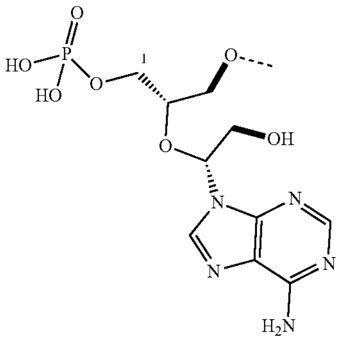

terminal UNA-A

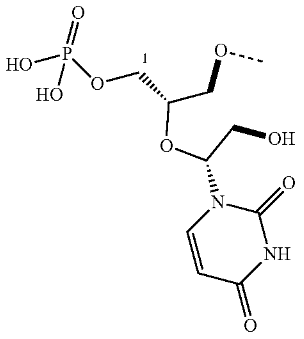

terminal UNA-U

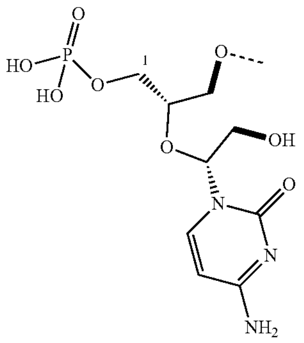

terminal UNA-C

-continued

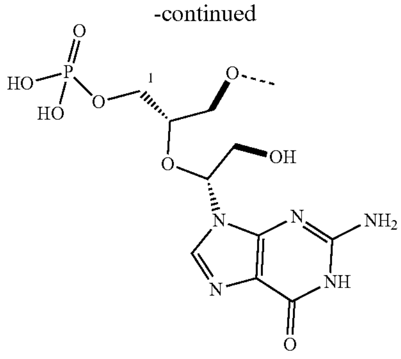

terminal UNA-G

Because a UNA monomer can be a flexible molecule, a UNA monomer as a terminal monomer can assume widely differing conformations. An example of an energy minimized UNA monomer conformation as a terminal monomer attached at the propane-3-yl position is shown below.

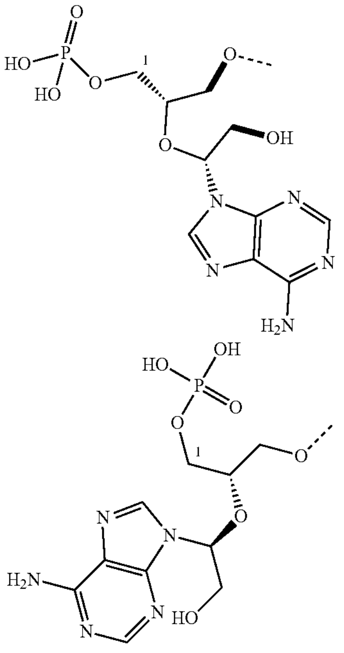

UNA-A terminal forms: the dashed bond shows the propane-3-yl attachment

Thus, UNA oligomers having a terminal UNA monomer are significantly different in structure from conventional nucleic acid agents, such as siRNAs. For example, siRNAs may require that terminal monomers or overhangs in a duplex be stabilized. In contrast, the conformability of a terminal UNA monomer can provide UNA oligomers with different properties.

Among other things, the structure of the UNA monomer allows it to be attached to naturally-occurring nucleotides. A UNA oligomer can be a chain composed of UNA monomers, as well as various nucleotides that may be based on naturally-occurring nucleosides.

In some embodiments, the functional group $R^3$ of a UNA monomer can be —$OR^4$, —$SR^4$, —$NR^4_2$, —NH(C═O)$R^4$, morpholino, morpholin-1-yl, piperazin-1-yl, or 4-alkanoyl-piperazin-1-yl, where $R^4$ is the same or different for each occurrence, and can be H, alkyl, a cholesterol, a lipid molecule, a polyamine, an amino acid, or a polypeptide.

The UNA monomers are organic molecules. UNA monomers are not nucleic acid monomers or nucleotides, nor are they naturally-occurring nucleosides or modified naturally-occurring nucleosides.

A UNA oligomer of this invention is a synthetic chain molecule. A UNA oligomer of this invention is not a nucleic acid, nor an oligonucleotide.

In some embodiments, as shown above, a UNA monomer can be UNA-A (designated Ã), UNA-U (designated Ŭ), UNA-C (designated Č), and UNA-G (designated Ğ).

Designations that may be used herein include mA, mG, mC, and mU, which refer to the 2'-O-Methyl modified ribonucleotides.

Designations that may be used herein include lower case c and u, which refer to the 2'-O-methyl modified ribonucleotides.

Designations that may be used herein include dT, which refers to a 2'-deoxy T nucleotide.

Additional Monomers for Oligomeric Agents

As used herein, in the context of oligomer sequences, the symbol X represents a UNA monomer.

As used herein, in the context of oligomer sequences, the symbol N represents any natural nucleotide monomer, or a modified nucleotide monomer.

As used herein, in the context of oligomer sequences, the symbol Q represents a non-natural, modified, or chemically-modified nucleotide monomer. When a Q monomer appears in one strand of the oligomer, and is unpaired with the other strand, the monomer can have any base attached. When a Q monomer appears in one strand of the oligomer, and is paired with a monomer in the other strand, the Q monomer can have any base attached that would be complementary to the monomer in the corresponding paired position in the other strand.

Examples of nucleic acid monomers include non-natural, modified, and chemically-modified nucleotides, including any such nucleotides known in the art.

Examples of non-natural, modified, and chemically-modified nucleotide monomers include any such nucleotides known in the art, for example, 2'-O-methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5-C-methyl-nucleotides, and inverted deoxyabasic monomer residues.

Examples of non-natural, modified, and chemically-modified nucleotide monomers include 3'-end stabilized nucleotides, 3'-glyceryl nucleotides, 3'-inverted abasic nucleotides, 3'-inverted thymidine, and L-thymidine.

Examples of non-natural, modified, and chemically-modified nucleotide monomers include locked nucleic acid nucleotides, 2'-O,4'-C-methylene-(D-ribofuranosyl) nucleotides, 2'-methoxyethoxy (MOE) nucleotides, 2'-methyl-thioethyl, 2'-deoxy-2'-fluoro nucleotides, and 2'-O-methyl nucleotides.

Examples of non-natural, modified, and chemically-modified nucleotide monomers include 2'-amino nucleotides, 2'-O-amino nucleotides, 2'-C-allyl nucleotides, and 2'-O-allyl nucleotides.

Examples of non-natural, modified, and chemically-modified nucleotide monomers include $N^6$-methyladenosine nucleotides.

Examples of non-natural, modified, and chemically-modified nucleotide monomers include nucleotide monomers with modified bases 5-(3-amino)propyluridine, 5-(2-mercapto)ethyluridine, 5-bromouridine; 8-bromoguanosine, or 7-deazaadenosine.

Examples of non-natural, modified, and chemically-modified nucleotide monomers include 2'-O-aminopropyl substituted nucleotides.

Examples of non-natural, modified, and chemically-modified nucleotide monomers include 2'-O-guanidinopropyl substituted nucleotides.

Examples of non-natural, modified, and chemically-modified nucleotide monomers include Pseudouridines.

Examples of non-natural, modified, and chemically-modified nucleotide monomers include replacing the 2'-OH group of a nucleotide with a 2'-R, a 2'-OR, a 2'-halogen, a 2'-SR, or a 2'-amino, 2'-azido, where R can be H, alkyl, fluorine-substituted alkyl, alkenyl, or alkynyl.

Examples of non-natural, modified, and chemically-modified nucleotide monomers include replacing the 2'-OH group of a nucleotide with a 2'-R or 2'-OR, where R can be CN, $CF_3$, alkylamino, or aralkyl.

Examples of non-natural, modified, and chemically-modified nucleotide monomers include nucleotides with a modified sugar such as an F-HNA, an HNA, a CeNA, a bicyclic sugar, or an LNA.

Examples of non-natural, modified, and chemically-modified nucleotide monomers include 2'-oxa-3'-aza-4'a-carbanucleoside monomers, 3-hydroxymethyl-5-(1H-1,2,3-triazol)-isoxazolidine monomers, and 5'-triazolyl-2'-oxa-3'-aza-4'a-carbanucleoside monomers.

Some examples of modified nucleotides are given in Saenger, Principles of Nucleic Acid Structure, Springer-Verlag, 1984.

Oligomeric Compounds Containing UNA Monomers

Aspects of this invention can provide structures and compositions for UNA-containing oligomeric compounds. The oligomeric agents may incorporate one or more UNA monomers. Oligomeric molecules of this invention can be used as active agents in formulations for gene regulating or gene silencing therapeutics.

In some embodiments, this invention provides oligomeric compounds having a structure that incorporates novel combinations of UNA monomers with certain natural nucleotides, non-natural nucleotides, modified nucleotides, or chemically-modified nucleotides.

In further aspects, the oligomeric compounds can be pharmacologically active molecules. UNA oligomers of this invention can be used as active pharmaceutical ingredients for regulating gene expression, and in RNA interference methods, as well as antisense, RNA blocking, and micro-RNA strategies.

A UNA oligomer of this invention can have the structure of Formula I

Formula I

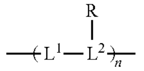

wherein $L^1$ is a linkage, n is from 19 to 29, and for each occurrence $L^2$ is a UNA linker group having the formula —$C^1$—$C^2$—$C^3$— where R is attached to $C^2$ and has the formula —$OCH(CH_2R^3)R^5$, where $R^3$ is —$OR^4$, —$SR^4$, —$NR^4_2$, —NH(C═O)$R^4$, morpholino, morpholin-1-yl, piperazin-1-yl, or 4-alkanoyl-piperazin-1-yl, where $R^4$ is the same or different for each occurrence and is H, alkyl, a cholesterol, a lipid molecule, a polyamine, an amino acid, or a polypeptide, and where $R^5$ is a nucleobase, or $L^2$(R) is a sugar such as a ribose and R is a nucleobase, or $L^2$ is a modified sugar such as a modified ribose and R is a nucleobase. In certain embodiments, a nucleobase can be a modified nucleobase. $L^1$ can be a phosphodiester linkage.

A UNA oligomer of this invention can be a short chain molecule. A UNA oligomer can be a duplex pair. Thus, a UNA oligomer can have a first strand of the duplex and a second strand of the duplex, which is complementary to the first strand with respect to the nucleobases, although up to three mismatches can occur. A UNA oligomer duplex can have overhangs.

Some UNA oligomers are discussed in U.S. Pat. No. 8,314,227, as well as US Patent Publication No. 20110313020 A1.

The target of a UNA oligomer can be a target nucleic acid. In some embodiments, the target can be any mRNA of a subject. A UNA oligomer can be active for gene silencing in RNA interference.

A UNA oligomer may comprise two strands that together provide a duplex. The duplex may be composed of a first strand, which may also be referred to as a passenger strand or sense strand, and a second strand, which may also be referred to as a guide strand or antisense strand.

In some aspects, a UNA oligomer of this invention can have any number of phosphorothioate intermonomer linkages in any position in any strand, or in both strands of a duplex structure.

In some embodiments, any one or more of the intermonomer linkages of a UNA oligomer can be a phosphodiester, a phosphorothioate including dithioates, a chiral phosphorothioate, and other chemically modified forms.

Examples of UNA oligomers of this invention include duplex pairs, which are in general complementary. Thus, for example, SEQ ID NO:1 can represent a first strand of a duplex and SEQ ID NO:2 can represent a second strand of the duplex, which is complementary to the first strand.

For example, the symbol "N" in the first strand can represent any nucleotide that is complementary to the monomer in the corresponding position in the second strand. Example UNA oligomers of this disclosure are shown with 2-monomer length overhangs, although overhangs of from 1 to 8 monomers, or longer, can be used.

The symbol "X" in a strand or oligomer represents a UNA monomer. When a UNA monomer appears in one strand of the oligomer, and is unpaired with the other strand, the monomer can have any base attached. When a UNA monomer appears in one strand of the oligomer, and is paired with a monomer in the other strand, the UNA monomer can have any base attached that would be complementary to the monomer in the corresponding paired position in the other strand.

Further, when the oligomer terminates in a UNA monomer, the terminal position has a 1-end, according to the positional numbering shown above, instead of a 5'-end as for a nucleotide, or the terminal position has a 3-end, according to the positional numbering shown above, instead of a 3'-end as for a nucleotide. For example, the UNA oligomer

SEQ ID NO: 1
```
1-X-N-N-N-N-N-N-N-N-N-N-N-N-N-N-N-N-N-N-N-X-X-3
```

SEQ ID NO: 2
```
3-X-X-N-N-N-N-N-N-N-N-N-N-N-N-X-X-X-X-X-X-X-N-5'
```

has a UNA monomer 1-end on the first strand, a UNA monomer 3-end on the first strand, a UNA monomer 3-end on the second strand, and a nucleotide 5'-end on the second strand.

Complementarity of strands can involve mismatches. In certain embodiments, complementarity of strands can include one to three, or more, mismatches.

In some embodiments, a UNA oligomer of this invention can have one or more UNA monomers at the 1-end of the first strand, and one or more UNA monomers at the 3-end of the first strand.

In further embodiments, a UNA oligomer of this invention can have one or more UNA monomers at the 3-end of the second strand.

In certain embodiments, a duplex UNA oligomer of this invention can have one or more UNA monomers at the 1-end of the first strand, one or more UNA monomers at the 3-end of the first strand, and one or more UNA monomers at the 3-end of the second strand.

A UNA oligomer of this invention the oligomer may have a first strand and a second strand, each of the strands independently being 19-23 monomers in length.

In certain embodiments, a UNA oligomer of this invention may have a first strand that is 19-23 monomers in length.

In certain embodiments, a UNA oligomer of this invention may have a duplex region that is 19-21 monomers in length.

In further embodiments, a UNA oligomer of this invention may have a second strand that is 19-23 monomers in length.

In certain embodiments, a UNA oligomer of this invention may have a first strand that is 19 monomers in length, and a second strand that is 21 monomers in length.

In certain embodiments, a UNA oligomer of this invention may have a first strand that is 20 monomers in length, and a second strand that is 21 monomers in length.

In certain embodiments, a UNA oligomer of this invention may have a first strand that is 21 monomers in length, and a second strand that is 21 monomers in length.

In certain embodiments, a UNA oligomer of this invention may have a first strand that is 22 monomers in length, and a second strand that is 21 monomers in length.

A UNA oligomer of this invention for inhibiting gene expression can have a first strand and a second strand, each of the strands being 19-29 monomers in length. The monomers can be UNA monomers and nucleic acid nucleoside monomers. The oligomer can have a duplex structure of from 14 to 29 monomers in length. The UNA oligomer can be targeted to a target gene and can exhibit reduced off-target effects as compared to a conventional siRNA. In some embodiments, a UNA oligomer of this invention can have a first strand and a second strand, each of the strands being 19-23 monomers in length.

In another aspect, the UNA oligomer may have a blunt end, or may have one or more overhangs. In some embodiments, the first and second strands may be connected with a connecting oligomer in between the strands, and form a duplex region with a connecting loop at one end.

In certain embodiments, an overhang can be one or two monomers in length.

Examples of an overhang can contain one or more UNA monomers, natural nucleotides, non-natural nucleotides, modified nucleotides, or chemically-modified nucleotides, and combinations thereof.

Examples of an overhang can contain one or more deoxythymidine nucleotides, 2'-O-methyl nucleotides, inverted abasic monomers, inverted thymidine monomers, L-thymidine monomers, or glyceryl nucleotides.

A UNA oligomer can mediate cleavage of a target nucleic acid in a cell. In some processes, the second strand of the UNA oligomer, at least a portion of which can be complementary to the target nucleic acid, can act as a guide strand that can hybridize to the target nucleic acid.

The second strand can be incorporated into an RNA Induced Silencing Complex (RISC).

A UNA oligomer of this disclosure may comprise naturally-occurring nucleic acid nucleotides, and modifications thereof that are compatible with gene silencing activity.

In some aspects, a UNA oligomer is a double stranded construct molecule that is able to inhibit gene expression.

As used herein, the term strand refers to a single, contiguous chain of monomers, the chain having any number of internal monomers and two end monomers, where each end monomer is attached to one internal monomer on one side, and is not attached to a monomer on the other side, so that it ends the chain.

The monomers of a UNA oligomer may be attached via phosphodiester linkages, phosphorothioate linkages, gapped linkages, and other variations.

In some embodiments, a UNA oligomer can include mismatches in complementarity between the first and second strands. In other embodiments, a UNA oligomer may have 1, or 2, or 3 mismatches. The mismatches may occur at any position in the duplex region.

The target of a UNA oligomer can be a target nucleic acid of a target gene.

A UNA oligomer may have one or two overhangs outside the duplex region. The overhangs can be an unpaired portion at the end of the first strand or second strand. The lengths of the overhang portions of the first and second strands can be the same or different.

A UNA oligomer may have at least one blunt end. A blunt end does not have an overhang portion, and the duplex region at a blunt end terminates at the same position for both the first and second strands.

A UNA oligomer can be RISC length, which means that it has a duplex length of less than 25 base pairs.

In certain embodiments, a UNA oligomer can be a single strand that folds upon itself and hybridizes to itself to form a double stranded region having a connecting loop at the end of the double stranded region.

Examples of UNA oligomers containing five UNA monomers, and which contain one or more Q monomers are shown in Table 1.

TABLE 1

Oligomeric compounds containing five UNA monomers and additional Q monomers

| SEQ ID NO: | OLIGOMER |
|---|---|
| 3 | X Q-N-N-Q-N-Q-N-Q-Q-Q-N-Q-N-Q-N-Q-N-Q-N-X-X |
| 4 | X-X-Q-N-Q-N-Q-N-N-N-N-N-Q-N-Q-N-Q-N-Q-N-Q |
| 5 | X-Q-N-N-Q-N-Q-N-Q-N-Q-N-Q-N-Q-N-Q-N-Q-N-X-X |
| 6 | X-X-Q-N-Q-N-Q-N-Q-N-Q-N-Q-N-Q-N-Q-N-Q-N-Q |
| 7 | X-Q-N-N-Q-N-Q-N-N-N-N-N-Q-N-Q-N-Q-N-Q-N-X-X |
| 8 | X-X-Q-N-Q-N-Q-N-Q-N-N-N-Q-N-Q-N-Q-N-Q-N-Q |
| 9 | X-Q-N-N-Q-N-Q-N-N-N-N-N-Q-N-Q-N-Q-N-Q-N-X-X |
| 10 | X-X-Q-N-Q-N-Q-N-N-N-N-N-N-N-Q-N-Q-N-Q-N-Q |

TABLE 1-continued

| Oligomeric compounds containing five UNA monomers and additional Q monomers | |
|---|---|
| SEQ ID NO: | OLIGOMER |
| 11 | X-Q-N-N-Q-N-Q-N-N-N-N-N-N-N-Q-N-Q-N-Q-N-X-X |
| 12 | X-X-Q-N-Q-N-Q-N-N-N-N-N-N-N-N-N-Q-N-Q-N-Q |
| 13 | X-Q-N-N-Q-N-Q-N-N-N-N-N-N-N-N-N-Q-N-Q-N-X-X |
| 14 | X-X-Q-N-Q-N-Q-N-N-N-N-N-N-N-N-N-Q-N-Q-N-Q |
| 15 | X-Q-N-N-Q-N-Q-N-N-N-N-N-N-N-N-N-Q-N-Q-N-X-X |
| 16 | X-X-Q-N-Q-N-Q-N-N-N-N-N-N-N-N-N-N-N-Q-N-Q |
| 17 | X-Q-N-N-Q-N-N-N-N-N-N-N-N-N-N-N-Q-N-Q-N-X-X |
| 18 | X-X-Q-N-Q-N-Q-N-N-N-N-N-N-N-N-N-N-N-Q-N-Q |
| 19 | X Q-N-N-Q-N-N-N-N-N-N-N-N-N-N-N-Q-N-Q-N-X-X |
| 20 | X-X-Q-N-Q-N-N-N-N-N-N-N-N-N-N-N-N-N-Q-N-Q |
| 21 | X-Q-N-N-N-N-N-N-N-N-N-N-N-N-N-N-Q-N-Q-N-X-X |
| 22 | X-X-Q-N-Q-N-N-N-N-N-N-N-N-N-N-N-N-N-Q-N-Q |
| 23 | X Q-N-N-N-N-N-N-N-N-N-N-N-N-N-N-N-N-Q-N-X-X |
| 24 | X-X-Q-N-Q-N-N-N-N-N-N-N-N-N-N-N-N-N-Q-N-Q |
| 25 | X-Q-N-N-N-N-N-N-N-N-N-N-N-N-N-N-N-Q-N-X-X |
| 26 | X-X-Q-N-N-N-N-N-N-N-N-N-N-N-N-N-N-N-Q-N-Q |
| 27 | X-Q-N-N-N-N-N-N-N-N-N-N-N-N-N-N-N-Q-N-X-X |
| 28 | X-X-Q-N-N-N-N-N-N-N-N-N-N-N-N-N-N-N-N-N-Q |
| 29 | X-Q-N-N-N-N-N-N-N-N-N-N-N-N-N-N-N-N-N-X-X |
| 30 | X-X-Q-N-N-N-N-N-N-N-N-N-N-N-N-N-N-N-N-N-Q |

Examples of UNA oligomers containing four UNA monomers and additional Q monomers are shown in Table 2.

TABLE 2

| Oligomeric compounds containing four UNA monomers and additional Q monomers | |
|---|---|
| SEQ ID NO: | OLIGOMER |
| 31 | X Q-N-N-Q-N-Q-N-Q-Q-Q-N-Q-N-Q-N-Q-N-Q-N-X-Q |
| 32 | X-X-Q-N-Q-N-Q-N-N-N-N-N-Q-N-Q-N-Q-N-Q-N-Q |
| 33 | X Q-N-N-Q-N-Q-N-Q-N-Q-N-Q-N-Q-N-Q-N-Q-N-X-Q |
| 34 | X-X-Q-N-Q-N-Q-N-Q-N-Q-N-Q-N-Q-N-Q-N-Q-N-Q |
| 35 | X-Q-N-N-Q-N-Q-N-N-N-N-N-Q-N-Q-N-Q-N-Q-N-X-Q |
| 36 | X-X-Q-N-Q-N-Q-N-Q-N-N-N-Q-N-Q-N-Q-N-Q-N-Q |
| 37 | X-Q-N-N-Q-N-Q-N-N-N-N-N-Q-N-Q-N-Q-N-Q-N-X-Q |
| 38 | X-X-Q-N-Q-N-Q-N-N-N-N-N-N-N-Q-N-Q-N-Q-N-Q |
| 39 | X Q-N-N-Q-N-Q-N-N-N-N-N-N-N-Q-N-Q-N-Q-N-X-Q |
| 40 | X-X-Q-N-Q-N-Q-N-N-N-N-N-N-N-N-N-Q-N-Q-N-Q |
| 41 | X-Q-N-N-Q-N-Q-N-N-N-N-N-N-N-N-N-Q-N-Q-N-X-Q |
| 42 | X-X-Q-N-Q-N-Q-N-N-N-N-N-N-N-N-N-Q-N-Q-N-Q |
| 43 | X Q-N-N-Q-N-Q-N-N-N-N-N-N-N-N-N-Q-N-Q-N-X-Q |
| 44 | X-X-Q-N-Q-N-Q-N-N-N-N-N-N-N-N-N-N-N-Q-N-Q |
| 45 | X Q-N-N-Q-N-N-N-N-N-N-N-N-N-N-N-Q-N-Q-N-X-Q |
| 46 | X-X-Q-N-Q-N-Q-N-N-N-N-N-N-N-N-N-N-N-Q-N-Q |
| 47 | X Q-N-N-Q-N-N-N-N-N-N-N-N-N-N-N-Q-N-Q-N-X-Q |
| 48 | X-X-Q-N-Q-N-N-N-N-N-N-N-N-N-N-N-N-N-Q-N-Q |
| 49 | X Q-N-N-N-N-N-N-N-N-N-N-N-N-N-N-Q-N-Q-N-X-Q |
| 50 | X-X-Q-N-Q-N-N-N-N-N-N-N-N-N-N-N-N-N-Q-N-Q |

TABLE 2-continued

| Oligomeric compounds containing four UNA monomers and additional Q monomers | |
|---|---|
| SEQ ID NO: | OLIGOMER |
| 51 | X Q-N-N-N-N-N-N-N-N-N-N-N-N-N-N-N-N-Q-N-X-Q |
| 52 | X-X-Q-N-Q-N-N-N-N-N-N-N-N-N-N-N-N-N-Q-N-Q |
| 53 | X-Q-N-N-N-N-N-N-N-N-N-N-N-N-N-N-N-Q-N-X-Q |
| 54 | X-X-Q-N-N-N-N-N-N-N-N-N-N-N-N-N-N-N-Q-N-Q |
| 55 | X Q-N-N-N-N-N-N-N-N-N-N-N-N-N-N-N-N-Q-N-X-Q |
| 56 | X-X-Q-N-N-N-N-N-N-N-N-N-N-N-N-N-N-N-N-N-Q |
| 57 | X Q-N-N-N-N-N-N-N-N-N-N-N-N-N-N-N-N-N-N-X-Q |
| 58 | X-X-Q-N-N-N-N-N-N-N-N-N-N-N-N-N-N-N-N-N-Q |

Examples of UNA oligomers containing four UNA Monomers and additional Q monomers are shown in Table 3.

TABLE 3

| Oligomeric compounds containing four UNA monomers and additional Q monomers | |
|---|---|
| SEQ ID NO: | OLIGOMER |
| 59 | X-Q-N-Q-N-Q-N-Q-Q-Q-N-Q-N-Q-N-Q-N-Q-N-X-X |
| 60 | Q-X-Q-N-Q-N-Q-N-N-N-N-N-Q-N-Q-N-Q-N-Q-N-Q |
| 61 | X-Q-N-Q-N-Q-N-Q-N-Q-N-Q-N-Q-N-Q-N-Q-N-X-X |
| 62 | Q-X-Q-N-Q-N-Q-N-Q-N-Q-N-Q-N-Q-N-Q-N-Q-N-Q |
| 63 | X-Q-N-Q-N-Q-N-N-N-N-N-Q-N-Q-N-Q-N-Q-N-X-X |
| 64 | Q-X-Q-N-Q-N-Q-N-Q-N-N-N-Q-N-Q-N-Q-N-Q-N-Q |
| 65 | X-Q-N-Q-N-Q-N-N-N-N-N-Q-N-Q-N-Q-N-Q-N-X-X |
| 66 | Q-X-Q-N-Q-N-Q-N-N-N-N-N-N-N-Q-N-Q-N-Q-N-Q |
| 67 | X-Q-N-Q-N-Q-N-N-N-N-N-N-N-Q-N-Q-N-Q-N-X-X |
| 68 | Q-X-Q-N-Q-N-Q-N-N-N-N-N-N-N-N-N-Q-N-Q-N-Q |
| 69 | X-Q-N-Q-N-Q-N-N-N-N-N-N-N-N-N-Q-N-Q-N-X-X |
| 70 | Q-X-Q-N-Q-N-Q-N-N-N-N-N-N-N-N-N-Q-N-Q-N-Q |
| 71 | X-Q-N-Q-N-Q-N-N-N-N-N-N-N-N-N-Q-N-Q-N-X-X |
| 72 | Q-X-Q-N-Q-N-Q-N-N-N-N-N-N-N-N-N-N-N-Q-N-Q |
| 73 | X-Q-N-Q-N-N-N-N-N-N-N-N-N-N-N-Q-N-Q-N-X-X |
| 74 | Q-X-Q-N-Q-N-Q-N-N-N-N-N-N-N-N-N-N-N-Q-N-Q |
| 75 | X-Q-N-Q-N-N-N-N-N-N-N-N-N-N-N-Q-N-Q-N-X-X |
| 76 | Q-X-Q-N-Q-N-N-N-N-N-N-N-N-N-N-N-N-N-Q-N-Q |
| 77 | X-Q-N-N-N-N-N-N-N-N-N-N-N-N-N-Q-N-Q-N-X-X |
| 78 | Q-X-Q-N-Q-N-N-N-N-N-N-N-N-N-N-N-N-N-Q-N-Q |
| 79 | X-Q-N-N-N-N-N-N-N-N-N-N-N-N-N-N-N-Q-N-X-X |
| 80 | Q-X-Q-N-Q-N-N-N-N-N-N-N-N-N-N-N-N-N-Q-N-Q |
| 81 | X-Q-N-N-N-N-N-N-N-N-N-N-N-N-N-N-N-Q-N-X-X |
| 82 | Q-X-Q-N-N-N-N-N-N-N-N-N-N-N-N-N-N-N-Q-N-Q |
| 83 | X-Q-N-N-N-N-N-N-N-N-N-N-N-N-N-N-N-Q-N-X-X |
| 84 | Q-X-Q-N-N-N-N-N-N-N-N-N-N-N-N-N-N-N-N-N-Q |
| 85 | X-Q-N-N-N-N-N-N-N-N-N-N-N-N-N-N-N-N-N-X-X |
| 86 | Q-X-Q-N-N-N-N-N-N-N-N-N-N-N-N-N-N-N-N-N-Q |

Examples of UNA oligomers containing three UNA monomers and additional Q monomers are shown in Table 4.

TABLE 4

| Oligomeric compounds containing three UNA monomers and additional Q monomers | |
|---|---|
| SEQ ID NO: | OLIGOMER |
| 87 | X-Q-N-Q-N-Q-N-Q-Q-Q-N-Q-N-Q-N-Q-N-Q-N-X-Q |
| 88 | Q-X-Q-N-Q-N-Q-N-N-N-N-N-Q-N-Q-N-Q-N-Q-N-Q |
| 89 | X-Q-N-Q-N-Q-N-Q-N-Q-N-Q-N-Q-N-Q-N-Q-N-X-Q |
| 90 | Q-X-Q-N-Q-N-Q-N-Q-N-Q-N-Q-N-Q-N-Q-N-Q-N-Q |
| 91 | X-Q-N-Q-N-Q-N-N-N-N-N-Q-N-Q-N-Q-N-Q-N-X-Q |
| 92 | Q-X-Q-N-Q-N-Q-N-Q-N-N-N-Q-N-Q-N-Q-N-Q-N-Q |
| 93 | X-Q-N-Q-N-Q-N-N-N-N-N-Q-N-Q-N-Q-N-Q-N-X-Q |
| 94 | Q-X-Q-N-Q-N-Q-N-N-N-N-N-N-N-Q-N-Q-N-Q-N-Q |
| 95 | X-Q-N-Q-N-Q-N-N-N-N-N-N-N-Q-N-Q-N-Q-N-X-Q |
| 96 | Q-X-Q-N-Q-N-Q-N-N-N-N-N-N-N-N-N-Q-N-Q-N-Q |
| 97 | X-Q-N-Q-N-Q-N-N-N-N-N-N-N-N-N-Q-N-Q-N-X-Q |
| 98 | Q-X-Q-N-Q-N-Q-N-N-N-N-N-N-N-N-N-Q-N-Q-N-Q |
| 99 | X-Q-N-Q-N-Q-N-N-N-N-N-N-N-N-N-Q-N-Q-N-X-Q |
| 100 | Q-X-Q-N-Q-N-Q-N-N-N-N-N-N-N-N-N-N-N-Q-N-Q |
| 101 | X-Q-N-Q-N-N-N-N-N-N-N-N-N-N-N-Q-N-Q-N-X-Q |
| 102 | Q-X-Q-N-Q-N-Q-N-N-N-N-N-N-N-N-N-N-N-Q-N-Q |
| 103 | X-Q-N-Q-N-N-N-N-N-N-N-N-N-N-N-Q-N-Q-N-X-Q |
| 104 | Q-X-Q-N-Q-N-N-N-N-N-N-N-N-N-N-N-N-N-Q-N-Q |
| 105 | X-Q-N-N-N-N-N-N-N-N-N-N-N-N-N-Q-N-Q-N-X-Q |
| 106 | Q-X-Q-N-Q-N-N-N-N-N-N-N-N-N-N-N-N-N-Q-N-Q |
| 107 | X-Q-N-N-N-N-N-N-N-N-N-N-N-N-N-N-N-Q-N-X-Q |
| 108 | Q-X-Q-N-Q-N-N-N-N-N-N-N-N-N-N-N-N-N-Q-N-Q |
| 109 | X-Q-N-N-N-N-N-N-N-N-N-N-N-N-N-N-N-Q-N-X-Q |
| 110 | Q-X-Q-N-N-N-N-N-N-N-N-N-N-N-N-N-N-N-Q-N-Q |
| 111 | X-Q-N-N-N-N-N-N-N-N-N-N-N-N-N-N-N-Q-N-X-Q |
| 112 | Q-X-Q-N-N-N-N-N-N-N-N-N-N-N-N-N-N-N-N-N-Q |
| 113 | X-Q-N-N-N-N-N-N-N-N-N-N-N-N-N-N-N-N-N-X-Q |
| 114 | Q-X-Q-N-N-N-N-N-N-N-N-N-N-N-N-N-N-N-N-N-Q |

Examples of UNA oligomers containing six UNA Monomers and additional Q monomers are shown in Table 5.

TABLE 5

| Oligomeric compounds containing six UNA monomers and additional Q monomers | |
|---|---|
| SEQ ID NO: | OLIGOMER |
| 115 | X-Q-N-Q-N-Q-N-Q-Q-Q-N-Q-N-Q-N-Q-N-Q-N-X-X |
| 116 | X-X-Q-N-Q-N-Q-N-N-N-N-N-Q-N-Q-N-Q-N-Q-X-Q |
| 117 | X-Q-N-Q-N-Q-N-Q-Q-Q-N-Q-N-Q-N-Q-N-Q-N-X-X |
| 118 | X-X-Q-N-Q-N-Q-N-N-N-N-N-Q-N-Q-N-Q-N-X-N-Q |
| 119 | X-Q-N-Q-N-Q-N-Q-Q-Q-N-Q-N-Q-N-Q-N-Q-N-X-X |
| 120 | X-X-Q-N-Q-N-Q-N-N-N-N-N-Q-N-Q-N-Q-X-Q-N-Q |
| 121 | X-Q-N-Q-N-Q-N-Q-Q-Q-N-Q-N-Q-N-Q-N-Q-N-X-X |
| 122 | X-X-Q-N-Q-N-Q-N-N-N-N-N-Q-N-Q-N-X-N-Q-N-Q |
| 123 | X-Q-N-Q-N-Q-N-Q-Q-Q-N-Q-N-Q-N-Q-N-Q-N-X-X |
| 124 | X-X-Q-N-Q-N-Q-N-N-N-N-N-Q-N-Q-X-Q-N-Q-N-Q |
| 125 | X-Q-N-Q-N-Q-N-Q-Q-Q-N-Q-N-Q-N-Q-N-Q-N-X-X |
| 126 | X-X-Q-N-Q-N-Q-N-N-N-N-N-Q-N-X-N-Q-N-Q-N-Q |

TABLE 5-continued

| Oligomeric compounds containing six UNA monomers and additional Q monomers | |
|---|---|
| SEQ ID NO: | OLIGOMER |
| 127 | X-Q-N-Q-N-Q-N-Q-Q-Q-N-Q-N-Q-N-Q-N-Q-N-X-X |
| 128 | X-X-Q-N-Q-N-Q-N-N-N-N-N-Q-X-Q-N-Q-N-Q-N-Q |

Examples of UNA oligomers containing seven UNA monomers and additional Q monomers are shown in Table 6.

TABLE 6

| Oligomeric compounds containing seven UNA monomers and additional Q monomers | |
|---|---|
| SEQ ID NO: | OLIGOMER |
| 129 | X-Q-N-Q-N-Q-N-Q-Q-Q-N-Q-N-Q-N-Q-N-Q-N-X-X |
| 130 | X-X-Q-N-Q-N-Q-N-N-N-N-N-Q-N-Q-N-Q-N-X-X-Q |
| 131 | X-Q-N-Q-N-Q-N-Q-Q-Q-N-Q-N-Q-N-Q-N-Q-N-X-X |
| 132 | X-X-Q-N-Q-N-Q-N-N-N-N-N-Q-N-Q-N-Q-X-Q-X-Q |
| 133 | X-Q-N-Q-N-Q-N-Q-Q-Q-N-Q-N-Q-N-Q-N-Q-N-X-X |
| 134 | X-X-Q-N-Q-N-Q-N-N-N-N-N-Q-N-Q-N-X-N-Q-X-Q |
| 135 | X-Q-N-Q-N-Q-N-Q-Q-Q-N-Q-N-Q-N-Q-N-Q-N-X-X |
| 136 | X-X-Q-N-Q-N-Q-N-N-N-N-N-Q-N-Q-X-Q-N-X-N-Q |
| 137 | X-Q-N-Q-N-Q-N-Q-Q-Q-N-Q-N-Q-N-Q-N-Q-N-X-X |
| 138 | X-X-Q-N-Q-N-Q-N-N-N-N-N-Q-N-Q-N-X-X-Q-N-Q |
| 139 | X-Q-N-Q-N-Q-N-Q-Q-Q-N-Q-N-Q-N-Q-N-Q-N-X-X |
| 140 | X-X-Q-N-Q-N-Q-N-N-N-N-N-Q-N-X-N-Q-X-Q-N-Q |
| 141 | X-Q-N-Q-N-Q-N-Q-Q-Q-N-Q-N-Q-N-Q-N-Q-N-X-X |
| 142 | X-X-Q-N-Q-N-Q-N-N-N-N-N-Q-N-Q-X-X-N-Q-N-Q |

Examples of UNA oligomers containing five UNA monomers and additional Q monomers are shown in Table 7.

TABLE 7

| Oligomeric compounds containing five UNA monomers and additional Q monomers | |
|---|---|
| SEQ ID NO: | OLIGOMER |
| 143 | X-Q-N-Q-N-Q-N-Q-Q-Q-N-Q-N-Q-N-Q-N-Q-N-X-Q |
| 144 | X-X-Q-N-Q-N-Q-N-N-N-N-N-Q-N-Q-N-Q-N-Q-X-Q |
| 145 | X-Q-N-Q-N-Q-N-Q-Q-Q-N-Q-N-Q-N-Q-N-Q-N-X-Q |
| 146 | X-X-Q-N-Q-N-Q-N-N-N-N-N-Q-N-Q-N-Q-N-X-N-Q |
| 147 | X-Q-N-Q-N-Q-N-Q-Q-Q-N-Q-N-Q-N-Q-N-Q-N-X-Q |
| 148 | X-X-Q-N-Q-N-Q-N-N-N-N-N-Q-N-Q-N-Q-X-Q-N-Q |
| 149 | X-Q-N-Q-N-Q-N-Q-Q-Q-N-Q-N-Q-N-Q-N-Q-N-X-Q |
| 150 | X-X-Q-N-Q-N-Q-N-N-N-N-N-Q-N-Q-N-X-N-Q-N-Q |
| 151 | X-Q-N-Q-N-Q-N-Q-Q-Q-N-Q-N-Q-N-Q-N-Q-N-X-Q |
| 152 | X-X-Q-N-Q-N-Q-N-N-N-N-N-Q-N-Q-X-Q-N-Q-N-Q |
| 153 | X-Q-N-Q-N-Q-N-Q-Q-Q-N-Q-N-Q-N-Q-N-Q-N-X-Q |
| 154 | X-X-Q-N-Q-N-Q-N-N-N-N-N-Q-N-X-N-Q-N-Q-N-Q |

TABLE 7-continued

Oligomeric compounds containing five UNA monomers and additional Q monomers

| SEQ ID NO: | OLIGOMER |
|---|---|
| 155 | X-Q-N-Q-N-Q-N-Q-Q-Q-N-Q-N-Q-N-Q-N-Q-N-X-Q |
| 156 | X-X-Q-N-Q-N-Q-N-N-N-N-N-Q-X-Q-N-Q-N-Q-N-Q |

Examples of UNA oligomers containing six UNA monomers and additional Q monomers are shown in Table 8.

TABLE 8

Oligomeric compounds containing six UNA monomers and additional Q monomers

| SEQ ID NO: | OLIGOMER |
|---|---|
| 157 | X-Q-N-Q-N-Q-N-Q-Q-Q-N-Q-N-Q-N-Q-N-Q-N-X-Q |
| 158 | X-X-Q-N-Q-N-Q-N-N-N-N-N-Q-N-Q-N-Q-N-X-X-Q |
| 159 | X-Q-N-Q-N-Q-N-Q-Q-Q-N-Q-N-Q-N-Q-N-Q-N-X-Q |
| 160 | X-X-Q-N-Q-N-Q-N-N-N-N-N-Q-N-Q-N-Q-X-Q-X-Q |
| 161 | X-Q-N-Q-N-Q-N-Q-Q-Q-N-Q-N-Q-N-Q-N-Q-N-X-Q |
| 162 | X-X-Q-N-Q-N-Q-N-N-N-N-N-Q-N-Q-N-X-N-Q-X-Q |
| 163 | X-Q-N-Q-N-Q-N-Q-Q-Q-N-Q-N-Q-N-Q-N-Q-N-X-Q |
| 164 | X-X-Q-N-Q-N-Q-N-N-N-N-N-Q-N-Q-X-Q-N-X-N-Q |
| 165 | X-Q-N-Q-N-Q-N-Q-Q-Q-N-Q-N-Q-N-Q-N-Q-N-X-Q |
| 166 | X-X-Q-N-Q-N-Q-N-N-N-N-N-Q-N-Q-N-X-X-Q-N-Q |
| 167 | X-Q-N-Q-N-Q-N-Q-Q-Q-N-Q-N-Q-N-Q-N-Q-N-X-Q |
| 168 | X-X-Q-N-Q-N-Q-N-N-N-N-N-Q-N-X-N-Q-X-Q-N-Q |
| 169 | X-Q-N-Q-N-Q-N-Q-Q-Q-N-Q-N-Q-N-Q-N-Q-N-X-Q |
| 170 | X-X-Q-N-Q-N-Q-N-N-N-N-N-Q-N-Q-X-X-N-Q-N-Q |

Examples of UNA oligomers containing five UNA monomers and additional Q monomers are shown in Table 9.

TABLE 9

Oligomeric compounds containing five UNA monomers and additional Q monomers

| SEQ ID NO: | OLIGOMER |
|---|---|
| 171 | X-Q-N-Q-N-Q-N-Q-Q-Q-N-Q-N-Q-N-Q-N-Q-N-X-X |
| 172 | Q-X-Q-N-Q-N-Q-N-N-N-N-N-Q-N-Q-N-Q-N-Q-X-Q |
| 173 | X-Q-N-Q-N-Q-N-Q-Q-Q-N-Q-N-Q-N-Q-N-Q-N-X-X |
| 174 | Q-X-Q-N-Q-N-Q-N-N-N-N-N-Q-N-Q-N-Q-N-X-N-Q |
| 175 | X-Q-N-Q-N-Q-N-Q-Q-Q-N-Q-N-Q-N-Q-N-Q-N-X-X |
| 176 | Q-X-Q-N-Q-N-Q-N-N-N-N-N-Q-N-Q-N-Q-X-Q-N-Q |
| 177 | X-Q-N-Q-N-Q-N-Q-Q-Q-N-Q-N-Q-N-Q-N-Q-N-X-X |
| 178 | Q-X-Q-N-Q-N-Q-N-N-N-N-N-Q-N-Q-N-X-N-Q-N-Q |
| 179 | X-Q-N-Q-N-Q-N-Q-Q-Q-N-Q-N-Q-N-Q-N-Q-N-X-X |
| 180 | Q-X-Q-N-Q-N-Q-N-N-N-N-N-Q-N-Q-X-Q-N-Q-N-Q |
| 181 | X-Q-N-Q-N-Q-N-Q-Q-Q-N-Q-N-Q-N-Q-N-Q-N-X-X |
| 182 | Q-X-Q-N-Q-N-Q-N-N-N-N-N-Q-N-X-N-Q-N-Q-N-Q |
| 183 | X-Q-N-Q-N-Q-N-Q-Q-Q-N-Q-N-Q-N-Q-N-Q-N-X-X |
| 184 | Q-X-Q-N-Q-N-Q-N-N-N-N-N-Q-X-Q-N-Q-N-Q-N-Q |

Examples of UNA oligomers containing six UNA monomers and additional Q monomers are shown in Table 10.

TABLE 10

Oligomeric compounds containing six UNA monomers and additional Q monomers

| SEQ ID NO: | OLIGOMER |
|---|---|
| 185 | X-Q-N-Q-N-Q-N-Q-Q-Q-N-Q-N-Q-N-Q-N-Q-N-X-X |
| 186 | Q-X-Q-N-Q-N-Q-N-N-N-N-N-Q-N-Q-N-Q-N-X-X-Q |
| 187 | X-Q-N-Q-N-Q-N-Q-Q-Q-N-Q-N-Q-N-Q-N-Q-N-X-X |
| 188 | Q-X-Q-N-Q-N-Q-N-N-N-N-N-Q-N-Q-N-Q-X-Q-X-Q |
| 189 | X-Q-N-Q-N-Q-N-Q-Q-Q-N-Q-N-Q-N-Q-N-Q-N-X-X |
| 190 | Q-X-Q-N-Q-N-Q-N-N-N-N-N-Q-N-Q-N-X-N-Q-X-Q |
| 191 | X-Q-N-Q-N-Q-N-Q-Q-Q-N-Q-N-Q-N-Q-N-Q-N-X-X |
| 192 | Q-X-Q-N-Q-N-Q-N-N-N-N-N-Q-N-Q-X-Q-N-X-N-Q |
| 193 | X-Q-N-Q-N-Q-N-Q-Q-Q-N-Q-N-Q-N-Q-N-Q-N-X-X |
| 194 | Q-X-Q-N-Q-N-Q-N-N-N-N-N-Q-N-Q-N-X-X-Q-N-Q |
| 195 | X-Q-N-Q-N-Q-N-Q-Q-Q-N-Q-N-Q-N-Q-N-Q-N-X-X |
| 196 | Q-X-Q-N-Q-N-Q-N-N-N-N-N-Q-N-X-N-Q-X-Q-N-Q |
| 197 | X-Q-N-Q-N-Q-N-Q-Q-Q-N-Q-N-Q-N-Q-N-Q-N-X-X |
| 198 | Q-X-Q-N-Q-N-Q-N-N-N-N-N-Q-N-Q-X-X-N-Q-N-Q |

Examples of UNA oligomers containing four UNA monomers and additional Q monomers are shown in Table 11.

TABLE 11

Oligomeric compounds containing four UNA monomers and additional Q monomers

| SEQ ID NO: | OLIGOMER |
|---|---|
| 199 | X-Q-N-Q-N-Q-N-Q-Q-Q-N-Q-N-Q-N-Q-N-Q-N-X-Q |
| 200 | Q-X-Q-N-Q-N-Q-N-N-N-N-N-Q-N-Q-N-Q-N-Q-X-Q |
| 201 | X-Q-N-Q-N-Q-N-Q-Q-Q-N-Q-N-Q-N-Q-N-Q-N-X-Q |
| 202 | Q-X-Q-N-Q-N-Q-N-N-N-N-N-Q-N-Q-N-Q-N-X-N-Q |
| 203 | X-Q-N-Q-N-Q-N-Q-Q-Q-N-Q-N-Q-N-Q-N-Q-N-X-Q |
| 204 | Q-X-Q-N-Q-N-Q-N-N-N-N-N-Q-N-Q-N-Q-X-Q-N-Q |
| 205 | X-Q-N-Q-N-Q-N-Q-Q-Q-N-Q-N-Q-N-Q-N-Q-N-X-Q |
| 206 | Q-X-Q-N-Q-N-Q-N-N-N-N-N-Q-N-Q-N-X-N-Q-N-Q |
| 207 | X-Q-N-Q-N-Q-N-Q-Q-Q-N-Q-N-Q-N-Q-N-Q-N-X-Q |
| 208 | Q-X-Q-N-Q-N-Q-N-N-N-N-N-Q-N-Q-X-Q-N-Q-N-Q |
| 209 | X-Q-N-Q-N-Q-N-Q-Q-Q-N-Q-N-Q-N-Q-N-Q-N-X-Q |
| 210 | Q-X-Q-N-Q-N-Q-N-N-N-N-N-Q-N-X-N-Q-N-Q-N-Q |
| 211 | X-Q-N-Q-N-Q-N-Q-Q-Q-N-Q-N-Q-N-Q-N-Q-N-X-Q |
| 212 | Q-X-Q-N-Q-N-Q-N-N-N-N-N-Q-X-Q-N-Q-N-Q-N-Q |

Examples of UNA oligomers containing five UNA monomers and additional Q monomers are shown in Table 12.

TABLE 12

| Oligomeric compounds containing five UNA monomers and additional Q monomers | |
|---|---|
| SEQ ID NO: | OLIGOMER |
| 213 | X-Q-N-Q-N-Q-N-Q-Q-Q-N-Q-N-Q-N-Q-N-Q-N-X-Q |
| 214 | Q-X-Q-N-Q-N-Q-N-N-N-N-N-Q-N-Q-N-Q-N-X-X-Q |
| 215 | X-Q-N-Q-N-Q-N-Q-Q-Q-N-Q-N-Q-N-Q-N-Q-N-X-Q |
| 216 | Q-X-Q-N-Q-N-Q-N-N-N-N-N-Q-N-Q-N-Q-X-Q-X-Q |
| 217 | X-Q-N-Q-N-Q-N-Q-Q-Q-N-Q-N-Q-N-Q-N-Q-N-X-Q |
| 218 | Q-X-Q-N-Q-N-Q-N-N-N-N-N-Q-N-Q-N-X-N-Q-X-Q |
| 219 | X-Q-N-Q-N-Q-N-Q-Q-Q-N-Q-N-Q-N-Q-N-Q-N-X-Q |
| 220 | Q-X-Q-N-Q-N-Q-N-N-N-N-N-Q-N-Q-X-Q-N-X-N-Q |
| 221 | X-Q-N-Q-N-Q-N-Q-Q-Q-N-Q-N-Q-N-Q-N-Q-N-X-Q |
| 222 | Q-X-Q-N-Q-N-Q-N-N-N-N-N-Q-N-Q-N-X-X-Q-N-Q |
| 223 | X-Q-N-Q-N-Q-N-Q-Q-Q-N-Q-N-Q-N-Q-N-Q-N-X-Q |
| 224 | Q-X-Q-N-Q-N-Q-N-N-N-N-N-Q-N-X-N-Q-X-Q-N-Q |
| 225 | X-Q-N-Q-N-Q-N-Q-Q-Q-N-Q-N-Q-N-Q-N-Q-N-X-Q |
| 226 | Q-X-Q-N-Q-N-Q-N-N-N-N-N-Q-N-Q-X-X-N-Q-N-Q |

Examples of UNA oligomers containing seven or more UNA monomers and additional Q monomers are shown in Table 13.

TABLE 13

| Oligomeric compounds containing seven or more UNA monomers and additional Q monomers | |
|---|---|
| SEQ ID NO: | OLIGOMER |
| 227 | X-Q-N-Q-N-Q-N-Q-Q-Q-N-Q-N-Q-N-Q-N-Q-N-X-X |
| 228 | X-X-Q-N-Q-N-Q-N-N-N-N-N-Q-N-Q-X-Q-X-Q-X-Q |
| 229 | X-Q-N-Q-N-Q-N-Q-Q-Q-N-Q-N-Q-N-Q-N-Q-N-X-Q |
| 230 | X-X-Q-N-Q-N-Q-N-N-N-N-N-Q-N-Q-N-Q-X-X-X-Q |
| 231 | X-Q-N-Q-N-Q-N-Q-Q-Q-N-Q-N-Q-N-Q-N-Q-N-X-X |
| 232 | Q-X-Q-N-Q-N-Q-N-N-N-N-N-Q-N-X-X-X-N-Q-N-Q |
| 233 | X-Q-N-Q-N-Q-N-Q-Q-Q-N-Q-N-Q-N-Q-N-Q-N-X-Q |
| 234 | Q-X-Q-N-Q-N-Q-N-N-N-N-N-Q-N-X-X-X-X-X-X-Q |
| 235 | X-Q-N-Q-N-Q-N-Q-Q-Q-N-Q-N-Q-N-Q-N-Q-N-X-X |
| 236 | X-X-Q-N-Q-N-Q-N-N-N-N-N-Q-N-X-X-X-X-X-X-Q |

An oligomeric compound of this invention may have any one of the structures shown in Tables 1 to 13.

In some embodiments, an oligomeric compound of this invention may have a first strand and a second strand, each of the strands independently being 19-23 monomers in length, where any monomer that is not a UNA monomer can be a Q monomer.

In some embodiments, an oligomeric compound of this invention may have a first strand and a second strand, each of the strands independently being 19-23 monomers in length, where any monomer that is not a UNA monomer can be a Q monomer, and where the number of Q monomers is less than twenty.

In some embodiments, an oligomeric compound of this invention may have a first strand and a second strand, each of the strands independently being 19-23 monomers in length, where any monomer that is not a UNA monomer can be a Q monomer, and where the number of Q monomers is less than twelve.

In some embodiments, an oligomeric compound of this invention may have a first strand and a second strand, each of the strands independently being 19-23 monomers in length, where any monomer that is not a UNA monomer can be a Q monomer, and where the number of Q monomers is less than ten.

In some embodiments, an oligomeric compound of this invention may have a first strand and a second strand, each of the strands independently being 19-23 monomers in length, where any monomer that is not a UNA monomer can be a Q monomer, and where the number of Q monomers is less than eight.

In some embodiments, an oligomeric compound of this invention may have a first strand and a second strand, each of the strands independently being 19-23 monomers in length, where any monomer that is not a UNA monomer can be a Q monomer, and where the number of Q monomers is from 1 to 20.

In some embodiments, an oligomeric compound of this invention may have a first strand and a second strand, each of the strands independently being 19-23 monomers in length, where any monomer that is not a UNA monomer can be a Q monomer, and where the number of Q monomers is from 1 to 15.

In some embodiments, an oligomeric compound of this invention may have a first strand and a second strand, each of the strands independently being 19-23 monomers in length, where any monomer that is not a UNA monomer can be a Q monomer, and where the number of Q monomers is from 1 to 9.

In some embodiments, an oligomeric compound of this invention may have a first strand and a second strand, each of the strands independently being 19-23 monomers in length, where any monomer that is not a UNA monomer can be a 2' Methyl modified ribonucleotide.

In some embodiments, an oligomeric compound of this invention may have a first strand and a second strand, each of the strands independently being 19-23 monomers in length, where any monomer that is not a UNA monomer can be a 2'-O-Methyl modified ribonucleotide, and where the number of 2'-O-Methyl modified ribonucleotides is less than twenty.

In some embodiments, an oligomeric compound of this invention may have a first strand and a second strand, each of the strands independently being 19-23 monomers in length, where any monomer that is not a UNA monomer can be a 2'-O-Methyl modified ribonucleotide, and where the number of 2'-O-Methyl modified ribonucleotides is less than twelve.

In some embodiments, an oligomeric compound of this invention may have a first strand and a second strand, each of the strands independently being 19-23 monomers in length, where any monomer that is not a UNA monomer can be a 2'-O-Methyl modified ribonucleotide, and where the number of 2'-O-Methyl modified ribonucleotides is less than ten.

In some embodiments, an oligomeric compound of this invention may have a first strand and a second strand, each of the strands independently being 19-23 monomers in length, where any monomer that is not a UNA monomer can be a 2'-O-Methyl modified ribonucleotide, and where the number of 2'-O-Methyl modified ribonucleotides is less than eight.

In some embodiments, an oligomeric compound of this invention may have a first strand and a second strand, each of the strands independently being 19-23 monomers in length, where any monomer that is not a UNA monomer can be a 2'-O-Methyl modified ribonucleotide, and where the number of 2'-O-Methyl modified ribonucleotides is from 1 to 20.

In some embodiments, an oligomeric compound of this invention may have a first strand and a second strand, each of the strands independently being 19-23 monomers in length, where any monomer that is not a UNA monomer can be a 2' Methyl modified ribonucleotide, and where the number of 2'-O-Methyl modified ribonucleotides is from 1 to 15.

In some embodiments, an oligomeric compound of this invention may have a first strand and a second strand, each of the strands independently being 19-23 monomers in length, where any monomer that is not a UNA monomer can be a 2'-O-Methyl modified ribonucleotide, and where the number of 2'-O-Methyl modified ribonucleotides is from 1 to 9.

In further aspects, an oligomeric compound of this invention may have a first strand and a second strand, each of the strands independently being 19-23 monomers in length, where any monomer that is not a UNA monomer can be a Q monomer, and where the oligomeric compound does not contain fluorine.

Embodiments of this invention advantageously provide oligomeric compounds, which are active agents against HBV and do not contain fluorine.

Methods of this invention include the treatment and/or prevention of HBV disease in a subject. A subject can be a mammalian subject, including a human subject.

HBV Component Target Sequences

As used herein, "Ref Pos" refers to reference position, which is the numerical position of a reference nucleotide in an HBV genome. The reference position is the position that corresponds target-wise to the 5' end of the sense strand of the oligomeric compound of this invention. The reference positions are numerical nucleotide positions based on a reference genome, which as used herein is HBV Genotype A2, Accession No. HE974376. Thus, a reference position number by itself refers to one sequence from the reference genome, and each sequence can be used in an oligomeric compound of this invention. Table 14 shows genomic positions for the HBV reference genome.

TABLE 14

| HBV genomic positions | | |
|---|---|---|
| Start | End | Gene |
| 1 | 835 | S |
| 1 | 1623 | Pol |
| 1374 | 1838 | X |
| 1901 | 2458 | C |
| 2307 | 3221 | Pol |
| 2854 | 3221 | S |

Figure 1:
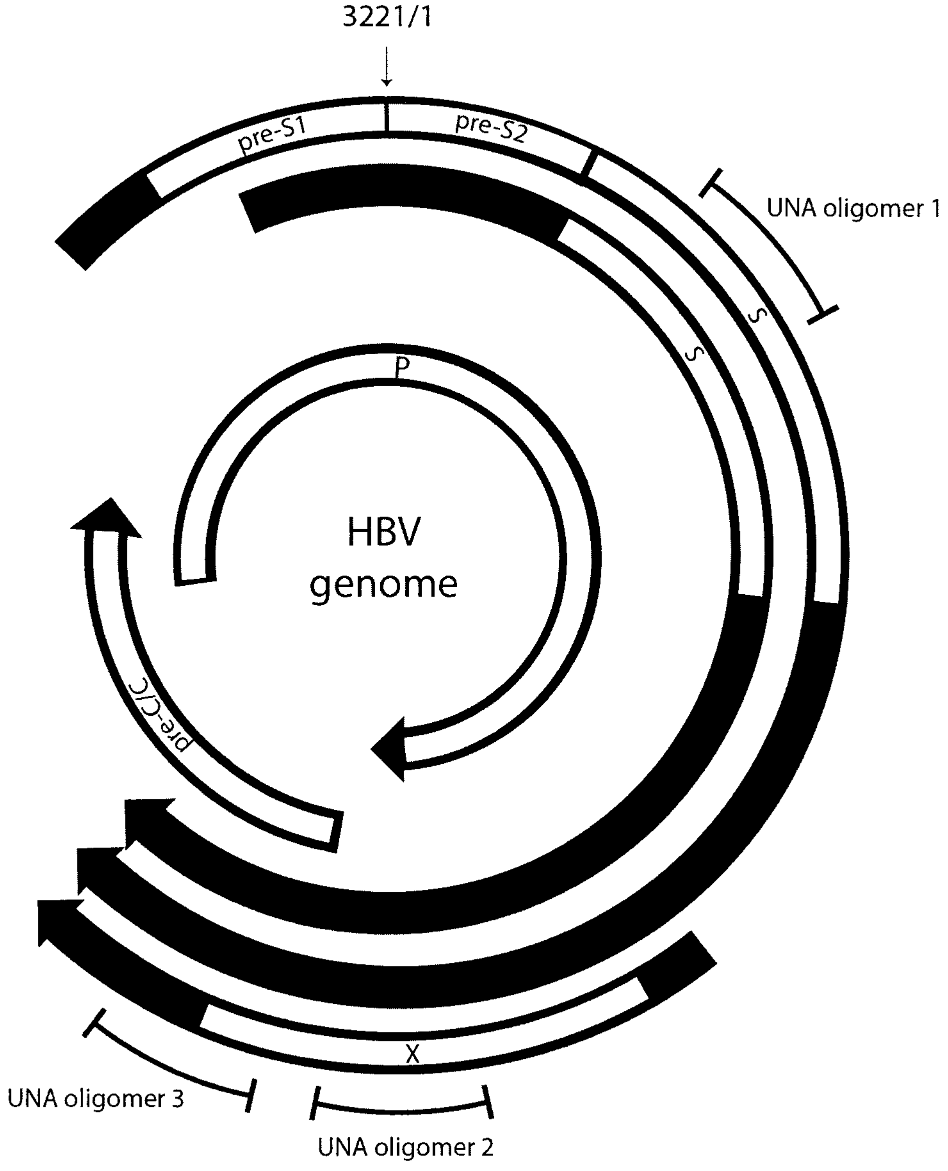
FIG. 1 shows a map of HBV protein coding regions and selected transcripts for a reference genome. Nucleotide position 1/3221 is designated at the top. Further designations are as follows: pre-S1, large HBsAg; pre-S2, medium HBsAg; S, HBsAg; P, polymerase; X, HBx protein; pre-C, pre-core/HBeAg; C, HB core Ag. The 2.4 kb, 2.1 kb, and 0.7 kb transcripts coding for the pre-S1/pre-S2/S, as well as the transcript coding the X protein are shown. The pre-Core/HBeAg protein is generated from a long, 3.5 kb transcript (not shown) originating at position ~1700, while the core and polymerase proteins and the pre-genomic RNA used as a template for viral replication are generated from a ~200 nt shorter transcript. The ranges of reference positions for certain UNA oligomers, designated UNA oligomer 1, UNA oligomer 2, and UNA oligomer 3, are shown.

In FIG. 1 is shown a map of HBV protein coding regions and selected transcripts for the reference genome HE974376. Nucleotide position 1/3221 is designated at the top. Further designations are as follows: pre-S1, large HBsAg; pre-S2, medium HBsAg; S, HBsAg; P, polymerase; X, HBx protein; pre-C, pre-core/HBeAg; C, HB core Ag. The 2.4 kb, 2.1 kb, and 0.7 kb transcripts coding for the pre-S1/pre-S2/S, as well as the transcript coding the X protein are shown. The pre-Core/HBeAg protein is generated from a long, 3.5 kb transcript (not shown) originating at position ~1700, while the core and polymerase proteins and the pre-genomic RNA used as a template for viral replication are generated from a ~200 nt shorter transcript.

The ranges of reference positions for certain UNA oligomers, designated UNA oligomer 1, UNA oligomer 2, and UNA oligomer 3, are shown in FIG. 1.

In some aspects, the inventive oligomers of this disclosure may target the long transcript coding for HBV core and polymerase proteins.

UNA Oligomers Targeting HBV

Examples of base sequences of this invention targeted to an HBV component are shown in Table 15.

An oligomeric compound of this invention can be formed having a first strand and a second strand each being 21 monomers in length. The first strand can have 19 contiguous monomers with a sequence of attached bases shown in Table 15 (sense), and two additional overhang monomers on the 3' end. The second strand can have 19 contiguous monomers with a sequence of attached bases shown in Table 15 (antisense), and two additional overhang monomers on the 3' end. The overhang monomers can be any of NN, QQ, XX, NX, NQ, XN, XQ, QN, and QX. For example, XQ can be UNA-U/mU, or UNA-U/*/dT.

An oligomeric compound of this invention can be composed of monomers. The monomers can have attached bases. An oligomeric compound of this invention can have a sequence of attached bases. The sequences of bases shown in Table 15 do not indicate to which monomer each of the bases in the sequence is attached. Thus, each sequence shown in Table 15 refers to a large number of small molecules, each of which is composed of UNA monomers, as well as nucleic acid monomers.

In some aspects, an oligomeric compound of this invention can be described by a sequence of attached bases, for example as shown in Table 15, and being substituted forms thereof. As used herein, substituted forms include differently substituted UNA monomers, as well as differently substituted or modified nucleic acid monomers, as are further described herein.

In some embodiments, one or more of three monomers at each end of each strand can be connected by a phosphorothioate, a chiral phosphorothioate, or a phosphorodithioate linkage.

For example, a compound may have one phosphorothioate linkage between two monomers at the 5' end of the first strand, one phosphorothioate linkage between two monomers at the 3' end of the first strand, one phosphorothioate linkage between monomers at the second and third positions from the 3' end of the first strand, and one phosphorothioate linkage between two monomers at the 3' end of the second strand.

In certain embodiments, a compound may have two or three phosphorothioate linkages at the 5' end of the first strand, two or three phosphorothioate linkages at the 3' end of the first strand, and one phosphorothioate linkage at the 3' end of the second strand.

In additional embodiments, a compound may have one to three phosphorothioate linkages at the 5' end of the first strand, two or three phosphorothioate linkages at the 3' end of the first strand, two phosphorothioate linkages at the 5' end of the second strand, and two phosphorothioate linkages at the 3' end of the second strand.

In some examples, a compound may have a deoxythymidine nucleotide at the 3' end of the first strand, at the 3' end of the second strand, or at both the 3' end of the first strand and the 3' end of the second strand.

In some aspects, a compound may contain one to five UNA monomers.

In certain aspects, a compound may contain three UNA monomers.

In some embodiments, a compound may contain a UNA monomer at the 1-end of the first strand (5' end), a UNA monomer at the 3-end of the first strand (3' end), and a UNA monomer at the second position from the 3' end of the second strand.

In certain embodiments, a compound may contain a UNA monomer at any one or more of positions 2 to 8 from the 5' end of the second strand (seed region).

TABLE 15

HBV sense and antisense sequences

| REF POS | SEQ ID NO | Sense (5'-3') SEQ ID NOS: 237 to 548 | SEQ ID NO | Antisense (5'-3') SEQ ID NOS: 549 to 860 |
|---|---|---|---|---|
| 1525 | 237 | CGCACCUCUCUUUACGCGG | 549 | CCGCGUAAAGAGAGGUGCG |
| 251 | 238 | GACUCGUGGUGGACUUCUC | 550 | GAGAAGUCCACCACGAGUC |
| 254 | 239 | UCGUGGUGGACUUCUCUCA | 551 | UGAGAGAAGUCCACCACGA |
| 374 | 240 | UGGAUGUGUCUGCGGCGUU | 552 | AACGCCGCAGACACAUCCA |
| 1575 | 241 | CCGUGUGCACUUCGCUUCA | 553 | UGAAGCGAAGUGCACACGG |
| 1577 | 242 | GUGUGCACUUCGCUUCACC | 554 | GGUGAAGCGAAGUGCACAC |
| 1578 | 243 | UGUGCACUUCGCUUCACCU | 555 | AGGUGAAGCGAAGUGCACA |
| 1579 | 244 | GUGCACUUCGCUUCACCUC | 556 | GAGGUGAAGCGAAGUGCAC |
| 1581 | 245 | GCACUUCGCUUCACCUCUG | 557 | CAGAGGUGAAGCGAAGUGC |
| 1863 | 246 | UUCAAGCCUCCAAGCUGUG | 558 | CACAGCUUGGAGGCUUGAA |
| 1864 | 247 | UCAAGCCUCCAAGCUGUGC | 559 | GCACAGCUUGGAGGCUUGA |
| 1865 | 248 | CAAGCCUCCAAGCUGUGCC | 560 | GGCACAGCUUGGAGGCUUG |
| 1866 | 249 | AAGCCUCCAAGCUGUGCCU | 561 | AGGCACAGCUUGGAGGCUU |
| 247 | 250 | UCUAGACUCGUGGUGGACU | 562 | AGUCCACCACGAGUCUAGA |
| 248 | 251 | CUAGACUCGUGGUGGACUU | 563 | AAGUCCACCACGAGUCUAG |
| 249 | 252 | UAGACUCGUGGUGGACUUC | 564 | GAAGUCCACCACGAGUCUA |
| 250 | 253 | AGACUCGUGGUGGACUUCU | 565 | AGAAGUCCACCACGAGUCU |
| 376 | 254 | GAUGUGUCUGCGGCGUUUU | 566 | AAAACGCCGCAGACACAUC |
| 378 | 255 | UGUGUCUGCGGCGUUUUAU | 567 | AUAAAACGCCGCAGACACA |
| 380 | 256 | UGUCUGCGGCGUUUUAUCA | 568 | UGAUAAAACGCCGCAGACA |
| 1776 | 257 | GGAGGCUGUAGGCAUAAAU | 569 | AUUUAUGCCUACAGCCUCC |
| 1777 | 258 | GAGGCUGUAGGCAUAAAUU | 570 | AAUUUAUGCCUACAGCCUC |
| 1779 | 259 | GGCUGUAGGCAUAAAUUGG | 571 | CCAAUUUAUGCCUACAGCC |
| 1780 | 260 | GCUGUAGGCAUAAAUUGGU | 572 | ACCAAUUUAUGCCUACAGC |
| 1818 | 261 | AACUUUUUCACCUCUGCCU | 573 | AGGCAGAGGUGAAAAAGUU |
| 244 | 262 | GAGUCUAGACUCGUGGUGG | 574 | CCACCACGAGUCUAGACUC |
| 245 | 263 | AGUCUAGACUCGUGGUGGA | 575 | UCCACCACGAGUCUAGACU |
| 246 | 264 | GUCUAGACUCGUGGUGGAC | 576 | GUCCACCACGAGUCUAGAC |
| 409 | 265 | CAUCCUGCUGCUAUGCCUC | 577 | GAGGCAUAGCAGCAGGAUG |
| 411 | 266 | UCCUGCUGCUAUGCCUCAU | 578 | AUGAGGCAUAGCAGCAGGA |
| 412 | 267 | CCUGCUGCUAUGCCUCAUC | 579 | GAUGAGGCAUAGCAGCAGG |
| 413 | 268 | CUGCUGCUAUGCCUCAUCU | 580 | AGAUGAGGCAUAGCAGCAG |

TABLE 15-continued

| HBV sense and antisense sequences | | | | |
|---|---|---|---|---|
| REF POS | SEQ ID NO | Sense (5'-3') SEQ ID NOS: 237 to 548 | SEQ ID NO | Antisense (5'-3') SEQ ID NOS: 549 to 860 |
| 414 | 269 | UGCUGCUAUGCCUCAUCUU | 581 | AAGAUGAGGCAUAGCAGCA |
| 1781 | 270 | CUGUAGGCAUAAAUUGGUC | 582 | GACCAAUUUAUGCCUACAG |
| 1782 | 271 | UGUAGGCAUAAAUUGGUCU | 583 | AGACCAAUUUAUGCCUACA |
| 252 | 272 | ACUCGUGGUGGACUUCUCU | 584 | AGAGAAGUCCACCACGAGU |
| 253 | 273 | CUCGUGGUGGACUUCUCUC | 585 | GAGAGAAGUCCACCACGAG |
| 1576 | 274 | CGUGUGCACUUCGCUUCAC | 586 | GUGAAGCGAAGUGCACACG |
| 1580 | 275 | UGCACUUCGCUUCACCUCU | 587 | AGAGGUGAAGCGAAGUGCA |
| 1582 | 276 | CACUUCGCUUCACCUCUGC | 588 | GCAGAGGUGAAGCGAAGUG |
| 1583 | 277 | ACUUCGCUUCACCUCUGCA | 589 | UGCAGAGGUGAAGCGAAGU |
| 1867 | 278 | AGCCUCCAAGCUGUGCCUU | 590 | AAGGCACAGCUUGGAGGCU |
| 1868 | 279 | GCCUCCAAGCUGUGCCUUG | 591 | CAAGGCACAGCUUGGAGGC |
| 2382 | 280 | GAACUCCCUCGCCUCGCAG | 592 | CUGCGAGGCGAGGGAGUUC |
| 2383 | 281 | AACUCCCUCGCCUCGCAGA | 593 | UCUGCGAGGCGAGGGAGUU |
| 2384 | 282 | ACUCCCUCGCCUCGCAGAC | 594 | GUCUGCGAGGCGAGGGAGU |
| 2385 | 283 | CUCCCUCGCCUCGCAGACG | 595 | CGUCUGCGAGGCGAGGGAG |
| 56 | 284 | CCUGCUGGUGGCUCCAGUU | 596 | AACUGGAGCCACCAGCAGG |
| 57 | 285 | CUGCUGGUGGCUCCAGUUC | 597 | GAACUGGAGCCACCAGCAG |
| 375 | 286 | GGAUGUGUCUGCGGCGUUU | 598 | AAACGCCGCAGACACAUCC |
| 377 | 287 | AUGUGUCUGCGGCGUUUUA | 599 | UAAAACGCCGCAGACACAU |
| 379 | 288 | GUGUCUGCGGCGUUUUAUC | 600 | GAUAAAACGCCGCAGACAC |
| 381 | 289 | GUCUGCGGCGUUUUAUCAU | 601 | AUGAUAAAACGCCGCAGAC |
| 637 | 290 | CCUAUGGGAGUGGGCCUCA | 602 | UGAGGCCCACUCCCAUAGG |
| 638 | 291 | CUAUGGGAGUGGGCCUCAG | 603 | CUGAGGCCCACUCCCAUAG |
| 1584 | 292 | CUUCGCUUCACCUCUGCAC | 604 | GUGCAGAGGUGAAGCGAAG |
| 1585 | 293 | UUCGCUUCACCUCUGCACG | 605 | CGUGCAGAGGUGAAGCGAA |
| 1586 | 294 | UCGCUUCACCUCUGCACGU | 606 | ACGUGCAGAGGUGAAGCGA |
| 1778 | 295 | AGGCUGUAGGCAUAAAUUG | 607 | CAAUUUAUGCCUACAGCCU |
| 1819 | 296 | ACUUUUUCACCUCUGCCUA | 608 | UAGGCAGAGGUGAAAAAGU |
| 410 | 297 | AUCCUGCUGCUAUGCCUCA | 609 | UGAGGCAUAGCAGCAGGAU |
| 415 | 298 | GCUGCUAUGCCUCAUCUUC | 610 | GAAGAUGAGGCAUAGCAGC |
| 416 | 299 | CUGCUAUGCCUCAUCUUCU | 611 | AGAAGAUGAGGCAUAGCAG |
| 417 | 300 | UGCUAUGCCUCAUCUUCUU | 612 | AAGAAGAUGAGGCAUAGCA |
| 1783 | 301 | GUAGGCAUAAAUUGGUCUG | 613 | CAGACCAAUUUAUGCCUAC |
| 1869 | 302 | CCUCCAAGCUGUGCCUUGG | 614 | CCAAGGCACAGCUUGGAGG |
| 255 | 303 | CGUGGUGGACUUCUCUCAA | 615 | UUGAGAGAAGUCCACCACG |
| 256 | 304 | GUGGUGGACUUCUCUCAAU | 616 | AUUGAGAGAAGUCCACCAC |
| 257 | 305 | UGGUGGACUUCUCUCAAUU | 617 | AAUUGAGAGAAGUCCACCA |

TABLE 15-continued

HBV sense and antisense sequences

| REF POS | SEQ ID NO | Sense (5'-3') SEQ ID NOS: 237 to 548 | SEQ ID NO | Antisense (5'-3') SEQ ID NOS: 549 to 860 |
|---|---|---|---|---|
| 258 | 306 | GGUGGACUUCUCUCAAUUU | 618 | AAAUUGAGAGAAGUCCACC |
| 259 | 307 | GUGGACUUCUCUCAAUUUU | 619 | AAAAUUGAGAGAAGUCCAC |
| 260 | 308 | UGGACUUCUCUCAAUUUUC | 620 | GAAAAUUGAGAGAAGUCCA |
| 262 | 309 | GACUUCUCUCAAUUUUCUA | 621 | UAGAAAAUUGAGAGAAGUC |
| 263 | 310 | ACUUCUCUCAAUUUUCUAG | 622 | CUAGAAAAUUGAGAGAAGU |
| 264 | 311 | CUUCUCUCAAUUUUCUAGG | 623 | CCUAGAAAAUUGAGAGAAG |
| 265 | 312 | UUCUCUCAAUUUUCUAGGG | 624 | CCCUAGAAAAUUGAGAGAA |
| 266 | 313 | UCUCUCAAUUUUCUAGGGG | 625 | CCCCUAGAAAAUUGAGAGA |
| 1264 | 314 | AUCCAUACUGCGGAACUCC | 626 | GGAGUUCCGCAGUAUGGAU |
| 1265 | 315 | UCCAUACUGCGGAACUCCU | 627 | AGGAGUUCCGCAGUAUGGA |
| 2376 | 316 | GAAGAAGAACUCCCUCGCC | 628 | GGCGAGGGAGUUCUUCUUC |
| 2377 | 317 | AAGAAGAACUCCCUCGCCU | 629 | AGGCGAGGGAGUUCUUCUU |
| 2378 | 318 | AGAAGAACUCCCUCGCCUC | 630 | GAGGCGAGGGAGUUCUUCU |
| 2379 | 319 | GAAGAACUCCCUCGCCUCG | 631 | CGAGGCGAGGGAGUUCUUC |
| 2380 | 320 | AAGAACUCCCUCGCCUCGC | 632 | GCGAGGCGAGGGAGUUCUU |
| 2381 | 321 | AGAACUCCCUCGCCUCGCA | 633 | UGCGAGGCGAGGGAGUUCU |
| 243 | 322 | AGAGUCUAGACUCGUGGUG | 634 | CACCACGAGUCUAGACUCU |
| 261 | 323 | GGACUUCUCUCAAUUUUCU | 635 | AGAAAAUUGAGAGAAGUCC |
| 1263 | 324 | GAUCCAUACUGCGGAACUC | 636 | GAGUUCCGCAGUAUGGAUC |
| 1815 | 325 | UGCAACUUUUUCACCUCUG | 637 | CAGAGGUGAAAAAGUUGCA |
| 1816 | 326 | GCAACUUUUUCACCUCUGC | 638 | GCAGAGGUGAAAAAGUUGC |
| 1817 | 327 | CAACUUUUUCACCUCUGCC | 639 | GGCAGAGGUGAAAAAGUUG |
| 301 | 328 | UGGCCAAAAUUCGCAGUCC | 640 | GGACUGCGAAUUUUGGCCA |
| 302 | 329 | GGCCAAAAUUCGCAGUCCC | 641 | GGGACUGCGAAUUUUGGCC |
| 1261 | 330 | CCGAUCCAUACUGCGGAAC | 642 | GUUCCGCAGUAUGGAUCGG |
| 1262 | 331 | CGAUCCAUACUGCGGAACU | 643 | AGUUCCGCAGUAUGGAUCG |
| 1820 | 332 | CUUUUUCACCUCUGCCUAA | 644 | UUAGGCAGAGGUGAAAAAG |
| 1821 | 333 | UUUUUCACCUCUGCCUAAU | 645 | UUAGGCAGAGGUGAAAAAA |
| 1822 | 334 | UUUUCACCUCUGCCUAAUC | 646 | UAGGCAGAGGUGAAAAGAU |
| 1823 | 335 | UUUCACCUCUGCCUAAUCA | 647 | UGAUUAGGCAGAGGUGAAA |
| 1874 | 336 | AAGCUGUGCCUUGGGUGGC | 648 | GCCACCCAAGGCACAGCUU |
| 1875 | 337 | AGCUGUGCCUUGGGUGGCU | 649 | AGCCACCCAAGGCACAGCU |
| 1876 | 338 | GCUGUGCCUUGGGUGGCUU | 650 | AAGCCACCCAAGGCACAGC |
| 1877 | 339 | CUGUGCCUUGGGUGGCUUU | 651 | AAAGCCACCCAAGGCACAG |
| 2267 | 340 | GGAGUGUGGAUUCGCACUC | 652 | GAGUGCGAAUCCACACUCC |
| 2268 | 341 | GAGUGUGGAUUCGCACUCC | 653 | GGAGUGCGAAUCCACACUC |
| 242 | 342 | CAGAGUCUAGACUCGUGGU | 654 | ACCACGAGUCUAGACUCUG |

TABLE 15-continued

HBV sense and antisense sequences

| REF POS | SEQ ID NO | Sense (5'-3') SEQ ID NOS: 237 to 548 | SEQ ID NO | Antisense (5'-3') SEQ ID NOS: 549 to 860 |
|---|---|---|---|---|
| 1654 | 343 | AUAAGAGGACUCUUGGACU | 655 | AGUCCAAGAGUCCUCUUAU |
| 1774 | 344 | UAGGAGGCUGUAGGCAUAA | 656 | UUAUGCCUACAGCCUCCUA |
| 1775 | 345 | AGGAGGCUGUAGGCAUAAA | 657 | UUUAUGCCUACAGCCUCCU |
| 1813 | 346 | CAUGCAACUUUUUCACCUC | 658 | GAGGUGAAAAAGUUGCAUG |
| 1814 | 347 | AUGCAACUUUUUCACCUCU | 659 | AGAGGUGAAAAAGUUGCAU |
| 1824 | 348 | UUCACCUCUGCCUAAUCAU | 660 | AUGAUUAGGCAGAGGUGAA |
| 1825 | 349 | UCACCUCUGCCUAAUCAUC | 661 | GAUGAUUAGGCAGAGGUGA |
| 1826 | 350 | CACCUCUGCCUAAUCAUCU | 662 | AGAUGAUUAGGCAGAGGUG |
| 1870 | 351 | CUCCAAGCUGUGCCUUGGG | 663 | CCCAAGGCACAGCUUGGAG |
| 1871 | 352 | UCCAAGCUGUGCCUUGGGU | 664 | ACCCAAGGCACAGCUUGGA |
| 1872 | 353 | CCAAGCUGUGCCUUGGGUG | 665 | CACCCAAGGCACAGCUUGG |
| 1873 | 354 | CAAGCUGUGCCUUGGGUGG | 666 | CCACCCAAGGCACAGCUUG |
| 2373 | 355 | CUAGAAGAAGAACUCCCUC | 667 | GAGGGAGUUCUUCUUCUAG |
| 2374 | 356 | UAGAAGAAGAACUCCCUCG | 668 | CGAGGGAGUUCUUCUUCUA |
| 2375 | 357 | AGAAGAAGAACUCCCUCGC | 669 | GCGAGGGAGUUCUUCUUCU |
| 1862 | 358 | GUUCAAGCCUCCAAGCUGU | 670 | ACAGCUUGGAGGCUUGAAC |
| 2297 | 359 | AGACCACCAAAUGCCCCUA | 671 | UAGGGGCAUUUGGUGGUCU |
| 2298 | 360 | GACCACCAAAUGCCCCUAU | 672 | AUAGGGGCAUUUGGUGGUC |
| 2299 | 361 | ACCACCAAAUGCCCCUAUC | 673 | GAUAGGGGCAUUUGGUGGU |
| 599 | 362 | UGUAUUCCCAUCCCAUCAU | 674 | AUGAUGGGAUGGGAAUACA |
| 600 | 363 | GUAUUCCCAUCCCAUCAUC | 675 | GAUGAUGGGAUGGGAAUAC |
| 703 | 364 | CGUAGGGCUUUCCCCCACU | 676 | AGUGGGGGAAAGCCCUACG |
| 704 | 365 | GUAGGGCUUUCCCCCACUG | 677 | CAGUGGGGGAAAGCCCUAC |
| 705 | 366 | UAGGGCUUUCCCCCACUGU | 678 | ACAGUGGGGGAAAGCCCUA |
| 1259 | 367 | UGCCGAUCCAUACUGCGGA | 679 | UCCGCAGUAUGGAUCGGCA |
| 1260 | 368 | GCCGAUCCAUACUGCGGAA | 680 | UUCCGCAGUAUGGAUCGGC |
| 1518 | 369 | CACGGGGCGCACCUCUCUU | 681 | AAGAGAGGUGCGCCCCGUG |
| 1519 | 370 | ACGGGGCGCACCUCUCUUU | 682 | AAAGAGAGGUGCGCCCCGU |
| 1520 | 371 | CGGGGCGCACCUCUCUUUA | 683 | UAAAGAGAGGUGCGCCCCG |
| 1521 | 372 | GGGGCGCACCUCUCUUUAC | 684 | GUAAAGAGAGGUGCGCCCC |
| 1522 | 373 | GGGCGCACCUCUCUUUACG | 685 | CGUAAAGAGAGGUGCGCCC |
| 1523 | 374 | GGCGCACCUCUCUUUACGC | 686 | GCGUAAAGAGAGGUGCGCC |
| 1524 | 375 | GCGCACCUCUCUUUACGCG | 687 | CGCGUAAAGAGAGGUGCGC |
| 1859 | 376 | ACUGUUCAAGCCUCCAAGC | 688 | GCUUGGAGGCUUGAACAGU |
| 1860 | 377 | CUGUUCAAGCCUCCAAGCU | 689 | AGCUUGGAGGCUUGAACAG |
| 1861 | 378 | UGUUCAAGCCUCCAAGCUG | 690 | CAGCUUGGAGGCUUGAACA |
| 459 | 379 | GUAUGUUGCCCGUUUGUCC | 691 | GGACAAACGGGCAACAUAC |

TABLE 15-continued

HBV sense and antisense sequences

| REF POS | SEQ ID NO | Sense (5'-3') SEQ ID NOS: 237 to 548 | SEQ ID NO | Antisense (5'-3') SEQ ID NOS: 549 to 860 |
|---|---|---|---|---|
| 460 | 380 | UAUGUUGCCCGUUUGUCCU | 692 | AGGACAAACGGGCAACAUA |
| 462 | 381 | UGUUGCCCGUUUGUCCUCU | 693 | AGAGGACAAACGGGCAACA |
| 1136 | 382 | UGAACCUUUACCCCGUUGC | 694 | GCAACGGGGUAAAGGUUCA |
| 1266 | 383 | CCAUACUGCGGAACUCCUA | 695 | UAGGAGUUCCGCAGUAUGG |
| 1267 | 384 | CAUACUGCGGAACUCCUAG | 696 | CUAGGAGUUCCGCAGUAUG |
| 1268 | 385 | AUACUGCGGAACUCCUAGC | 697 | GCUAGGAGUUCCGCAGUAU |
| 1517 | 386 | CCACGGGGCGCACCUCUCU | 698 | AGAGAGGUGCGCCCCGUGG |
| 2371 | 387 | CCCUAGAAGAAGAACUCCC | 699 | GGGAGUUCUUCUUCUAGGG |
| 2372 | 388 | CCUAGAAGAAGAACUCCCU | 700 | AGGGAGUUCUUCUUCUAGG |
| 2380 | 389 | UCCCUCGCCUCGCAGACGA | 701 | UCGUCUGCGAGGCGAGGGA |
| 401 | 390 | UUCCUCUUCAUCCUGCUGC | 702 | GCAGCAGGAUGAAGAGGAA |
| 402 | 391 | UCCUCUUCAUCCUGCUGCU | 703 | AGCAGCAGGAUGAAGAGGA |
| 403 | 392 | CCUCUUCAUCCUGCUGCUA | 704 | UAGCAGCAGGAUGAAGAGG |
| 404 | 393 | CUCUUCAUCCUGCUGCUAU | 705 | AUAGCAGCAGGAUGAAGAG |
| 405 | 394 | UCUUCAUCCUGCUGCUAUG | 706 | CAUAGCAGCAGGAUGAAGA |
| 406 | 395 | CUUCAUCCUGCUGCUAUGC | 707 | GCAUAGCAGCAGGAUGAAG |
| 407 | 396 | UUCAUCCUGCUGCUAUGCC | 708 | GGCAUAGCAGCAGGAUGAA |
| 408 | 397 | UCAUCCUGCUGCUAUGCCU | 709 | AGGCAUAGCAGCAGGAUGA |
| 458 | 398 | GGUAUGUUGCCCGUUUGUC | 710 | GACAAACGGGCAACAUACC |
| 461 | 399 | AUGUUGCCCGUUUGUCCUC | 711 | GAGGACAAACGGGCAACAU |
| 1426 | 400 | UACGUCCCGUCGGCGCUGA | 712 | UCAGCGCCGACGGGACGUA |
| 1427 | 401 | ACGUCCCGUCGGCGCUGAA | 713 | UUCAGCGCCGACGGGACGU |
| 1428 | 402 | CGUCCCGUCGGCGCUGAAU | 714 | AUUCAGCGCCGACGGGACG |
| 1429 | 403 | GUCCCGUCGGCGCUGAAUC | 715 | GAUUCAGCGCCGACGGGAC |
| 1430 | 404 | UCCCGUCGGCGCUGAAUCC | 716 | GGAUUCAGCGCCGACGGGA |
| 2269 | 405 | AGUGUGGAUUCGCACUCCU | 717 | AGGAGUGCGAAUCCACACU |
| 2370 | 406 | CCCCUAGAAGAAGAACUCC | 718 | GGAGUUCUUCUUCUAGGGG |
| 455 | 407 | CAAGGUAUGUUGCCCGUUU | 719 | AAACGGGCAACAUACCUUG |
| 456 | 408 | AAGGUAUGUUGCCCGUUUG | 720 | CAAACGGGCAACAUACCUU |
| 457 | 409 | AGGUAUGUUGCCCGUUUGU | 721 | ACAAACGGGCAACAUACCU |
| 1513 | 410 | CCGACCACGGGGCGCACCU | 722 | AGGUGCGCCCCGUGGUCGG |
| 1514 | 411 | CGACCACGGGGCGCACCUC | 723 | GAGGUGCGCCCCGUGGUCG |
| 1515 | 412 | GACCACGGGGCGCACCUCU | 724 | AGAGGUGCGCCCCGUGGUC |
| 1516 | 413 | ACCACGGGGCGCACCUCUC | 725 | GAGAGGUGCGCCCCGUGGU |
| 1545 | 414 | CUCCCCGUCUGUGCCUUCU | 726 | AGAAGGCACAGACGGGGAG |
| 1546 | 415 | UCCCCGUCUGUGCCUUCUC | 727 | GAGAAGGCACAGACGGGGA |
| 2417 | 416 | CCGCGUCGCAGAAGAUCUC | 728 | GAGAUCUUCUGCGACGCGG |

TABLE 15-continued

HBV sense and antisense sequences

| REF POS | SEQ ID NO | Sense (5'-3') SEQ ID NOS: 237 to 548 | SEQ ID NO | Antisense (5'-3') SEQ ID NOS: 549 to 860 |
|---|---|---|---|---|
| 2418 | 417 | CGCGUCGCAGAAGAUCUCA | 729 | UGAGAUCUUCUGCGACGCG |
| 2419 | 418 | GCGUCGCAGAAGAUCUCAA | 730 | UUGAGAUCUUCUGCGACGC |
| 2420 | 419 | CGUCGCAGAAGAUCUCAAU | 731 | AUUGAGAUCUUCUGCGACG |
| 2421 | 420 | GUCGCAGAAGAUCUCAAUC | 732 | GAUUGAGAUCUUCUGCGAC |
| 2422 | 421 | UCGCAGAAGAUCUCAAUCU | 733 | AGAUUGAGAUCUUCUGCGA |
| 181 | 422 | AGGACCCCUGCUCGUGUUA | 734 | UAACACGAGCAGGGGUCCU |
| 182 | 423 | GGACCCCUGCUCGUGUUAC | 735 | GUAACACGAGCAGGGGUCC |
| 183 | 424 | GACCCCUGCUCGUGUUACA | 736 | UGUAACACGAGCAGGGGUC |
| 184 | 425 | ACCCCUGCUCGUGUUACAG | 737 | CUGUAACACGAGCAGGGGU |
| 185 | 426 | CCCCUGCUCGUGUUACAGG | 738 | CCUGUAACACGAGCAGGGG |
| 368 | 427 | UAUCGCUGGAUGUGUCUGC | 739 | GCAGACACAUCCAGCGAUA |
| 369 | 428 | AUCGCUGGAUGUGUCUGCG | 740 | CGCAGACACAUCCAGCGAU |
| 370 | 429 | UCGCUGGAUGUGUCUGCGG | 741 | CCGCAGACACAUCCAGCGA |
| 371 | 430 | CGCUGGAUGUGUCUGCGGC | 742 | GCCGCAGACACAUCCAGCG |
| 372 | 431 | GCUGGAUGUGUCUGCGGCG | 743 | CGCCGCAGACACAUCCAGC |
| 373 | 432 | CUGGAUGUGUCUGCGGCGU | 744 | ACGCCGCAGACACAUCCAG |
| 463 | 433 | GUUGCCCGUUUGUCCUCUA | 745 | UAGAGGACAAACGGGCAAC |
| 686 | 434 | CCAUUUGUUCAGUGGUUCG | 746 | CGAACCACUGAACAAAUGG |
| 800 | 435 | UUACCAAUUUUCUUUUGUC | 747 | GACAAAAGAAAAUUGGUAA |
| 1102 | 436 | CCAACUUACAAGGCCUUUC | 748 | GAAAGGCCUUGUAAGUUGG |
| 1103 | 437 | CAACUUACAAGGCCUUUCU | 749 | AGAAAGGCCUUGUAAGUUG |
| 1183 | 438 | UUUGCUGACGCAACCCCCA | 750 | UGGGGGUUGCGUCAGCAAA |
| 1184 | 439 | UUGCUGACGCAACCCCCAC | 751 | GUGGGGGUUGCGUCAGCAA |
| 1185 | 440 | UGCUGACGCAACCCCCACU | 752 | AGUGGGGGUUGCGUCAGCA |
| 1186 | 441 | GCUGACGCAACCCCCACUG | 753 | CAGUGGGGGUUGCGUCAGC |
| 1187 | 442 | CUGACGCAACCCCCACUGG | 754 | CCAGUGGGGGUUGCGUCAG |
| 1553 | 443 | CUGUGCCUUCUCAUCUGCC | 755 | GGCAGAUGAGAAGGCACAG |
| 1554 | 444 | UGUGCCUUCUCAUCUGCCG | 756 | CGGCAGAUGAGAAGGCACA |
| 1555 | 445 | GUGCCUUCUCAUCUGCCGG | 757 | CCGGCAGAUGAGAAGGCAC |
| 1805 | 446 | ACCAGCACCAUGCAACUUU | 758 | AAAGUUGCAUGGUGCUGGU |
| 1806 | 447 | CCAGCACCAUGCAACUUUU | 759 | AAAAGUUGCAUGGUGCUGG |
| 1807 | 448 | CAGCACCAUGCAACUUUUU | 760 | AAAAAGUUGCAUGGUGCUG |
| 1808 | 449 | AGCACCAUGCAACUUUUUC | 761 | GAAAAAGUUGCAUGGUGCU |
| 1809 | 450 | GCACCAUGCAACUUUUUCA | 762 | UGAAAAAGUUGCAUGGUGC |
| 1810 | 451 | CACCAUGCAACUUUUUCAC | 763 | GUGAAAAAGUUGCAUGGUG |
| 1811 | 452 | ACCAUGCAACUUUUUCACC | 764 | GGUGAAAAAGUUGCAUGGU |
| 1812 | 453 | CCAUGCAACUUUUUCACCU | 765 | AGGUGAAAAAGUUGCAUGG |

TABLE 15-continued

| HBV sense and antisense sequences | | | | |
|---|---|---|---|---|
| REF POS | SEQ ID NO | Sense (5'-3') SEQ ID NOS: 237 to 548 | SEQ ID NO | Antisense (5'-3') SEQ ID NOS: 549 to 860 |
| 2423 | 454 | CGCAGAAGAUCUCAAUCUC | 766 | GAGAUUGAGAUCUUCUGCG |
| 177 | 455 | UCCUAGGACCCCUGCUCGU | 767 | ACGAGCAGGGGUCCUAGGA |
| 178 | 456 | CCUAGGACCCCUGCUCGUG | 768 | CACGAGCAGGGGUCCUAGG |
| 179 | 457 | CUAGGACCCCUGCUCGUGU | 769 | ACACGAGCAGGGGUCCUAG |
| 180 | 458 | UAGGACCCCUGCUCGUGUU | 770 | AACACGAGCAGGGGUCCUA |
| 186 | 459 | CCCUGCUCGUGUUACAGGC | 771 | GCCUGUAACACGAGCAGGG |
| 187 | 460 | CCUGCUCGUGUUACAGGCG | 772 | CGCCUGUAACACGAGCAGG |
| 188 | 461 | CUGCUCGUGUUACAGGCGG | 773 | CCGCCUGUAACACGAGCAG |
| 685 | 462 | GCCAUUUGUUCAGUGGUUC | 774 | GAACCACUGAACAAAUGGC |
| 1099 | 463 | UCGCCAACUUACAAGGCCU | 775 | AGGCCUUGUAAGUUGGCGA |
| 1100 | 464 | CGCCAACUUACAAGGCCUU | 776 | AAGGCCUUGUAAGUUGGCG |
| 1101 | 465 | GCCAACUUACAAGGCCUUU | 777 | AAAGGCCUUGUAAGUUGGC |
| 1230 | 466 | GCGCAUGCGUGGAACCUUU | 778 | AAAGGUUCCACGCAUGCGC |
| 1258 | 467 | CUGCCGAUCCAUACUGCGG | 779 | CCGCAGUAUGGAUCGGCAG |
| 1606 | 468 | GCAUGGAGACCACCGUGAA | 780 | UUCACGGUGGUCUCCAUGC |
| 1607 | 469 | CAUGGAGACCACCGUGAAC | 781 | GUUCACGGUGGUCUCCAUG |
| 1608 | 470 | AUGGAGACCACCGUGAACG | 782 | CGUUCACGGUGGUCUCCAU |
| 1609 | 471 | UGGAGACCACCGUGAACGC | 783 | GCGUUCACGGUGGUCUCCA |
| 1610 | 472 | GGAGACCACCGUGAACGCC | 784 | GGCGUUCACGGUGGUCUCC |
| 1611 | 473 | GAGACCACCGUGAACGCCC | 785 | GGGCGUUCACGGUGGUCUC |
| 1804 | 474 | CACCAGCACCAUGCAACUU | 786 | AAGUUGCAUGGUGCUGGUG |
| 2381 | 475 | CCCUCGCCUCGCAGACGAA | 787 | UUCGUCUGCGAGGCGAGGG |
| 3077 | 476 | UGGGGUGGAGCCCUCAGGC | 788 | GCCUGAGGGCUCCACCCCA |
| 303 | 477 | GCCAAAAUUCGCAGUCCCC | 789 | GGGGACUGCGAAUUUUGGC |
| 304 | 478 | CCAAAAUUCGCAGUCCCCA | 790 | UGGGGACUGCGAAUUUUGG |
| 305 | 479 | CAAAAUUCGCAGUCCCCAA | 791 | UUGGGGACUGCGAAUUUUG |
| 801 | 480 | UACCAAUUUUCUUUUGUCU | 792 | AGACAAAAGAAAAUUGGUA |
| 1174 | 481 | UGCCAAGUGUUUGCUGACG | 793 | CGUCAGCAAACACUUGGCA |
| 1175 | 482 | GCCAAGUGUUUGCUGACGC | 794 | GCGUCAGCAAACACUUGGC |
| 1176 | 483 | CCAAGUGUUUGCUGACGCA | 795 | UGCGUCAGCAAACACUUGG |
| 2382 | 484 | CCUCGCCUCGCAGACGAAG | 796 | CUUCGUCUGCGAGGCGAGG |
| 2408 | 485 | UCUCAAUCGCCGCGUCGCA | 797 | UGCGACGCGGCGAUUGAGA |
| 2409 | 486 | CUCAAUCGCCGCGUCGCAG | 798 | CUGCGACGCGGCGAUUGAG |
| 2410 | 487 | UCAAUCGCCGCGUCGCAGA | 799 | UCUGCGACGCGGCGAUUGA |
| 2463 | 488 | CCUUGGACUCAUAAGGUGG | 800 | CCACCUUAUGAGUCCAAGG |
| 2464 | 489 | CUUGGACUCAUAAGGUGGG | 801 | CCCACCUUAUGAGUCCAAG |
| 55 | 490 | UCCUGCUGGUGGCUCCAGU | 802 | ACUGGAGCCACCAGCAGGA |

TABLE 15-continued

| HBV sense and antisense sequences | | | | |
|---|---|---|---|---|
| REF POS | SEQ ID NO | Sense (5'-3') SEQ ID NOS: 237 to 548 | SEQ ID NO | Antisense (5'-3') SEQ ID NOS: 549 to 860 |
| 668 | 491 | UGGCUCAGUUUACUAGUGC | 803 | GCACUAGUAAACUGAGCCA |
| 701 | 492 | UUCGUAGGGCUUUCCCCCA | 804 | UGGGGGAAAGCCCUACGAA |
| 1177 | 493 | CAAGUGUUUGCUGACGCAA | 805 | UUGCGUCAGCAAACACUUG |
| 1178 | 494 | AAGUGUUUGCUGACGCAAC | 806 | GUUGCGUCAGCAAACACUU |
| 1179 | 495 | AGUGUUUGCUGACGCAACC | 807 | GGUUGCGUCAGCAAACACU |
| 1180 | 496 | GUGUUUGCUGACGCAACCC | 808 | GGGUUGCGUCAGCAAACAC |
| 1181 | 497 | UGUUUGCUGACGCAACCCC | 809 | GGGGUUGCGUCAGCAAACA |
| 1182 | 498 | GUUUGCUGACGCAACCCCC | 810 | GGGGGUUGCGUCAGCAAAC |
| 1680 | 499 | AUGUCAACGACCGACCUUG | 811 | CAAGGUCGGUCGUUGACAU |
| 1681 | 500 | UGUCAACGACCGACCUUGA | 812 | UCAAGGUCGGUCGUUGACA |
| 1682 | 501 | GUCAACGACCGACCUUGAG | 813 | CUCAAGGUCGGUCGUUGAC |
| 1683 | 502 | UCAACGACCGACCUUGAGG | 814 | CCUCAAGGUCGGUCGUUGA |
| 1684 | 503 | CAACGACCGACCUUGAGGC | 815 | GCCUCAAGGUCGGUCGUUG |
| 2411 | 504 | CAAUCGCCGCGUCGCAGAA | 816 | UUCUGCGACGCGGCGAUUG |
| 2412 | 505 | AAUCGCCGCGUCGCAGAAG | 817 | CUUCUGCGACGCGGCGAUU |
| 2413 | 506 | AUCGCCGCGUCGCAGAAGA | 818 | UCUUCUGCGACGCGGCGAU |
| 2414 | 507 | UCGCCGCGUCGCAGAAGAU | 819 | AUCUUCUGCGACGCGGCGA |
| 2415 | 508 | CGCCGCGUCGCAGAAGAUC | 820 | GAUCUUCUGCGACGCGGCG |
| 2416 | 509 | GCCGCGUCGCAGAAGAUCU | 821 | AGAUCUUCUGCGACGCGGC |
| 54 | 510 | UUCCUGCUGGUGGCUCCAG | 822 | CUGGAGCCACCAGCAGGAA |
| 700 | 511 | GUUCGUAGGGCUUUCCCCC | 823 | GGGGGAAAGCCCUACGAAC |
| 702 | 512 | UCGUAGGGCUUUCCCCCAC | 824 | GUGGGGGAAAGCCCUACGA |
| 1253 | 513 | CUCCUCUGCCGAUCCAUAC | 825 | GUAUGGAUCGGCAGAGGAG |
| 1254 | 514 | UCCUCUGCCGAUCCAUACU | 826 | AGUAUGGAUCGGCAGAGGA |
| 1255 | 515 | CCUCUGCCGAUCCAUACUG | 827 | CAGUAUGGAUCGGCAGAGG |
| 1439 | 516 | CGCUGAAUCCCGCGGACGA | 828 | UCGUCCGCGGGAUUCAGCG |
| 1547 | 517 | CCCCGUCUGUGCCUUCUCA | 829 | UGAGAAGGCACAGACGGGG |
| 1548 | 518 | CCCGUCUGUGCCUUCUCAU | 830 | AUGAGAAGGCACAGACGGG |
| 1549 | 519 | CCGUCUGUGCCUUCUCAUC | 831 | GAUGAGAAGGCACAGACGG |
| 1550 | 520 | CGUCUGUGCCUUCUCAUCU | 832 | AGAUGAGAAGGCACAGACG |
| 1653 | 521 | CAUAAGAGGACUCUUGGAC | 833 | GUCCAAGAGUCCUCUUAUG |
| 1910 | 522 | GACCCUUAUAAAGAAUUUG | 834 | CAAAUUCUUUAUAAGGGUC |
| 2270 | 523 | GUGUGGAUUCGCACUCCUC | 835 | GAGGAGUGCGAAUCCACAC |
| 2361 | 524 | GAGGCAGGUCCCCUAGAAG | 836 | CUUCUAGGGGACCUGCCUC |
| 2362 | 525 | AGGCAGGUCCCCUAGAAGA | 837 | UCUUCUAGGGGACCUGCCU |
| 316 | 526 | GUCCCCAACCUCCAAUCAC | 838 | GUGAUUGGAGGUUGGGGAC |
| 317 | 527 | UCCCCAACCUCCAAUCACU | 839 | AGUGAUUGGAGGUUGGGGA |

TABLE 15-continued

| HBV sense and antisense sequences | | | | |
|---|---|---|---|---|
| REF POS | SEQ ID NO | Sense (5'-3') SEQ ID NOS: 237 to 548 | SEQ ID NO | Antisense (5'-3') SEQ ID NOS: 549 to 860 |
| 452 | 528 | UAUCAAGGUAUGUUGCCCG | 840 | CGGGCAACAUACCUUGAUA |
| 453 | 529 | AUCAAGGUAUGUUGCCCGU | 841 | ACGGGCAACAUACCUUGAU |
| 687 | 530 | CAUUUGUUCAGUGGUUCGU | 842 | ACGAACCACUGAACAAAUG |
| 689 | 531 | UUUGUUCAGUGGUUCGUAG | 843 | CUACGAACCACUGAACAAA |
| 690 | 532 | UUGUUCAGUGGUUCGUAGG | 844 | CCUACGAACCACUGAACAA |
| 691 | 533 | UGUUCAGUGGUUCGUAGGG | 845 | CCCUACGAACCACUGAACA |
| 692 | 534 | GUUCAGUGGUUCGUAGGGC | 846 | GCCCUACGAACCACUGAAC |
| 693 | 535 | UUCAGUGGUUCGUAGGGCU | 847 | AGCCCUACGAACCACUGAA |
| 694 | 536 | UCAGUGGUUCGUAGGGCUU | 848 | AAGCCCUACGAACCACUGA |
| 695 | 537 | CAGUGGUUCGUAGGGCUUU | 849 | AAAGCCCUACGAACCACUG |
| 696 | 538 | AGUGGUUCGUAGGGCUUUC | 850 | GAAAGCCCUACGAACCACU |
| 697 | 539 | GUGGUUCGUAGGGCUUUCC | 851 | GGAAAGCCCUACGAACCAC |
| 698 | 540 | UGGUUCGUAGGGCUUUCCC | 852 | GGGAAAGCCCUACGAACCA |
| 699 | 541 | GGUUCGUAGGGCUUUCCCC | 853 | GGGGAAAGCCCUACGAACC |
| 1228 | 542 | CAGCGCAUGCGUGGAACCU | 854 | AGGUUCCACGCAUGCGCUG |
| 1229 | 543 | AGCGCAUGCGUGGAACCUU | 855 | AAGGUUCCACGCAUGCGCU |
| 1231 | 544 | CGCAUGCGUGGAACCUUUG | 856 | CAAAGGUUCCACGCAUGCG |
| 1256 | 545 | CUCUGCCGAUCCAUACUGC | 857 | GCAGUAUGGAUCGGCAGAG |
| 1257 | 546 | UCUGCCGAUCCAUACUGCG | 858 | CGCAGUAUGGAUCGGCAGA |
| 1438 | 547 | GCGCUGAAUCCCGCGGACG | 859 | CGUCCGCGGGAUUCAGCGC |
| 1827 | 548 | ACCUCUGCCUAAUCAUCUC | 860 | GAGAUGAUUAGGCAGAGGU |

UNA Oligomers Targeting HBV

Examples of base sequences of this invention targeted to an HBV component are shown in Table 16.

An oligomeric compound of this invention can be formed having a first strand and a second strand each being 21 monomers in length. The first strand can have 19 contiguous monomers with a sequence of attached bases shown in Table 16 (sense), and two additional overhang monomers on the 3' end. The second strand can have 19 contiguous monomers with a sequence of attached bases shown in Table 16 (antisense), and two additional overhang monomers on the 3' end. The overhang monomers can be any of NN, QQ, XX, NX, NQ, XN, XQ, QN, and QX. For example, XQ can be UNA-U/mU, or UNA-U/*/dT.

TABLE 16

| HBV sense and antisense sequences | | | | |
|---|---|---|---|---|
| REF POS | SEQ ID NO | Sense (5'-3') SEQ ID NOS: 861 to 901 | SEQ ID NO | Antisense (5'-3') SEQ ID NOS: 902 to 942 |
| 1525 | 861 | CGCACCUCUCUUUACGCGG | 902 | CCGCGUAAAGAGAGGUGCG |
| 251 | 862 | GACUCGUGGUGGACUUCUC | 903 | GAGAAGUCCACCACGAGUC |
| 254 | 863 | UCGUGGUGGACUUCUCUCA | 904 | UGAGAGAAGUCCACCACGA |
| 374 | 864 | UGGAUGUGUCUGCGGCGUU | 905 | AACGCCGCAGACACAUCCA |
| 1575 | 865 | CCGUGUGCACUUCGCUUCA | 906 | UGAAGCGAAGUGCACACGG |
| 1577 | 866 | GUGUGCACUUCGCUUCACC | 907 | GGUGAAGCGAAGUGCACAC |
| 1578 | 867 | UGUGCACUUCGCUUCACCU | 908 | AGGUGAAGCGAAGUGCACA |

TABLE 16 -continued

HBV sense and antisense sequences

| REF POS | SEQ ID NO | Sense (5'-3') SEQ ID NOS: 861 to 901 | SEQ ID NO | Antisense (5'-3') SEQ ID NOS: 902 to 942 |
|---|---|---|---|---|
| 1579 | 868 | GUGCACUUCGCUUCACCUC | 909 | GAGGUGAAGCGAAGUGCAC |
| 1581 | 869 | GCACUUCGCUUCACCUCUG | 910 | CAGAGGUGAAGCGAAGUGC |
| 247 | 870 | UCUAGACUCGUGGUGGACU | 911 | AGUCCACCACGAGUCUAGA |
| 248 | 871 | CUAGACUCGUGGUGGACUU | 912 | AAGUCCACCACGAGUCUAG |
| 249 | 872 | UAGACUCGUGGUGGACUUC | 913 | GAAGUCCACCACGAGUCUA |
| 250 | 873 | AGACUCGUGGUGGACUUCU | 914 | AGAAGUCCACCACGAGUCU |
| 1776 | 874 | GGAGGCUGUAGGCAUAAAU | 915 | AUUUAUGCCUACAGCCUCC |
| 1777 | 875 | GAGGCUGUAGGCAUAAAUU | 916 | AAUUUAUGCCUACAGCCUC |
| 1779 | 876 | GGCUGUAGGCAUAAAUUGG | 917 | CCAAUUUAUGCCUACAGCC |
| 1780 | 877 | GCUGUAGGCAUAAAUUGGU | 918 | ACCAAUUUAUGCCUACAGC |
| 1781 | 878 | CUGUAGGCAUAAAUUGGUC | 919 | GACCAAUUUAUGCCUACAG |
| 1782 | 879 | UGUAGGCAUAAAUUGGUCU | 920 | AGACCAAUUUAUGCCUACA |
| 256 | 880 | GUGGUGGACUUCUCUCAAU | 921 | AUUGAGAGAAGUCCACCAC |
| 1863 | 881 | UUCAAGCCUCCAAGCUGUG | 922 | CACAGCUUGGAGGCUUGAA |
| 1864 | 882 | UCAAGCCUCCAAGCUGUGC | 923 | GCACAGCUUGGAGGCUUGA |
| 1865 | 883 | CAAGCCUCCAAGCUGUGCC | 924 | GGCACAGCUUGGAGGCUUG |
| 1866 | 884 | AAGCCUCCAAGCUGUGCCU | 925 | AGGCACAGCUUGGAGGCUU |
| 376 | 885 | GAUGUGUCUGCGGCGUUUU | 926 | AAAACGCCGCAGACACAUC |
| 378 | 886 | UGUGUCUGCGGCGUUUUAU | 927 | AUAAAACGCCGCAGACACA |
| 380 | 887 | UGUCUGCGGCGUUUUAUCA | 928 | UGAUAAAACGCCGCAGACA |
| 1818 | 888 | AACUUUUUCACCUCUGCCU | 929 | AGGCAGAGGUGAAAAAGUU |
| 244 | 889 | GAGUCUAGACUCGUGGUGG | 930 | CCACCACGAGUCUAGACUC |
| 245 | 890 | AGUCUAGACUCGUGGUGGA | 931 | UCCACCACGAGUCUAGACU |
| 246 | 891 | GUCUAGACUCGUGGUGGAC | 932 | GUCCACCACGAGUCUAGAC |
| 409 | 892 | CAUCCUGCUGCUAUGCCUC | 933 | GAGGCAUAGCAGCAGGAUG |
| 411 | 893 | UCCUGCUGCUAUGCCUCAU | 934 | AUGAGGCAUAGCAGCAGGA |
| 412 | 894 | CCUGCUGCUAUGCCUCAUC | 935 | GAUGAGGCAUAGCAGCAGG |
| 413 | 895 | CUGCUGCUAUGCCUCAUCU | 936 | AGAUGAGGCAUAGCAGCAG |
| 414 | 896 | UGCUGCUAUGCCUCAUCUU | 937 | AAGAUGAGGCAUAGCAGCA |
| 252 | 897 | ACUCGUGGUGGACUUCUCU | 938 | AGAGAAGUCCACCACGAGU |
| 253 | 898 | CUCGUGGUGGACUUCUCUC | 939 | GAGAGAAGUCCACCACGAG |
| 1576 | 899 | CGUGUGCACUUCGCUUCAC | 940 | GUGAAGCGAAGUGCACACG |
| 1580 | 900 | UGCACUUCGCUUCACCUCU | 941 | AGAGGUGAAGCGAAGUGCA |
| 1582 | 901 | CACUUCGCUUCACCUCUGC | 942 | GCAGAGGUGAAGCGAAGUG |

UNA Oligomers Targeting HBV

Embodiments of this invention can provide oligomeric molecules that are active agents targeted to HBV.

Examples of UNA oligomers of this invention that are targeted to an HBV component are shown in Table 17. Table 17 shows "sense" and "antisense" pairs.

TABLE 17

UNA oligomers targeted to HBV (Sense (S)-Antisense (AS))

| REF POS | SEQ ID NO | S/AS | HBV (Sense (S)-Antisense (AS)) (5'-3') |
|---|---|---|---|
| 244 | 943 | S | UNA-G/mAGmUCmUAmGACUmCGmUGmGUmGG/UNA-U/mU |
| 244 | 944 | AS | mCCmACmCAmCGmAGmUmCmUAmGAmCUmC/UNA-U/mU |
| 245 | 945 | S | UNA-A/mGUmCUmAGmACUCmGUmGGmUGmGA/UNA-U/mU |
| 245 | 946 | AS | mUCmCAmCCmACmGAmGmUmCUmAGmACmU/UNA-U/mU |
| 246 | 947 | S | UNA-G/mUCmUAmGAmCUCGmUGmGUmGGmAC/UNA-U/mU |
| 246 | 948 | AS | mGUmCCmACmCAmCGmAmGmUCmUAmGAmC/UNA-U/mU |
| 247 | 949 | S | UNA-U/mCUmAGmACmUCGUmGGmUGmGAmCU/UNA-U/mU |
| 247 | 950 | AS | mAGmUCmCAmCCmACmGmAmGUmCUmAGmA/UNA-U/mU |
| 248 | 951 | S | UNA-C/mUAmGAmCUmCGUGmGUmGGmACmUU/UNA-U/mU |
| 248 | 952 | AS | mAAmGUmCCmACmCAmCmGmAGmUCmUAmG/UNA-U/mU |
| 249 | 953 | S | UNA-U/mAGmACmUCmGUGGmUGmGAmCUmUC/UNA-U/mU |
| 249 | 954 | AS | mGAmAGmUCmCAmCCmAmCmGAmGUmCUmA/UNA-U/mU |
| 250 | 955 | S | UNA-A/mGAmCUmCGmUGGUmGGmACmUUmCU/UNA-U/mU |
| 250 | 956 | AS | mAGmAAmGUmCCmACmCmAmCGmAGmUCmU/UNA-U/mU |
| 251 | 957 | S | UNA-G/mACmUCmGUmGGUGmGAmCUmUCmUC/UNA-U/mU |
| 251 | 958 | AS | mGAmGAmAGmUCmCAmCmCmACmGAmGUmC/UNA-U/mU |
| 252 | 959 | S | UNA-A/mCUmCGmUGmGUGGmACmUUmCUmCU/UNA-U/mU |
| 252 | 960 | AS | mAGmAGmAAmGUmCCmAmCmCAmCGmAGmU/UNA-U/mU |
| 253 | 961 | S | UNA-C/mUCmGUmGGmUGGAmCUmUCmUCmUC/UNA-U/mU |
| 253 | 962 | AS | mGAmGAmGAmAGmUCmCmAmCCmACmGAmG/UNA-U/mU |
| 254 | 963 | S | UNA-U/mCGmUGmGUmGGACmUUmCUmCUmCA/UNA-U/mU |
| 254 | 964 | AS | mUGmAGmAGmAAmGUmCmCmACmCAmCGmA/UNA-U/mU |
| 256 | 965 | S | UNA-G/mUGmGUmGGmACUUmCUmCUmCAmAU/UNA-U/mU |
| 256 | 966 | AS | mAUmUGmAGmAGmAAmGmUmCCmACmCAmC/UNA-U/mU |
| 374 | 967 | S | UNA-U/mGGmAUmGUmGUCUmGCmGGmCGmUU/UNA-U/mU |
| 374 | 968 | AS | mAAmCGmCCmGCmAGmAmCmACmAUmCCmA/UNA-U/mU |
| 376 | 969 | S | UNA-G/mAUmGUmGUmCUGCmGGmCGmUUmUU/UNA-U/mU |
| 376 | 970 | AS | mAAmAAmCGmCCmGCmAmGmACmACmAUmC/UNA-U/mU |
| 378 | 971 | S | UNA-U/mGUmGUmCUmGCGGmCGmUUmUUmAU/UNA-U/mU |
| 378 | 972 | AS | mAUmAAmAAmCGmCCmGmCmAGmACmACmA/UNA-U/mU |
| 380 | 973 | S | UNA-U/mGUmCUmGCmGGCGmUUmUUmAUmCA/UNA-U/mU |
| 380 | 974 | AS | mUGmAUmAAmAAmCGmCmCmGCmAGmACmA/UNA-U/mU |
| 409 | 975 | S | UNA-C/mAUmCCmUGmCUGCmUAmUGmCCmUC/UNA-U/mU |
| 409 | 976 | AS | mGAmGGmCAmUAmGCmAmGmCAmGGmAUmG/UNA-U/mU |
| 411 | 977 | S | UNA-U/mCCmUGmCUmGCUAmUGmCCmUCmAU/UNA-U/mU |
| 411 | 978 | AS | mAUmGAmGGmCAmUAmGmCmAGmCAmGGmA/UNA-U/mU |
| 412 | 979 | S | UNA-C/mCUmGCmUGmCUAUmGCmCUmCAmUC/UNA-U/mU |

TABLE 17 -continued

UNA oligomers targeted to HBV (Sense (S)-Antisense (AS))

| REF POS | SEQ ID NO | S/AS | HBV (Sense (S)-Antisense (AS)) (5'-3') |
|---|---|---|---|
| 412 | 980 | AS | mGAmUGmAGmGCmAUmAmGmCAmGCmAGmG/UNA-U/mU |
| 413 | 981 | S | UNA-C/mUGmCUmGCmUAUGmCCmUCmAUmCU/UNA-U/mU |
| 413 | 982 | AS | mAGmAUmGAmGGmCAmUmAmGCmAGmCAmG/UNA-U/mU |
| 414 | 983 | S | UNA-U/mGCmUGmCUmAUGCmCUmCAmUCmUU/UNA-U/mU |
| 414 | 984 | AS | mAAmGAmUGmAGmGCmAmUmAGmCAmGCmA/UNA-U/mU |
| 1525 | 985 | S | UNA-C/mGCmACmCUmCUCUmUUmACmGCmGG/UNA-U/mU |
| 1525 | 986 | AS | mCCmGCmGUmAAmAGmAmGmAGmGUmGCmG/UNA-U/mU |
| 1575 | 987 | S | UNA-C/mCGmUGmUGmCACUmUCmGCmUUmCA/UNA-U/mU |
| 1575 | 988 | AS | mUGmAAmGCmGAmAGmUmGmCAmCAmCGmG/UNA-U/mU |
| 1576 | 989 | S | UNA-C/mGUmGUmGCmACUUmCGmCUmUCmAC/UNA-U/mU |
| 1576 | 990 | AS | mGUmGAmAGmCGmAAmGmUmGCmACmACmG/UNA-U/mU |
| 1577 | 991 | S | UNA-G/mUGmUGmCAmCUUCmGCmUUmCAmCC/UNA-U/mU |
| 1577 | 992 | AS | mGGmUGmAAmGCmGAmAmGmUGmCAmCAmC/UNA-U/mU |
| 1578 | 993 | S | UNA-U/mGUmGCmACmUUCGmCUmUCmACmCU/UNA-U/mU |
| 1578 | 994 | AS | mAGmGUmGAmAGmCGmAmAmGUmGCmACmA/UNA-U/mU |
| 1579 | 995 | S | UNA-G/mUGmCAmCUmUCGCmUUmCAmCCmUC/UNA-U/mU |
| 1579 | 996 | AS | mGAmGGmUGmAAmGCmGmAmAGmUGmCAmC/UNA-U/mU |
| 1580 | 997 | S | UNA-U/mGCmACmUUmCGCUmUCmACmCUmCU/UNA-U/mU |
| 1580 | 998 | AS | mAGmAGmGUmGAmAGmCmGmAAmGUmGCmA/UNA-U/mU |
| 1581 | 999 | S | UNA-G/mCAmCUmUCmGCUUmCAmCCmUCmUG/UNA-U/mU |
| 1581 | 1000 | AS | mCAmGAmGGmUGmAAmGmCmGAmAGmUGmC/UNA-U/mU |
| 1582 | 1001 | S | UNA-C/mACmUUmCGmCUUCmACmCUmCUmGC/UNA-U/mU |
| 1582 | 1002 | AS | mGCmAGmAGmGUmGAmAmGmCGmAAmGUmG/UNA-U/mU |
| 1776 | 1003 | S | UNA-G/mGAmGGmCUmGUAGmGCmAUmAAmAU/UNA-U/mU |
| 1776 | 1004 | AS | mAUmUUmAUmGCmCUmAmCmAGmCCmUCmC/UNA-U/mU |
| 1777 | 1005 | S | UNA-G/mAGmGCmUGmUAGGmCAmUAmAAmUU/UNA-U/mU |
| 1777 | 1006 | AS | mAAmUUmUAmUGmCCmUmAmCAmGCmCUmC/UNA-U/mU |
| 1779 | 1007 | S | UNA-G/mGCmUGmUAmGGCAmUAmAAmUUmGG/UNA-U/mU |
| 1779 | 1008 | AS | mCCmAAmUUmUAmUGmCmCmUAmCAmGCmC/UNA-U/mU |
| 1780 | 1009 | S | UNA-G/mCUmGUmAGmGCAUmAAmAUmUGmGU/UNA-U/mU |
| 1780 | 1010 | AS | mACmCAmAUmUUmAUmGmCmCUmACmAGmC/UNA-U/mU |
| 1781 | 1011 | S | UNA-C/mUGmUAmGGmCAUAmAAmUUmGGmUC/UNA-U/mU |
| 1781 | 1012 | AS | mGAmCCmAAmUUmUAmUmGmCCmUAmCAmG/UNA-U/mU |
| 1782 | 1013 | S | UNA-U/mGUmAGmGCmAUAAmAUmUGmGUmCU/UNA-U/mU |
| 1782 | 1014 | AS | mAGmACmCAmAUmUUmAmUmGCmCUmACmA/UNA-U/mU |
| 1818 | 1015 | S | UNA-A/mACmUUmUUmUCACmCUmCUmGCmCU/UNA-U/mU |
| 1818 | 1016 | AS | mAGmGCmAGmAGmGUmGmAmAAmAAmGUmU/UNA-U/mU |

TABLE 17 -continued

UNA oligomers targeted to HBV (Sense (S)-Antisense (AS))

| REF POS | SEQ ID NO | S/AS | HBV (Sense (S)-Antisense (AS)) (5'-3') |
|---|---|---|---|
| 1863 | 1017 | S | UNA-U/mUCmAAmGCmCUCCmAAmGCmUGmUG/UNA-U/mU |
| 1863 | 1018 | AS | mCAmCAmGCmUUmGGmAmGmGCmUUmGAmA/UNA-U/mU |
| 1864 | 1019 | S | UNA-U/mCAmAGmCCmUCCAmAGmCUmGUmGC/UNA-U/mU |
| 1864 | 1020 | AS | mGCmACmAGmCUmUGmGmAmGGmCUmUGmA/UNA-U/mU |
| 1865 | 1021 | S | UNA-C/mAAmGCmCUmCCAAmGCmUGmUGmCC/UNA-U/mU |
| 1865 | 1022 | AS | mGGmCAmCAmGCmUUmGmGmAGmGCmUUmG/UNA-U/mU |
| 1866 | 1023 | S | UNA-A/mAGmCCmUCmCAAGmCUmGUmGCmCU/UNA-U/mU |
| 1866 | 1024 | AS | mAGmGCmACmAGmCUmUmGmGAmGGmCUmU/UNA-U/mU |

UNA Oligomers Targeting HBV

Embodiments of this invention can provide oligomeric molecules that are active agents targeted to HBV.

Examples of UNA oligomers of this invention that are targeted to an HBV component are shown in Table 18. Table 18 shows "sense" and "antisense" pairs.

TABLE 18

UNA oligomers targeted to HBV (Sense (S)-Antisense (AS))

| REF POS | SEQ ID NO | S/AS | HBV (Sense (S)-Antisense (AS)) (5'-3') |
|---|---|---|---|
| 1576 | 1025 | S | UNA-C/mGrUmGrUmGrCmArCrUrUmCrGmCrUmUrCmArC/UNA-U/mU |
| 1576 | 1026 | AS | mGrUmGrAmArGmC/UNA-G/mArAmGmUmGrCmArCmArCmG/UNA-U/mU |
| 1576 | 1027 | S | UNA-C*/mGrUmGrUmGrCmArCrUrUmCrGmCrUmUrCmArC*/UNA-U*/mU |
| 1576 | 1028 | AS | mGrUmGrAmArGmC/UNA-G/mArAmGmUmGrCmArCmArCmG/UNA-U*/mU |
| 1576 | 1029 | S | UNA-C*/mG*rU*mGrUmGrCmArCrUrUmCrGmCrUmUrCmArC*/UNA-U*/mU |
| 1576 | 1030 | AS | mGrUmGrAmArGmC/UNA-G/mArAmGmUmGrCmArCmArCmG/UNA-U*/mU |
| 1576 | 1031 | S | UNA-C*/mG*rU*mGrUmGrCmArCrUrUmCrGmCrUmUrCmA*rC*/UNA-U*/mU |
| 1576 | 1032 | AS | mGrUmGrAmArGmC/UNA-G/mArAmGmUmGrCmArCmArCmG/UNA-U*/mU |
| 1576 | 1033 | S | UNA-C*/mGrUmGrUmGrCmArCrUrUmCrGmCrUmUrCmArC*/UNA-U*/mU |
| 1576 | 1034 | AS | mG*rU*mGrAmArGmC/UNA-G/mArAmGmUmGrCmArCmArCmG*/UNA-U*/mU |
| 1576 | 1035 | S | UNA-C*/mG*rUmGrUmGrCmArCrUrUmCrGmCrUmUrCmArC*/UNA-U*/mU |
| 1576 | 1036 | AS | mG*rU*mGrAmArGmC/UNA-G/mArAmGmUmGrCmArCmArCmG*/UNA-U*/mU |
| 1576 | 1037 | S | UNA-C*/mG*rU*mGrUmGrCmArCrUrUmCrGmCrUmUrCmArC*/UNA-U*/mU |
| 1576 | 1038 | AS | mG*rU*mGrAmArGmC/UNA-G/mArAmGmUmGrCmArCmArCmG*/UNA-U*/mU |
| 1576 | 1039 | S | UNA-C*/mG*rU*mGrUmGrCmArCrUrUmCrGmCrUmUrCmA*rC*/UNA-U*/mU |
| 1576 | 1040 | AS | mG*rU*mGrAmArGmC/UNA-G/mArAmGmUmGrCmArCmArCmG*/UNA-U*/mU |
| 1575 | 1041 | S | UNA-C*/mC*rGmUrGmUrGmCrArCrUmUrCmGrCmUrUmCrA*/UNA-U*/mU |
| 1575 | 1042 | AS | mUrGmArA/UNA-G/rCmGrAmArGmUmGmCrAmCrAmCrGmG/UNA-U*/mU |
| 1575 | 1043 | S | UNA-C*/mC*rGmUrGmUrGmCrArCrUmUrCmGrCmUrUmCrA*/UNA-U*/mU |
| 1575 | 1044 | AS | mUrGmArAmGrC/UNA-G/rAmArGmUmGmCrAmCrAmCrGmG/UNA-U*/mU |
| 1575 | 1045 | S | UNA-C*/mC*rGmUrGmUrGmCrArCrUmUrCmGrCmUrUmCrA*/UNA-U*/mU |

TABLE 18 -continued

UNA oligomers targeted to HBV (Sense (S)-Antisense (AS))

| REF POS | SEQ ID NO | S/AS | HBV (Sense (S)-Antisense (AS)) (5'-3') |
|---|---|---|---|
| 1575 | 1046 | AS | mUrGmArAmGrCmG/UNA-A/mArGmUmGmCrAmCrAmCrGmG/UNA-U*/mU |
| 1578 | 1047 | S | UNA-U*/mG*rU*mGrCmArCmUrUrCrGmCrUmUrCmArCmC*rU*/UNA-U*/mU |
| 1578 | 1048 | AS | mArGmGrU/UNA-G/rAmArGmCrGmAmAmGrUmGrCmArCmA/UNA-U*/mU |
| 1578 | 1049 | S | UNA-U*/mG*rU*mGrCmArCmUrUrCrGmCrUmUrCmArCmC*rU*/UNA-U*/mU |
| 1578 | 1050 | AS | mArGmGrUmG/UNA-A/mArGmCrGmAmAmGrUmGrCmArCmA/UNA-U*/mU |
| 1578 | 1051 | S | UNA-U*/mG*rU*mGrCmArCmUrUrCrGmCrUmUrCmArCmC*rU*/UNA-U*/mU |
| 1578 | 1052 | AS | mArGmGrUmGrAmA/UNA-G/mCrGmAmAmGrUmGrCmArCmA/UNA-U*/mU |
| 1818 | 1053 | S | UNA-A/mArCmUrUmUrUmUrCrArCmCrUmCrUmGrCmCrU/UNA-U/mU |
| 1818 | 1054 | AS | mArGmGrC/UNA-A/rGmArGmGrUmGmAmArAmArAmGrUmU/UNA-U/mU |
| 1818 | 1055 | S | UNA-A/mArCmUrUmUrUmUrCrArCmCrUmCrUmGrCmCrU/UNA-U/mU |
| 1818 | 1056 | AS | mArGmGrCmA/UNA-G/mArGmGrUmGmAmArAmArAmGrUmU/UNA-U/mU |
| 1818 | 1057 | S | UNA-A/mArCmUrUmUrUmUrCrArCmCrUmCrUmGrCmCrU/UNA-U/mU |
| 1818 | 1058 | AS | mArGmGrCmArG/UNA-A/rGmGrUmGmAmArAmArAmGrUmU/UNA-U/mU |
| 245 | 1059 | S | UNA-A/mGrUmCrUmArGmArCrUrCmGrUmGrGmUrGmGrA/UNA-U/mU |
| 245 | 1060 | AS | mUrCmCrAmCrC/-UNA-A/rCmGrAmGmUmCrUmArGmArCmU/UNA-U/mU |
| 1580 | 1061 | S | UNA-U/mGrCmArCmUrUmCrGrCrUmUrCmArCmCrUmCrU/UNA-U/mU |
| 1580 | 1062 | AS | mArGmArG/UNA-G/rUmGrAmArGmCmGmArAmGrUmGrCmA/UNA-U/mU |
| 1580 | 1063 | S | UNA-U/mGrCmArCmUrUmCrGrCrUmUrCmArCmCrUmCrU/UNA-U/mU |
| 1580 | 1064 | AS | mArGmArGmG/UNA-U/mGrAmArGmCmGmArAmGrUmGrCmA/UNA-U/mU |
| 1580 | 1065 | S | UNA-U/mGrCmArCmUrUmCrGrCrUmUrCmArCmCrUmCrU/UNA-U/mU |
| 1580 | 1066 | AS | mArGmArGmGrU/UNA-G/rAmArGmCmGmArAmGrUmGrCmA/UNA-U/mU |
| 1580 | 1067 | S | UNA-U/mGrCmArCmUrUmCrGrCrUmUrCmArCmCrUmCrU/UNA-U/mU |
| 1580 | 1068 | AS | mArGmArGmGrUmG/UNA-A/mArGmCmGmArAmGrUmGrCmA/UNA-U/mU |

UNA Oligomers Targeting HBV

Embodiments of this invention can provide oligomeric molecules that are active agents targeted to HBV.

Examples of UNA oligomers of this invention that are targeted to an HBV component are shown in Table 19. Table 19 shows "sense" and "antisense" pairs.

TABLE 19

UNA oligomers targeted to HBV (Sense (S)-Antisense (AS))

| REF POS | SEQ ID NO | S/AS | HBV (Sense (S)-Antisense (AS)) (5'-3') |
|---|---|---|---|
| 1578 | 1069 | S | UNA-U*/mGrUmGrCmArCmUrUrCrGmCrUmUrCmArCmCrU'VUNA-U*/mU |
| 1578 | 1070 | AS | mArGmGrUmGrAmArGmCrGmAmAmGrUmGrCmArCmA/UNA-U*/mU |
| 1578 | 1071 | S | UNA-U*/mG*rUmGrCmArCmUrUrCrGmCrUmUrCmArCmCrU'VUNA-U*/mU |
| 1578 | 1072 | AS | mArGmGrUmGrAmArGmCrGmAmAmGrUmGrCmArCmA/UNA-U*/mU |
| 1578 | 1073 | S | UNA-U*/mG*rU*mGrCmArCmUrUrCrGmCrUmUrCmArCmCrU'VUNA-U*/mU |
| 1578 | 1074 | AS | mArGmGrUmGrAmArGmCrGmAmAmGrUmGrCmArCmA/UNA-U*/mU |
| 1578 | 1075 | S | UNA-U*/mG*rU*mGrCmArCmUrUrCrGmCrUmUrCmArCmC*rU'VUNA-U*/mU |

TABLE 19 -continued

| UNA oligomers targeted to HBV (Sense (S)-Antisense (AS)) | | | |
|---|---|---|---|
| REF POS | SEQ ID NO | S/AS | HBV (Sense (S)-Antisense (AS)) (5'-3') |
| 1578 | 1076 | AS | mArGmGrUmGrAmArGmCrGmAmAmGrUmGrCmArCmA/UNA-U*/mU |
| 1578 | 1077 | S | UNA-U*/mGrUmGrCmArCmUrUrCrGmCrUmUrCmArCmCrU'VUNA-U*/mU |
| 1578 | 1078 | AS | mA*rGmGrUmGrAmArGmCrGmAmAmGrUmGrCmArCmA/UNA-U*/mU |
| 1578 | 1079 | S | UNA-U*/mG*rUmGrCmArCmUrUrCrGmCrUmUrCmArCmCrU'VUNA-U*/mU |
| 1578 | 1080 | AS | mA*rGmGrUmGrAmArGmCrGmAmAmGrUmGrCmArCmA/UNA-U*/mU |
| 1578 | 1081 | S | UNA-U*/mG*rWmGrCmArCmUrUrCrGmCrUmUrCmArCmCrU'VUNA-U*/mU |
| 1578 | 1082 | AS | mA*rGmGrUmGrAmArGmCrGmAmAmGrUmGrCmArCmA/UNA-U*/mU |
| 1578 | 1083 | S | UNA-U*/mG*rWmGrCmArCmUrUrCrGmCrUmUrCmArCmC*rU'VUNA-U*/mU |
| 1578 | 1084 | AS | mA*rGmGrUmGrAmArGmCrGmAmAmGrUmGrCmArCmA/UNA-U*/mU |
| 1578 | 1085 | S | UNA-U*/mGrUmGrCmArCmUrUrCrGmCrUmUrCmArCmCrU'VUNA-U*/mU |
| 1578 | 1086 | AS | mA*rGmGrUmGrAmArGmCrGmAmAmGrUmGrCmArCmA*/UNA-U*/mU |
| 1578 | 1087 | S | UNA-U*/mG*rUmGrCmArCmUrUrCrGmCrUmUrCmArCmCrU'VUNA-U*/mU |
| 1578 | 1088 | AS | mA*rGmGrUmGrAmArGmCrGmAmAmGrUmGrCmArCmA*/UNA-U*/mU |
| 1578 | 1089 | S | UNA-U*/mG*rWmGrCmArCmUrUrCrGmCrUmUrCmArCmCrU'VUNA-U*/mU |
| 1578 | 1090 | AS | mA*rGmGrUmGrAmArGmCrGmAmAmGrUmGrCmArCmA*/UNA-U*/mU |
| 1578 | 1091 | S | UNA-U*/mG*rWmGrCmArCmUrUrCrGmCrUmUrCmArCmC*rU'VUNA-U*/mU |
| 1578 | 1092 | AS | mA*rGmGrUmGrAmArGmCrGmAmAmGrUmGrCmArCmA*/UNA-U*/mU |
| 1578 | 1093 | S | UNA-U*/mGrUmGrCmArCmUrUrCrGmCrUmUrCmArCmCrU'VUNA-U*/mU |
| 1578 | 1094 | AS | mA*rG*mGrUmGrAmArGmCrGmAmAmGrUmGrCmArCmA*/UNA-U*/mU |
| 1578 | 1095 | S | UNA-U*/mG*rUmGrCmArCmUrUrCrGmCrUmUrCmArCmCrU'VUNA-U*/mU |
| 1578 | 1096 | AS | mA*rG*mGrUmGrAmArGmCrGmAmAmGrUmGrCmArCmA*/UNA-U*/mU |
| 1578 | 1097 | S | UNA-U*/mG*rWmGrCmArCmUrUrCrGmCrUmUrCmArCmCrU'VUNA-U*/mU |
| 1578 | 1098 | AS | mA*rG*mGrUmGrAmArGmCrGmAmAmGrUmGrCmArCmA*/UNA-U*/mU |
| 1578 | 1099 | S | UNA-U*/mG*rU*mGrCmArCmUrUrCrGmCrUmUrCmArCmC*rU*/UNA-U*/mU |
| 1578 | 1100 | AS | mA*rG*mGrUmGrAmArGmCrGmAmAmGrUmGrCmArCmA*/UNA-U*/mU |
| 1777 | 1101 | S | UNA-G*/mArGmGrCmUrGmUrArGrGmCrAmUrAmArAmUrW/UNA-U*/mU |
| 1777 | 1102 | AS | mArAmUrUmUrAmUrGmCrCmUmAmCrAmGrCmCrUmC/UNA-U*/mU |
| 1777 | 1103 | S | UNA-G*/mA*rGmGrCmUrGmUrArGrGmCrAmUrAmArAmUrU*/UNA-U*/mU |
| 1777 | 1104 | AS | mArAmUrUmUrAmUrGmCrCmUmAmCrAmGrCmCrUmC*/UNA-U*/mU |
| 1777 | 1105 | S | UNA-G*/mA*rG*mGrCmUrGmUrArGrGmCrAmUrAmArAmUrW/UNA-U*/mU |
| 1777 | 1106 | AS | mArAmUrUmUrAmUrGmCrCmUmAmCrAmGrCmCrU*mC*/UNA-U*/mU |
| 380 | 1107 | S | UNA-U*/mGrUmCrUmGrCmGrGrCrGmUrUmUrUmArUmCrA*/UNA-U*/mU |
| 380 | 1108 | AS | mUrGmArUmArAmArAmCrGmCmCmGrCmArGmArCmA/UNA-U*/mU |
| 380 | 1109 | S | UNA-U*/mG*rUmCrUmGrCmGrGrCrGmUrUmUrUmArUmCrA*/UNA-U*/mU |
| 380 | 1110 | AS | mUrGmArUmArAmArAmCrGmCmCmGrCmArGmArCmA/UNA-U*/mU |
| 380 | 1111 | S | UNA-U*/mGrUmCrUmGrCmGrGrCrGmUrUmUrUmArUmCrA*/UNA-U*/mU |
| 380 | 1112 | AS | mU*rGmArUmArAmArAmCrGmCmCmGrCmArGmArCmA/UNA-U*/mU |

TABLE 19 -continued

UNA oligomers targeted to HBV (Sense (S)-Antisense (AS))

| REF POS | SEQ ID NO | S/AS | HBV (Sense (S)-Antisense (AS)) (5'-3') |
|---|---|---|---|
| 380 | 1113 | S | UNA-U*/mG*rU*mCrUmGrCmGrGrCrGmUrUmUrUmArUmC*rA*/UNA-U*/mU |
| 380 | 1114 | AS | mU*rGmArUmArAmArAmCrGmCmCmGrCmArGmArCmA/UNA-U*/mU |
| 1576 | 1115 | S | UNA-C*/mGrUmGrUmGrCmArCrUrUmCrGmCrUmUrCmArC*/UNA-U*/mU |
| 1576 | 1116 | AS | mGrUmGrAmArGmCrGmArAmGmUmGrCmArCmArCmG/UNA-U*/mU |
| 1575 | 1117 | S | UNA-C*/mC*rGmUrGmUrGmCrArCrUmUrCmGrCmUrUmCrA*/UNA-U*/mU |
| 1575 | 1118 | AS | mUrGmArAmGrCmGrAmArGmUmGmCrAmCrAmCrGmG/UNA-U*/mU |
| 1580 | 1119 | S | UNA-U*/mG*rC*mArCmUrUmCrGrCrUmUrCmArCmCrUmCrU*/UNA-U*/mU |
| 1580 | 1120 | AS | mArGmArGmGrUmGrAmArGmCmGmArAmGrUmGrCmA*/UNA-U*/mU |

UNA Oligomers Targeting HBV

Embodiments of this invention can provide oligomeric molecules that are active agents targeted to HBV.

Examples of UNA oligomers of this invention that are targeted to an HBV component are shown in Table 20. Table 20 shows "sense" and "antisense" pairs.

TABLE 20

UNA oligomers targeted to HBV (Sense (S)-Antisense (AS))

| REF POS | SEQ ID NO | S/AS | HBV (Sense (S)-Antisense (AS)) (5'-3') |
|---|---|---|---|
| 1578 | 1121 | S | UNA-U/*/mGrUmGrCmArCmUrUrCrGmCrUmUrCmArCmCrU/*/UNA-UPYT |
| 1578 | 1122 | AS | mArGmGrUmGrAmArGmCrGmAmAmGrUmGrCmArCmA/UNA-UPYT |
| 1578 | 1123 | S | UNA-U/*/fGrUfGrCfArCfUrUrCrGfCrUfUrCfArCfCrU/*/UNA-U/*/dT |
| 1578 | 1124 | AS | fArGfGrUfGrAfArGfCrGfAfAfGrUfGrCfArCfA/UNA-U/*/dT |
| 1578 | 1125 | S | UNA-U/*/rGfUrGfCrAfCfUfUfCrGfCfUfUfCrAfCfCfU/*/UNA-U/*/dT |
| 1578 | 1126 | AS | rArGrGfUrGrArArGfCrGrArArGfUrGfCrAfCrA/UNA-U/*/dT |
| 1578 | 1127 | S | UNA-U/*/mGfUmGfCmAfCmUfUfCfGmCfUmUfCmAfCmCfU/*/UNA-U/*/T |
| 1578 | 1128 | AS | mAfGmGfUmGfAmAfGmCfGmAmAmGfUmGfCmAfCmA/UNA-U/*/T |
| 1777 | 1129 | S | UNA-G/*/mArGmGrCmUrGmUrArGrGmCrAmUrAmArAmUrU/*/UNA-U/*/T |
| 1777 | 1130 | AS | UNA-G/*/mArGmGrCmUrGmUrArGrGmCrAmUrAmArAmUrU/*/UNA-U/*/T |
| 1777 | 1131 | S | UNA-G/*/fArGfGrCfUrGfUrArGrGfCrAfUrAfArAfUrU/*/UNA-U/*/T |
| 1777 | 1132 | AS | fArAfUrUfUrAfUrGfCrCfUfAfCrAfGrCfCrUfC/UNA-U/*/T |
| 1777 | 1133 | S | UNA-G/*/rArGrGfCfUrGfUrArGrGfCrAfUrArArAfUfU/*/UNA-U/*/T |
| 1777 | 1134 | AS | rArAfUfUfUrAfUrGfCfCfUrAfCrArGfCfCfUfC/UNA-U/*/T |
| 1777 | 1135 | S | UNA-G/*/mAfGmGfCmUfGmUfAfGfGmCfAmUfAmAfAmUfU/*/UNA-U/*/T |
| 1777 | 1136 | AS | UNA-G/*/mAfGmGfCmUfGmUfAfGfGmCfAmUfAmAfAmUfU/*/UNA-U/*/T |
| 380 | 1137 | S | UNA-G/*/mAfGmGfCmUfGmUfAfGfGmCfAmUfAmAfAmUfU/*/UNA-U/*/T |
| 380 | 1138 | AS | mUrGmArUmArAmArAmCrGmCmCmGrCmArGmArCmA/UNA-U/*/mU |
| 380 | 1139 | S | UNA-U/*/fGrUfCrUfGrCfGrGrCrGfUrUfUrUfArUfCrA/*/UNA-U/*/fU |
| 380 | 1140 | AS | fUrGfArUfArAfArAfCrGfCfCfGrCfArGfArCfA/UNA-U/*/fU |
| 380 | 1141 | S | UNA-U/*/rGfUfCfUrGfCrGrGfCrGfUfUfUfUrAfUfCrA/*/UNA-U/*/fU |

TABLE 20-continued

UNA oligomers targeted to HBV (Sense (S)-Antisense (AS))

| REF POS | SEQ ID NO | S/AS | HBV (Sense (S)-Antisense (AS)) (5'-3') |
|---|---|---|---|
| 380 | 1142 | AS | fUrGrAfUrArArArAfCrGfCfCrGfCrArGrAfCrA/UNA-U/*/fU |
| 380 | 1143 | S | UNA-U/*/mGfUmCfUmGfCmGfGfCfGmUfUmUfUmAfUmCfA/*/UNA-U/*/mU |
| 380 | 1144 | AS | UNA-U/*/mGfUmCfUmGfCmGfGfCfGmUfUmUfUmAfUmCfA/*/UNA-U/*/mU |

In Tables herein, rN refers to N, which is a ribonucleotide, mN refers to a chemically-modified 2'-OMe ribonucleotide, an asterisk * between characters refers to a phosphorothioate linkage, dN refers to a deoxyribonucleotide, f refers to a 2'-deoxy-2'-fluoro ribonucleotide.

Additional compounds of this invention are shown in Table 21.

TABLE 21

UNA oligomers targeted to HBV (Sense (S)-Antisense (AS))

| REF POS | SEQ ID NO | S/AS | HBV (Sense (S)-Antisense (AS)) (5'-3') |
|---|---|---|---|
| 1575 | 1145 | S | UNA-C*/mCrGmUrGmUrGmCrArCrUmUrCmGrCmUrUmCrA*/UNA-U*/dT |
| 1575 | 1146 | AS | mUrGmArAmGrCmGrAmArGmUmGmCrAmCrAmCrGmG/UNA-U*/dT |
| 1576 | 1147 | S | UNA-C*/mGrUmGrUmGrCmArCrUrUmCrGmCrUmUrCmArC*/UNA-U*/dT |
| 1576 | 1148 | AS | mGrUmGrAmArGmCrGmArAmGmUmGrCmArCmArCmG/UNA-U*/dT |
| 1581 | 1149 | S | UNA-G*/mCAmCUmUCmGCUUmCAmCCmUCmUG*IUNA-U*IdT |
| 1581 | 1150 | AS | mCAmGAmGGmUGmAAmGmCmGAmAGmUGmC/UNA-U*/dT |
| 1580 | 1151 | S | UNA-U*/mGrCmArCmUrUmCrGrCrUmUrCmArCmCrUmCrU*/UNA-U*/dT |
| 1580 | 1152 | AS | mArGmArGmGrUmGrAmArGmCmGmArAmGrUmGrCmA/UNA-U*/dT |
| 376 | 1153 | A | UNA-G*/mAUmGUmGUmCUGCmGGmCGmUUmUU*/UNA-U*/dT |
| 376 | 1154 | AS | mAAmAAmCGmCCmGCmAmGmACmACmAUmC/UNA-U*/dT |
| 378 | 1155 | S | UNA-U*/mGUmGUmCUmGCGGmCGmUUmUUmAU*/UNA-U*/dT |
| 378 | 1156 | AS | mAUmAAmAAmCGmCCmGmCmAGmACmACmA/UNA-U*/dT |
| 380 | 1157 | S | UNA-U/*mGrUmCrUmGrCmGrGrCrGmUrUmUrUmArUmCrA/*UNA-U/*dT |
| 380 | 1158 | AS | mUrGmArUmArAmArAmCrGmCmCmGrCmArGmArCmA/UNA-U/*dT |
| 413 | 1159 | S | UNA-C/*mUGmCUmGCmUAUGmCCmUCmAUmCU/*UNA-U/*dT |
| 413 | 1160 | AS | mAGmAUmGAmGGmCAmUmAmGCmAGmCAmG/UNA-U/*dT |
| 411 | 1161 | S | UNA-U/*mCCmUGmCUmGCUAmUGmCCmUCmAU/*UNA-U/*dT |
| 411 | 1162 | AS | mAUmGAmGGmCAmUAmGmCmAGmCAmGGmA/UNA-U/*dT |
| 1777 | 1163 | S | UNA-G/*mArGmGrCmUrGmUrArGrGmCrAmUrAmArAmUrU/*UNA-U/*dT |
| 1777 | 1164 | AS | mArAmUrUmUrAmUrGmCrCmUmAmCrAmGrCmCrUmC/UNA-U/*dT |
| 1780 | 1165 | S | UNA-G/*mCUmGUmAGmGCAUmAAmAUmUGmGU/*UNA-U/*dT |
| 1780 | 1166 | AS | mACmCAmAUmUUmAUmGmCmCUmACmAGmC/UNA-U/*dT |
| 1781 | 1167 | S | UNA-C/*mUGmUAmGGmCAUAmAAmUUmGGmUC/*UNA-U/*dT |
| 1781 | 1168 | AS | mGAmCCmAAmUUmUAmUmGmCCmUAmCAmG/UNA-U/*dT |
| 1782 | 1169 | S | UNA-U/*mGUmAGmGCmAUAAmAUmUGmGUmCU/*UNA-U/*dT |
| 1782 | 1170 | AS | mAGmACmCAmAUmUUmAmUmGCmCUmACmA/UNA-U/*dT |

Compositions for Use Against HBV

Embodiments of this invention can provide compositions of oligomeric molecules that are active agents targeted to HBV.

A composition for use against HBV viral infection can provide targeting for suppressing multiple viral gene products.

Without wishing to be bound by any one particular theory, certain open reading frames (ORF) encoding the P, S, C, and X genes of HBV can overlap.

In some embodiments, a composition of this invention may contain an oligomeric compound targeted to an HBV genomic transcript or ORF for HBsAg. For example, these embodiments can inhibit expression of HBsAg, regardless of the location of the HBV genomic DNA.

In additional embodiments, a composition may contain an oligomeric compound targeted to an HBV genomic transcript or ORF for HBeAg.

In further embodiments, a composition may contain an oligomeric compound targeted to an HBV genomic transcript or ORF for X protein.

In further embodiments, a composition may contain an oligomeric compound targeted to an HBV genomic transcript or ORF for DNA polymerase (P).

In certain embodiments, a composition may contain an oligomeric compound targeted to a conserved HBV genomic region of the transcripts or open reading frames from genes X, S, and C.

In certain embodiments, a composition may contain an oligomeric compound targeted to a conserved HBV genomic region of the transcripts or open reading frames from genes X, S, C and P.

In some aspects, a composition of this invention includes a dyad of oligomeric compounds as the active agents targeted to HBV.

Examples of dyad compositions include a composition containing a compound with a reference position in the range 1403 to 1623, and a compound with a reference position in the range 155 to 550.

Examples of dyad compositions include a composition containing a compound with a reference position in the range 1575 to 1581, and a compound with a reference position in the range 245 to 414.

Examples of dyad compositions include a composition containing a compound with a reference position in the range 1525 to 1604, and a compound with a reference position in the range 374 to 414.

Examples of dyad compositions include a composition containing a compound with a reference position in the range 1525 to 1604, and a compound with a reference position in the range 1776 to 1818.

Examples of dyad compositions include a composition containing a compound with a reference position in the range 374 to 414, and a compound with a reference position in the range 1776 to 1782.

Examples of dyad compositions include a composition containing a compound with the reference position 1578 and a compound with the reference position 380. Examples of dyad compositions include a composition containing a compound with the reference position 1578 and a compound with the reference position 376 or 411.

Examples of dyad compositions include compositions containing compounds with the reference positions 1575 and 376, 1575 and 380, 1575 and 511, 1581 and 376, 1581 and 380, as well as 1581 and 411.

Examples of dyad compositions include compositions containing a compound with the reference position 1578 and a compound with the reference position 1777.

Examples of dyad compositions include compositions containing compounds with the reference positions 1578 and 1780, or 1578 and 1782, or 1575 and 1777, or 1575 and 1780, or 1575 and 1782, or 1581 and 1777, or 1581 and 1780, or 1581 and 1782, or 1576 and 1777, or 1576 and 1780, or 1576 and 1782.

For example, a dyad composition may contain the compounds 1578 and 380 shown in Table 22.

TABLE 22

Dyad composition of UNA oligomers targeted to HBV (Sense (S)-Antisense (AS))

| REF POS | SEQ ID NO | S/AS | HBV (Sense (S)-Antisense (AS)) (5'-3') |
|---|---|---|---|
| 1578 | 1171 | S | UNA-U/*mGrUmGrCmArCmUrUrCrGmCrUm UrCmArCmCrU/*UNA-U/*dT |
| 1578 | 1172 | AS | mArGmGrUmGrAmArGmCrGmAmAmGrUmGrCm ArCmA/UNA-U/*dT |
| 380 | 1173 | S | UNA-U/*mGrUmCrUmGrCmGrGrCrGmUrUmUr UmArUmCrA/*UNA-U/*mU |
| 380 | 1174 | AS | mUrGmArUmArAmArAmCrGmCmCmGrCmArGm ArCmA/UNA-U/*mU |

UNA Oligomer Triad Compositions for HBV

In some aspects, a composition of this invention includes triads of oligomeric compounds as the active agents targeted to HBV.

Examples of triad compositions include a composition containing a compound with a reference position in the range 1403 to 1623, a compound with a reference position in the range 155 to 550, and a compound with a reference position in the range 1624 to 1930.

Examples of triad compositions include a composition containing a compound with a reference position in the range 1525 to 1582, a compound with a reference position in the range 245 to 414, and a compound with a reference position in the range 1777 to 1818.

Examples of triad compositions include a composition containing a compound with a reference position in the range 1525 to 1604, a compound with a reference position in the range 374 to 414, and a compound with a reference position in the range 1776 to 1782.

Examples of triad compositions include a composition containing a compound with a reference position in the range 1525 to 1582, a compound with a reference position in the range 374 to 414, and a compound with a reference position in the range 1776 to 1782.

Examples of triad compositions include a composition containing a compound with the reference position 1578, a compound with the reference position 380, and a compound with the reference position 1777.

Examples of triad compositions include a composition containing a compound with the reference position 1576, a compound with the reference position 380, and a compound with the reference position 1777.

Examples of triad compositions include a composition containing a compound with the reference position 1575, a compound with the reference position 380, and a compound with the reference position 1777.

Examples of triad compositions include a composition containing a compound with the reference position 1578, a compound with the reference position 1777, and a compound with the reference position 376 or 411.

Examples of triad compositions include a composition containing a compound with the reference position 1578, a compound with the reference position 1780 or 1782, and a compound with the reference position 376 or 411.

Examples of triad compositions include compositions containing compounds with the reference positions:

1578, 1777 and 376; 1578, 1777 and 380; 1578, 1777 and 411; 1578, 1780 and 376; 1578, 1780 and 380; 1578, 1780 and 411; 1578, 1782 and 376; 1578, 1782 and 380; 1578, 1782 and 411;

1575, 1777 and 376; 1575, 1777 and 380; 1575, 1777 and 411; 1575, 1780 and 376; 1575, 1780 and 380; 1575, 1780 and 411; 1575, 1782 and 376; 1575, 1782 and 380; 1575, 1782 and 411;

1581, 1777 and 376; 1581, 1777 and 380; 1581, 1777 and 411; 1581, 1780 and 376; 1581, 1780 and 380; 1581, 1780 and 411; 1581, 1782 and 376; 1581, 1782 and 380; 1581, 1782 and 411;

1576, 1777 and 376; 1576, 1777 and 380; 1576, 1777 and 411; 1576, 1780 and 376; 1576, 1780 and 380; 1576, 1780 and 411; 1576, 1782 and 376; 1576, 1782 and 380; 1576, 1782 and 411;

1578, 1818 and 376; 1578, 1818 and 380; 1578, 1818 and 411;

1575, 1818 and 376; 1575, 1818 and 380; 1575, 1818 and 411.

For example, a triad composition may contain the compounds 1578, 380 and 1777 shown in Table 23.

TABLE 23

Triad composition of UNA oligomers targeted to HBV (Sense (S)-Antisense (AS))

| REF POS | SEQ ID NO | S/AS | HBV (Sense (S)-Antisense (AS)) (5'-3') |
|---|---|---|---|
| 1578 | 1175 | S | UNA-U/*mGrUmGrCmArCmUrUrCrGmCrUmUrCmArCmCrU/*UNA-U/*dT |
| 1578 | 1176 | As | mArGmGrUmGrAmArGmCrGmAmAmGrUmGrCmArCmA/UNA-U/*dT |
| 380 | 1177 | S | UNA-U/*mGrUmCrUmGrCmGrGrCrGmUrUmUrUmArUmCrA/*UNA-U/*dT |
| 380 | 1178 | As | mUrGmArUmArAmArAmCrGmCmCmGrCmArGmArCmA/UNA-U/*dT |
| 1777 | 1179 | S | UNA-G/*mArGmGrCmUrGmUrArGrGmCrAmUrAmArAmUrU/*UNA-U/*dT |
| 1777 | 1180 | AS | mArAmUrUmUrAmUrGmCrCmUmAmCrAmGrCmCrUmC/UNA-U/*dT |

In Tables herein, rN refers to N, which is a ribonucleotide, mN refers to a chemically-modified 2'-OMe ribonucleotide, an * between characters refers to a phosphorothioate linkage, and dN refers to a deoxyribonucleotide.

This invent includes a compounds containing a UNA monomer at the 1-end (5' end for non-UNA) of the first strand, a UNA monomer at the 3-end or second position from the 3-end (3' end for non-UNA) of the sense strand, and a UNA monomer at the 3-end or second position from the 3-end (3' end for non-UNA) of the antisense strand.

Embodiments of this invention include a compound wherein the sense strand comprises SEQ ID NO:271 and the antisense strand comprises SEQ ID NO:583.

Embodiments of this invention include a compound wherein the sense strand comprises SEQ ID NO:266 and the antisense strand comprises SEQ ID NO:578.

Embodiments of this invention include a compound wherein the sense strand comprises SEQ ID NO:275 and the antisense strand comprises SEQ ID NO:587.

Embodiments of this invention include compounds wherein the first and second strands are a sense-antisense pair selected from any of Tables 33 to 38.

This invention includes compositions comprising a triad of compounds, wherein the triad is selected from the following: the first compound comprises SEQ ID NO:867 and 908, the second compound comprises SEQ ID NO:887 and 928, and the third compound comprises SEQ ID NO:879 and 920; the first compound comprises SEQ ID NO: 867 and 908, the second compound comprises SEQ ID NO:893 and 934, and the third compound comprises SEQ ID NO:875 and 916; the first compound comprises SEQ ID NO:900 and 941, the second compound comprises SEQ ID NO:887 and 928, and the third compound comprises SEQ ID NO:875 and 916.

siRNA Structures

In further aspects, this invention describes siRNA molecules comprising nucleotides, wherein the siRNA is targeted to HBV. The siRNA molecules are not composed of any UNA monomers.

A siRNA may have a first strand and a second strand, each of the strands being 19-29 nucleotides in length, wherein the siRNA has a duplex region of from 14 to 29 contiguous monomers in length, wherein the first strand is a sense strand for RNA interference and the second strand is an antisense strand for RNA interference, and wherein the compound comprises a sequence of bases targeted to inhibit expression of an HBV genome. Each of the strands may be 19-21 nucleotides in length.

A siRNA molecule of this invention may comprise SEQ ID NOs:900 and 941, and substituted forms thereof.

A siRNA molecule of this invention may comprise SEQ ID NO:893 and 934, and substituted forms thereof.

A siRNA molecule of this invention may comprise SEQ ID NO:879 and 920, and substituted forms thereof.

This invent further contemplates methods for preventing, ameliorating or treating a disease or condition associated with HBV infection in a subject in need, the method comprising administering to the subject an effective amount of a composition of a siRNA above. The administration of the siRNA, or a c composition thereof, can reduce HBV viral titer in the subject. The subject may have been diagnosed with a disease associated with Hepatitis B virus infection, or a liver disease.

Methods of this invention include inhibiting the replication, maturation, growth, or transmission of a Hepatitis B virus in a subject in need, by administering to the subject an effective amount of a siRNA above, or a composition thereof. The administration can reduce serum concentration of HBsAg in the subject by 2-$\log_{10}$-fold for at least 7 days. The administration can reduce HBeAg in the subject, or reduce HBV DNA in the subject.

In some embodiments, this invention includes methods for inhibiting expression of a Hepatitis B virus polynucleotide in a subject in need, by administering to the subject a siRNA above, or a composition thereof.

HBV Sequences

Some examples of known sequences for HBV are shown in Table 24.

TABLE 24

| Sequences for HBV | | |
|---|---|---|
| ACC # | Genotype | Description |
| HE974383.1 | A | HBV genotype A2 complete genome, isolate Mart-B74 |
| HE974381.1 | A | HBV genotype A1 complete genome, isolate Mart-B64 |
| HE974376.1 | A | HBV genotype A2 complete genome, isolate Mart-B45 |
| HE974375.1 | A | HBV genotype A1 complete genome, isolate Mart-B43 |
| HE974374.1 | A | HBV genotype A2 complete genome, isolate Mart-B42 |
| HE974371.1 | A | HBV genotype A2 complete genome, isolate Mart-B34 |
| HE974370.1 | A | HBV genotype A1 complete genome, isolate Mart-B27 |
| HE974367.1 | A | HBV genotype A2 complete genome, isolate Mart-B22 |
| HE974365.1 | A | HBV genotype A1 complete genome, isolate Mart-B16 |
| HE974364.1 | A | HBV genotype A2 complete genome, isolate Mart-B15 |
| HE974363.1 | A | HBV genotype A1 complete genome, isolate Mart-B06 |
| HE974362.1 | A | HBV genotype A1 complete genome, isolate Mart-B01 |
| AB778116.1 | A | HBV genotype A gene for polymerase, complete cds, strain: OCU01 |
| AB299858.1 | adr | Hepatitis B virus subtype adr DNA, complete genome, clone: HBVFH0204 |
| AB176642.1 | adr | Hepatitis B virus subtype ADR DNA, complete genome, isolate: HBV-115 |
| HW390268.1 | adw | JP 2013537423-A/508: RNA Interference Mediated Inhibition of Hepatitis B Virus (HBV) |
| AM282986.1 | adw | Hepatitis B virus (SUBTYPE ADW2), genotype A, complete genome |
| D00331.1 | adw | HPBADW3 Hepatitis B virus subtype ADW genomic DNA, complete genome, clone: pIDW420 |
| D00330.1 | adw | HPBADW2 Hepatitis B virus subtype ADW genomic DNA, complete genome, clone: pODW282 |
| D00329.1 | adw | HPBADW1 Hepatitis B virus subtype ADW genomic DNA, complete genome, clone: pIDW233 |
| AB540582.1 | B | HBV genotype B DNA, complete genome, strain: B0901189(NT15) |
| AB554017.1 | B | HBV genotype B DNA, complete genome, isolate: NMB09010 |
| AB602818.1 | B | HBV genotype B DNA, complete genome, isolate: AH-2 |
| AB644287.1 | C | HBV genotype C DNA, complete genome, isolate: NAB52 |
| AB644286.1 | C | HBV genotype C DNA, complete genome, isolate: NAB47 |
| AB644284.1 | C | HBV genotype C DNA, complete genome, isolate: NAB32 |
| AB644283.1 | C | HBV genotype C DNA, complete genome, isolate: NAB28 |
| AB644281.1 | C | HBV genotype C DNA, complete genome, isolate: NAB9 |
| AB644280.1 | C | HBV genotype C DNA, complete genome, isolate: NAB1 |
| AB560662.1 | C | HBV genotype C DNA, complete genome, isolate: 60PU |
| AB560661.1 | C | HBV genotype C DNA, complete genome, isolate: 58PU |
| AB554025.1 | C | HBV genotype C DNA, complete genome, isolate: MRK89073 |
| AB554022.1 | C | HBV genotype C DNA, complete genome, isolate: GRS08325 |
| AB554021.1 | C | HBV genotype C DNA, complete genome, isolate: GRS08298 |
| AB554020.1 | C | HBV genotype C DNA, complete genome, isolate: NMB09124 |
| AB554019.1 | C | HBV genotype C DNA, complete genome, isolate: NMB09122 |
| AB554018.1 | C | HBV genotype C DNA, complete genome, |

TABLE 24-continued

| Sequences for HBV | | |
|---|---|---|
| ACC # | Genotype | Description |
| | | isolate: NMB09075 |
| AB554015.1 | C | HBV genotype C DNA, complete genome, isolate: TRF08111 |
| AB554014.1 | C | HBV genotype C DNA, complete genome, isolate: TRF08029 |
| AB540585.1 | C | HBV genotype C DNA, complete genome, strain: C0901192(NT18) |
| AB540584.1 | C | HBV genotype C DNA, complete genome, strain: C0901190(NT16) |
| AB540583.1 | C | HBV genotype C DNA, complete genome, strain: C0901177(NT3) |
| HE974382.1 | D | HBV genotype D4 complete genome, isolate Mart-B70 |
| HE974379.1 | D | HBV genotype D3 complete genome, isolate Mart-B58 |
| HE974378.1 | D | HBV genotype D4 complete genome, isolate Mart-B50 |
| HE974377.1 | D | HBV genotype D3 complete genome, isolate Mart-B47 |
| HE974373.1 | D | HBV genotype D4 complete genome, isolate Mart-B37 |
| HE974372.1 | D | HBV genotype D4 complete genome, isolate Mart-B36 |
| HE815465.1 | D | HBV genotype D, serotype ayw3, complete genome |
| AB554024.1 | D | HBV genotype D DNA, complete genome, isolate: GRS08538 |
| AB554023.1 | D | HBV genotype D DNA, complete genome, isolate: GRS08457 |
| AB554016.1 | D | HBV genotype D DNA, complete genome, isolate: TRF08226 |
| AB267090.1 | D | Hepatitis B virus ayw/Japan/Ehime 22-HS/2005 DNA, complete genome |
| HE974384.1 | E | HBV genotype E complete genome, isolate Mart-B84 |
| HE974380.1 | E | HBV genotype E complete genome, isolate Mart-B63 |
| AP007262.1 | E | HBV genotype E DNA, complete genome, isolate: HB-JI411F |
| HE974369.1 | F | HBV genotype F2 complete genome, isolate Mart-B26 |
| HE974368.1 | F | HBV genotype F4 complete genome, isolate Mart-B24 |
| HE974366.1 | F | HBV genotype F2 complete genome, isolate Mart-B18 |
| AB625343.1 | G | HBV genotype G DNA, complete genome, isolate: MEX921M |
| AB625342.1 | G | HBV genotype G DNA, complete genome, isolate: MEX918M |
| AP007264.1 | G | HBV genotype G DNA, complete genome, isolate: HB-JI444GF |
| AB846650.1 | H | HBV genotype H DNA, complete genome, isolate: B-MHJ9014 |
| AB516395.1 | H | HBV genotype H DNA, complete genome, isolate: MEX914M |
| AB516394.1 | H | HBV genotype H DNA, complete genome, isolate: MEX912M |
| AB516393.1 | H | HBV genotype H DNA, complete genome, isolate: 904MEXM |
| AP007261.1 | H | HBV genotype H DNA, complete genome, isolate: HB-JI260F |
| AB298362.1 | H | HBV genotype H DNA, complete genome, isolate: HBV ST0404 |
| AB246338.1 | Ae | Hepatitis B virus DNA, complete genome, clone: Ae_JPN |
| AB246341.1 | Bj | Hepatitis B virus DNA, complete genome, clone: Bj_JPN35 |
| AB246345.1 | C | Hepatitis B virus DNA, complete genome, clone: C_JPNAT |
| AB246347.1 | D | Hepatitis B virus DNA, complete genome, clone: D_IND60 |

Methods for Treating HBV Disease

Methods of this invention include the treatment and prevention of various diseases in mammalian subjects. A subject can be a human or mammal.

In the methods of this invention, a subject in need of treatment or prevention can be administered an effective amount of an oligomeric compound of this invention.

An effective amount of an oligomeric compound of this invention can be a dose ranging from 0.001 mg/kg to 50.0 mg/kg.

In the methods of this invention, target mRNA expression can be reduced in a subject for at least 5 days. In certain embodiments, target mRNA expression can be reduced in a subject for at least 10 days, or 15 days.

In the methods of this disclosure, the administration of an oligomeric compound may not result in an inflammatory response.

In further embodiments, this invention includes methods for inhibiting expression of a target gene in a cell, by treating the cell with an oligomeric compound of this invention.

In additional embodiments, this invention includes methods for inhibiting expression of a target gene in a mammal, by administering to the mammal a composition containing an oligomeric compound of this invention.

Pharmaceutical Compositions

In some aspects, this invention provides pharmaceutical compositions containing an oligomeric compound and a pharmaceutically acceptable carrier.

A pharmaceutical composition can be capable of local or systemic administration. In some aspects, a pharmaceutical composition can be capable of any modality of administration. In certain aspects, the administration can be intravenous, subcutaneous, pulmonary, intramuscular, intraperitoneal, dermal, oral, or nasal administration.

Embodiments of this invention include pharmaceutical compositions containing an oligomeric compound in a lipid formulation.

In some embodiments, a pharmaceutical composition may comprise one or more lipids selected from cationic lipids, anionic lipids, sterols, pegylated lipids, and any combination of the foregoing.

In certain embodiments, a pharmaceutical composition can be substantially free of liposomes.

In further embodiments, a pharmaceutical composition can include liposomes or nanoparticles.

Some examples of lipids and lipid compositions for delivery of an active molecule of this invention are given in WO/2015/074085, which is hereby incorporated by reference in its entirety.

In additional embodiments, a pharmaceutical composition can contain an oligomeric compound within a viral or bacterial vector.

A pharmaceutical composition of this disclosure may include carriers, diluents or excipients as are known in the art. Examples of pharmaceutical compositions are described, for example, in *Remington's Pharmaceutical Sciences*, Mack Publishing Co. (A. R. Gennaro ed. 1985).

Examples of excipients for a pharmaceutical composition include antioxidants, suspending agents, dispersing agents, preservatives, buffering agents, tonicity agents, and surfactants.

EXAMPLES

Example 1: Luciferase Reporter Assay

Luciferase-based reporter plasmid was constructed based on psiCHECK™2 vector (Promega, Madison, Wis.). Reporter p (1-20) was generated with oligonucleotides containing the sequence from position 1 through 2500 relative to Eco RI digestion site cloned into the multiple cloning region downstream of the stop codon of the SV40 promoted *Renilla* luciferase gene in psiCHECK™2, which made the expression of *Renilla* luciferase gene under the regulation of the artificial 3'UTR sequence. *Renilla* luciferase activity was then used as an indicator of the effect of the artificial 3'UTR on transcript stability and translation efficiency. The psiCHECK™-2 Vector also contained a constitutively expressed *Firefly* luciferase gene, which served as an internal control to normalize transfection efficiency.

A total of 5,000 HepB3 cells (American Type Culture Collection) were plated onto a well of 96-well plate one day before the transfectrion. The cells were incubated at 37° C. in 100 μl of DMEM (Life Technologies, Carlsbad, Calif.) supplemented with 0.1 mM nonessential amino acids and 10% FBS (Life Technologies, Carlsbad, Calif.). The culture medium was changed to 90 μl of fresh medium just before the transfection. The reporter plasmid and UNA Oligomer were co-transfected with transfection reagent, Lipofectamine™ 3000 (Life Technologies, Carlsbad, Calif.) was used to transfect reporter plasmid (100 ng) and a various amount of UNA Oligomer together with P3000 into the cells according to manufacturer's instruction.

Dual-Luciferase Reporter Assay System (DLR assay system, Promega, Madison, Wis.) was used to perform dual-reporter assays on psiCHECK2 based reporter systems. Twenty-four hours after transfection, the cells were washed gently with phosphate buffered saline once. A 500 well of Passive Lysis Buffer (Promega, Madison, Wis.) was added to the cells and incubated with gentle rocking for 20 min at room temperature. Luciferase activities were measured using Cytation 3 imaging reader (BioTek, Winooski, Vt.) and the effect of the UNA Oligomer on reporter expression was calculated based on ratio of *Renilla/Firefly* to normalize cell number and transfection efficiency.

Example 2: The HBV inhibitory effect of UNA oligomers was observed with a psiCHECK2 assay. At 1 nM concentration for 6 days, the percent inhibition of target expression for each of the UNA oligomeric compounds in Table 19 designated as having Reference Position 1578 was determined to be from 77% to 97%. Thus, all of the UNA oligomeric compounds in Table 19 having Reference Position 1578 were operable for silencing target expression.

Example 3: The HBV inhibitory effect of UNA oligomers was observed with a psiCHECK2 assay. At 1 nM concentration for 6 days, the percent inhibition of target expression for each of the UNA oligomeric compounds in Table 19 designated as having Reference Position 1777 was determined to be from 77% to 92%. Thus, all of the UNA oligomeric compounds in Table 19 having Reference Position 1777 were operable for silencing target expression.

Example 4: The HBV inhibitory effect of UNA oligomers was observed with a psiCHECK2 assay. At 1 nM concentration for 6 days, the percent inhibition of target expression for each of the UNA oligomeric compounds in Table 19 designated as having Reference Position 380 was determined to be from 87% to 94%. Thus, all of the UNA oligomeric compounds in Table 19 having Reference Position 380 were operable for silencing target expression.

Example 5: The HBV inhibitory effect of UNA oligomers was observed with a psiCHECK2 assay. At 1 nM concentration for 6 days, the percent inhibition of target expression for the UNA oligomeric compound in Table 19 designated as having Reference Position 1576 was determined to be 93%.

Thus, UNA oligomeric compounds having Reference Position 1576 were operable for modulating target expression.

Example 6: The HBV inhibitory effect of UNA oligomers was observed with a psiCHECK2 assay. At 1 nM concentration for 6 days, the percent inhibition of target expression for the UNA oligomeric compound in Table 19 designated as having Reference Position 1575 was determined to be 90%. Thus, UNA oligomeric compounds having Reference Position 1575 were operable for modulating target expression.

Example 7: The HBV inhibitory effect of UNA oligomers was observed with a psiCHECK2 assay. At 1 nM concentration for 6 days, the percent inhibition of target expression for the UNA oligomeric compound in Table 19 designated as having Reference Position 1580 was determined to be 95%. Thus, UNA oligomeric compounds having Reference Position 1580 were operable for modulating target expression.

Example 8: The HBV inhibitory effect of UNA oligomers was observed with a psiCHECK2 assay. UNA oligomers of this invention in Table 17 were found to exhibit IC50 for inhibiting target expression as shown in Table 25.

TABLE 25

IC50 of UNA oligomers targeted to HBV

| Reference Position | IC50 pM (6 days) |
|---|---|
| 244 | 917 |
| 245 | 328 |
| 246 | 816 |
| 248 | 148 |
| 251 | 554 |
| 252 | 374 |
| 253 | 703 |
| 254 | 44 |
| 256 | 8 |
| 376 | 16 |
| 378 | 114 |
| 380 | 6.7 |
| 409 | 328 |
| 411 | 58 |
| 412 | 298 |
| 413 | 123 |
| 414 | 363 |
| 1575 | 65 |
| 1576 | 137 |
| 1577 | 472 |
| 1578 | 63 |
| 1580 | 255 |
| 1581 | 22 |
| 1776 | 461 |
| 1777 | 26 |
| 1779 | 348 |
| 1780 | 151 |
| 1781 | 227 |
| 1782 | 177 |
| 1818 | 49 |

Thus, UNA oligomeric compounds of this invention were operable for modulating HBV target expression. The UNA oligomeric compounds of this invention exhibited picomolar activity in vitro for inhibiting target expression. In some embodiments, the UNA oligomeric compounds of this invention exhibited surprisingly high activity in vitro of about IC50<200 pM for inhibiting target expression.

Example 9: The HBV inhibitory effect in vivo for UNA oligomers was observed in a humanized PXB Mouse model of HBV infection. The UNA oligomers of this invention exhibited profound reduction of HBV serum infection parameters in vivo. In this study, the UNA oligomers were contained in lipid nanoparticle formulations, −1 and −2.

The UNA oligomers were formulated or co-formulated in lipid nanoparticles and injected intravenously into HBV-infected Phoenix Bio (PXB) mice. The mice were Genotype: cDNA-uPA$^{wild/+}$/SCID [cDNA-uPA$^{wild/+}$: B6; 129SvEv-Plau, SCID: C.B-17/Icr-scid/scid Jcl] containing human hepatocytes with an estimated replacement index of 70% or more.

The study used an ascending dose in which mice were treated with 3 mg/kg on day 0, then 5 mg/kg on day 4, then 10 mg/kg on day 8.

As shown in FIG. 2, treatment with both UNA oligomer 1576 and UNA oligomer triad (1576, 380, 177) caused a rapid and sustained reduction in viral endpoint serum HBsAg compared to PBS control group. (Mean±SEM).

As shown in Table 26, treatment with both UNA oligomer 1576 and UNA oligomer triad (1576, 380, 177) caused a sustained reduction in viral endpoint serum HBeAg compared to PBS control group. (Mean±SEM).

TABLE 26

Serum HBeAg viral endpoint

| UNA oligomer formulation | HBeAg (% control) (normalized to hAlb) Day 12 |
|---|---|
| PBS control | 100 |
| 1576-1 | 48.2 |
| 1576-2 | 59.8 |
| (1576, 380, 177)-1 | 10.5 |
| (1576, 380, 177)-2 | 15.0 |

As shown in Table 27, treatment with both UNA oligomer 1576 and UNA oligomer triad (1576, 380, 177) caused a sustained reduction in viral endpoint serum HBV DNA compared to PBS control group. (Mean±SEM).

TABLE 27

Serum HBV DNA viral endpoint

| UNA oligomer formulation | HBV DNA (% control) (normalized to hAlb) Day 12 |
|---|---|
| PBS control | 100 |
| 1576-1 | 31.2 |
| 1576-2 | 52.4 |
| (1576, 380, 1777)-1 | 4.1 |
| (1576, 380, 1777)-2 | 7.7 |

The compositions in FIG. 2 and Tables 26 and 27 were UNA oligomer triad composition (1777 (SEQ ID NO:1005 and 1006), 380 (SEQ ID NO:973 and 974), 1576 (SEQ ID NO:989 and 990)).

Thus, the UNA oligomers of this invention demonstrated significant and unexpectedly advantageous HBV inhibition efficacy in vivo. For all viral endpoints, HBsAg, HBeAg, and HBV DNA, the treatment with UNA oligomer triad composition (1576, 380, 177) was significantly superior to UNA oligomer 1576.

Example 10: The HBV inhibitory effect in vivo for UNA oligomers was observed in a PXB Mouse model of HBV infection. The UNA oligomers of this invention exhibited profound reduction of HBV serum infection parameters in vivo. In this study, the UNA oligomers were contained in lipid nanoparticle formulation.

The UNA oligomers were co-formulated in lipid nanoparticles and injected intravenously into HBV-infected Phoenix Bio (PXB) mice. The mice were Genotype: cDNA-uPA$^{wild/+}$/SCID [cDNA-uPA$^{wild/+}$: B6; 129SvEv-Plau, SCID:

C.B-17/Icr-scid/scid Jcl] containing human hepatocytes with an estimated replacement index of 70% or more.

The study used an ascending dose in which mice were administered every 4 days, up to day 40, and viral endpoints were monitored every 4 days through day 44.

As shown in FIG. 3, treatment with UNA oligomer triad (1576, 380, 1777) caused a rapid and sustained reduction in viral endpoint serum HBsAg compared to PBS control group. (Mean±SEM). The dose-dependent response in vivo shows a pharmacological effect of the UNA oligomer composition. The composition in FIG. 3 was UNA oligomer triad composition (1777 (SEQ ID NO:1005 and 1006), 380 (SEQ ID NO:973 and 974), 1576 (SEQ ID NO:989 and 990)).

As shown in FIG. 4, treatment with UNA oligomer triad (1576, 380, 1777) caused a rapid and sustained reduction in viral endpoint serum HBeAg compared to PBS control group. (Mean±SEM). The dose-dependent response in vivo shows a pharmacological effect of the UNA oligomer composition. The composition in FIG. 4 was UNA oligomer triad composition (1777 (SEQ ID NO:1005 and 1006), 380 (SEQ ID NO:973 and 974), 1576 (SEQ ID NO:989 and 990)).

As shown in FIG. 5, treatment with UNA oligomer triad (1576, 380, 1777) caused a rapid and sustained reduction in viral endpoint serum HBV DNA compared to PBS control group. (Mean±SEM). The dose-dependent response in vivo shows a pharmacological effect of the UNA oligomer composition. The composition in FIG. 5 was UNA oligomer triad composition (1777 (SEQ ID NO:1005 and 1006), 380 (SEQ ID NO:973 and 974), 1576 (SEQ ID NO:989 and 990)).

Thus, the UNA oligomers of this invention demonstrated significant and unexpectedly advantageous HBV inhibition efficacy in vivo.

Example 11: The HBV inhibitory effect in vivo for UNA oligomers was observed in a PXB Mouse model of HBV infection. The UNA oligomers of this invention exhibited profound reduction of HBV serum infection parameters in vivo. In this study, the UNA oligomers were contained in lipid nanoparticle formulation.

The UNA oligomers were formulated or co-formulated in lipid nanoparticles and injected intravenously into HBV-infected Phoenix Bio (PXB) mice. The mice were Genotype: cDNA-uPA$^{wild/+}$/SCID [cDNA-uPA$^{wild/+}$: B6; 129SvEv-Plau, SCID: C.B-17/Icr-scid/scid Jcl] containing human hepatocytes with an estimated replacement index of 70% or more.

Serum viral endpoints were monitored up to 15 days after the single injection.

As shown in FIG. 6, treatment with each of UNA oligomers 1777 (SEQ ID NO:1179 and 1180), 380 (SEQ ID NO:1173 and 1174) and 1578 (SEQ ID NO:1175 and 1176) caused a rapid and sustained reduction in viral endpoint serum HBsAg compared to PBS control group. (Mean±SEM).

As shown in FIG. 7, treatment with each of UNA oligomers 1777 (SEQ ID NO:1179 and 1180), 380 (SEQ ID NO:1173 and 1174) and 1578 (SEQ ID NO:1175 and 1176) caused a rapid and sustained reduction in viral endpoint serum HBeAg compared to PBS control group. (Mean±SEM).

As shown in FIG. 8, treatment with each of UNA oligomers 1777 (SEQ ID NO:1179 and 1180), 380 (SEQ ID NO:1173 and 1174) and 1578 (SEQ ID NO:1175 and 1176) caused a rapid and sustained reduction in viral endpoint serum HBV DNA compared to PBS control group. (Mean±SEM).

As shown in FIG. 9, treatment with UNA oligomer triad composition (1777 (SEQ ID NO:1179 and 1180), 380 (SEQ ID NO:1173 and 1174), 1578 (SEQ ID NO:1175 and 1176)) caused a rapid and sustained reduction in viral endpoint serum HBsAg compared to PBS control group. (Mean±SEM). The dose-dependent response in vivo shows a pharmacological effect of the UNA oligomer composition.

As shown in FIG. 10, treatment with UNA oligomer triad composition (1777 (SEQ ID NO:1179 and 1180), 380 (SEQ ID NO:1173 and 1174), 1578 (SEQ ID NO:1175 and 1176)) caused a rapid and sustained reduction in viral endpoint serum HBeAg compared to PBS control group. (Mean±SEM). The dose-dependent response in vivo shows a pharmacological effect of the UNA oligomer composition.

As shown in FIG. 11, treatment with UNA oligomer triad composition (1777 (SEQ ID NO:1179 and 1180), 380 (SEQ ID NO:1173 and 1174), 1578 (SEQ ID NO:1175 and 1176)) caused a rapid and sustained reduction in viral endpoint serum HBV DNA compared to PBS control group. (Mean±SEM). The dose-dependent response in vivo shows a pharmacological effect of the UNA oligomer composition.

Thus, the UNA oligomers of this invention demonstrated significant and unexpectedly advantageous HBV inhibition efficacy in vivo.

Example 12: The HBV inhibitory effect in vivo for UNA oligomers was observed in an AAV-HBV mouse model of HBV infection. The UNA oligomers of this invention exhibited profound reduction of HBV serum infection parameters in vivo. In general, the AAV-HBV mouse model is a robust model for investigating HBV infection, and can provide direct clinical pertinence for drug efficacy and potency. In this study, the UNA oligomers were contained in lipid nanoparticle formulation.

The UNA oligomers were formulated or co-formulated in lipid nanoparticles and injected intravenously into C57Bl/6 mice with active HBV replication after AAV-mediated delivery of a recombinant HBV genome to the liver.

The study was an ascending dose design in which mice were treated with 3 mg/kg on day 0, then 5 mg/kg on day 4, then 10 mg/kg on day 8.

Serum viral endpoints were monitored 15 days before, and at least 22 days after treatment.

As shown in FIG. 12, treatment with each of UNA oligomers 380 (SEQ ID NO:973 and 974), 1777 (SEQ ID NO:1005 and 1006), and 1576 (SEQ ID NO:1003 and 1004) caused a rapid and sustained reduction in viral endpoint serum HBsAg compared to PBS control group. (Mean±SEM).

As shown in FIG. 13, treatment with each of UNA oligomers 380 (SEQ ID NO:973 and 974), 1777 (SEQ ID NO:1005 and 1006), and 1576 (SEQ ID NO:1003 and 1004), as well as the UNA oligomer triad composition of the same compounds (1576, 380, 1777) caused a rapid and sustained reduction in viral endpoint serum HBeAg compared to PBS control group. (Mean±SEM). This head-to-head comparison shows that the triad composition provided surprisingly increased potency throughout the duration of the effect, relative to the individual oligomers.

As shown in FIG. 14, treatment with each of UNA oligomers 380 (SEQ ID NO:973 and 974), 1777 (SEQ ID NO:1005 and 1006), and 1576 (SEQ ID NO:1003 and 1004) caused a rapid and sustained reduction in viral endpoint serum HBV DNA compared to PBS control group. (Mean±SEM).

Thus, the UNA oligomers of this invention demonstrated significant and unexpectedly advantageous HBV inhibition efficacy in vivo.

Example 13: The HBV inhibitory effect in vivo for UNA oligomers was observed in an AAV-HBV mouse model of HBV infection. The UNA oligomers of this invention exhibited profound reduction of HBV serum infection parameters in vivo. In this study, the UNA oligomers were contained in lipid nanoparticle formulation.

The UNA oligomers were co-formulated in lipid nanoparticles and injected intravenously into C57Bl/6 mice with active HBV replication after AAV-mediated delivery of a recombinant HBV genome to the liver.

The study was an ascending dose design in which mice were treated with 3 mg/kg on day 0, then 5 mg/kg on day 4, then 10 mg/kg on day 8.

Serum viral endpoints were monitored up to day 12 after treatment.

As shown in FIG. 15, treatment with the UNA oligomer triad composition (1777 (SEQ ID NO:1179 and 1180), 380 (SEQ ID NO:1173 and 1174), 1578 (SEQ ID NO:1175 and 1176)) caused a rapid and sustained reduction in viral endpoint serum HBsAg compared to PBS control group. (Mean±SEM). The dose-dependent response in vivo shows a pharmacological effect of the UNA oligomer composition.

Thus, the UNA oligomers of this invention demonstrated significant and unexpectedly advantageous HBV inhibition efficacy in vivo.

Example 14: The HBV inhibitory effect in vivo for UNA oligomers was observed in an AAV-HBV mouse model of HBV infection. The UNA oligomers of this invention exhibited profound reduction of HBV serum infection parameters in vivo. In general, the AAV-HBV mouse model is a robust model for investigating HBV infection, and can provide direct clinical pertinence for drug efficacy and potency. In this study, the UNA oligomers were contained in lipid nanoparticle formulation.

The UNA oligomers were formulated or co-formulated in lipid nanoparticles and injected intravenously into C57Bl/6 mice with active HBV replication after AAV-mediated delivery of a recombinant HBV genome to the liver.

The study was an ascending dose design in which mice were treated with 3 mg/kg on day 0, then 5 mg/kg on day 4, then 10 mg/kg on day 8.

Serum viral endpoints were monitored 15 days before, and at least 22 days after treatment.

As shown in FIG. 16, treatment with each of UNA oligomers 1578 (SEQ ID NO:993 and 994) and 1575 (SEQ ID NO:988 and 989) caused a rapid and sustained reduction in viral endpoint serum HBsAg compared to PBS control group. (Mean±SEM).

As shown in FIG. 17, treatment with each of UNA oligomers 1578 (SEQ ID NO:993 and 994) and 1575 (SEQ ID NO:988 and 989) caused a rapid and sustained reduction in viral endpoint serum HBeAg compared to PBS control group. (Mean±SEM).

As shown in FIG. 18, treatment with each of UNA oligomers 1578 (SEQ ID NO:993 and 994) and 1575 (SEQ ID NO:988 and 989) caused a rapid and sustained reduction in viral endpoint serum HBV DNA compared to PBS control group. (Mean±SEM).

Thus, the UNA oligomers of this invention demonstrated significant and unexpectedly advantageous HBV inhibition efficacy in vivo.

Example 15: The HBV inhibitory effect of UNA oligomers was observed with a psiCHECK2 assay. The percent inhibition of target expression for UNA oligomeric compounds containing one or more 2'-deoxy-2'-fluoro ribonucleotides was measured.

As shown in Table 28, UNA oligomeric compounds exhibited at least 87% inhibition of target expression at 10 nM.

TABLE 28

| Activity of UNA oligomer | |
|---|---|
| UNA oligomer | Relative RLuc/FLuc at 0.1 nM, 1 nM, 10 nM |
| 1578 (SEQ ID NO: 1127 and 1128) | 0.65, 0.18, 0.08 |
| 1777 (SEQ ID NO: 1135 and 1136) | 0.56, 0.14, 0.13 |
| 380 (SEQ ID NO: 1143 and 1144) | 0.40, 0.14, 0.13 |

Thus, the UNA oligomers of this invention demonstrated advantageous HBV inhibition efficacy in vitro.

Example 16: The HBV inhibitory effect in vivo for UNA oligomers was observed in a PXB Mouse model of HBV infection. The UNA oligomers of this invention exhibited profound reduction of HBV serum infection parameters in vivo. In this study, the UNA oligomers were contained in lipid nanoparticle formulation.

The UNA oligomers were formulated or co-formulated in lipid nanoparticles and injected intravenously into HBV-infected Phoenix Bio (PXB) mice. The mice were Genotype: cDNA-uPA$^{wild/+}$/SCID [cDNA-uPA$^{wild/+}$: B6; 129SvEv-Plau, SCID: C.B-17/Icr-scid/scid Jcl] containing human hepatocytes with an estimated replacement index of 70% or more.

As shown in Table 29, treatment with both UNA oligomers caused a rapid and sustained reduction in viral endpoint serum HBsAg compared to a PBS control group.

TABLE 29

| HBsAg (% control) (normalized to hAlb) | | | | |
|---|---|---|---|---|
| UNA oligomer Ref Pos. | % Inhibition Day 5 3.3 nM | % Inhibition Day 10 3.3 nM | % Inhibition Day 15 3.3 nM | % Inhibition Day 20 3.3 nM |
| 1580 (SEQ ID NO: 997 and 998) | 72.0 | 71.0 | 59.0 | 49.0 |
| 1578 (SEQ ID NO: 993 and 994) | 70.0 | 59.0 | 39.0 | 25.3 |
| 1575 (SEQ ID NO: 987 and 988) | 75.0 | 58.0 | 39.0 | 22.2 |
| 1818 (SEQ ID NO: 1015 and 1016) | 55.0 | 56.0 | 56.0 | 17.7 |
| 380 (SEQ ID NO: 973 and 974) | 62.0 | 55.0 | 33.0 | 30.5 |
| 1576 (SEQ ID NO: 989 and 990) | 42.0 | 48.0 | 44.0 | 38.2 |
| 1777 (SEQ ID NO: 1005 and 1006) | 65.0 | 43.0 | 21.0 | 12.7 |
| 1782 (SEQ ID NO: 1013 and 1014) | 65.0 | 43.0 | 25.0 | 20.4 |
| 1581 (SEQ ID NO: 999 and 1000) | 50.0 | 42.0 | 28.0 | 11.7 |

Thus, the UNA oligomers of this invention demonstrated significant and unexpectedly advantageous HBV inhibition efficacy in vivo.

Example 17: The HBV inhibitory effect in vivo for UNA oligomers was observed in a PXB Mouse model of HBV infection. The UNA oligomers of this invention exhibited profound reduction of HBV serum infection parameters in vivo. In this study, the UNA oligomers were contained in lipid nanoparticle formulation.

The UNA oligomers were formulated or co-formulated in lipid nanoparticles and injected intravenously into HBV-infected Phoenix Bio (PXB) mice. The mice were Genotype: cDNA-uPA$^{wild/+}$/SCID [cDNA-uPA$^{wild/+}$: B6; 129SvEv-Plau, SCID: C.B-17/Icr-scid/scid Jcl] containing human hepatocytes with an estimated replacement index of 70% or more.

As shown in Table 30, treatment with a triad UNA oligomer composition caused a rapid and sustained reduction in viral endpoint serum HBsAg compared to a PBS control group.

TABLE 30

| Serum HBsAg (% control) (normalized to hAlb) | | | | |
|---|---|---|---|---|
| UNA oligomer composition Ref Pos. | % Inhibition Day 5 3.3 nM | % Inhibition Day 10 3.3 nM | % Inhibition Day 15 3.3 nM | % Inhibition Day 20 3.3 nM |
| 380/1777/1575 | 82.0 | 67.0 | 39.9 | 28.0 |
| 380/1777/1578 | 82.0 | 70.0 | 47.3 | 33.2 |
| 380/1777/1576 | 79.0 | 64.0 | 44.8 | 29.1 |

The compositions in Table 30 were:

UNA oligomer triad composition (1777 (SEQ ID NO:1005 and 1006), 380 (SEQ ID NO:973 and 974), 1575 (SEQ ID NO:987 and 988));

UNA oligomer triad composition (1777 (SEQ ID NO:1005 and 1006), 380 (SEQ ID NO:973 and 974), 1578 (SEQ ID NO:993 and 994)); and UNA oligomer triad composition (1777 (SEQ ID NO:1005 and 1006), 380 (SEQ ID NO:973 and 974), 1576 (SEQ ID NO:989 and 990)).

Thus, the triad UNA oligomer compositions of this invention demonstrated significant and unexpectedly advantageous HBV inhibition efficacy in vivo.

Example 18: The HBV inhibitory effect in vivo for UNA oligomers was observed in a PXB Mouse model of HBV infection. The UNA oligomers of this invention exhibited profound reduction of HBV serum infection parameters in vivo. In this study, the UNA oligomers were contained in lipid nanoparticle formulation.

The UNA oligomers were formulated or co-formulated in lipid nanoparticles and injected intravenously into HBV-infected Phoenix Bio (PXB) mice. The mice were Genotype: cDNA-uPA$^{wild/+}$/SCID [cDNA-uPA$^{wild/+}$: B6; 129SvEv-Plau, SCID: C.B-17/Icr-scid/scid Jcl] containing human hepatocytes with an estimated replacement index of 70% or more.

As shown in Table 31, treatment with a triad UNA oligomer composition caused a rapid and sustained reduction in viral endpoint serum HBsAg compared to a PBS control group, for Genotypes Ae, Bj, C, and D.

TABLE 31

| Serum HBsAg (% control) (normalized to hAlb) | | | | | |
|---|---|---|---|---|---|
| UNA oligomer composition (Ref Pos.) | Genotype | % Inhibition Day 5 3 nM | % Inhibition Day 10 3 nM | % Inhibition Day 5 15 nM | % Inhibition Day 10 15 nM |
| 380/1777/1578 | Ae | 79.2 | 71.0 | 87.5 | 79.0 |
| 380/1777/1578 | Bj | 75.4 | 62.2 | 85.0 | 79.0 |
| 380/1777/1578 | C | — | 68.8 | — | 82.8 |
| 380/1777/1578 | D | 80.7 | 68.9 | 88.5 | 81.4 |

The composition in Table 31 was UNA oligomer triad composition (1777 (SEQ ID NO:1005 and 1006), 380 (SEQ ID NO:973 and 974), 1578 (SEQ ID NO:993 and 994)).

Thus, the triad UNA oligomer compositions of this invention demonstrated significant and unexpectedly advantageous HBV inhibition efficacy in vivo over a range of genotypes.

Example 19: The HBV inhibitory effect in vivo for UNA oligomers was observed in a PXB Mouse model of HBV infection. The UNA oligomers of this invention exhibited profound reduction of HBV serum infection parameters in vivo with phosphorothioate linkages present. In this study, the UNA oligomers were contained in lipid nanoparticle formulation.

The UNA oligomers were formulated or co-formulated in lipid nanoparticles and injected intravenously into HBV-infected Phoenix Bio (PXB) mice. The mice were Genotype: cDNA-uPA$^{wild/+}$/SCID [cDNA-uPA$^{wild/+}$: B6; 129SvEv-Plau, SCID: C.B-17/Icr-scid/scid Jcl] containing human hepatocytes with an estimated replacement index of 70% or more.

As shown in Table 32, treatment with UNA oligomers caused a rapid and sustained reduction in viral endpoint serum HBsAg compared to a PBS control group.

TABLE 32

| HBsAg (% control) (normalized to hAlb) | | | | |
|---|---|---|---|---|
| UNA oligomer Ref Pos. | % Inhibition Day 5 3.3 nM | % Inhibition Day 10 3.3 nM | % Inhibition Day 15 3.3 nM | % Inhibition Day 20 3.3 nM |
| 1575 (SEQ ID NO: 987 and 988) | 76.2 | 60.4 | 25.0 | 3.0 |
| 1575PS (SEQ ID NO: 1117 and 1118) | 79.0 | 77.5 | 58.5 | 35.7 |
| 1578 (SEQ ID NO: 993 and 994) | 77.0 | 65.6 | 34.4 | 5.7 |
| 1578PS (SEQ ID NO: 1069 and 1070) | 78.1 | 72.7 | 53.5 | 18.3 |
| 380 (SEQ ID NO: 973 and 974) | 72.4 | 69.5 | 48.1 | 23.9 |
| 380PS (SEQ ID NO: 1107 and 1108) | 68.1 | 69.9 | 52.4 | 35.2 |

Thus, the UNA oligomers of this invention with phosphorothioate linkages (PS) demonstrated significant and unexpectedly advantageous HBV inhibition efficacy in vivo with longer duration (Day 15 to Day 20). The phosphorothioate linkages were as follows: one phosphorothioate linkage between two monomers at the 5' end of the first strand, one phosphorothioate linkage between two monomers at the 3' end of the first strand, one phosphorothioate linkage between monomers at the second and third positions from the 3' end of the first strand, and one phosphorothioate linkage between two monomers at the 3' end of the second strand.

Example 20: HBV reference genome HB974376 (3221bp).

SEQ ID NO: 1181

```
   1 ttccactgcc ttccaccaag ctctgcagga tcccagagtc aggggtctgt attttcctgc
  61 tggtggctcc agttcaggaa cagtaaaccc tgctccgaat attgcctctc acatctcgtc
 121 aatctccgcg aggactgggg accctgtgac gaacatggag aacatcacat caggattcct
 181 aggacccctg ctcgtgttac aggcggggtt tttcttgttg acaagaatcc tcacaatacc
 241 gcagagtcta gactcgtggt ggacttctct caattttcta gggggatcac ccgtgtgtct
 301 tggccaaaat tcgcagtccc caacctccaa tcactcacca acctcctgtc ctccaatttg
 361 tcctggttat cgctggatgt gtctgcggcg ttttatcata ttcctcttca tcctgctgct
 421 atgcctcatc ttcttattgg ttcttctgga ttatcaaggt atgttgcccg tttgtcctct
 481 aattccagga tcaacaacaa ccagtacggg accatgcaaa acctgcacga ctcctgctca
 541 aggcaactct atgtttccct catgttgctg tacaaaacct acggatggaa attgcacctg
 601 tattcccatc ccatcgtcct gggctttcgc aaaataccta tgggagtggg cctcagtccg
 661 tttctcttgg ctcagtttac tagtgccatt tgttcagtgg ttcgtagggc tttcccccac
 721 tgtttggctt tcagctatat ggatgatgtg gtattggggg ccaagtctgt acagcatcgt
 781 gagtcccttt ataccgctgt taccaatttt cttttgtctc tgggtataca tttaaaccct
 841 aacaaaacaa aaagatgggg ttattcccta aacttcatgg gttacataat tggaagttgg
 901 ggaactttgc cacaggatca tattgtacaa aagatcaaac actgttttag aaaacttcct
 961 gttaacaggc ctattgattg gaaagtatgt caaagaattg tgggtctttt gggctttgct
1021 gctccattta cacaatgtgg atatcctgcc ttaatgcctt tgtatgcatg tatacaagct
1081 aaacaggctt tcactttctc gccaacttac aaggcctttc taagtaaaca gtacatgaac
1141 ctttaccccg ttgctcggca acggcctggt ctgtgccaag tgtttgctga cgcaaccccc
1201 actggctggg gcttggccat aggccatcag cgcatgcgtg gaacctttgt ggctcctctg
1261 ccgatccata ctgcggaact cctagccgct tgttttgctc gcagccggtc tggagcaaag
1321 ctcatcggaa ctgacaattc tgtcgtcctc tcgcggaaat atacatcgtt tccatggctg
1381 ctaggctgta ctgccaactg gatccttcgc gggacgtcct ttgtttacgt cccgtcggcg
1441 ctgaatcccg cggacgaccc ctctcggggc cgcttgggac tctctcgtcc ccttctccgt
1501 ctgccgttcc agccgaccac ggggcgcacc tctctttacg cggtctcccc gtctgtgcct
1561 tctcatctgc cggtccgtgt gcacttcgct tcacctctgc acgttgcatg gagaccaccg
1621 tgaacgccca tcagatcctg cccaaggtct tacataagag gactcttgga ctcccagcaa
1681 tgtcaacgac cgaccttgag gcctacttca aagactgtgt gtttaaagac tgggaggagc
1741 tgggggagga gattaggtta aaggtctttg tattaggagg ctgtaggcat aaattggtct
1801 gcgcaccagc accatgcaac tttttcacct ctgcctaatc atctcttgta catgtcccac
1861 tgttcaagcc tccaagctgt gccttgggtg gctttggggc atggacattg acccttataa
1921 agaatttgga gctactgtgg agttactctc gtttttgcct tctgacttct ttccttccgt
1981 cagagatctc ctagacaccg cctcagctct gtatcgagaa gccttagaat ctcctgagca
2041 ttgctcacct caccatactg cactcaggca agccattctc tgctgggggg aattgatgac
2101 tctagctacc tgggtgggta ataatttgga agatccagca tccagggatc tagtagtcaa
2161 ttatgttaat actaacatgg gtttaaagat caggcaacta ttgtggtttc atatatcttg
2221 ccttactttt ggaagagaga ctgtacttga atatttggtc tctttcggag tgtggattcg
2281 cactcctcca gcctatagac caccaaatgc ccctatctta tcaacacttc cggaaactac
2341 tgttgttaga cgacgggacc gaggcaggtc ccctagaaga agaactccct cgcctcgcag
```

-continued

```
2401 acgcagatct caatcgccgc gtcgcagaag atctcaatct cgggaatctc aatgttagta

2461 ttccttggac tcataaggtg ggaaacttta cggggcttta ttcctctaca gtacctatct

2521 ttaatcctga atggcaaact ccttcctttc ctaagattca tttacaagag gacattatta

2581 ataggtgtca acaatttgtg ggccctctca ctgtaaatga aaagagaaga ttgaaattaa

2641 ttatgcctgc tagattctat cctactcaca ctaaatattt gcccttagac aaaggaatta

2701 aaccttatta tccagatcag gtagttaatc attacttcca aaccagacat tatttacata

2761 ctctttggaa ggctggtatt ctatataaga gggaaaccac acgtagcgca tcattttgtg

2821 ggtcaccata ttcttgggaa caagagctac agcatgggag gttggtcatc aaaacctcgc

2881 aaaggcatgg ggacgaatct ttctgttccc aaccctctgg gattctttcc cgatcatcag

2941 ttggaccctg cattcggagc caactcaaac aatccagatt gggacttcaa ccccatcaag

3001 gaccactggc cagcagccaa ccaggtagga gcgggagcat tcgggccagg gctcacccct

3061 ccacacggcg gtattctggg gtggagccct caggctcagg gcatattgac cacagtgtca

3121 acaattcctc ctcctgcctc caccaatcgg cagtcaggaa ggcagcctac tcccatctct

3181 ccacctctaa gagacagtca tcctcaggcc atgcagtgga a
```

Example 21: Additional compounds of this invention are shown in Table 33.

Additional compounds of this invention are shown in Table 33.

Designations used in Table 33 include rN for RNA, mN for 2'-O-methyl, rN* for RNA-3'-phosphorothioate, dN for DNA, and fN for 2'-fluoro. Underline bold indicates mismatch.

TABLE 33

UNA oligomers targeted to HBV (Sense (S)-Antisense (AS))

| REF POS | SEQ ID NO | S/AS | HBV (Sense (S)-Antisense (AS)) (5'-3') |
|---|---|---|---|
| 1577 | 1182 | S | UNA-G/*/mArGmGrCmUrGmUrArGrGmCrAmUrAmArAmUrU/*/UNA-U/*/dT |
| 1577 | 1183 | AS | mArAmUrUmUrAmUrGmCrCmUmAmCrAmGrCmCrUmC/UNA-U/*/dT |
| 1577 | 1184 | S | UNA-G/*/rArGrGmCmUrGmUrArGrGmCrAmUrArArAmUmU/*/UNA-U/*/dT |
| 1577 | 1185 | AS | mArA/*/mUrUmUrAmUrGmCrCmUmAmCrAmGrCmCrUmC/UNA-U/*/dT |
| 1577 | 1186 | S | UNA-G/*/rArGrGmCmUrGmUrArGrGmCrAmUrArArAmUmU/*/UNA-U/*/dT |
| 1577 | 1187 | AS | mArArUmUmUrArUrGmCrCmUrArCrAmGmCmCrUmC/UNA-U/*/dT |
| 1577 | 1188 | S | UNA-G/*/rArGrGmCmUrGmUrArGrGmCrAmUrArArAmUmU/*/UNA-U/*/dT |
| 1577 | 1189 | AS | mArAmUrUmU/*/rAmU/*/rGmCrCmU/*/mAmC/*/rAmGrCmCrUmC/UNA-U/*/dT |
| 1577 | 1190 | S | UNA-G/*/rArGrGmCmUrGmUrArGrGmCrAmUrArArAmUmU/*/UNA-U/*/dT |
| 1577 | 1191 | AS | mArAmUrUmUrAmUrGmCrCmUmAmCrAmGrCmCrUm**A**/UNA-U/*/dT |
| 1577 | 1192 | S | UNA-G/*/rArGrGmCmUrGmUrArGrGmCrAmUrArArAmUmU/*/UNA-U/*/dT |
| 1577 | 1193 | AS | mArAmUrUdUrAmUrGmCrCmUmAmCrAdGrCmCrUmC/UNA-U/*/dT |
| 1577 | 1194 | S | UNA-G/*/rArGrGmCmUrGmUrArGrGmCrAmUrArArAmUmU/*/UNA-U/*/dT |
| 1577 | 1195 | AS | rArAmUmUmUrAmUrGmCmCmUrAmCrArGmCmCmUmC/UNA-U/*/dT |
| 1577 | 1196 | S | UNA-G/*/rArGrGfCfUrGfUrArGrGfCrAfUrArArAfUfU/*/UNA-U/*/dT |
| 1577 | 1197 | AS | rArAfUrUfUrAfUrGfCfCfUrAfCrArGfCfCfUfC/UNA-U/*/dT |
| 1577 | 1198 | S | UNA-G/*/fArGfGrCfUrGfUrArGrGfCrAfUrAfArAfUrU/*/UNA-U/*/dT |
| 1577 | 1199 | AS | fArAfUrUfUrAfUrGfCrCfUfAfCrAfGrCfCrUfC/UNA-U/*/dT |

Example 22: Additional compounds of this invention are shown in Table 34.

Additional compounds of this invention are shown in Table 34.

TABLE 34

| UNA oligomers targeted to HBV (Sense (S)-Antisense (AS)) | | | |
|---|---|---|---|
| REF POS | SEQ ID NO | S/AS | HBV (Sense (S)-Antisense (AS)) (5'-3') |
| 380 | 1200 | S | UNA-U/*/mGrUmCrUmGrCmGrGrCrGmUrUmUrUmArUmCrA/*/UNA-U/*/dT |
| 380 | 1201 | As | mUrGmArUmArAmArAmCrGmCmCmGrCmArGmArCmA/UNA-U/*/dT |
| 380 | 1202 | S | UNA-U/*/rGmUmCmUrGmCrGrGmCrGmUmUmUmUrAmUmCrA/*/UNA-U/*/dT |
| 380 | 1203 | AS | mUrG/*/mArUmArAmArAmCrGmCmCmGrCmArGmArCmA/UNA-U/*/dT |
| 380 | 1204 | S | UNA-U/*/rGmUmCmUrGmCrGrGmCrGmUmUmUmUrAmUmCrA/*/UNA-U/*/dT |
| 380 | 1205 | AS | mUrGrAmUmArArArAmCrGmCrCrGrCmAmGmArCmA/UNA-U/*/dT |
| 380 | 1206 | S | UNA-U/*/rGmUmCmUrGmCrGrGmCrGmUmUmUmUrAmUmCrA/*/UNA-U/*/dT |
| 380 | 1207 | AS | mU/*/rGmArU/*/mArAmArAmCrGmCmCmGrC/*/mArGmArC/*/mA/UNA-U/*/dT |
| 380 | 1208 | S | UNA-U/*/rGmUmCmUrGmCrGrGmCrGmUmUmUmUrAmUmCrA/*/UNA-U/*/dT |
| 380 | 1209 | AS | mUrGmArUmArAmArAmCrGmCmCmGrCmArGmArCm**C**/UNA-U/*/dT |
| 380 | 1210 | S | UNA-U/*/rGmUmCmUrGmCrGrGmCrGmUmUmUmUrAmUmCrA/*/UNA-U/*/dT |
| 380 | 1211 | AS | mUrGmArUdArAmArAmCrGmCmCmGrCdArGmArCmA/UNA-U/*/dT |
| 380 | 1212 | S | UNA-U/*/rGmUmCmUrGmCrGrGmCrGmUmUmUmUrAmUmCrA/*/UNA-U/*/dT |
| 380 | 1213 | AS | mUrGrAmUrArArArAmCrGmCmCrGmCrArGrAmCrA/UNA-U/*/dT |
| 380 | 1214 | S | UNA-U/*/rGfUfCfUrGfCrGrGfCrGfUfUfUfUrAfUfCrA/*/UNA-U/*/dT |
| 380 | 1215 | AS | fUrGrAfUrArArArAfCrGfCfCrGfCrArGrAfCrA/UNA-U/*/dT |
| 380 | 1216 | S | UNA-U/*/fGrUfCrUfGrCfGrGrCrGfUrUfUrUfArUfCrA/*/UNA-U/*/dT |
| 380 | 1217 | AS | fUrGfArUfArAfArAfCrGfCfCfGrCfArGfArCfA/UNA-U/*/dT |

Designations used in Table 34 include rN for RNA, mN for 2'-O-methyl, rN* for RNA-3'-phosphorothioate, dN for DNA, and fN for 2'-fluoro. Underline bold indicates mismatch.

Example 23: Additional compounds of this invention are shown in Table 35.

Additional compounds of this invention are shown in Table 35.

TABLE 35

| UNA oligomers targeted to HBV (Sense (S)-Antisense (AS)) | | | |
|---|---|---|---|
| REF POS | SEQ ID NO | S/AS | HBV (Sense (S)-Antisense (AS)) (5'-3') |
| 1575 | 1218 | S | UNA-C/*/mCrGmUrGmUrGmCrArCrUmUrCmGrCmUrUmCrA/*/UNA-U/*/dT |
| 1575 | 1219 | AS | mUrGmArAmGrCmGrAmArGmUmGmCrAmCrAmCrGmG/UNA-U/*/dT |
| 1575 | 1220 | S | UNA-C/*/mCrGmUrGmUrGmCrAmCmUrUrCmGmCmUmUmCrA/*/UNA-U/*/dT |
| 1575 | 1221 | AS | mUrG/*/mArAmGrCmGrAmArGmUmGmCrAmCrAmCrGmG/UNA-U/*/dT |
| 1575 | 1222 | S | UNA-C/*/mCrGmUrGmUrGmCrAmCmUrUrCmGmCmUmUmCrA/*/UNA-U/*/dT |
| 1575 | 1223 | AS | mUrGrAmAmGrCrGrAmArGmUrGrCrAmCmAmCrGmG/UNA-U/*/dT |
| 1575 | 1224 | S | UNA-C/*/mCrGmUrGmUrGmCrAmCmUrUrCmGmCmUmUmCrA/*/UNA-U/*/dT |

TABLE 35 -continued

| UNA oligomers targeted to HBV (Sense (S)-Antisense (AS)) | | | |
|---|---|---|---|
| REF POS | SEQ ID NO | S/AS | HBV (Sense (S)-Antisense (AS)) (5'-3') |
| 1575 | 1225 | AS | mU/*/rGmArAmGrCmGrAmArGmU/*/mGmC/*/rAmC/*/rAmCrGmG/UNA-U/*/dT |
| 1575 | 1226 | S | UNA-C/*/mCrGmUrGmUrGmCrAmCmUrUrCmGmCmUmUmCrA/*/UNA-U/*/dT |
| 1575 | 1227 | AS | mUrGmArAmGrCmGrAmArGmUmGmCrAmCrAmCrGm**A**/UNA-U/*/dT |
| 1575 | 1228 | S | UNA-C/*/mCrGmUrGmUrGmCrAmCmUrUrCmGmCmUmUmCrA/*/UNA-U/*/dT |
| 1575 | 1229 | AS | mUrGmArAdGrCmGrAmArGmUmGmCrAdCrAmCrGmG/UNA-U/*/dT |
| 1575 | 1230 | S | UNA-C/*/mCrGmUrGmUrGmCrAmCmUrUrCmGmCmUmUmCrA/*/UNA-U/*/dT |
| 1575 | 1231 | AS | mUrGrArArGmCrGrArArGmUrGmCrAmCrAmCrGrG/UNA-U/*/dT |
| 1575 | 1232 | S | UNA-C/*/fCrGfUrGfUrGfCrAfCfUfUfCrGfCfUrUfCrA/*/UNA-U/*/dT |
| 1575 | 1233 | AS | fUrGrArArGfCrGrArArGfUrGfCrAfCrAfCrGrG/UNA-U/*/dT |
| 1575 | 1234 | S | UNA-C/*/fCrGfUrGfUrGfCrArCrUfUrCfGrCfUrUfCrA/*/UNA-U/*/dT |
| 1575 | 1235 | AS | fUrGfArAfGrCfGrAfArGfUfGfCrAfCrAfCrGfG/UNA-U/*/dT |
| 1575 | 1236 | S | UNA-U/*/mGrUmGrCmArCmUrUrCrGmCrUmUrCmArCmCrU/*/UNA-U/*/dT |
| 1575 | 1237 | AS | mArGmGrUmGrAmArGmCrGmAmAmGrUmGrCmArCmA/UNA-U/*/dT |

Designations used in Table 35 include rN for RNA, mN for 2'-O-methyl, rN* for RNA-3'-phosphorothioate, dN for DNA, and fN for 2'-fluoro. Underline bold indicates mismatch.

Example 24: Additional compounds of this invention are shown in Table 36.

Additional compounds of this invention are shown in Table 36.

TABLE 36

| UNA oligomers targeted to HBV (Sense (S)-Antisense (AS)) | | | |
|---|---|---|---|
| REF POS | SEQ ID NO | S/AS | HBV (Sense (S)-Antisense (AS)) (5'-3') |
| 1578 | 1238 | S | UNA-U/*/mGrUmGrCmArCmUrUrCrGmCrUmUrCmArCmCrUPVUNA-UPVdT |
| 1578 | 1239 | AS | mArGmGrUmGrAmArGmCrGmAmAmGrUmGrCmArCmA/UNA-UPVdT |
| 1578 | 1240 | S | UNA-UPYrGmUrGmCrAmCmUmUmCrGmCmUmUmCrAmCmCmU/*/UNA-UPVdT |
| 1578 | 1241 | AS | mArG/*/mGrUmGrAmArGmCrGmAmAmGrUmGrCmArCmA/UNA-UPVdT |
| 1578 | 1242 | S | UNA-UPYrGmUrGmCrAmCmUmUmCrGmCmUmUmCrAmCmCmU/*/UNA-UPVdT |
| 1578 | 1243 | AS | mArGrGmUmGrArArGmCrGmArArGrUmGmCmArCmA/UNA-UPVdT |
| 1578 | 1244 | S | UNA-UPYrGmUrGmCrAmCmUmUmCrGmCmUmUmCrAmCmCmU/*/UNA-UPVdT |
| 1578 | 1245 | AS | mArGmGrU/*/mGrAmArGmCrGmAmAmGrU/*/mGrC/*/mArC/*/mA/UNA-U/*/dT |
| 1578 | 1246 | S | UNA-UPYrGmUrGmCrAmCmUmUmCrGmCmUmUmCrAmCmCmU/*/UNA-UPVdT |
| 1578 | 1247 | AS | mArGmGrUmGrAmArGmCrGmAmAmGrUmGrCmArCmC/UNA-UPVdT |
| 1578 | 1248 | S | UNA-UPYrGmUrGmCrAmCmUmUmCrGmCmUmUmCrAmCmCmU/*/UNA-UPVdT |
| 1578 | 1249 | AS | mArGmGrUdGrAmArGmCrGmAmAmGrUdGrCmArCmA/UNA-UPVdT |
| 1578 | 1250 | S | UNA-UPYrGmUrGmCrAmCmUmUmCrGmCmUmUmCrAmCmCmU/*/UNA-UPVdT |
| 1578 | 1251 | AS | rArGrGmUrGrArArGmCrGrArArGmUrGmCrAmCrA/UNA-UPVdT |
| 1578 | 1252 | S | UNA-UPYrGfUrGfCrAfCfUfUfCrGfCfUfUfCrAfCfCfU/*/UNA-U/*/dT |
| 1578 | 1253 | AS | rArGrGfUrGrArArGfCrGrArArGfUrGfCrAfCrA/UNA-UPVdT |

TABLE 36 -continued

| UNA oligomers targeted to HBV (Sense (S)-Antisense (AS)) | | | |
|---|---|---|---|
| REF POS | SEQ ID NO | S/AS | HBV (Sense (S)-Antisense (AS)) (5'-3') |
| 1578 | 1254 | S | UNA-U/*/fGrUfGrCfArCfUrUrCrGfCrUfUrCfArCfCrUPVUNA-UPVdT |
| 1578 | 1255 | AS | fArGfGrUfGrAfArGfCrGfAfAfGrUfGrCfArCfA/UNA-UPVdT |

Designations used in Table 36 include rN for RNA, mN for 2'-O-methyl, rN* for RNA-3'-phosphorothioate, dN for DNA, and fN for 2'-fluoro. Underline bold indicates mismatch.

Example 25: Additional compounds of this invention are shown in Table 37.

Additional compounds of this invention are shown in Table 37.

TABLE 37

| UNA oligomers targeted to HBV (Sense (S)-Antisense (AS)) | | | |
|---|---|---|---|
| REF POS | SEQ ID NO | S/AS | HBV (Sense (S)-Antisense (AS)) (5'-3') |
| 1576 | 1256 | S | UNA-C/*/mGrUmGrUmGrCmArCrUrUmCrGmCrUmUrCmArC/*/UNA-U/*/dT |
| 1576 | 1257 | AS | mGrUmGrAmArGmC/UNA-G/mArAmGmUmGrCmArCmArCmG/UNA-U/*/dT |
| 1576 | 1258 | S | UNA-C/*/rGmUrGmUrGmCrAmCmUmUmCrGmCmUmUrCrAmC/*/UNA-U/*/dT |
| 1576 | 1259 | AS | mGrU/*/mGrAmArGmC/UNA-G/mArAmGmUmGrCmArCmArCmG/UNA-U/*/dT |
| 1576 | 1260 | S | UNA-C/*/rGmUrGmUrGmCrAmCmUmUmCrGmCmUmUrCrAmC/*/UNA-U/*/dT |
| 1576 | 1261 | AS | mGrU/*/rGmAmArGrC/UNA-G/mArAmGrUrGrCmAmCmArCmG/UNA-U/*/dT |
| 1576 | 1262 | S | UNA-C/*/rGmUrGmUrGmCrAmCmUmUmCrGmCmUmUrCrAmC/*/UNA-U/*/dT |
| 1576 | 1263 | AS | mGrU/*/mGrAmArGmC/UNA-G/mArAmGmU/*/mGrC/*/mArC/*/mArCmG/UNA-U/*/dT |
| 1576 | 1264 | S | UNA-C/*/rGmUrGmUrGmCrAmCmUmUmCrGmCmUmUrCrAmC/*/UNA-U/*/dT |
| 1576 | 1265 | AS | mGrUmGrAmArGmC/UNA-G/mArAmGmUmGrCmArCmArCmA/UNA-U/*/dT |
| 1576 | 1266 | S | UNA-C/*/rGmUrGmUrGmCrAmCmUmUmCrGmCmUmUrCrAmC/*/UNA-U/*/dT |
| 1576 | 1267 | AS | mGrU/*/rGmAdArGrC/UNA-G/mArAmGrUrGrCdAmCmArCmG/UNA-U/*/dT |
| 1576 | 1268 | S | UNA-C/*/rGmUrGmUrGmCrAmCmUmUmCrGmCmUmUrCrAmC/*/UNA-U/*/dT |
| 1576 | 1269 | AS | rGmUrGrArArGmC/UNA-G/rArArGmUrGmCrAmCrAmCrG/UNA-U/*/dT |
| 1576 | 1270 | S | UNA-C/*/rGfUrGfUrGfCrAfCfUfUfCrGfCfUfUfCrAfC/*/UNA-U/*/dT |
| 1576 | 1271 | AS | rGfUrGrArArGfC/UNA-G/rArArGfUrGfCrAfCrAfCrG/UNA-U/*/dT |
| 1576 | 1272 | S | UNA-C/*/fGrUfGrUfGrCfArCrUrUfCrGfCrUfUrCfArC/*/UNA-U/*/dT |
| 1576 | 1273 | AS | fGrUfGrAfArGfC/UNA-G/fArAfGfUfGrCfArCfArCfG/UNA-U/*/dT |

Designations used in Table 37 include rN for RNA, mN for 2'-O-methyl, rN* for RNA-3'-phosphorothioate, dN for DNA, and fN for 2'-fluoro. Underline bold indicates mismatch.

Example 26: Additional compounds of this invention are shown in Table 38.

Additional compounds of this invention are shown in Table 38.

TABLE 38

| UNA oligomers targeted to HBV (Sense (S)-Antisense (AS)) | | | |
|---|---|---|---|
| REF POS | SEQ ID NO | S/AS | HBV (Sense (S)-Antisense (AS)) (5'-3') |
| 1578 | 1274 | S | UNA-U/mGrUmGrCmArCmUrUrCrGmCrUmUrCmArCmCrU/UNA-U/mU |
| 1578 | 1275 | AS | mArGmGrUmGrAmArGmCrGmAmAmGrUmGrCmArCmA/UNA-U/mU |
| 1578 | 1276 | S | UNA-U/mGrUmGrCmArCmUrUrCrGmCrUmUrCmArCmCrU/UNA-U/mU |
| 1578 | 1277 | AS | 5Phos/mArGmGrUmGrAmArGmCrGmAmAmGrUmGrCmArCmA/UNA-U/mU |
| 1777 | 1278 | S | UNA-G/mArGmGrCmUrGmUrArGrGmCrAmUrAmArAmUrU/UNA-U/mU |
| 1777 | 1279 | AS | mArAmUrUmUrAmUrGmCrCmUmAmCrAmGrCmCrUmC/UNA-U/mU |
| 1777 | 1280 | S | UNA-G/mArGmGrCmUrGmUrArGrGmCrAmUrAmArAmUrU/UNA-U/mU |
| 1777 | 1281 | AS | 5Phos/mArAmUrUmUrAmUrGmCrCmUmAmCrAmGrCmCrUmC/UNA-U/mU |
| 380 | 1282 | S | UNA-U/mGrUmCrUmGrCmGrGrCrGmUrUmUrUmArUmCrA/UNA-U/mU |
| 380 | 1283 | AS | mUrGmArUmArAmArAmCrGmCmCmGrCmArGmArCmA/UNA-U/mU |
| 380 | 1284 | S | UNA-U/mGrUmCrUmGrCmGrGrCrGmUrUmUrUmArUmCrA/UNA-U/mU |
| 380 | 1285 | AS | 5Phos/mUrGmArUmArAmArAmCrGmCmCmGrCmArGmArCmA/UNA-U/mU |

Designations used in Table 38 include rN for RNA, mN for 2'-O-methyl, rN* for RNA-3'-phosphorothioate, and Phos for phosphoro.

All publications, patents and literature specifically mentioned herein are incorporated by reference for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be encompassed by the appended claims.

It must be noted that as used herein and in the appended claims, the singular forms “a”, “an”, and “the” include plural reference unless the context clearly dictates otherwise. As well, the terms “a” (or “an”), “one or more” and “at least one” can be used interchangeably herein. It is also to be noted that the terms “comprises,” “comprising”, “containing,” “including”, and “having” can be used interchangeably.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A compound comprising a first strand and a second strand, each of the strands being 19-29 monomers in length, the monomers comprising UNA monomers and nucleic acid monomers, wherein the compound has a duplex region of from 14 to 29 contiguous monomers in length, wherein the first strand is a sense strand for RNA interference and the second strand is an antisense strand for RNA interference, wherein the compound comprises a sequence of bases targeted to inhibit expression of an HBV genome, wherein the sense strand and the antisense strand are each independently selected from the group consisting of:

| REF POS | SEQ ID NO | S/ AS | HBV (Sense (S)-Antisense (AS)) (5'-3') |
|---|---|---|---|
| 1777 | 1182 | S | UNA-G/*/mArGmGrCmUrGmUrArGrGmCr AmUrAmArAmUrU/*/UNA-U/*/dT |
| 1777 | 1183 | AS | mArAmUrUmUrAmUrGmCrCmUmAmCr AmGrCmCrUmC/UNA-U/*/dT |
| 1777 | 1184 | S | UNA-G/*/rArGrGmCmUrGmUrArGrGm CrAmUrArArAmUmU/*/UNA-U/*/dT |
| 1777 | 1185 | AS | mArA/*/mUrUmUrAmUrGmCrCmUmAm CrAmGrCmCrUmC/UNA-U/*/dT |
| 1777 | 1186 | S | UNA-G/*/rArGrGmCmUrGmUrArGrGm CrAmUrArArAmUmU/*/UNA-U/*/dT |
| 1777 | 1187 | AS | mArArUmUmUrArUrGmCrCmUrArCrAm GmCmCrUmC/UNA-U/*/dT |
| 1777 | 1188 | S | UNA-G/*/rArGrGmCmUrGmUrArGrGmCr AmUrArArAmUmU/*/UNA-U/*/dT |
| 1777 | 1189 | AS | mArAmUrUmU/*/rAmU/*/rGmCrCmU/ */mAmC/*/rAmGrCmCrUmC/UNA-U/*/dT |
| 1777 | 1190 | S | UNA-G/*/rArGrGmCmUrGmUrArGrGm CrAmUrArArAmUmU/*/UNA-U/*/dT |
| 1777 | 1191 | AS | mArAmUrUmUrAmUrGmCrCmUmAmCrAm GrCmCrUmA/UNA-U/*/dT |
| 1777 | 1192 | S | UNA-G/*/rArGrGmCmUrGmUrArGrGm CrAmUrArArAmUmU/*/UNA-U/*/dT |
| 1777 | 1193 | AS | mArAmUrUdUrAmUrGmCrCmUmAmCr AdGrCmCrUmC/UNA-U/*/dT |
| 1777 | 1194 | S | UNA-G/*/rArGrGmCmUrGmUrArGrGm CrAmUrArArAmUmU/*/UNA-U/*/dT |
| 1777 | 1195 | AS | rArAmUmUmUrAmUrGmCmCmUrAmCr ArGmCmCmUmC/UNA-U/*/dT |
| 1777 | 1196 | S | UNA-G/*/rArGrGfCfUrGfUrArGrGf CrAfUrArArAfUfU/*/UNA-U/*/dT |
| 1777 | 1197 | AS | rArAfUrUfUrAfUrGfCfCfUrAfCr ArGfCfCfUfC/UNA-U/*/dT |
| 1777 | 1198 | S | UNA-G/*/fArGfGrCfUrGfUrArGrGf CrAfUrAfArAfUrU/*/UNA-U/*/dT |
| 1777 | 1199 | AS | fArAfUrUfUrAfUrGfCrCfUfAfCr AfGrCfCrUfC/UNA-U/*/dT |
| 380 | 1200 | S | UNA-U/*/mGrUmCrUmGrCmGrGrCrGm UrUmUrUmArUmCrA/*/UNA-U/*/dT |
| 380 | 1201 | AS | mUrGmArUmArAmArAmCrGmCmCmGr CmArGmArCmA/UNA-U/*/dT |
| 380 | 1202 | S | UNA-U/*/rGmUmCmUrGmCrGrGmCrGm UmUmUmUrAmUmCrA/*/UNA-U/*/dT |
| 380 | 1203 | AS | mUrG/*/mArUmArAmArAmCrGmCmCm GrCmArGmArCmA/UNA-U/*/dT |
| 380 | 1204 | S | UNA-U/*/rGmUmCmUrGmCrGrGmCrGm UmUmUmUrAmUmCrA/*/UNA-U/*/dT |
| 380 | 1205 | AS | mUrGrAmUmArArArAmCrGmCrCrGr CmAmGmArCmA/UNA-U/*/dT |
| 380 | 1206 | S | UNA-U/*/rGmUmCmUrGmCrGrGmCr GmUmUmUmUrAmUmCrA/*/UNA-U/*/dT |
| 380 | 1207 | AS | mU/*/rGmArU/*/mArAmArAmCrGm CmCmGrC/*/mArGmArC/*/mA/UNA-U/*/dT |
| 380 | 1208 | S | UNA-U/*/rGmUmCmUrGmCrGrGmCr GmUmUmUmUrAmUmCrA/*/UNA-U/*/dT |
| 380 | 1209 | AS | mUrGmArUmArAmArAmCrGmCmCm GrCmArGmArCmC/UNA-U/*/dT |
| 380 | 1210 | S | UNA-U/*/rGmUmCmUrGmCrGrGmCr GmUmUmUmUrAmUmCrA/*/UNA-U/*/dT |
| 380 | 1211 | AS | mUrGmArUdArAmArAmCrGmCmCm GrCdArGmArCmA/UNA-U/*/dT |
| 380 | 1212 | S | UNA-U/*/rGmUmCmUrGmCrGrGmCr GmUmUmUmUrAmUmCrA/*/UNA-U/*/dT |
| 380 | 1213 | AS | mUrGrAmUrArArArAmCrGmCmCrGm CrArGrAmCrA/UNA-U/*/dT |
| 380 | 1214 | S | UNA-U/*/rGfUfCfUrGfCrGrGfCr GfUfUfUfUrAfUfCrA/*/UNA-U/*/dT |
| 380 | 1215 | AS | fUrGrAfUrArArArAfCrGfCfCrGf CrArGrAfCrA/UNA-U/*/dT |
| 380 | 1216 | S | UNA-U/*/fGrUfCrUfGrCfGrGrCrGf UrUfUrUfArUfCrA/*/UNA-U/*/dT |
| 380 | 1217 | AS | fUrGfArUfArAfArAfCrGfCfCfGr CfArGfArCfA/UNA-U/*/dT |
| 1575 | 1218 | S | UNA-C/*/mCrGmUrGmUrGmCrArCr UmUrCmGrCmUrUmCrA/*/UNA-U/*/dT |
| 1575 | 1219 | AS | mUrGmArAmGrCmGrAmArGmUmGm CrAmCrAmCrGmG/UNA-U/*/dT |
| 1575 | 1220 | S | UNA-C/*/mCrGmUrGmUrGmCrAmCm UrUrCmGmCmUmUmCrA/*/UNA-U/*/dT |
| 1575 | 1221 | AS | mUrG/*/mArAmGrCmGrAmArGmUm GmCrAmCrAmCrGmG/UNA-U/*/dT |
| 1575 | 1222 | S | UNA-C/*/mCrGmUrGmUrGmCrAmCm UrUrCmGmCmUmUmCrA/*/UNA-U/*/dT |
| 1575 | 1223 | AS | mUrGrAmAmGrCrGrAmArGmUrGrCr AmCmAmCrGmG/UNA-U/*/dT |
| 1575 | 1224 | S | UNA-C/*/mCrGmUrGmUrGmCrAmCmUr UrCmGmCmUmUmCrA/*/UNA-U/*/dT |
| 1575 | 1225 | AS | mU/*/rGmArAmGrCmGrAmArGmU/*/ mGmC/*/rAmC/*/rAmCrGmG/UNA-U/*/dT U/*/dT |
| 1575 | 1226 | S | UNA-C/*/mCrGmUrGmUrGmCrAmCmUr UrCmGmCmUmUmCrA/*/UNA-U/*/dT |
| 1575 | 1227 | AS | mUrGmArAmGrCmGrAmArGmUmGmCr AmCrAmCrGmA/UNA-U/*/dT |

-continued

| REF POS | SEQ ID NO | S/ AS | HBV (Sense (S)-Antisense (AS)) (5'-3') |
|---|---|---|---|
| 1575 | 1228 | S | UNA-C/*/mCrGmUrGmUrGmCrAmCmUr UrCmGmCmUmUmCrA/*/UNA-U/*/dT |
| 1575 | 1229 | AS | mUrGmArAdGrCmGrAmArGmUmGmCr AdCrAmCrGmG/UNA-U/*/dT |
| 1575 | 1230 | S | UNA-C/*/mCrGmUrGmUrGmCrAmCm UrUrCmGmCmUmUmCrA/*/UNA-U/*/dT |
| 1575 | 1231 | AS | mUrGrArArGmCrGrArArGmUrGmCr AmCrAmCrGrG/UNA-U/*/dT |
| 1575 | 1232 | S | UNA-C/*/fCrGfUrGfUrGfCrAfCfUf UfCrGfCfUrUfCrA/*/UNA-U/*/dT |
| 1575 | 1233 | AS | fUrGrArArGfCrGrArArGfUrGfCr AfCrAfCrGrG/UNA-U/*/dT |
| 1575 | 1234 | S | UNA-C/*/fCrGfUrGfUrGfCrArCr UfUrCfGrCfUrUfCrA/*/UNA-U/*/dT |
| 1575 | 1235 | AS | fUrGfArAfGrCfGrAfArGfUfGfCr AfCrAfCrGfG/UNA-U/*/dT |
| 1575 | 1236 | S | UNA-U/*/mGrUmGrCmArCmUrUrCr GmCrUmUrCmArCmCrU/*/UNA-U/*/dT |
| 1575 | 1237 | AS | mArGmGrUmGrAmArGmCrGmAmAmGr UmGrCmArCmA/UNA-U/*/dT |
| 1578 | 1238 | S | UNA-U/*/mGrUmGrCmArCmUrUrCrGm CrUmUrCmArCmCrU/*/UNA-U/*/dT |
| 1578 | 1239 | AS | mArGmGrUmGrAmArGmCrGmAmAmGr UmGrCmArCmA/UNA-U/*/dT |
| 1578 | 1240 | S | UNA-U/*/rGmUrGmCrAmCmUmUmCrGm CmUmUmCrAmCmCmU/*/UNA-U/*/dT |
| 1578 | 1241 | AS | mArG/*/mGrUmGrAmArGmCrGmAmAm GrUmGrCmArCmA/UNA-U/*/dT |
| 1578 | 1242 | S | UNA-U/*/rGmUrGmCrAmCmUmUmCrGm CmUmUmCrAmCmCmU/*/UNA-U/*/dT |
| 1578 | 1243 | AS | mArGrGmUmGrArArGmCrGmArArGrUm GmCmArCmA/UNA-U/*/dT |
| 1578 | 1244 | S | UNA-U/*/rGmUrGmCrAmCmUmUmCrGmCm UmUmCrAmCmCmU/*/UNA-U/*/dT |
| 1578 | 1245 | AS | mArGmGrU/*/mGrAmArGmCrGmAmAmGr U/*/mGrC/*/mArC/*/mA/UNA-U/*/dT |
| 1578 | 1246 | S | UNA-U/*/rGmUrGmCrAmCmUmUmCrGm CmUmUmCrAmCmCmU/*/UNA-U/*/dT |
| 1578 | 1247 | AS | mArGmGrUmGrAmArGmCrGmAmAmGr UmGrCmArCmC/UNA-U/*/dT |
| 1578 | 1248 | S | UNA-U/*/rGmUrGmCrAmCmUmUmCrGm CmUmUmCrAmCmCmU/*/UNA-U/*/dT |
| 1578 | 1249 | AS | mArGmGrUdGrAmArGmCrGmAmAmGrUd GrCmArCmA/UNA-U/*/dT |
| 1578 | 1250 | S | UNA-U/*/rGmUrGmCrAmCmUmUmCrGm CmUmUmCrAmCmCmU/*/UNA-U/*/dT |
| 1578 | 1251 | AS | rArGrGmUrGrArArGmCrGrArArGmUr GmCrAmCrA/UNA-U/*/dT |
| 1578 | 1252 | S | UNA-U/*/rGfUrGfCrAfCfUfUfCrGf CfUfUfCrAfCfCfU/*/UNA-U/*/dT |

-continued

| REF POS | SEQ ID NO | S/ AS | HBV (Sense (S)-Antisense (AS)) (5'-3') |
|---|---|---|---|
| 1578 | 1253 | AS | rArGrGfUrGrArArGfCrGrArArGf UrGfCrAfCrA/UNA-U/*/dT |
| 1578 | 1254 | S | UNA-U/*/fGrUfGrCfArCfUrUrCrGf CrUfUrCfArCfCrU/*/UNA-U/*/dT |
| 1578 | 1255 | AS | fArGfGrUfGrAfArGfCrGfAfAfGr UfGrCfArCfA/UNA-U/*/dT |
| 1576 | 1256 | S | UNA-C/*/rGmUrGmUrGmCrAmCmUmUm CrGmCmUmUrCrAmC/*/UNA-U/*/dT |
| 1576 | 1257 | AS | mGrU/*/mGrAmArGmC/UNA-G/mArAm GmUmGrCmArCmArCmG/UNA-U/*/dT |
| 1576 | 1258 | S | UNA-C/*/rGmUrGmUrGmCrAmCmUmUm CrGmCmUmUrCrAmC/*/UNA-U/*/dT |
| 1576 | 1259 | AS | mGrU/*/rGmAmArGrC/UNA-G/mAr AmGrUrGrCmAmCmArCmG/UNA-U/*/dT |
| 1576 | 1260 | S | UNA-C/*/rGmUrGmUrGmCrAmCmUmUm CrGmCmUmUrCrAmC/*/UNA-U/*/dT |
| 1576 | 1261 | AS | mGrU/*/mGrAmArGmC/UNA-G/mArAmGmU/ */mGrC/*/mArC/*/mArCmG/UNA-U/*/dT |
| 1576 | 1262 | S | UNA-C/*/rGmUrGmUrGmCrAmCmUm UmCrGmCmUmUrCrAmC/*/UNA-U/*/dT |
| 1576 | 1263 | AS | mGrUmGrAmArGmC/UNA-G/mArAmGm UmGrCmArCmArCmA/UNA-U/*/dT |
| 1576 | 1264 | S | UNA-C/*/rGmUrGmUrGmCrAmCmUmUm CrGmCmUmUrCrAmC/*/UNA-U/*/dT |
| 1576 | 1265 | AS | mGrU/*/rGmAdArGrC/UNA-G/mArAm GrUrGrCdAmCmArCmG/UNA-U/*/dT |
| 1576 | 1266 | S | UNA-C/*/rGmUrGmUrGmCrAmCmUmUm CrGmCmUmUrCrAmC/*/UNA-U/*/dT |
| 1576 | 1267 | AS | rGmUrGrArArGmC/UNA-G/rArArGmUr GmCrAmCrAmCrG/UNA-U/*/dT |
| 1576 | 1268 | S | UNA-C/*/rGfUrGfUrGfCrAfCfUfUfCr GfCfUfUfCrAfC/*/UNA-U/*/dT |
| 1576 | 1269 | AS | rGfUrGrArArGfC/UNA-G/rArArGfUr GfCrAfCrAfCrG/UNA-U/*/dT |
| 1576 | 1270 | S | UNA-C/*/fGrUfGrUfGrCfArCrUrUfCr GfCrUfUrCfArC/*/UNA-U/*/dT |
| 1576 | 1271 | AS | fGrUfGrAfArGfC/UNA-G/fArAfGfUf GrCfArCfArCfG/UNA-U/*/dT |
| 1578 | 1274 | S | UNA-U/mGrUmGrCmArCmUrUrCrGmCrUm UrCmArCmCrU/UNA-U/mU |
| 1578 | 1275 | AS | mArGmGrUmGrAmArGmCrGmAmAmGrUm GrCmArCmA/UNA-U/mU |
| 1578 | 1276 | S | UNA-U/mGrUmGrCmArCmUrUrCrGmCrUm UrCmArCmCrU/UNA-U/mU |
| 1578 | 1277 | AS | 5Phos/mArGmGrUmGrAmArGmCrGmAmAm GrUmGrCmArCmA/UNA-U/mU |
| 1777 | 1278 | S | UNA-G/mArGmGrCmUrGmUrArGrGmCrAmUr AmArAmUrU/UNA-U/mU |
| 1777 | 1279 | AS | mArAmUrUmUrAmUrGmCrCmUmAmCrAmGr CmCrUmC/UNA-U/mU |

-continued

| REF POS | SEQ ID NO | S/ AS | HBV (Sense (S)-Antisense (AS)) (5'-3') |
|---|---|---|---|
| 1777 | 1280 | S | UNA-G/mArGmGrCmUrGmUrArGrGmCrAmUr AmArAmUrU/UNA-U/mU |
| 1777 | 1281 | AS | 5Phos/mArAmUrUmUrAmUrGmCrCmUmAmCr AmGrCmCrUmC/UNA-U/mU |
| 380 | 1282 | S | UNA-U/mGrUmCrUmGrCmGrGrCrGmUrUmUr UmArUmCrA/UNA-U/mU |
| 380 | 1283 | AS | mUrGmArUmArAmArAmCrGmCmCmGrCm ArGmArCmA/UNA-U/mU |
| 380 | 1284 | S | UNA-U/mGrUmCrUmGrCmGrGrCrGmUrUm UrUmArUmCrA/UNA-U/mU |
| 380 | 1285 | AS | 5Phos/mUrGmArUmArAmArAmCrGmCmCm GrCmArGmArCmA/UNA-U/mU, |

SEQ ID NO:1107 (UNA-U*/mGrUmCrUmGrCmGrGr-CrGmUrUmUrUmArUmCrA*/UNA-U*/mU) and SEQ ID NO:1108 (mUrGmArUmArAmArAmCrGmCmCmGrC-mArGmArCmA/UNA-U*/mU);

and wherein "m" before a nucleotide denotes a chemically-modified 2'-OMe ribonucleotide, "r" before a nucleotide denotes a ribonucleotide, an asterisk * between characters refers to a phosphorothioate linkage, "d" before a nucleotide denotes a deoxyribonucleotide, "UNA" before a nucleotide denotes an unlocked nucleotide, and "f" before a nucleotide denotes a 2'-deoxy-2'-fluoro ribonucleotide.

2. The compound of claim 1, wherein the compound is conjugated to a delivery moiety.

3. The compound of claim 1, wherein the compound is conjugated to a delivery moiety that binds to a glycoprotein receptor, wherein the delivery moiety comprises a galactose, a galactosamine, or a N-acetylgalactosamine.

4. The compound of claim 1, wherein the compound is conjugated to a GalNAc delivery moiety or a cholesterol delivery moiety.

5. A lipid nanoparticle-oligomer compound comprising one or more compounds of claim 1 attached to the lipid nanoparticle.

6. A composition comprising one or more compounds of claim 1 and a pharmaceutically acceptable carrier.

7. The composition of claim 6, wherein the carrier comprises lipid nanoparticles or liposomes.

8. A method for preventing, ameliorating or treating a disease or condition associated with HBV infection in a subject in need, the method comprising administering to the subject an effective amount of a composition of claim 6.

9. The method of claim 8, wherein the administration of the composition reduces HBV viral titer in the subject.

10. The method of claim 8, wherein the subject has been diagnosed with a disease associated with Hepatitis B virus infection.

11. The method of claim 8, wherein the subject has been diagnosed with liver disease.

* * * * *

SEQUENCE LISTING

```
<160> NUMBER OF SEQ ID NOS: 1285

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 1

nnnnnnnnnn nnnnnnnnnn nn                                          22


<210> SEQ ID NO 2
<211> LENGTH: 21
<212> TYPE: RNA
<213> ORGANISM: Artificial Sequence
```

<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 2
nnnnnnnnnn nnnnnnnnnn n 21

<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(22)
<223> OTHER INFORMATION: Any natural, non-natural, modified, or
chemically-modified nucleotide; may or may not be modified
based on a propane-1,2,3-tri-yl-trisoxy structure

<400> SEQUENCE: 3
nnnnnnnnnn nnnnnnnnnn nn 22

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 4
nnnnnnnnnn nnnnnnnnnn n 21

<210> SEQ ID NO 5
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(22)
<223> OTHER INFORMATION: Any natural, non-natural, modified, or
chemically-modified nucleotide; may or may not be modified
based on a propane-1,2,3-tri-yl-trisoxy structure

<400> SEQUENCE: 5
nnnnnnnnnn nnnnnnnnnn nn 22

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide <220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 6
nnnnnnnnnn nnnnnnnnnn n 21

<210> SEQ ID NO 7
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(22)
<223> OTHER INFORMATION: Any natural, non-natural, modified, or chemically-modified nucleotide; may or may not be modified based on a propane-1,2,3-tri-yl-trisoxy structure

<400> SEQUENCE: 7
nnnnnnnnnn nnnnnnnnnn nn 22

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 8
nnnnnnnnnn nnnnnnnnnn n 21

<210> SEQ ID NO 9
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(22)
<223> OTHER INFORMATION: Any natural, non-natural, modified, or chemically-modified nucleotide; may or may not be modified based on a propane-1,2,3-tri-yl-trisoxy structure

<400> SEQUENCE: 9
nnnnnnnnnn nnnnnnnnnn nn 22

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)

<223> OTHER INFORMATION: Any natural, non-natural, modified, or
      chemically-modified nucleotide; may or may not be modified
      based on a propane-1,2,3-tri-yl-trisoxy structure

<400> SEQUENCE: 10
nnnnnnnnnn nnnnnnnnnn n 21

<210> SEQ ID NO 11
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 11
nnnnnnnnnn nnnnnnnnnn nn 22

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 12
nnnnnnnnnn nnnnnnnnnn n 21

<210> SEQ ID NO 13
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 13
nnnnnnnnnn nnnnnnnnnn nn 22

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 14
nnnnnnnnnn nnnnnnnnnn n 21

<210> SEQ ID NO 15
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(22)
<223> OTHER INFORMATION: Any natural, non-natural, modified, or chemically-modified nucleotide; may or may not be modified based on a propane-1,2,3-tri-yl-trisoxy structure

<400> SEQUENCE: 15
nnnnnnnnnn nnnnnnnnnn nn 22

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 16
nnnnnnnnnn nnnnnnnnnn n 21

<210> SEQ ID NO 17
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(22)
<223> OTHER INFORMATION: Any natural, non-natural, modified, or chemically-modified nucleotide; may or may not be modified based on a propane-1,2,3-tri-yl-trisoxy structure

<400> SEQUENCE: 17
nnnnnnnnnn nnnnnnnnnn nn 22

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 18
nnnnnnnnnn nnnnnnnnnn n 21

<210> SEQ ID NO 19
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(22)
<223> OTHER INFORMATION: Any natural, non-natural, modified, or chemically-modified nucleotide; may or may not be modified based on a propane-1,2,3-tri-yl-trisoxy structure

<400> SEQUENCE: 19
nnnnnnnnnn nnnnnnnnnn nn 22

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 20
nnnnnnnnnn nnnnnnnnnn n 21

<210> SEQ ID NO 21
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(22)
<223> OTHER INFORMATION: Any natural, non-natural, modified, or chemically-modified nucleotide; may or may not be modified based on a propane-1,2,3-tri-yl-trisoxy structure

<400> SEQUENCE: 21
nnnnnnnnnn nnnnnnnnnn nn 22

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 22
nnnnnnnnnn nnnnnnnnnn n 21

```
<210> SEQ ID NO 23
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 23

nnnnnnnnnn nnnnnnnnnn nn                                              22


<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 24

nnnnnnnnnn nnnnnnnnnn n                                               21


<210> SEQ ID NO 25
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 25

nnnnnnnnnn nnnnnnnnnn nn                                              22


<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 26

nnnnnnnnnn nnnnnnnnnn n                                               21


<210> SEQ ID NO 27
<211> LENGTH: 22
<212> TYPE: RNA
```

<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(22)
<223> OTHER INFORMATION: Any natural, non-natural, modified, or
chemically-modified nucleotide; may or may not be modified
based on a propane-1,2,3-tri-yl-trisoxy structure

<400> SEQUENCE: 27
nnnnnnnnnn nnnnnnnnnn nn 22

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 28
nnnnnnnnnn nnnnnnnnnn n 21

<210> SEQ ID NO 29
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(22)
<223> OTHER INFORMATION: Any natural, non-natural, modified, or
chemically-modified nucleotide; may or may not be modified
based on a propane-1,2,3-tri-yl-trisoxy structure

<400> SEQUENCE: 29
nnnnnnnnnn nnnnnnnnnn nn 22

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 30
nnnnnnnnnn nnnnnnnnnn n 21

<210> SEQ ID NO 31
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(22)
<223> OTHER INFORMATION: Any natural, non-natural, modified, or chemically-modified nucleotide; may or may not be modified based on a propane-1,2,3-tri-yl-trisoxy structure

<400> SEQUENCE: 31
nnnnnnnnnn nnnnnnnnnn nn 22

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 32
nnnnnnnnnn nnnnnnnnnn n 21

<210> SEQ ID NO 33
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(22)
<223> OTHER INFORMATION: Any natural, non-natural, modified, or chemically-modified nucleotide; may or may not be modified based on a propane-1,2,3-tri-yl-trisoxy structure

<400> SEQUENCE: 33
nnnnnnnnnn nnnnnnnnnn nn 22

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 34
nnnnnnnnnn nnnnnnnnnn n 21

<210> SEQ ID NO 35
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 35
nnnnnnnnnn nnnnnnnnnn nn 22

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 36
nnnnnnnnnn nnnnnnnnnn n 21

<210> SEQ ID NO 37
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 37
nnnnnnnnnn nnnnnnnnnn nn 22

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 38
nnnnnnnnnn nnnnnnnnnn n 21

<210> SEQ ID NO 39
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified based on a propane-1,2,3-tri-yl-trisoxy structure

<400> SEQUENCE: 39
nnnnnnnnnn nnnnnnnnnn nn 22

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 40
nnnnnnnnnn nnnnnnnnnn n 21

<210> SEQ ID NO 41
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(22)
<223> OTHER INFORMATION: Any natural, non-natural, modified, or chemically-modified nucleotide; may or may not be modified based on a propane-1,2,3-tri-yl-trisoxy structure

<400> SEQUENCE: 41
nnnnnnnnnn nnnnnnnnnn nn 22

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 42
nnnnnnnnnn nnnnnnnnnn n 21

<210> SEQ ID NO 43
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(22)
<223> OTHER INFORMATION: Any natural, non-natural, modified, or chemically-modified nucleotide; may or may not be modified based on a propane-1,2,3-tri-yl-trisoxy structure

<400> SEQUENCE: 43

```
nnnnnnnnnn nnnnnnnnnn nn                                              22


<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 44

nnnnnnnnnn nnnnnnnnnn n                                               21


<210> SEQ ID NO 45
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 45

nnnnnnnnnn nnnnnnnnnn nn                                              22


<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 46

nnnnnnnnnn nnnnnnnnnn n                                               21


<210> SEQ ID NO 47
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 47

nnnnnnnnnn nnnnnnnnnn nn                                              22
```

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 48
nnnnnnnnnn nnnnnnnnnn n 21

<210> SEQ ID NO 49
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(22)
<223> OTHER INFORMATION: Any natural, non-natural, modified, or chemically-modified nucleotide; may or may not be modified based on a propane-1,2,3-tri-yl-trisoxy structure

<400> SEQUENCE: 49
nnnnnnnnnn nnnnnnnnnn nn 22

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 50
nnnnnnnnnn nnnnnnnnnn n 21

<210> SEQ ID NO 51
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(22)
<223> OTHER INFORMATION: Any natural, non-natural, modified, or chemically-modified nucleotide; may or may not be modified based on a propane-1,2,3-tri-yl-trisoxy structure

<400> SEQUENCE: 51
nnnnnnnnnn nnnnnnnnnn nn 22

<210> SEQ ID NO 52
<211> LENGTH: 21

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 52

nnnnnnnnnn nnnnnnnnnn n                                              21


<210> SEQ ID NO 53
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 53

nnnnnnnnnn nnnnnnnnnn nn                                             22


<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 54

nnnnnnnnnn nnnnnnnnnn n                                              21


<210> SEQ ID NO 55
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 55

nnnnnnnnnn nnnnnnnnnn nn                                             22


<210> SEQ ID NO 56
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 56

nnnnnnnnnn nnnnnnnnnn n                                              21


<210> SEQ ID NO 57
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 57

nnnnnnnnnn nnnnnnnnnn nn                                             22


<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 58

nnnnnnnnnn nnnnnnnnnn n                                              21


<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 59

nnnnnnnnnn nnnnnnnnnn n                                              21


<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 60
nnnnnnnnnn nnnnnnnnnn n                                              21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 61
nnnnnnnnnn nnnnnnnnnn n                                              21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 62
nnnnnnnnnn nnnnnnnnnn n                                              21

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 63
nnnnnnnnnn nnnnnnnnnn n                                              21

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or

```
      chemically-modified nucleotide; may or may not be modified
      based on a propane-1,2,3-tri-yl-trisoxy structure

<400> SEQUENCE: 64

nnnnnnnnnn nnnnnnnnnn n                                               21


<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 65

nnnnnnnnnn nnnnnnnnnn n                                               21


<210> SEQ ID NO 66
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 66

nnnnnnnnnn nnnnnnnnnn n                                               21


<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 67

nnnnnnnnnn nnnnnnnnnn n                                               21


<210> SEQ ID NO 68
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure
```

<400> SEQUENCE: 68
nnnnnnnnnn nnnnnnnnnn n 21

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 69
nnnnnnnnnn nnnnnnnnnn n 21

<210> SEQ ID NO 70
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 70
nnnnnnnnnn nnnnnnnnnn n 21

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 71
nnnnnnnnnn nnnnnnnnnn n 21

<210> SEQ ID NO 72
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 72
nnnnnnnnnn nnnnnnnnnn n 21

```
<210> SEQ ID NO 73
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 73

nnnnnnnnnn nnnnnnnnnn n                                              21


<210> SEQ ID NO 74
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 74

nnnnnnnnnn nnnnnnnnnn n                                              21


<210> SEQ ID NO 75
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 75

nnnnnnnnnn nnnnnnnnnn n                                              21


<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 76

nnnnnnnnnn nnnnnnnnnn n                                              21


<210> SEQ ID NO 77
```

<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 77
nnnnnnnnnn nnnnnnnnnn n 21

<210> SEQ ID NO 78
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 78
nnnnnnnnnn nnnnnnnnnn n 21

<210> SEQ ID NO 79
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 79
nnnnnnnnnn nnnnnnnnnn n 21

<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 80
nnnnnnnnnn nnnnnnnnnn n 21

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 81
nnnnnnnnnn nnnnnnnnnn n 21

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 82
nnnnnnnnnn nnnnnnnnnn n 21

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 83
nnnnnnnnnn nnnnnnnnnn n 21

<210> SEQ ID NO 84
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 84
nnnnnnnnnn nnnnnnnnnn n 21

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 85
nnnnnnnnnn nnnnnnnnnn n 21

<210> SEQ ID NO 86
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 86
nnnnnnnnnn nnnnnnnnnn n 21

<210> SEQ ID NO 87
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 87
nnnnnnnnnn nnnnnnnnnn n 21

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 88
nnnnnnnnnn nnnnnnnnnn n 21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)

<223> OTHER INFORMATION: Any natural, non-natural, modified, or chemically-modified nucleotide; may or may not be modified based on a propane-1,2,3-tri-yl-trisoxy structure

<400> SEQUENCE: 89
nnnnnnnnnn nnnnnnnnnn n 21

<210> SEQ ID NO 90
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 90
nnnnnnnnnn nnnnnnnnnn n 21

<210> SEQ ID NO 91
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 91
nnnnnnnnnn nnnnnnnnnn n 21

<210> SEQ ID NO 92
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 92
nnnnnnnnnn nnnnnnnnnn n 21

<210> SEQ ID NO 93
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 93
nnnnnnnnnn nnnnnnnnnn n 21

<210> SEQ ID NO 94
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 94
nnnnnnnnnn nnnnnnnnnn n 21

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 95
nnnnnnnnnn nnnnnnnnnn n 21

<210> SEQ ID NO 96
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 96
nnnnnnnnnn nnnnnnnnnn n 21

<210> SEQ ID NO 97
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 97

-continued

```
nnnnnnnnnn nnnnnnnnnn n                                              21


<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 98

nnnnnnnnnn nnnnnnnnnn n                                              21


<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 99

nnnnnnnnnn nnnnnnnnnn n                                              21


<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 100

nnnnnnnnnn nnnnnnnnnn n                                              21


<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 101

nnnnnnnnnn nnnnnnnnnn n                                              21
```

<210> SEQ ID NO 102
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 102
nnnnnnnnnn nnnnnnnnnn n 21

<210> SEQ ID NO 103
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 103
nnnnnnnnnn nnnnnnnnnn n 21

<210> SEQ ID NO 104
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 104
nnnnnnnnnn nnnnnnnnnn n 21

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 105
nnnnnnnnnn nnnnnnnnnn n 21

<210> SEQ ID NO 106
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 106
nnnnnnnnnn nnnnnnnnnn n 21

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 107
nnnnnnnnnn nnnnnnnnnn n 21

<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 108
nnnnnnnnnn nnnnnnnnnn n 21

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 109
nnnnnnnnnn nnnnnnnnnn n 21

<210> SEQ ID NO 110
<211> LENGTH: 21
<212> TYPE: RNA
<213> ORGANISM: Artificial Sequence
<220> FEATURE:
<223> OTHER INFORMATION: Description of Artificial Sequence: Synthetic

```
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 110

nnnnnnnnnn nnnnnnnnnn n                                             21


<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 111

nnnnnnnnnn nnnnnnnnnn n                                             21


<210> SEQ ID NO 112
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 112

nnnnnnnnnn nnnnnnnnnn n                                             21


<210> SEQ ID NO 113
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 113

nnnnnnnnnn nnnnnnnnnn n                                             21


<210> SEQ ID NO 114
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 114
nnnnnnnnnn nnnnnnnnnn n 21

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 115
nnnnnnnnnn nnnnnnnnnn n 21

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 116
nnnnnnnnnn nnnnnnnnnn n 21

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 117
nnnnnnnnnn nnnnnnnnnn n 21

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified based on a propane-1,2,3-tri-yl-trisoxy structure

<400> SEQUENCE: 118
nnnnnnnnnn nnnnnnnnnn n 21

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 119
nnnnnnnnnn nnnnnnnnnn n 21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 120
nnnnnnnnnn nnnnnnnnnn n 21

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 121
nnnnnnnnnn nnnnnnnnnn n 21

<210> SEQ ID NO 122
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 122
nnnnnnnnnn nnnnnnnnnn n 21

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 123
nnnnnnnnnn nnnnnnnnnn n 21

<210> SEQ ID NO 124
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 124
nnnnnnnnnn nnnnnnnnnn n 21

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 125
nnnnnnnnnn nnnnnnnnnn n 21

<210> SEQ ID NO 126
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 126
nnnnnnnnnn nnnnnnnnnn n 21

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 127
nnnnnnnnnn nnnnnnnnnn n 21

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 128
nnnnnnnnnn nnnnnnnnnn n 21

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 129
nnnnnnnnnn nnnnnnnnnn n 21

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 130
nnnnnnnnnn nnnnnnnnnn n 21

<210> SEQ ID NO 131
<211> LENGTH: 21

<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 131
nnnnnnnnnn nnnnnnnnnn n                                                21

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 132
nnnnnnnnnn nnnnnnnnnn n                                                21

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 133
nnnnnnnnnn nnnnnnnnnn n                                                21

<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 134
nnnnnnnnnn nnnnnnnnnn n                                                21

<210> SEQ ID NO 135
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 135
nnnnnnnnnn nnnnnnnnnn n 21

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 136
nnnnnnnnnn nnnnnnnnnn n 21

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 137
nnnnnnnnnn nnnnnnnnnn n 21

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 138
nnnnnnnnnn nnnnnnnnnn n 21

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:

<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 139
nnnnnnnnnn nnnnnnnnnn n 21

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 140
nnnnnnnnnn nnnnnnnnnn n 21

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 141
nnnnnnnnnn nnnnnnnnnn n 21

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 142
nnnnnnnnnn nnnnnnnnnn n 21

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 143
nnnnnnnnnn nnnnnnnnnn n 21

<210> SEQ ID NO 144
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 144
nnnnnnnnnn nnnnnnnnnn n 21

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 145
nnnnnnnnnn nnnnnnnnnn n 21

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 146
nnnnnnnnnn nnnnnnnnnn n 21

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 147
nnnnnnnnnn nnnnnnnnnn n 21

<210> SEQ ID NO 148
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 148
nnnnnnnnnn nnnnnnnnnn n 21

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 149
nnnnnnnnnn nnnnnnnnnn n 21

<210> SEQ ID NO 150
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 150
nnnnnnnnnn nnnnnnnnnn n 21

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 151
nnnnnnnnnn nnnnnnnnnn n 21

<210> SEQ ID NO 152
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 152
nnnnnnnnnn nnnnnnnnnn n 21

<210> SEQ ID NO 153
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 153
nnnnnnnnnn nnnnnnnnnn n 21

<210> SEQ ID NO 154
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 154
nnnnnnnnnn nnnnnnnnnn n 21

<210> SEQ ID NO 155
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 155
nnnnnnnnnn nnnnnnnnnn n 21

<210> SEQ ID NO 156

<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 156
nnnnnnnnnn nnnnnnnnnn n 21

<210> SEQ ID NO 157
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 157
nnnnnnnnnn nnnnnnnnnn n 21

<210> SEQ ID NO 158
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 158
nnnnnnnnnn nnnnnnnnnn n 21

<210> SEQ ID NO 159
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 159
nnnnnnnnnn nnnnnnnnnn n 21

<210> SEQ ID NO 160
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 160
nnnnnnnnnn nnnnnnnnnn n 21

<210> SEQ ID NO 161
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 161
nnnnnnnnnn nnnnnnnnnn n 21

<210> SEQ ID NO 162
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 162
nnnnnnnnnn nnnnnnnnnn n 21

<210> SEQ ID NO 163
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 163
nnnnnnnnnn nnnnnnnnnn n 21

<210> SEQ ID NO 164
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide <220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 164
nnnnnnnnnn nnnnnnnnnn n 21

<210> SEQ ID NO 165
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 165
nnnnnnnnnn nnnnnnnnnn n 21

<210> SEQ ID NO 166
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 166
nnnnnnnnnn nnnnnnnnnn n 21

<210> SEQ ID NO 167
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 167
nnnnnnnnnn nnnnnnnnnn n 21

<210> SEQ ID NO 168
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)

<223> OTHER INFORMATION: Any natural, non-natural, modified, or chemically-modified nucleotide; may or may not be modified based on a propane-1,2,3-tri-yl-trisoxy structure

<400> SEQUENCE: 168
nnnnnnnnnn nnnnnnnnnn n 21

<210> SEQ ID NO 169
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 169
nnnnnnnnnn nnnnnnnnnn n 21

<210> SEQ ID NO 170
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 170
nnnnnnnnnn nnnnnnnnnn n 21

<210> SEQ ID NO 171
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 171
nnnnnnnnnn nnnnnnnnnn n 21

<210> SEQ ID NO 172
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 172
nnnnnnnnnn nnnnnnnnnn n 21

<210> SEQ ID NO 173
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 173
nnnnnnnnnn nnnnnnnnnn n 21

<210> SEQ ID NO 174
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 174
nnnnnnnnnn nnnnnnnnnn n 21

<210> SEQ ID NO 175
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 175
nnnnnnnnnn nnnnnnnnnn n 21

<210> SEQ ID NO 176
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 176
nnnnnnnnnn nnnnnnnnnn n 21

<210> SEQ ID NO 177
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 177
nnnnnnnnnn nnnnnnnnnn n 21

<210> SEQ ID NO 178
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 178
nnnnnnnnnn nnnnnnnnnn n 21

<210> SEQ ID NO 179
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 179
nnnnnnnnnn nnnnnnnnnn n 21

<210> SEQ ID NO 180
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 180
nnnnnnnnnn nnnnnnnnnn n 21

<210> SEQ ID NO 181
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 181
nnnnnnnnnn nnnnnnnnnn n 21

<210> SEQ ID NO 182
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 182
nnnnnnnnnn nnnnnnnnnn n 21

<210> SEQ ID NO 183
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 183
nnnnnnnnnn nnnnnnnnnn n 21

<210> SEQ ID NO 184
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 184
nnnnnnnnnn nnnnnnnnnn n 21

<210> SEQ ID NO 185
<211> LENGTH: 21
<212> TYPE: RNA

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 185
nnnnnnnnnn nnnnnnnnnn n                                              21

<210> SEQ ID NO 186
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 186
nnnnnnnnnn nnnnnnnnnn n                                              21

<210> SEQ ID NO 187
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 187
nnnnnnnnnn nnnnnnnnnn n                                              21

<210> SEQ ID NO 188
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 188
nnnnnnnnnn nnnnnnnnnn n                                              21

<210> SEQ ID NO 189
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 189
nnnnnnnnnn nnnnnnnnnn n 21

<210> SEQ ID NO 190
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 190
nnnnnnnnnn nnnnnnnnnn n 21

<210> SEQ ID NO 191
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 191
nnnnnnnnnn nnnnnnnnnn n 21

<210> SEQ ID NO 192
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 192
nnnnnnnnnn nnnnnnnnnn n 21

<210> SEQ ID NO 193
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 193
nnnnnnnnnn nnnnnnnnnn n 21

<210> SEQ ID NO 194
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 194
nnnnnnnnnn nnnnnnnnnn n 21

<210> SEQ ID NO 195
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 195
nnnnnnnnnn nnnnnnnnnn n 21

<210> SEQ ID NO 196
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 196
nnnnnnnnnn nnnnnnnnnn n 21

<210> SEQ ID NO 197
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified based on a propane-1,2,3-tri-yl-trisoxy structure

<400> SEQUENCE: 197
nnnnnnnnnn nnnnnnnnnn n 21

<210> SEQ ID NO 198
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 198
nnnnnnnnnn nnnnnnnnnn n 21

<210> SEQ ID NO 199
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 199
nnnnnnnnnn nnnnnnnnnn n 21

<210> SEQ ID NO 200
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 200
nnnnnnnnnn nnnnnnnnnn n 21

<210> SEQ ID NO 201
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 201
nnnnnnnnnn nnnnnnnnnn n 21

<210> SEQ ID NO 202
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 202
nnnnnnnnnn nnnnnnnnnn n 21

<210> SEQ ID NO 203
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 203
nnnnnnnnnn nnnnnnnnnn n 21

<210> SEQ ID NO 204
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 204
nnnnnnnnnn nnnnnnnnnn n 21

<210> SEQ ID NO 205
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 205
nnnnnnnnnn nnnnnnnnnn n 21

<210> SEQ ID NO 206
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 206
nnnnnnnnnn nnnnnnnnnn n 21

<210> SEQ ID NO 207
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 207
nnnnnnnnnn nnnnnnnnnn n 21

<210> SEQ ID NO 208
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 208
nnnnnnnnnn nnnnnnnnnn n 21

<210> SEQ ID NO 209
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 209
nnnnnnnnnn nnnnnnnnnn n 21

<210> SEQ ID NO 210
<211> LENGTH: 21

<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 210
nnnnnnnnnn nnnnnnnnnn n 21

<210> SEQ ID NO 211
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 211
nnnnnnnnnn nnnnnnnnnn n 21

<210> SEQ ID NO 212
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 212
nnnnnnnnnn nnnnnnnnnn n 21

<210> SEQ ID NO 213
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 213
nnnnnnnnnn nnnnnnnnnn n 21

<210> SEQ ID NO 214
<211> LENGTH: 21
<212> TYPE: RNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 214

nnnnnnnnnn nnnnnnnnnn n                                              21


<210> SEQ ID NO 215
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 215

nnnnnnnnnn nnnnnnnnnn n                                              21


<210> SEQ ID NO 216
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 216

nnnnnnnnnn nnnnnnnnnn n                                              21


<210> SEQ ID NO 217
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 217

nnnnnnnnnn nnnnnnnnnn n                                              21


<210> SEQ ID NO 218
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 218

nnnnnnnnnn nnnnnnnnnn n                                              21


<210> SEQ ID NO 219
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 219

nnnnnnnnnn nnnnnnnnnn n                                              21


<210> SEQ ID NO 220
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 220

nnnnnnnnnn nnnnnnnnnn n                                              21


<210> SEQ ID NO 221
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 221

nnnnnnnnnn nnnnnnnnnn n                                              21


<210> SEQ ID NO 222
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
```

chemically-modified nucleotide; may or may not be modified
based on a propane-1,2,3-tri-yl-trisoxy structure

<400> SEQUENCE: 222
nnnnnnnnnn nnnnnnnnnn n 21

<210> SEQ ID NO 223
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 223
nnnnnnnnnn nnnnnnnnnn n 21

<210> SEQ ID NO 224
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 224
nnnnnnnnnn nnnnnnnnnn n 21

<210> SEQ ID NO 225
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 225
nnnnnnnnnn nnnnnnnnnn n 21

<210> SEQ ID NO 226
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: Any natural, non-natural, modified, or
chemically-modified nucleotide; may or may not be modified
based on a propane-1,2,3-tri-yl-trisoxy structure

<400> SEQUENCE: 226
nnnnnnnnnn nnnnnnnnnn n 21

<210> SEQ ID NO 227
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 227
nnnnnnnnnn nnnnnnnnnn n 21

<210> SEQ ID NO 228
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 228
nnnnnnnnnn nnnnnnnnnn n 21

<210> SEQ ID NO 229
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 229
nnnnnnnnnn nnnnnnnnnn n 21

<210> SEQ ID NO 230
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: Any natural, non-natural, modified, or chemically-modified nucleotide; may or may not be modified based on a propane-1,2,3-tri-yl-trisoxy structure

<400> SEQUENCE: 230
nnnnnnnnnn nnnnnnnnnn n 21

<210> SEQ ID NO 231
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 231
nnnnnnnnnn nnnnnnnnnn n 21

<210> SEQ ID NO 232
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 232
nnnnnnnnnn nnnnnnnnnn n 21

<210> SEQ ID NO 233
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 233
nnnnnnnnnn nnnnnnnnnn n 21

<210> SEQ ID NO 234
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 234
nnnnnnnnnn nnnnnnnnnn n 21

<210> SEQ ID NO 235

<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 235
nnnnnnnnnn nnnnnnnnnn n 21

<210> SEQ ID NO 236
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 236
nnnnnnnnnn nnnnnnnnnn n 21

<210> SEQ ID NO 237
<211> LENGTH: 19
<212> TYPE: RNA
<213> ORGANISM: Hepatitis B virus

<400> SEQUENCE: 237
cgcaccucuc uuuacgcgg 19

<210> SEQ ID NO 238
<211> LENGTH: 19
<212> TYPE: RNA
<213> ORGANISM: Hepatitis B virus

<400> SEQUENCE: 238
gacucguggu ggacuucuc 19

<210> SEQ ID NO 239
<211> LENGTH: 19
<212> TYPE: RNA
<213> ORGANISM: Hepatitis B virus

<400> SEQUENCE: 239
ucguggugga cuucucuca 19

<210> SEQ ID NO 240
<211> LENGTH: 19
<212> TYPE: RNA
<213> ORGANISM: Hepatitis B virus

<400> SEQUENCE: 240
uggauguguc ugcggcguu 19

<210> SEQ ID NO 241
<211> LENGTH: 19

<212> TYPE: RNA
<213> ORGANISM: Hepatitis B virus

<400> SEQUENCE: 241
ccgugugcac uucgcuuca 19

<210> SEQ ID NO 242
<211> LENGTH: 19
<212> TYPE: RNA
<213> ORGANISM: Hepatitis B virus

<400> SEQUENCE: 242
gugugcacuu cgcuucacc 19

<210> SEQ ID NO 243
<211> LENGTH: 19
<212> TYPE: RNA
<213> ORGANISM: Hepatitis B virus

<400> SEQUENCE: 243
ugugcacuuc gcuucaccu 19

<210> SEQ ID NO 244
<211> LENGTH: 19
<212> TYPE: RNA
<213> ORGANISM: Hepatitis B virus

<400> SEQUENCE: 244
gugcacuucg cuucaccuc 19

<210> SEQ ID NO 245
<211> LENGTH: 19
<212> TYPE: RNA
<213> ORGANISM: Hepatitis B virus

<400> SEQUENCE: 245
gcacuucgcu ucaccucug 19

<210> SEQ ID NO 246
<211> LENGTH: 19
<212> TYPE: RNA
<213> ORGANISM: Hepatitis B virus

<400> SEQUENCE: 246
uucaagccuc caagcugug 19

<210> SEQ ID NO 247
<211> LENGTH: 19
<212> TYPE: RNA
<213> ORGANISM: Hepatitis B virus

<400> SEQUENCE: 247
ucaagccucc aagcugugc 19

<210> SEQ ID NO 248
<211> LENGTH: 19
<212> TYPE: RNA
<213> ORGANISM: Hepatitis B virus

<400> SEQUENCE: 248
caagccucca agcugugcc 19

<210> SEQ ID NO 249

<211> LENGTH: 19
<212> TYPE: RNA
<213> ORGANISM: Hepatitis B virus

<400> SEQUENCE: 249
aagccuccaa gcugugccu 19

<210> SEQ ID NO 250
<211> LENGTH: 19
<212> TYPE: RNA
<213> ORGANISM: Hepatitis B virus

<400> SEQUENCE: 250
ucuagacucg ugguggacu 19

<210> SEQ ID NO 251
<211> LENGTH: 19
<212> TYPE: RNA
<213> ORGANISM: Hepatitis B virus

<400> SEQUENCE: 251
cuagacucgu gguggacuu 19

<210> SEQ ID NO 252
<211> LENGTH: 19
<212> TYPE: RNA
<213> ORGANISM: Hepatitis B virus

<400> SEQUENCE: 252
uagacucgug guggacuuc 19

<210> SEQ ID NO 253
<211> LENGTH: 19
<212> TYPE: RNA
<213> ORGANISM: Hepatitis B virus

<400> SEQUENCE: 253
agacucgugg uggacuucu 19

<210> SEQ ID NO 254
<211> LENGTH: 19
<212> TYPE: RNA
<213> ORGANISM: Hepatitis B virus

<400> SEQUENCE: 254
gaugugucug cggcguuuu 19

<210> SEQ ID NO 255
<211> LENGTH: 19
<212> TYPE: RNA
<213> ORGANISM: Hepatitis B virus

<400> SEQUENCE: 255
ugugucugcg gcguuuuau 19

<210> SEQ ID NO 256
<211> LENGTH: 19
<212> TYPE: RNA
<213> ORGANISM: Hepatitis B virus

<400> SEQUENCE: 256
ugucugcggc guuuuauca 19

<210> SEQ ID NO 257
<211> LENGTH: 19
<212> TYPE: RNA
<213> ORGANISM: Hepatitis B virus

<400> SEQUENCE: 257
ggaggcugua ggcauaaau 19

<210> SEQ ID NO 258
<211> LENGTH: 19
<212> TYPE: RNA
<213> ORGANISM: Hepatitis B virus

<400> SEQUENCE: 258
gaggcuguag gcauaaauu 19

<210> SEQ ID NO 259
<211> LENGTH: 19
<212> TYPE: RNA
<213> ORGANISM: Hepatitis B virus

<400> SEQUENCE: 259
ggcuguaggc auaaauugg 19

<210> SEQ ID NO 260
<211> LENGTH: 19
<212> TYPE: RNA
<213> ORGANISM: Hepatitis B virus

<400> SEQUENCE: 260
gcuguaggca uaaauuggu 19

<210> SEQ ID NO 261
<211> LENGTH: 19
<212> TYPE: RNA
<213> ORGANISM: Hepatitis B virus

<400> SEQUENCE: 261
aacuuuuuca ccucugccu 19

<210> SEQ ID NO 262
<211> LENGTH: 19
<212> TYPE: RNA
<213> ORGANISM: Hepatitis B virus

<400> SEQUENCE: 262
gagucuagac ucguggugg 19

<210> SEQ ID NO 263
<211> LENGTH: 19
<212> TYPE: RNA
<213> ORGANISM: Hepatitis B virus

<400> SEQUENCE: 263
agucuagacu cguggugga 19

<210> SEQ ID NO 264
<211> LENGTH: 19
<212> TYPE: RNA
<213> ORGANISM: Hepatitis B virus

<400> SEQUENCE: 264
gucuagacuc gugguggac 19

<210> SEQ ID NO 265
<211> LENGTH: 19
<212> TYPE: RNA
<213> ORGANISM: Hepatitis B virus

<400> SEQUENCE: 265
cauccugcug cuaugccuc 19

<210> SEQ ID NO 266
<211> LENGTH: 19
<212> TYPE: RNA
<213> ORGANISM: Hepatitis B virus

<400> SEQUENCE: 266
uccugcugcu augccucau 19

<210> SEQ ID NO 267
<211> LENGTH: 19
<212> TYPE: RNA
<213> ORGANISM: Hepatitis B virus

<400> SEQUENCE: 267
ccugcugcua ugccucauc 19

<210> SEQ ID NO 268
<211> LENGTH: 19
<212> TYPE: RNA
<213> ORGANISM: Hepatitis B virus

<400> SEQUENCE: 268
cugcugcuau gccucaucu 19

<210> SEQ ID NO 269
<211> LENGTH: 19
<212> TYPE: RNA
<213> ORGANISM: Hepatitis B virus

<400> SEQUENCE: 269
ugcugcuaug ccucaucuu 19

<210> SEQ ID NO 270
<211> LENGTH: 19
<212> TYPE: RNA
<213> ORGANISM: Hepatitis B virus

<400> SEQUENCE: 270
cuguaggcau aaauugguc 19

<210> SEQ ID NO 271
<211> LENGTH: 19
<212> TYPE: RNA
<213> ORGANISM: Hepatitis B virus

<400> SEQUENCE: 271
uguaggcaua aauuggucu 19

<210> SEQ ID NO 272
<211> LENGTH: 19
<212> TYPE: RNA
<213> ORGANISM: Hepatitis B virus

<400> SEQUENCE: 272
acucguggug gacuucucu 19

```
<210> SEQ ID NO 273
<211> LENGTH: 19
<212> TYPE: RNA
<213> ORGANISM: Hepatitis B virus

<400> SEQUENCE: 273

cucguggugg acuucucuc                                                    19

<210> SEQ ID NO 274
<211> LENGTH: 19
<212> TYPE: RNA
<213> ORGANISM: Hepatitis B virus

<400> SEQUENCE: 274

cgugugcacu ucgcuucac                                                    19

<210> SEQ ID NO 275
<211> LENGTH: 19
<212> TYPE: RNA
<213> ORGANISM: Hepatitis B virus

<400> SEQUENCE: 275

ugcacuucgc uucaccucu                                                    19

<210> SEQ ID NO 276
<211> LENGTH: 19
<212> TYPE: RNA
<213> ORGANISM: Hepatitis B virus

<400> SEQUENCE: 276

cacuucgcuu caccucugc                                                    19

<210> SEQ ID NO 277
<211> LENGTH: 19
<212> TYPE: RNA
<213> ORGANISM: Hepatitis B virus

<400> SEQUENCE: 277

acuucgcuuc accucugca                                                    19

<210> SEQ ID NO 278
<211> LENGTH: 19
<212> TYPE: RNA
<213> ORGANISM: Hepatitis B virus

<400> SEQUENCE: 278

agccuccaag cugugccuu                                                    19

<210> SEQ ID NO 279
<211> LENGTH: 19
<212> TYPE: RNA
<213> ORGANISM: Hepatitis B virus

<400> SEQUENCE: 279

gccuccaagc ugugccuug                                                    19

<210> SEQ ID NO 280
<211> LENGTH: 19
<212> TYPE: RNA
<213> ORGANISM: Hepatitis B virus

<400> SEQUENCE: 280
```

gaacucccuc gccucgcag 19

<210> SEQ ID NO 281
<211> LENGTH: 19
<212> TYPE: RNA
<213> ORGANISM: Hepatitis B virus

<400> SEQUENCE: 281
aacucccucg ccucgcaga 19

<210> SEQ ID NO 282
<211> LENGTH: 19
<212> TYPE: RNA
<213> ORGANISM: Hepatitis B virus

<400> SEQUENCE: 282
acucccucgc cucgcagac 19

<210> SEQ ID NO 283
<211> LENGTH: 19
<212> TYPE: RNA
<213> ORGANISM: Hepatitis B virus

<400> SEQUENCE: 283
cucccucgcc ucgcagacg 19

<210> SEQ ID NO 284
<211> LENGTH: 19
<212> TYPE: RNA
<213> ORGANISM: Hepatitis B virus

<400> SEQUENCE: 284
ccugcuggug gcuccaguu 19

<210> SEQ ID NO 285
<211> LENGTH: 19
<212> TYPE: RNA
<213> ORGANISM: Hepatitis B virus

<400> SEQUENCE: 285
cugcuggugg cuccaguuc 19

<210> SEQ ID NO 286
<211> LENGTH: 19
<212> TYPE: RNA
<213> ORGANISM: Hepatitis B virus

<400> SEQUENCE: 286 ggauguguc u gcggcguuu 19

<210> SEQ ID NO 287
<211> LENGTH: 19
<212> TYPE: RNA
<213> ORGANISM: Hepatitis B virus

<400> SEQUENCE: 287
augugucugc ggcguuuua 19

<210> SEQ ID NO 288
<211> LENGTH: 19
<212> TYPE: RNA
<213> ORGANISM: Hepatitis B virus

<400> SEQUENCE: 288
gugucugcgg cguuuuauc 19

<210> SEQ ID NO 289
<211> LENGTH: 19
<212> TYPE: RNA
<213> ORGANISM: Hepatitis B virus

<400> SEQUENCE: 289
gucugcggcg uuuuaucau 19

<210> SEQ ID NO 290
<211> LENGTH: 19
<212> TYPE: RNA
<213> ORGANISM: Hepatitis B virus

<400> SEQUENCE: 290
ccuaugggag ugggccuca 19

<210> SEQ ID NO 291
<211> LENGTH: 19
<212> TYPE: RNA
<213> ORGANISM: Hepatitis B virus

<400> SEQUENCE: 291
cuaugggagu gggccucag 19

<210> SEQ ID NO 292
<211> LENGTH: 19
<212> TYPE: RNA
<213> ORGANISM: Hepatitis B virus

<400> SEQUENCE: 292
cuucgcuuca ccucugcac 19

<210> SEQ ID NO 293
<211> LENGTH: 19
<212> TYPE: RNA
<213> ORGANISM: Hepatitis B virus

<400> SEQUENCE: 293
uucgcuucac cucugcacg 19

<210> SEQ ID NO 294
<211> LENGTH: 19
<212> TYPE: RNA
<213> ORGANISM: Hepatitis B virus

<400> SEQUENCE: 294
ucgcuucacc ucugcacgu 19

<210> SEQ ID NO 295
<211> LENGTH: 19
<212> TYPE: RNA
<213> ORGANISM: Hepatitis B virus

<400> SEQUENCE: 295
aggcuguagg cauaaauug 19

<210> SEQ ID NO 296
<211> LENGTH: 19
<212> TYPE: RNA
<213> ORGANISM: Hepatitis B virus

<400> SEQUENCE: 296
acuuuuucac cucugccua 19

<210> SEQ ID NO 297
<211> LENGTH: 19
<212> TYPE: RNA
<213> ORGANISM: Hepatitis B virus

<400> SEQUENCE: 297
auccugcugc uaugccuca 19

<210> SEQ ID NO 298
<211> LENGTH: 19
<212> TYPE: RNA
<213> ORGANISM: Hepatitis B virus

<400> SEQUENCE: 298
gcugcuaugc cucaucuuc 19

<210> SEQ ID NO 299
<211> LENGTH: 19
<212> TYPE: RNA
<213> ORGANISM: Hepatitis B virus

<400> SEQUENCE: 299
cugcuaugcc ucaucuucu 19

<210> SEQ ID NO 300
<211> LENGTH: 19
<212> TYPE: RNA
<213> ORGANISM: Hepatitis B virus

<400> SEQUENCE: 300
ugcuaugccu caucuucuu 19

<210> SEQ ID NO 301
<211> LENGTH: 19
<212> TYPE: RNA
<213> ORGANISM: Hepatitis B virus

<400> SEQUENCE: 301
guaggcauaa auuggucug 19

<210> SEQ ID NO 302
<211> LENGTH: 19
<212> TYPE: RNA
<213> ORGANISM: Hepatitis B virus

<400> SEQUENCE: 302
ccuccaagcu gugccuugg 19

<210> SEQ ID NO 303
<211> LENGTH: 19
<212> TYPE: RNA
<213> ORGANISM: Hepatitis B virus

<400> SEQUENCE: 303
cgugguggac uucucucaa 19

<210> SEQ ID NO 304
<211> LENGTH: 19
<212> TYPE: RNA
<213> ORGANISM: Hepatitis B virus

<400> SEQUENCE: 304
gugguggacu ucucucaau 19

<210> SEQ ID NO 305
<211> LENGTH: 19
<212> TYPE: RNA
<213> ORGANISM: Hepatitis B virus

<400> SEQUENCE: 305
ugguggacuu cucucaauu 19

<210> SEQ ID NO 306
<211> LENGTH: 19
<212> TYPE: RNA
<213> ORGANISM: Hepatitis B virus

<400> SEQUENCE: 306
gguggacuuc ucucaauuu 19

<210> SEQ ID NO 307
<211> LENGTH: 19
<212> TYPE: RNA
<213> ORGANISM: Hepatitis B virus

<400> SEQUENCE: 307
guggacuucu cucaauuuu 19

<210> SEQ ID NO 308
<211> LENGTH: 19
<212> TYPE: RNA
<213> ORGANISM: Hepatitis B virus

<400> SEQUENCE: 308
uggacuucuc ucaauuuuc 19

<210> SEQ ID NO 309
<211> LENGTH: 19
<212> TYPE: RNA
<213> ORGANISM: Hepatitis B virus

<400> SEQUENCE: 309
gacuucucuc aauuuucua 19

<210> SEQ ID NO 310
<211> LENGTH: 19
<212> TYPE: RNA
<213> ORGANISM: Hepatitis B virus

<400> SEQUENCE: 310
acuucucuca auuuucuag 19

<210> SEQ ID NO 311
<211> LENGTH: 19
<212> TYPE: RNA
<213> ORGANISM: Hepatitis B virus

<400> SEQUENCE: 311
cuucucucaa uuuucuagg 19

<210> SEQ ID NO 312
<211> LENGTH: 19
<212> TYPE: RNA

<213> ORGANISM: Hepatitis B virus

<400> SEQUENCE: 312
uucucucaau uuucuaggg 19

<210> SEQ ID NO 313
<211> LENGTH: 19
<212> TYPE: RNA
<213> ORGANISM: Hepatitis B virus

<400> SEQUENCE: 313
ucucucaauu uucuagggg 19

<210> SEQ ID NO 314
<211> LENGTH: 19
<212> TYPE: RNA
<213> ORGANISM: Hepatitis B virus

<400> SEQUENCE: 314
auccauacug cggaacucc 19

<210> SEQ ID NO 315
<211> LENGTH: 19
<212> TYPE: RNA
<213> ORGANISM: Hepatitis B virus

<400> SEQUENCE: 315
uccauacugc ggaacuccu 19

<210> SEQ ID NO 316
<211> LENGTH: 19
<212> TYPE: RNA
<213> ORGANISM: Hepatitis B virus

<400> SEQUENCE: 316
gaagaagaac ucccucgcc 19

<210> SEQ ID NO 317
<211> LENGTH: 19
<212> TYPE: RNA
<213> ORGANISM: Hepatitis B virus

<400> SEQUENCE: 317
aagaagaacu cccucgccu 19

<210> SEQ ID NO 318
<211> LENGTH: 19
<212> TYPE: RNA
<213> ORGANISM: Hepatitis B virus

<400> SEQUENCE: 318
agaagaacuc ccucgccuc 19

<210> SEQ ID NO 319
<211> LENGTH: 19
<212> TYPE: RNA
<213> ORGANISM: Hepatitis B virus

<400> SEQUENCE: 319
gaagaacucc cucgccucg 19

<210> SEQ ID NO 320
<211> LENGTH: 19

<212> TYPE: RNA
<213> ORGANISM: Hepatitis B virus

<400> SEQUENCE: 320
aagaacuccc ucgccucgc 19

<210> SEQ ID NO 321
<211> LENGTH: 19
<212> TYPE: RNA
<213> ORGANISM: Hepatitis B virus

<400> SEQUENCE: 321
agaacucccu cgccucgca 19

<210> SEQ ID NO 322
<211> LENGTH: 19
<212> TYPE: RNA
<213> ORGANISM: Hepatitis B virus

<400> SEQUENCE: 322
agagucuaga cucguggug 19

<210> SEQ ID NO 323
<211> LENGTH: 19
<212> TYPE: RNA
<213> ORGANISM: Hepatitis B virus

<400> SEQUENCE: 323
ggacuucucu caauuuucu 19

<210> SEQ ID NO 324
<211> LENGTH: 19
<212> TYPE: RNA
<213> ORGANISM: Hepatitis B virus

<400> SEQUENCE: 324
gauccauacu gcggaacuc 19

<210> SEQ ID NO 325
<211> LENGTH: 19
<212> TYPE: RNA
<213> ORGANISM: Hepatitis B virus

<400> SEQUENCE: 325
ugcaacuuuu ucaccucug 19

<210> SEQ ID NO 326
<211> LENGTH: 19
<212> TYPE: RNA
<213> ORGANISM: Hepatitis B virus

<400> SEQUENCE: 326
gcaacuuuuu caccucugc 19

<210> SEQ ID NO 327
<211> LENGTH: 19
<212> TYPE: RNA
<213> ORGANISM: Hepatitis B virus

<400> SEQUENCE: 327
caacuuuuuc accucugcc 19

<210> SEQ ID NO 328

<211> LENGTH: 19
<212> TYPE: RNA
<213> ORGANISM: Hepatitis B virus

<400> SEQUENCE: 328
uggccaaaau ucgcagucc 19

<210> SEQ ID NO 329
<211> LENGTH: 19
<212> TYPE: RNA
<213> ORGANISM: Hepatitis B virus

<400> SEQUENCE: 329
ggccaaaauu cgcaguccc 19

<210> SEQ ID NO 330
<211> LENGTH: 19
<212> TYPE: RNA
<213> ORGANISM: Hepatitis B virus

<400> SEQUENCE: 330
ccgauccaua cugcggaac 19

<210> SEQ ID NO 331
<211> LENGTH: 19
<212> TYPE: RNA
<213> ORGANISM: Hepatitis B virus

<400> SEQUENCE: 331
cgauccauac ugcggaacu 19

<210> SEQ ID NO 332
<211> LENGTH: 19
<212> TYPE: RNA
<213> ORGANISM: Hepatitis B virus

<400> SEQUENCE: 332
cuuuuucacc ucugccuaa 19

<210> SEQ ID NO 333
<211> LENGTH: 19
<212> TYPE: RNA
<213> ORGANISM: Hepatitis B virus

<400> SEQUENCE: 333
uuuuucaccu cugccuaau 19

<210> SEQ ID NO 334
<211> LENGTH: 19
<212> TYPE: RNA
<213> ORGANISM: Hepatitis B virus

<400> SEQUENCE: 334
uuuucaccuc ugccuaauc 19

<210> SEQ ID NO 335
<211> LENGTH: 19
<212> TYPE: RNA
<213> ORGANISM: Hepatitis B virus

<400> SEQUENCE: 335
uuucaccucu gccuaauca 19

```
<210> SEQ ID NO 336
<211> LENGTH: 19
<212> TYPE: RNA
<213> ORGANISM: Hepatitis B virus

<400> SEQUENCE: 336

aagcugugcc uuggguggc                                                19

<210> SEQ ID NO 337
<211> LENGTH: 19
<212> TYPE: RNA
<213> ORGANISM: Hepatitis B virus

<400> SEQUENCE: 337

agcugugccu uggguggcu                                                19

<210> SEQ ID NO 338
<211> LENGTH: 19
<212> TYPE: RNA
<213> ORGANISM: Hepatitis B virus

<400> SEQUENCE: 338

gcugugccuu ggguggcuu                                                19

<210> SEQ ID NO 339
<211> LENGTH: 19
<212> TYPE: RNA
<213> ORGANISM: Hepatitis B virus

<400> SEQUENCE: 339

cugugccuug gguggcuuu                                                19

<210> SEQ ID NO 340
<211> LENGTH: 19
<212> TYPE: RNA
<213> ORGANISM: Hepatitis B virus

<400> SEQUENCE: 340

ggagugugga uucgcacuc                                                19

<210> SEQ ID NO 341
<211> LENGTH: 19
<212> TYPE: RNA
<213> ORGANISM: Hepatitis B virus

<400> SEQUENCE: 341

gaguguggau ucgcacucc                                                19

<210> SEQ ID NO 342
<211> LENGTH: 19
<212> TYPE: RNA
<213> ORGANISM: Hepatitis B virus

<400> SEQUENCE: 342

cagagucuag acucguggu                                                19

<210> SEQ ID NO 343
<211> LENGTH: 19
<212> TYPE: RNA
<213> ORGANISM: Hepatitis B virus

<400> SEQUENCE: 343

auaagaggac ucuuggacu                                                19
```

<210> SEQ ID NO 344
<211> LENGTH: 19
<212> TYPE: RNA
<213> ORGANISM: Hepatitis B virus

<400> SEQUENCE: 344
uaggaggcug uaggcauaa 19

<210> SEQ ID NO 345
<211> LENGTH: 19
<212> TYPE: RNA
<213> ORGANISM: Hepatitis B virus

<400> SEQUENCE: 345
aggaggcugu aggcauaaa 19

<210> SEQ ID NO 346
<211> LENGTH: 19
<212> TYPE: RNA
<213> ORGANISM: Hepatitis B virus

<400> SEQUENCE: 346
caugcaacuu uuucaccuc 19

<210> SEQ ID NO 347
<211> LENGTH: 19
<212> TYPE: RNA
<213> ORGANISM: Hepatitis B virus

<400> SEQUENCE: 347
augcaacuuu uucaccucu 19

<210> SEQ ID NO 348
<211> LENGTH: 19
<212> TYPE: RNA
<213> ORGANISM: Hepatitis B virus

<400> SEQUENCE: 348
uucaccucug ccuaaucau 19

<210> SEQ ID NO 349
<211> LENGTH: 19
<212> TYPE: RNA
<213> ORGANISM: Hepatitis B virus

<400> SEQUENCE: 349
ucaccucugc cuaaucauc 19

<210> SEQ ID NO 350
<211> LENGTH: 19
<212> TYPE: RNA
<213> ORGANISM: Hepatitis B virus

<400> SEQUENCE: 350
caccucugcc uaaucaucu 19

<210> SEQ ID NO 351
<211> LENGTH: 19
<212> TYPE: RNA
<213> ORGANISM: Hepatitis B virus

<400> SEQUENCE: 351
cuccaagcug ugccuuggg 19

-continued

<210> SEQ ID NO 352
<211> LENGTH: 19
<212> TYPE: RNA
<213> ORGANISM: Hepatitis B virus

<400> SEQUENCE: 352
uccaagcugu gccuugggu 19

<210> SEQ ID NO 353
<211> LENGTH: 19
<212> TYPE: RNA
<213> ORGANISM: Hepatitis B virus

<400> SEQUENCE: 353
ccaagcugug ccuugggug 19

<210> SEQ ID NO 354
<211> LENGTH: 19
<212> TYPE: RNA
<213> ORGANISM: Hepatitis B virus

<400> SEQUENCE: 354
caagcugugc cuugggugg 19

<210> SEQ ID NO 355
<211> LENGTH: 19
<212> TYPE: RNA
<213> ORGANISM: Hepatitis B virus

<400> SEQUENCE: 355
cuagaagaag aacucccuc 19

<210> SEQ ID NO 356
<211> LENGTH: 19
<212> TYPE: RNA
<213> ORGANISM: Hepatitis B virus

<400> SEQUENCE: 356
uagaagaaga acucccucg 19

<210> SEQ ID NO 357
<211> LENGTH: 19
<212> TYPE: RNA
<213> ORGANISM: Hepatitis B virus

<400> SEQUENCE: 357
agaagaagaa cucccucgc 19

<210> SEQ ID NO 358
<211> LENGTH: 19
<212> TYPE: RNA
<213> ORGANISM: Hepatitis B virus

<400> SEQUENCE: 358
guucaagccu ccaagcugu 19

<210> SEQ ID NO 359
<211> LENGTH: 19
<212> TYPE: RNA
<213> ORGANISM: Hepatitis B virus

<400> SEQUENCE: 359
agaccaccaa augccccua 19

<210> SEQ ID NO 360
<211> LENGTH: 19
<212> TYPE: RNA
<213> ORGANISM: Hepatitis B virus

<400> SEQUENCE: 360
gaccaccaaa ugccccuau 19

<210> SEQ ID NO 361
<211> LENGTH: 19
<212> TYPE: RNA
<213> ORGANISM: Hepatitis B virus

<400> SEQUENCE: 361
accaccaaau gccccuauc 19

<210> SEQ ID NO 362
<211> LENGTH: 19
<212> TYPE: RNA
<213> ORGANISM: Hepatitis B virus

<400> SEQUENCE: 362
uguauuccca ucccaucau 19

<210> SEQ ID NO 363
<211> LENGTH: 19
<212> TYPE: RNA
<213> ORGANISM: Hepatitis B virus

<400> SEQUENCE: 363
guauucccau cccaucauc 19

<210> SEQ ID NO 364
<211> LENGTH: 19
<212> TYPE: RNA
<213> ORGANISM: Hepatitis B virus

<400> SEQUENCE: 364
cguagggcuu ucccccacu 19

<210> SEQ ID NO 365
<211> LENGTH: 19
<212> TYPE: RNA
<213> ORGANISM: Hepatitis B virus

<400> SEQUENCE: 365
guagggcuuu cccccacug 19

<210> SEQ ID NO 366
<211> LENGTH: 19
<212> TYPE: RNA
<213> ORGANISM: Hepatitis B virus

<400> SEQUENCE: 366
uagggcuuuc ccccacugu 19

<210> SEQ ID NO 367
<211> LENGTH: 19
<212> TYPE: RNA
<213> ORGANISM: Hepatitis B virus

<400> SEQUENCE: 367
ugccgaucca uacugcgga 19

<210> SEQ ID NO 368
<211> LENGTH: 19
<212> TYPE: RNA
<213> ORGANISM: Hepatitis B virus

<400> SEQUENCE: 368
gccgauccau acugcggaa 19

<210> SEQ ID NO 369
<211> LENGTH: 19
<212> TYPE: RNA
<213> ORGANISM: Hepatitis B virus

<400> SEQUENCE: 369
cacggggcgc accucucuu 19

<210> SEQ ID NO 370
<211> LENGTH: 19
<212> TYPE: RNA
<213> ORGANISM: Hepatitis B virus

<400> SEQUENCE: 370
acggggcgca ccucucuuu 19

<210> SEQ ID NO 371
<211> LENGTH: 19
<212> TYPE: RNA
<213> ORGANISM: Hepatitis B virus

<400> SEQUENCE: 371
cggggcgcac cucucuuua 19

<210> SEQ ID NO 372
<211> LENGTH: 19
<212> TYPE: RNA
<213> ORGANISM: Hepatitis B virus

<400> SEQUENCE: 372
ggggcgcacc ucucuuuac 19

<210> SEQ ID NO 373
<211> LENGTH: 19
<212> TYPE: RNA
<213> ORGANISM: Hepatitis B virus

<400> SEQUENCE: 373
gggcgcaccu cucuuuacg 19

<210> SEQ ID NO 374
<211> LENGTH: 19
<212> TYPE: RNA
<213> ORGANISM: Hepatitis B virus

<400> SEQUENCE: 374
ggcgcaccuc ucuuuacgc 19

<210> SEQ ID NO 375
<211> LENGTH: 19
<212> TYPE: RNA
<213> ORGANISM: Hepatitis B virus

<400> SEQUENCE: 375
gcgcaccucu cuuuacgcg 19

<210> SEQ ID NO 376
<211> LENGTH: 19
<212> TYPE: RNA
<213> ORGANISM: Hepatitis B virus

<400> SEQUENCE: 376
acuguucaag ccuccaagc 19

<210> SEQ ID NO 377
<211> LENGTH: 19
<212> TYPE: RNA
<213> ORGANISM: Hepatitis B virus

<400> SEQUENCE: 377
cuguucaagc cuccaagcu 19

<210> SEQ ID NO 378
<211> LENGTH: 19
<212> TYPE: RNA
<213> ORGANISM: Hepatitis B virus

<400> SEQUENCE: 378
uguucaagcc uccaagcug 19

<210> SEQ ID NO 379
<211> LENGTH: 19
<212> TYPE: RNA
<213> ORGANISM: Hepatitis B virus

<400> SEQUENCE: 379
guauguugcc cguuugucc 19

<210> SEQ ID NO 380
<211> LENGTH: 19
<212> TYPE: RNA
<213> ORGANISM: Hepatitis B virus

<400> SEQUENCE: 380
uauguugccc guuuguccu 19

<210> SEQ ID NO 381
<211> LENGTH: 19
<212> TYPE: RNA
<213> ORGANISM: Hepatitis B virus

<400> SEQUENCE: 381
uguugcccgu uuguccucu 19

<210> SEQ ID NO 382
<211> LENGTH: 19
<212> TYPE: RNA
<213> ORGANISM: Hepatitis B virus

<400> SEQUENCE: 382
ugaaccuuua ccccguugc 19

<210> SEQ ID NO 383
<211> LENGTH: 19
<212> TYPE: RNA
<213> ORGANISM: Hepatitis B virus

<400> SEQUENCE: 383
ccauacugcg gaacuccua 19

<210> SEQ ID NO 384
<211> LENGTH: 19
<212> TYPE: RNA
<213> ORGANISM: Hepatitis B virus

<400> SEQUENCE: 384
cauacugcgg aacuccuag 19

<210> SEQ ID NO 385
<211> LENGTH: 19
<212> TYPE: RNA
<213> ORGANISM: Hepatitis B virus

<400> SEQUENCE: 385
auacugcgga acuccuagc 19

<210> SEQ ID NO 386
<211> LENGTH: 19
<212> TYPE: RNA
<213> ORGANISM: Hepatitis B virus

<400> SEQUENCE: 386
ccacggggcg caccucucu 19

<210> SEQ ID NO 387
<211> LENGTH: 19
<212> TYPE: RNA
<213> ORGANISM: Hepatitis B virus

<400> SEQUENCE: 387
cccuagaaga agaacuccc 19

<210> SEQ ID NO 388
<211> LENGTH: 19
<212> TYPE: RNA
<213> ORGANISM: Hepatitis B virus

<400> SEQUENCE: 388
ccuagaagaa gaacucccu 19

<210> SEQ ID NO 389
<211> LENGTH: 19
<212> TYPE: RNA
<213> ORGANISM: Hepatitis B virus

<400> SEQUENCE: 389
ucccucgccu cgcagacga 19

<210> SEQ ID NO 390
<211> LENGTH: 19
<212> TYPE: RNA
<213> ORGANISM: Hepatitis B virus

<400> SEQUENCE: 390
uuccucuuca uccugcugc 19

<210> SEQ ID NO 391
<211> LENGTH: 19
<212> TYPE: RNA

<213> ORGANISM: Hepatitis B virus

<400> SEQUENCE: 391
uccucuucau ccugcugcu 19

<210> SEQ ID NO 392
<211> LENGTH: 19
<212> TYPE: RNA
<213> ORGANISM: Hepatitis B virus

<400> SEQUENCE: 392
ccucuucauc cugcugcua 19

<210> SEQ ID NO 393
<211> LENGTH: 19
<212> TYPE: RNA
<213> ORGANISM: Hepatitis B virus

<400> SEQUENCE: 393
cucuucaucc ugcugcuau 19

<210> SEQ ID NO 394
<211> LENGTH: 19
<212> TYPE: RNA
<213> ORGANISM: Hepatitis B virus

<400> SEQUENCE: 394
ucuucauccu gcugcuaug 19

<210> SEQ ID NO 395
<211> LENGTH: 19
<212> TYPE: RNA
<213> ORGANISM: Hepatitis B virus

<400> SEQUENCE: 395
cuucauccug cugcuaugc 19

<210> SEQ ID NO 396
<211> LENGTH: 19
<212> TYPE: RNA
<213> ORGANISM: Hepatitis B virus

<400> SEQUENCE: 396
uucauccugc ugcuaugcc 19

<210> SEQ ID NO 397
<211> LENGTH: 19
<212> TYPE: RNA
<213> ORGANISM: Hepatitis B virus

<400> SEQUENCE: 397
ucauccugcu gcuaugccu 19

<210> SEQ ID NO 398
<211> LENGTH: 19
<212> TYPE: RNA
<213> ORGANISM: Hepatitis B virus

<400> SEQUENCE: 398
gguauguugc ccguuuguc 19

<210> SEQ ID NO 399
<211> LENGTH: 19

<212> TYPE: RNA
<213> ORGANISM: Hepatitis B virus

<400> SEQUENCE: 399
auguugcccg uuuguccuc 19

<210> SEQ ID NO 400
<211> LENGTH: 19
<212> TYPE: RNA
<213> ORGANISM: Hepatitis B virus

<400> SEQUENCE: 400
uacgucccgu cggcgcuga 19

<210> SEQ ID NO 401
<211> LENGTH: 19
<212> TYPE: RNA
<213> ORGANISM: Hepatitis B virus

<400> SEQUENCE: 401
acgucccguc ggcgcugaa 19

<210> SEQ ID NO 402
<211> LENGTH: 19
<212> TYPE: RNA
<213> ORGANISM: Hepatitis B virus

<400> SEQUENCE: 402
cgucccgucg gcgcugaau 19

<210> SEQ ID NO 403
<211> LENGTH: 19
<212> TYPE: RNA
<213> ORGANISM: Hepatitis B virus

<400> SEQUENCE: 403
gucccgucgg cgcugaauc 19

<210> SEQ ID NO 404
<211> LENGTH: 19
<212> TYPE: RNA
<213> ORGANISM: Hepatitis B virus

<400> SEQUENCE: 404
ucccgucggc gcugaaucc 19

<210> SEQ ID NO 405
<211> LENGTH: 19
<212> TYPE: RNA
<213> ORGANISM: Hepatitis B virus

<400> SEQUENCE: 405
aguguggauu cgcacuccu 19

<210> SEQ ID NO 406
<211> LENGTH: 19
<212> TYPE: RNA
<213> ORGANISM: Hepatitis B virus

<400> SEQUENCE: 406
ccccuagaag aagaacucc 19

<210> SEQ ID NO 407

<211> LENGTH: 19
<212> TYPE: RNA
<213> ORGANISM: Hepatitis B virus

<400> SEQUENCE: 407
caagguaugu ugcccguuu 19

<210> SEQ ID NO 408
<211> LENGTH: 19
<212> TYPE: RNA
<213> ORGANISM: Hepatitis B virus

<400> SEQUENCE: 408
aagguauguu gcccguuug 19

<210> SEQ ID NO 409
<211> LENGTH: 19
<212> TYPE: RNA
<213> ORGANISM: Hepatitis B virus

<400> SEQUENCE: 409
agguauguug cccguuugu 19

<210> SEQ ID NO 410
<211> LENGTH: 19
<212> TYPE: RNA
<213> ORGANISM: Hepatitis B virus

<400> SEQUENCE: 410
ccgaccacgg ggcgcaccu 19

<210> SEQ ID NO 411
<211> LENGTH: 19
<212> TYPE: RNA
<213> ORGANISM: Hepatitis B virus

<400> SEQUENCE: 411
cgaccacggg gcgcaccuc 19

<210> SEQ ID NO 412
<211> LENGTH: 19
<212> TYPE: RNA
<213> ORGANISM: Hepatitis B virus

<400> SEQUENCE: 412
gaccacgggg cgcaccucu 19

<210> SEQ ID NO 413
<211> LENGTH: 19
<212> TYPE: RNA
<213> ORGANISM: Hepatitis B virus

<400> SEQUENCE: 413
accacggggc gcaccucuc 19

<210> SEQ ID NO 414
<211> LENGTH: 19
<212> TYPE: RNA
<213> ORGANISM: Hepatitis B virus

<400> SEQUENCE: 414
cuccccgucu gugccuucu 19

<210> SEQ ID NO 415
<211> LENGTH: 19
<212> TYPE: RNA
<213> ORGANISM: Hepatitis B virus

<400> SEQUENCE: 415
uccccgucug ugccuucuc 19

<210> SEQ ID NO 416
<211> LENGTH: 19
<212> TYPE: RNA
<213> ORGANISM: Hepatitis B virus

<400> SEQUENCE: 416
ccgcgucgca gaagaucuc 19

<210> SEQ ID NO 417
<211> LENGTH: 19
<212> TYPE: RNA
<213> ORGANISM: Hepatitis B virus

<400> SEQUENCE: 417
cgcgucgcag aagaucuca 19

<210> SEQ ID NO 418
<211> LENGTH: 19
<212> TYPE: RNA
<213> ORGANISM: Hepatitis B virus

<400> SEQUENCE: 418
gcgucgcaga agaucucaa 19

<210> SEQ ID NO 419
<211> LENGTH: 19
<212> TYPE: RNA
<213> ORGANISM: Hepatitis B virus

<400> SEQUENCE: 419
cgucgcagaa gaucucaau 19

<210> SEQ ID NO 420
<211> LENGTH: 19
<212> TYPE: RNA
<213> ORGANISM: Hepatitis B virus

<400> SEQUENCE: 420
gucgcagaag aucucaauc 19

<210> SEQ ID NO 421
<211> LENGTH: 19
<212> TYPE: RNA
<213> ORGANISM: Hepatitis B virus

<400> SEQUENCE: 421
ucgcagaaga ucucaaucu 19

<210> SEQ ID NO 422
<211> LENGTH: 19
<212> TYPE: RNA
<213> ORGANISM: Hepatitis B virus

<400> SEQUENCE: 422
aggaccccug cucguguua 19

<210> SEQ ID NO 423
<211> LENGTH: 19
<212> TYPE: RNA
<213> ORGANISM: Hepatitis B virus

<400> SEQUENCE: 423
ggaccccugc ucguguuac 19

<210> SEQ ID NO 424
<211> LENGTH: 19
<212> TYPE: RNA
<213> ORGANISM: Hepatitis B virus

<400> SEQUENCE: 424
gaccccugcu cguguuaca 19

<210> SEQ ID NO 425
<211> LENGTH: 19
<212> TYPE: RNA
<213> ORGANISM: Hepatitis B virus

<400> SEQUENCE: 425
accccugcuc guguuacag 19

<210> SEQ ID NO 426
<211> LENGTH: 19
<212> TYPE: RNA
<213> ORGANISM: Hepatitis B virus

<400> SEQUENCE: 426
ccccugcucg uguuacagg 19

<210> SEQ ID NO 427
<211> LENGTH: 19
<212> TYPE: RNA
<213> ORGANISM: Hepatitis B virus

<400> SEQUENCE: 427
uaucgcugga ugugucugc 19

<210> SEQ ID NO 428
<211> LENGTH: 19
<212> TYPE: RNA
<213> ORGANISM: Hepatitis B virus

<400> SEQUENCE: 428
aucgcuggau gugucugcg 19

<210> SEQ ID NO 429
<211> LENGTH: 19
<212> TYPE: RNA
<213> ORGANISM: Hepatitis B virus

<400> SEQUENCE: 429
ucgcuggaug ugucugcgg 19

<210> SEQ ID NO 430
<211> LENGTH: 19
<212> TYPE: RNA
<213> ORGANISM: Hepatitis B virus

<400> SEQUENCE: 430
cgcuggaugu gucugcggc 19

<210> SEQ ID NO 431
<211> LENGTH: 19
<212> TYPE: RNA
<213> ORGANISM: Hepatitis B virus

<400> SEQUENCE: 431
gcuggaugug ucugcggcg 19

<210> SEQ ID NO 432
<211> LENGTH: 19
<212> TYPE: RNA
<213> ORGANISM: Hepatitis B virus

<400> SEQUENCE: 432
cuggaugugu cugcggcgu 19

<210> SEQ ID NO 433
<211> LENGTH: 19
<212> TYPE: RNA
<213> ORGANISM: Hepatitis B virus

<400> SEQUENCE: 433
guugcccguu uguccucua 19

<210> SEQ ID NO 434
<211> LENGTH: 19
<212> TYPE: RNA
<213> ORGANISM: Hepatitis B virus

<400> SEQUENCE: 434
ccauuuguuc agugguucg 19

<210> SEQ ID NO 435
<211> LENGTH: 19
<212> TYPE: RNA
<213> ORGANISM: Hepatitis B virus

<400> SEQUENCE: 435
uuaccaauuu ucuuuuguc 19

<210> SEQ ID NO 436
<211> LENGTH: 19
<212> TYPE: RNA
<213> ORGANISM: Hepatitis B virus

<400> SEQUENCE: 436
ccaacuuaca aggccuuuc 19

<210> SEQ ID NO 437
<211> LENGTH: 19
<212> TYPE: RNA
<213> ORGANISM: Hepatitis B virus

<400> SEQUENCE: 437
caacuuacaa ggccuuucu 19

<210> SEQ ID NO 438
<211> LENGTH: 19
<212> TYPE: RNA
<213> ORGANISM: Hepatitis B virus

<400> SEQUENCE: 438
uuugcugacg caaccccca 19

<210> SEQ ID NO 439
<211> LENGTH: 19
<212> TYPE: RNA
<213> ORGANISM: Hepatitis B virus

<400> SEQUENCE: 439
uugcugacgc aacccccac 19

<210> SEQ ID NO 440
<211> LENGTH: 19
<212> TYPE: RNA
<213> ORGANISM: Hepatitis B virus

<400> SEQUENCE: 440
ugcugacgca acccccacu 19

<210> SEQ ID NO 441
<211> LENGTH: 19
<212> TYPE: RNA
<213> ORGANISM: Hepatitis B virus

<400> SEQUENCE: 441
gcugacgcaa cccccacug 19

<210> SEQ ID NO 442
<211> LENGTH: 19
<212> TYPE: RNA
<213> ORGANISM: Hepatitis B virus

<400> SEQUENCE: 442
cugacgcaac ccccacugg 19

<210> SEQ ID NO 443
<211> LENGTH: 19
<212> TYPE: RNA
<213> ORGANISM: Hepatitis B virus

<400> SEQUENCE: 443
cugugccuuc ucaucugcc 19

<210> SEQ ID NO 444
<211> LENGTH: 19
<212> TYPE: RNA
<213> ORGANISM: Hepatitis B virus

<400> SEQUENCE: 444
ugugccuucu caucugccg 19

<210> SEQ ID NO 445
<211> LENGTH: 19
<212> TYPE: RNA
<213> ORGANISM: Hepatitis B virus

<400> SEQUENCE: 445
gugccuucuc aucugccgg 19

<210> SEQ ID NO 446
<211> LENGTH: 19
<212> TYPE: RNA
<213> ORGANISM: Hepatitis B virus

<400> SEQUENCE: 446
accagcacca ugcaacuuu 19

<210> SEQ ID NO 447
<211> LENGTH: 19
<212> TYPE: RNA
<213> ORGANISM: Hepatitis B virus

<400> SEQUENCE: 447
ccagcaccau gcaacuuuu 19

<210> SEQ ID NO 448
<211> LENGTH: 19
<212> TYPE: RNA
<213> ORGANISM: Hepatitis B virus

<400> SEQUENCE: 448
cagcaccaug caacuuuuu 19

<210> SEQ ID NO 449
<211> LENGTH: 19
<212> TYPE: RNA
<213> ORGANISM: Hepatitis B virus

<400> SEQUENCE: 449
agcaccaugc aacuuuuuc 19

<210> SEQ ID NO 450
<211> LENGTH: 19
<212> TYPE: RNA
<213> ORGANISM: Hepatitis B virus

<400> SEQUENCE: 450
gcaccaugca acuuuuuca 19

<210> SEQ ID NO 451
<211> LENGTH: 19
<212> TYPE: RNA
<213> ORGANISM: Hepatitis B virus

<400> SEQUENCE: 451
caccaugcaa cuuuuucac 19

<210> SEQ ID NO 452
<211> LENGTH: 19
<212> TYPE: RNA
<213> ORGANISM: Hepatitis B virus

<400> SEQUENCE: 452
accaugcaac uuuuucacc 19

<210> SEQ ID NO 453
<211> LENGTH: 19
<212> TYPE: RNA
<213> ORGANISM: Hepatitis B virus

<400> SEQUENCE: 453
ccaugcaacu uuuucaccu 19

<210> SEQ ID NO 454
<211> LENGTH: 19
<212> TYPE: RNA
<213> ORGANISM: Hepatitis B virus

<400> SEQUENCE: 454
cgcagaagau cucaaucuc 19

<210> SEQ ID NO 455
<211> LENGTH: 19
<212> TYPE: RNA
<213> ORGANISM: Hepatitis B virus

<400> SEQUENCE: 455
uccuaggacc ccugcucgu 19

<210> SEQ ID NO 456
<211> LENGTH: 19
<212> TYPE: RNA
<213> ORGANISM: Hepatitis B virus

<400> SEQUENCE: 456
ccuaggaccc cugcucgug 19

<210> SEQ ID NO 457
<211> LENGTH: 19
<212> TYPE: RNA
<213> ORGANISM: Hepatitis B virus

<400> SEQUENCE: 457
cuaggacccc ugcucgugu 19

<210> SEQ ID NO 458
<211> LENGTH: 19
<212> TYPE: RNA
<213> ORGANISM: Hepatitis B virus

<400> SEQUENCE: 458
uaggaccccu gcucguguu 19

<210> SEQ ID NO 459
<211> LENGTH: 19
<212> TYPE: RNA
<213> ORGANISM: Hepatitis B virus

<400> SEQUENCE: 459
cccugcucgu guuacaggc 19

<210> SEQ ID NO 460
<211> LENGTH: 19
<212> TYPE: RNA
<213> ORGANISM: Hepatitis B virus

<400> SEQUENCE: 460
ccugcucgug uuacaggcg 19

<210> SEQ ID NO 461
<211> LENGTH: 19
<212> TYPE: RNA
<213> ORGANISM: Hepatitis B virus

<400> SEQUENCE: 461
cugcucgugu uacaggcgg 19

<210> SEQ ID NO 462
<211> LENGTH: 19
<212> TYPE: RNA
<213> ORGANISM: Hepatitis B virus

<400> SEQUENCE: 462
gccauuuguu cagugguuc 19

<210> SEQ ID NO 463
<211> LENGTH: 19
<212> TYPE: RNA
<213> ORGANISM: Hepatitis B virus

<400> SEQUENCE: 463
ucgccaacuu acaaggccu 19

<210> SEQ ID NO 464
<211> LENGTH: 19
<212> TYPE: RNA
<213> ORGANISM: Hepatitis B virus

<400> SEQUENCE: 464
cgccaacuua caaggccuu 19

<210> SEQ ID NO 465
<211> LENGTH: 19
<212> TYPE: RNA
<213> ORGANISM: Hepatitis B virus

<400> SEQUENCE: 465
gccaacuuac aaggccuuu 19

<210> SEQ ID NO 466
<211> LENGTH: 19
<212> TYPE: RNA
<213> ORGANISM: Hepatitis B virus

<400> SEQUENCE: 466
gcgcaugcgu ggaaccuuu 19

<210> SEQ ID NO 467
<211> LENGTH: 19
<212> TYPE: RNA
<213> ORGANISM: Hepatitis B virus

<400> SEQUENCE: 467
cugccgaucc auacugcgg 19

<210> SEQ ID NO 468
<211> LENGTH: 19
<212> TYPE: RNA
<213> ORGANISM: Hepatitis B virus

<400> SEQUENCE: 468
gcauggagac caccgugaa 19

<210> SEQ ID NO 469
<211> LENGTH: 19
<212> TYPE: RNA
<213> ORGANISM: Hepatitis B virus

<400> SEQUENCE: 469
cauggagacc accgugaac 19

<210> SEQ ID NO 470
<211> LENGTH: 19
<212> TYPE: RNA

```
<213> ORGANISM: Hepatitis B virus

<400> SEQUENCE: 470

auggagacca ccgugaacg                                              19

<210> SEQ ID NO 471
<211> LENGTH: 19
<212> TYPE: RNA
<213> ORGANISM: Hepatitis B virus

<400> SEQUENCE: 471

uggagaccac cgugaacgc                                              19

<210> SEQ ID NO 472
<211> LENGTH: 19
<212> TYPE: RNA
<213> ORGANISM: Hepatitis B virus

<400> SEQUENCE: 472

ggagaccacc gugaacgcc                                              19

<210> SEQ ID NO 473
<211> LENGTH: 19
<212> TYPE: RNA
<213> ORGANISM: Hepatitis B virus

<400> SEQUENCE: 473

gagaccaccg ugaacgccc                                              19

<210> SEQ ID NO 474
<211> LENGTH: 19
<212> TYPE: RNA
<213> ORGANISM: Hepatitis B virus

<400> SEQUENCE: 474

caccagcacc augcaacuu                                              19

<210> SEQ ID NO 475
<211> LENGTH: 19
<212> TYPE: RNA
<213> ORGANISM: Hepatitis B virus

<400> SEQUENCE: 475

cccucgccuc gcagacgaa                                              19

<210> SEQ ID NO 476
<211> LENGTH: 19
<212> TYPE: RNA
<213> ORGANISM: Hepatitis B virus

<400> SEQUENCE: 476

ugggguggag cccucaggc                                              19

<210> SEQ ID NO 477
<211> LENGTH: 19
<212> TYPE: RNA
<213> ORGANISM: Hepatitis B virus

<400> SEQUENCE: 477

gccaaaauuc gcagucccc                                              19

<210> SEQ ID NO 478
<211> LENGTH: 19
```

<212> TYPE: RNA
<213> ORGANISM: Hepatitis B virus

<400> SEQUENCE: 478
ccaaaauucg caguccca 19

<210> SEQ ID NO 479
<211> LENGTH: 19
<212> TYPE: RNA
<213> ORGANISM: Hepatitis B virus

<400> SEQUENCE: 479
caaaauucgc aguccccaa 19

<210> SEQ ID NO 480
<211> LENGTH: 19
<212> TYPE: RNA
<213> ORGANISM: Hepatitis B virus

<400> SEQUENCE: 480
uaccaauuuu cuuuugucu 19

<210> SEQ ID NO 481
<211> LENGTH: 19
<212> TYPE: RNA
<213> ORGANISM: Hepatitis B virus

<400> SEQUENCE: 481
ugccaagugu uugcugacg 19

<210> SEQ ID NO 482
<211> LENGTH: 19
<212> TYPE: RNA
<213> ORGANISM: Hepatitis B virus

<400> SEQUENCE: 482
gccaaguguu ugcugacgc 19

<210> SEQ ID NO 483
<211> LENGTH: 19
<212> TYPE: RNA
<213> ORGANISM: Hepatitis B virus

<400> SEQUENCE: 483
ccaaguguuu gcugacgca 19

<210> SEQ ID NO 484
<211> LENGTH: 19
<212> TYPE: RNA
<213> ORGANISM: Hepatitis B virus

<400> SEQUENCE: 484
ccucgccucg cagacgaag 19

<210> SEQ ID NO 485
<211> LENGTH: 19
<212> TYPE: RNA
<213> ORGANISM: Hepatitis B virus

<400> SEQUENCE: 485
ucucaaucgc cgcgucgca 19

<210> SEQ ID NO 486

```
<211> LENGTH: 19
<212> TYPE: RNA
<213> ORGANISM: Hepatitis B virus

<400> SEQUENCE: 486

cucaaucgcc gcgucgcag                                                 19

<210> SEQ ID NO 487
<211> LENGTH: 19
<212> TYPE: RNA
<213> ORGANISM: Hepatitis B virus

<400> SEQUENCE: 487

ucaaucgccg cgucgcaga                                                 19

<210> SEQ ID NO 488
<211> LENGTH: 19
<212> TYPE: RNA
<213> ORGANISM: Hepatitis B virus

<400> SEQUENCE: 488

ccuuggacuc auaaggugg                                                 19

<210> SEQ ID NO 489
<211> LENGTH: 19
<212> TYPE: RNA
<213> ORGANISM: Hepatitis B virus

<400> SEQUENCE: 489

cuuggacuca uaagguggg                                                 19

<210> SEQ ID NO 490
<211> LENGTH: 19
<212> TYPE: RNA
<213> ORGANISM: Hepatitis B virus

<400> SEQUENCE: 490

uccugcuggu ggcuccagu                                                 19

<210> SEQ ID NO 491
<211> LENGTH: 19
<212> TYPE: RNA
<213> ORGANISM: Hepatitis B virus

<400> SEQUENCE: 491

uggcucaguu uacuagugc                                                 19

<210> SEQ ID NO 492
<211> LENGTH: 19
<212> TYPE: RNA
<213> ORGANISM: Hepatitis B virus

<400> SEQUENCE: 492

uucguagggc uuuccccca                                                 19

<210> SEQ ID NO 493
<211> LENGTH: 19
<212> TYPE: RNA
<213> ORGANISM: Hepatitis B virus

<400> SEQUENCE: 493

caaguguuug cugacgcaa                                                 19
```

<210> SEQ ID NO 494
<211> LENGTH: 19
<212> TYPE: RNA
<213> ORGANISM: Hepatitis B virus

<400> SEQUENCE: 494
aaguguuugc ugacgcaac 19

<210> SEQ ID NO 495
<211> LENGTH: 19
<212> TYPE: RNA
<213> ORGANISM: Hepatitis B virus

<400> SEQUENCE: 495
aguguuugcu gacgcaacc 19

<210> SEQ ID NO 496
<211> LENGTH: 19
<212> TYPE: RNA
<213> ORGANISM: Hepatitis B virus

<400> SEQUENCE: 496
guguuugcug acgcaaccc 19

<210> SEQ ID NO 497
<211> LENGTH: 19
<212> TYPE: RNA
<213> ORGANISM: Hepatitis B virus

<400> SEQUENCE: 497
uguuugcuga cgcaacccc 19

<210> SEQ ID NO 498
<211> LENGTH: 19
<212> TYPE: RNA
<213> ORGANISM: Hepatitis B virus

<400> SEQUENCE: 498
guuugcugac gcaaccccc 19

<210> SEQ ID NO 499
<211> LENGTH: 19
<212> TYPE: RNA
<213> ORGANISM: Hepatitis B virus

<400> SEQUENCE: 499
augucaacga ccgaccuug 19

<210> SEQ ID NO 500
<211> LENGTH: 19
<212> TYPE: RNA
<213> ORGANISM: Hepatitis B virus

<400> SEQUENCE: 500
ugucaacgac cgaccuuga 19

<210> SEQ ID NO 501
<211> LENGTH: 19
<212> TYPE: RNA
<213> ORGANISM: Hepatitis B virus

<400> SEQUENCE: 501
gucaacgacc gaccuugag 19

<210> SEQ ID NO 502
<211> LENGTH: 19
<212> TYPE: RNA
<213> ORGANISM: Hepatitis B virus

<400> SEQUENCE: 502
ucaacgaccg accuugagg 19

<210> SEQ ID NO 503
<211> LENGTH: 19
<212> TYPE: RNA
<213> ORGANISM: Hepatitis B virus

<400> SEQUENCE: 503
caacgaccga ccuugaggc 19

<210> SEQ ID NO 504
<211> LENGTH: 19
<212> TYPE: RNA
<213> ORGANISM: Hepatitis B virus

<400> SEQUENCE: 504
caaucgccgc gucgcagaa 19

<210> SEQ ID NO 505
<211> LENGTH: 19
<212> TYPE: RNA
<213> ORGANISM: Hepatitis B virus

<400> SEQUENCE: 505
aaucgccgcg ucgcagaag 19

<210> SEQ ID NO 506
<211> LENGTH: 19
<212> TYPE: RNA
<213> ORGANISM: Hepatitis B virus

<400> SEQUENCE: 506
aucgccgcgu cgcagaaga 19

<210> SEQ ID NO 507
<211> LENGTH: 19
<212> TYPE: RNA
<213> ORGANISM: Hepatitis B virus

<400> SEQUENCE: 507
ucgccgcguc gcagaagau 19

<210> SEQ ID NO 508
<211> LENGTH: 19
<212> TYPE: RNA
<213> ORGANISM: Hepatitis B virus

<400> SEQUENCE: 508
cgccgcgucg cagaagauc 19

<210> SEQ ID NO 509
<211> LENGTH: 19
<212> TYPE: RNA
<213> ORGANISM: Hepatitis B virus

<400> SEQUENCE: 509
gccgcgucgc agaagaucu 19

<210> SEQ ID NO 510
<211> LENGTH: 19
<212> TYPE: RNA
<213> ORGANISM: Hepatitis B virus

<400> SEQUENCE: 510
uuccugcugg uggcuccag 19

<210> SEQ ID NO 511
<211> LENGTH: 19
<212> TYPE: RNA
<213> ORGANISM: Hepatitis B virus

<400> SEQUENCE: 511
guucguaggg cuuuccccc 19

<210> SEQ ID NO 512
<211> LENGTH: 19
<212> TYPE: RNA
<213> ORGANISM: Hepatitis B virus

<400> SEQUENCE: 512
ucguagggcu uucccccac 19

<210> SEQ ID NO 513
<211> LENGTH: 19
<212> TYPE: RNA
<213> ORGANISM: Hepatitis B virus

<400> SEQUENCE: 513
cuccucugcc gauccauac 19

<210> SEQ ID NO 514
<211> LENGTH: 19
<212> TYPE: RNA
<213> ORGANISM: Hepatitis B virus

<400> SEQUENCE: 514
uccucugccg auccauacu 19

<210> SEQ ID NO 515
<211> LENGTH: 19
<212> TYPE: RNA
<213> ORGANISM: Hepatitis B virus

<400> SEQUENCE: 515
ccucugccga uccauacug 19

<210> SEQ ID NO 516
<211> LENGTH: 19
<212> TYPE: RNA
<213> ORGANISM: Hepatitis B virus

<400> SEQUENCE: 516
cgcugaaucc cgcggacga 19

<210> SEQ ID NO 517
<211> LENGTH: 19
<212> TYPE: RNA
<213> ORGANISM: Hepatitis B virus

<400> SEQUENCE: 517

-continued ccccgucugu gccuucuca 19

<210> SEQ ID NO 518
<211> LENGTH: 19
<212> TYPE: RNA
<213> ORGANISM: Hepatitis B virus

<400> SEQUENCE: 518
cccgucugug ccuucucau 19

<210> SEQ ID NO 519
<211> LENGTH: 19
<212> TYPE: RNA
<213> ORGANISM: Hepatitis B virus

<400> SEQUENCE: 519
ccgucugugc cuucucauc 19

<210> SEQ ID NO 520
<211> LENGTH: 19
<212> TYPE: RNA
<213> ORGANISM: Hepatitis B virus

<400> SEQUENCE: 520
cgucugugcc uucucaucu 19

<210> SEQ ID NO 521
<211> LENGTH: 19
<212> TYPE: RNA
<213> ORGANISM: Hepatitis B virus

<400> SEQUENCE: 521
cauaagagga cucuuggac 19

<210> SEQ ID NO 522
<211> LENGTH: 19
<212> TYPE: RNA
<213> ORGANISM: Hepatitis B virus

<400> SEQUENCE: 522
gacccuuaua aagaauuug 19

<210> SEQ ID NO 523
<211> LENGTH: 19
<212> TYPE: RNA
<213> ORGANISM: Hepatitis B virus

<400> SEQUENCE: 523
guguggauuc gcacuccuc 19

<210> SEQ ID NO 524
<211> LENGTH: 19
<212> TYPE: RNA
<213> ORGANISM: Hepatitis B virus

<400> SEQUENCE: 524
gaggcagguc cccuagaag 19

<210> SEQ ID NO 525
<211> LENGTH: 19
<212> TYPE: RNA
<213> ORGANISM: Hepatitis B virus

<400> SEQUENCE: 525
aggcaggucc ccuagaaga                                                19

<210> SEQ ID NO 526
<211> LENGTH: 19
<212> TYPE: RNA
<213> ORGANISM: Hepatitis B virus

<400> SEQUENCE: 526
guccccaacc uccaaucac                                                19

<210> SEQ ID NO 527
<211> LENGTH: 19
<212> TYPE: RNA
<213> ORGANISM: Hepatitis B virus

<400> SEQUENCE: 527
uccccaaccu ccaaucacu                                                19

<210> SEQ ID NO 528
<211> LENGTH: 19
<212> TYPE: RNA
<213> ORGANISM: Hepatitis B virus

<400> SEQUENCE: 528
uaucaaggua uguugcccg                                                19

<210> SEQ ID NO 529
<211> LENGTH: 19
<212> TYPE: RNA
<213> ORGANISM: Hepatitis B virus

<400> SEQUENCE: 529
aucaagguau guugcccgu                                                19

<210> SEQ ID NO 530
<211> LENGTH: 19
<212> TYPE: RNA
<213> ORGANISM: Hepatitis B virus

<400> SEQUENCE: 530
cauuuguuca gugguucgu                                                19

<210> SEQ ID NO 531
<211> LENGTH: 19
<212> TYPE: RNA
<213> ORGANISM: Hepatitis B virus

<400> SEQUENCE: 531
uuuguucagu gguucguag                                                19

<210> SEQ ID NO 532
<211> LENGTH: 19
<212> TYPE: RNA
<213> ORGANISM: Hepatitis B virus

<400> SEQUENCE: 532
uuguucagug guucguagg                                                19

<210> SEQ ID NO 533
<211> LENGTH: 19
<212> TYPE: RNA
<213> ORGANISM: Hepatitis B virus

<400> SEQUENCE: 533
uguucagugg uucguaggg 19

<210> SEQ ID NO 534
<211> LENGTH: 19
<212> TYPE: RNA
<213> ORGANISM: Hepatitis B virus

<400> SEQUENCE: 534
guucaguggu ucguagggc 19

<210> SEQ ID NO 535
<211> LENGTH: 19
<212> TYPE: RNA
<213> ORGANISM: Hepatitis B virus

<400> SEQUENCE: 535
uucagugguu cguagggcu 19

<210> SEQ ID NO 536
<211> LENGTH: 19
<212> TYPE: RNA
<213> ORGANISM: Hepatitis B virus

<400> SEQUENCE: 536
ucagugguuc guagggcuu 19

<210> SEQ ID NO 537
<211> LENGTH: 19
<212> TYPE: RNA
<213> ORGANISM: Hepatitis B virus

<400> SEQUENCE: 537
cagugguucg uagggcuuu 19

<210> SEQ ID NO 538
<211> LENGTH: 19
<212> TYPE: RNA
<213> ORGANISM: Hepatitis B virus

<400> SEQUENCE: 538
agugguucgu agggcuuuc 19

<210> SEQ ID NO 539
<211> LENGTH: 19
<212> TYPE: RNA
<213> ORGANISM: Hepatitis B virus

<400> SEQUENCE: 539
gugguucgua gggcuuucc 19

<210> SEQ ID NO 540
<211> LENGTH: 19
<212> TYPE: RNA
<213> ORGANISM: Hepatitis B virus

<400> SEQUENCE: 540
ugguucguag ggcuuuccc 19

<210> SEQ ID NO 541
<211> LENGTH: 19
<212> TYPE: RNA
<213> ORGANISM: Hepatitis B virus

<400> SEQUENCE: 541
gguucguagg gcuuucccc 19

<210> SEQ ID NO 542
<211> LENGTH: 19
<212> TYPE: RNA
<213> ORGANISM: Hepatitis B virus

<400> SEQUENCE: 542
cagcgcaugc guggaaccu 19

<210> SEQ ID NO 543
<211> LENGTH: 19
<212> TYPE: RNA
<213> ORGANISM: Hepatitis B virus

<400> SEQUENCE: 543
agcgcaugcg uggaaccuu 19

<210> SEQ ID NO 544
<211> LENGTH: 19
<212> TYPE: RNA
<213> ORGANISM: Hepatitis B virus

<400> SEQUENCE: 544
cgcaugcgug gaaccuuug 19

<210> SEQ ID NO 545
<211> LENGTH: 19
<212> TYPE: RNA
<213> ORGANISM: Hepatitis B virus

<400> SEQUENCE: 545
cucugccgau ccauacugc 19

<210> SEQ ID NO 546
<211> LENGTH: 19
<212> TYPE: RNA
<213> ORGANISM: Hepatitis B virus

<400> SEQUENCE: 546
ucugccgauc cauacugcg 19

<210> SEQ ID NO 547
<211> LENGTH: 19
<212> TYPE: RNA
<213> ORGANISM: Hepatitis B virus

<400> SEQUENCE: 547
gcgcugaauc ccgcggacg 19

<210> SEQ ID NO 548
<211> LENGTH: 19
<212> TYPE: RNA
<213> ORGANISM: Hepatitis B virus

<400> SEQUENCE: 548
accucugccu aaucaucuc 19

<210> SEQ ID NO 549
<211> LENGTH: 19
<212> TYPE: RNA

<213> ORGANISM: Hepatitis B virus

<400> SEQUENCE: 549
ccgcguaaag agaggugcg 19

<210> SEQ ID NO 550
<211> LENGTH: 19
<212> TYPE: RNA
<213> ORGANISM: Hepatitis B virus

<400> SEQUENCE: 550
gagaagucca ccacgaguc 19

<210> SEQ ID NO 551
<211> LENGTH: 19
<212> TYPE: RNA
<213> ORGANISM: Hepatitis B virus

<400> SEQUENCE: 551
ugagagaagu ccaccacga 19

<210> SEQ ID NO 552
<211> LENGTH: 19
<212> TYPE: RNA
<213> ORGANISM: Hepatitis B virus

<400> SEQUENCE: 552
aacgccgcag acacaucca 19

<210> SEQ ID NO 553
<211> LENGTH: 19
<212> TYPE: RNA
<213> ORGANISM: Hepatitis B virus

<400> SEQUENCE: 553
ugaagcgaag ugcacacgg 19

<210> SEQ ID NO 554
<211> LENGTH: 19
<212> TYPE: RNA
<213> ORGANISM: Hepatitis B virus

<400> SEQUENCE: 554
ggugaagcga agugcacac 19

<210> SEQ ID NO 555
<211> LENGTH: 19
<212> TYPE: RNA
<213> ORGANISM: Hepatitis B virus

<400> SEQUENCE: 555
aggugaagcg aagugcaca 19

<210> SEQ ID NO 556
<211> LENGTH: 19
<212> TYPE: RNA
<213> ORGANISM: Hepatitis B virus

<400> SEQUENCE: 556
gaggugaagc gaagugcac 19

<210> SEQ ID NO 557
<211> LENGTH: 19

<212> TYPE: RNA
<213> ORGANISM: Hepatitis B virus

<400> SEQUENCE: 557
cagaggugaa gcgaagugc 19

<210> SEQ ID NO 558
<211> LENGTH: 19
<212> TYPE: RNA
<213> ORGANISM: Hepatitis B virus

<400> SEQUENCE: 558
cacagcuugg aggcuugaa 19

<210> SEQ ID NO 559
<211> LENGTH: 19
<212> TYPE: RNA
<213> ORGANISM: Hepatitis B virus

<400> SEQUENCE: 559
gcacagcuug gaggcuuga 19

<210> SEQ ID NO 560
<211> LENGTH: 19
<212> TYPE: RNA
<213> ORGANISM: Hepatitis B virus

<400> SEQUENCE: 560
ggcacagcuu ggaggcuug 19

<210> SEQ ID NO 561
<211> LENGTH: 19
<212> TYPE: RNA
<213> ORGANISM: Hepatitis B virus

<400> SEQUENCE: 561
aggcacagcu uggaggcuu 19

<210> SEQ ID NO 562
<211> LENGTH: 19
<212> TYPE: RNA
<213> ORGANISM: Hepatitis B virus

<400> SEQUENCE: 562
aguccaccac gagucuaga 19

<210> SEQ ID NO 563
<211> LENGTH: 19
<212> TYPE: RNA
<213> ORGANISM: Hepatitis B virus

<400> SEQUENCE: 563
aaguccacca cgagucuag 19

<210> SEQ ID NO 564
<211> LENGTH: 19
<212> TYPE: RNA
<213> ORGANISM: Hepatitis B virus

<400> SEQUENCE: 564
gaaguccacc acgagucua 19

<210> SEQ ID NO 565

-continued

<211> LENGTH: 19
<212> TYPE: RNA
<213> ORGANISM: Hepatitis B virus

<400> SEQUENCE: 565
agaaguccac cacgagucu 19

<210> SEQ ID NO 566
<211> LENGTH: 19
<212> TYPE: RNA
<213> ORGANISM: Hepatitis B virus

<400> SEQUENCE: 566
aaaacgccgc agacacauc 19

<210> SEQ ID NO 567
<211> LENGTH: 19
<212> TYPE: RNA
<213> ORGANISM: Hepatitis B virus

<400> SEQUENCE: 567
auaaaacgcc gcagacaca 19

<210> SEQ ID NO 568
<211> LENGTH: 19
<212> TYPE: RNA
<213> ORGANISM: Hepatitis B virus

<400> SEQUENCE: 568
ugauaaaacg ccgcagaca 19

<210> SEQ ID NO 569
<211> LENGTH: 19
<212> TYPE: RNA
<213> ORGANISM: Hepatitis B virus

<400> SEQUENCE: 569
auuuaugccu acagccucc 19

<210> SEQ ID NO 570
<211> LENGTH: 19
<212> TYPE: RNA
<213> ORGANISM: Hepatitis B virus

<400> SEQUENCE: 570
aauuuaugcc uacagccuc 19

<210> SEQ ID NO 571
<211> LENGTH: 19
<212> TYPE: RNA
<213> ORGANISM: Hepatitis B virus

<400> SEQUENCE: 571
ccaauuuaug ccuacagcc 19

<210> SEQ ID NO 572
<211> LENGTH: 19
<212> TYPE: RNA
<213> ORGANISM: Hepatitis B virus

<400> SEQUENCE: 572
accaauuuau gccuacagc 19

<210> SEQ ID NO 573
<211> LENGTH: 19
<212> TYPE: RNA
<213> ORGANISM: Hepatitis B virus

<400> SEQUENCE: 573
aggcagaggu gaaaaaguu 19

<210> SEQ ID NO 574
<211> LENGTH: 19
<212> TYPE: RNA
<213> ORGANISM: Hepatitis B virus

<400> SEQUENCE: 574
ccaccacgag ucuagacuc 19

<210> SEQ ID NO 575
<211> LENGTH: 19
<212> TYPE: RNA
<213> ORGANISM: Hepatitis B virus

<400> SEQUENCE: 575
uccaccacga gucuagacu 19

<210> SEQ ID NO 576
<211> LENGTH: 19
<212> TYPE: RNA
<213> ORGANISM: Hepatitis B virus

<400> SEQUENCE: 576
guccaccacg agucuagac 19

<210> SEQ ID NO 577
<211> LENGTH: 19
<212> TYPE: RNA
<213> ORGANISM: Hepatitis B virus

<400> SEQUENCE: 577
gaggcauagc agcaggaug 19

<210> SEQ ID NO 578
<211> LENGTH: 19
<212> TYPE: RNA
<213> ORGANISM: Hepatitis B virus

<400> SEQUENCE: 578
augaggcaua gcagcagga 19

<210> SEQ ID NO 579
<211> LENGTH: 19
<212> TYPE: RNA
<213> ORGANISM: Hepatitis B virus

<400> SEQUENCE: 579
gaugaggcau agcagcagg 19

<210> SEQ ID NO 580
<211> LENGTH: 19
<212> TYPE: RNA
<213> ORGANISM: Hepatitis B virus

<400> SEQUENCE: 580
agaugaggca uagcagcag 19

<210> SEQ ID NO 581
<211> LENGTH: 19
<212> TYPE: RNA
<213> ORGANISM: Hepatitis B virus

<400> SEQUENCE: 581
aagaugaggc auagcagca 19

<210> SEQ ID NO 582
<211> LENGTH: 19
<212> TYPE: RNA
<213> ORGANISM: Hepatitis B virus

<400> SEQUENCE: 582
gaccaauuua ugccuacag 19

<210> SEQ ID NO 583
<211> LENGTH: 19
<212> TYPE: RNA
<213> ORGANISM: Hepatitis B virus

<400> SEQUENCE: 583
agaccaauuu augccuaca 19

<210> SEQ ID NO 584
<211> LENGTH: 19
<212> TYPE: RNA
<213> ORGANISM: Hepatitis B virus

<400> SEQUENCE: 584
agagaagucc accacgagu 19

<210> SEQ ID NO 585
<211> LENGTH: 19
<212> TYPE: RNA
<213> ORGANISM: Hepatitis B virus

<400> SEQUENCE: 585
gagagaaguc caccacgag 19

<210> SEQ ID NO 586
<211> LENGTH: 19
<212> TYPE: RNA
<213> ORGANISM: Hepatitis B virus

<400> SEQUENCE: 586
gugaagcgaa gugcacacg 19

<210> SEQ ID NO 587
<211> LENGTH: 19
<212> TYPE: RNA
<213> ORGANISM: Hepatitis B virus

<400> SEQUENCE: 587
agaggugaag cgaagugca 19

<210> SEQ ID NO 588
<211> LENGTH: 19
<212> TYPE: RNA
<213> ORGANISM: Hepatitis B virus

<400> SEQUENCE: 588
gcagagguga agcgaagug 19

<210> SEQ ID NO 589
<211> LENGTH: 19
<212> TYPE: RNA
<213> ORGANISM: Hepatitis B virus

<400> SEQUENCE: 589
ugcagaggug aagcgaagu 19

<210> SEQ ID NO 590
<211> LENGTH: 19
<212> TYPE: RNA
<213> ORGANISM: Hepatitis B virus

<400> SEQUENCE: 590
aaggcacagc uuggaggcu 19

<210> SEQ ID NO 591
<211> LENGTH: 19
<212> TYPE: RNA
<213> ORGANISM: Hepatitis B virus

<400> SEQUENCE: 591
caaggcacag cuuggaggc 19

<210> SEQ ID NO 592
<211> LENGTH: 19
<212> TYPE: RNA
<213> ORGANISM: Hepatitis B virus

<400> SEQUENCE: 592
cugcgaggcg agggaguuc 19

<210> SEQ ID NO 593
<211> LENGTH: 19
<212> TYPE: RNA
<213> ORGANISM: Hepatitis B virus

<400> SEQUENCE: 593
ucugcgaggc gagggaguu 19

<210> SEQ ID NO 594
<211> LENGTH: 19
<212> TYPE: RNA
<213> ORGANISM: Hepatitis B virus

<400> SEQUENCE: 594
gucugcgagg cgagggagu 19

<210> SEQ ID NO 595
<211> LENGTH: 19
<212> TYPE: RNA
<213> ORGANISM: Hepatitis B virus

<400> SEQUENCE: 595
cgucugcgag gcgagggag 19

<210> SEQ ID NO 596
<211> LENGTH: 19
<212> TYPE: RNA
<213> ORGANISM: Hepatitis B virus

<400> SEQUENCE: 596
aacuggagcc accagcagg 19

<210> SEQ ID NO 597
<211> LENGTH: 19
<212> TYPE: RNA
<213> ORGANISM: Hepatitis B virus

<400> SEQUENCE: 597
gaacuggagc caccagcag 19

<210> SEQ ID NO 598
<211> LENGTH: 19
<212> TYPE: RNA
<213> ORGANISM: Hepatitis B virus

<400> SEQUENCE: 598
aaacgccgca gacacaucc 19

<210> SEQ ID NO 599
<211> LENGTH: 19
<212> TYPE: RNA
<213> ORGANISM: Hepatitis B virus

<400> SEQUENCE: 599
uaaaacgccg cagacacau 19

<210> SEQ ID NO 600
<211> LENGTH: 19
<212> TYPE: RNA
<213> ORGANISM: Hepatitis B virus

<400> SEQUENCE: 600
gauaaaacgc cgcagacac 19

<210> SEQ ID NO 601
<211> LENGTH: 19
<212> TYPE: RNA
<213> ORGANISM: Hepatitis B virus

<400> SEQUENCE: 601
augauaaaac gccgcagac 19

<210> SEQ ID NO 602
<211> LENGTH: 19
<212> TYPE: RNA
<213> ORGANISM: Hepatitis B virus

<400> SEQUENCE: 602
ugaggcccac ucccauagg 19

<210> SEQ ID NO 603
<211> LENGTH: 19
<212> TYPE: RNA
<213> ORGANISM: Hepatitis B virus

<400> SEQUENCE: 603
cugaggccca cucccauag 19

<210> SEQ ID NO 604
<211> LENGTH: 19
<212> TYPE: RNA
<213> ORGANISM: Hepatitis B virus

<400> SEQUENCE: 604
gugcagaggu gaagcgaag 19

<210> SEQ ID NO 605
<211> LENGTH: 19
<212> TYPE: RNA
<213> ORGANISM: Hepatitis B virus

<400> SEQUENCE: 605
cgugcagagg ugaagcgaa 19

<210> SEQ ID NO 606
<211> LENGTH: 19
<212> TYPE: RNA
<213> ORGANISM: Hepatitis B virus

<400> SEQUENCE: 606
acgugcagag gugaagcga 19

<210> SEQ ID NO 607
<211> LENGTH: 19
<212> TYPE: RNA
<213> ORGANISM: Hepatitis B virus

<400> SEQUENCE: 607
caauuuaugc cuacagccu 19

<210> SEQ ID NO 608
<211> LENGTH: 19
<212> TYPE: RNA
<213> ORGANISM: Hepatitis B virus

<400> SEQUENCE: 608
uaggcagagg ugaaaaagu 19

<210> SEQ ID NO 609
<211> LENGTH: 19
<212> TYPE: RNA
<213> ORGANISM: Hepatitis B virus

<400> SEQUENCE: 609
ugaggcauag cagcaggau 19

<210> SEQ ID NO 610
<211> LENGTH: 19
<212> TYPE: RNA
<213> ORGANISM: Hepatitis B virus

<400> SEQUENCE: 610
gaagaugagg cauagcagc 19

<210> SEQ ID NO 611
<211> LENGTH: 19
<212> TYPE: RNA
<213> ORGANISM: Hepatitis B virus

<400> SEQUENCE: 611
agaagaugag gcauagcag 19

<210> SEQ ID NO 612
<211> LENGTH: 19
<212> TYPE: RNA
<213> ORGANISM: Hepatitis B virus

<400> SEQUENCE: 612
aagaagauga ggcauagca 19

<210> SEQ ID NO 613
<211> LENGTH: 19
<212> TYPE: RNA
<213> ORGANISM: Hepatitis B virus

<400> SEQUENCE: 613
cagaccaauu uaugccuac 19

<210> SEQ ID NO 614
<211> LENGTH: 19
<212> TYPE: RNA
<213> ORGANISM: Hepatitis B virus

<400> SEQUENCE: 614
ccaaggcaca gcuuggagg 19

<210> SEQ ID NO 615
<211> LENGTH: 19
<212> TYPE: RNA
<213> ORGANISM: Hepatitis B virus

<400> SEQUENCE: 615
uugagagaag uccaccacg 19

<210> SEQ ID NO 616
<211> LENGTH: 19
<212> TYPE: RNA
<213> ORGANISM: Hepatitis B virus

<400> SEQUENCE: 616
auugagagaa guccaccac 19

<210> SEQ ID NO 617
<211> LENGTH: 19
<212> TYPE: RNA
<213> ORGANISM: Hepatitis B virus

<400> SEQUENCE: 617
aauugagaga aguccacca 19

<210> SEQ ID NO 618
<211> LENGTH: 19
<212> TYPE: RNA
<213> ORGANISM: Hepatitis B virus

<400> SEQUENCE: 618
aaauugagag aaguccacc 19

<210> SEQ ID NO 619
<211> LENGTH: 19
<212> TYPE: RNA
<213> ORGANISM: Hepatitis B virus

<400> SEQUENCE: 619
aaaauugaga gaaguccac 19

<210> SEQ ID NO 620
<211> LENGTH: 19
<212> TYPE: RNA
<213> ORGANISM: Hepatitis B virus

<400> SEQUENCE: 620
gaaaauugag agaagucca 19

<210> SEQ ID NO 621
<211> LENGTH: 19
<212> TYPE: RNA
<213> ORGANISM: Hepatitis B virus

<400> SEQUENCE: 621
uagaaaauug agagaaguc 19

<210> SEQ ID NO 622
<211> LENGTH: 19
<212> TYPE: RNA
<213> ORGANISM: Hepatitis B virus

<400> SEQUENCE: 622
cuagaaaauu gagagaagu 19

<210> SEQ ID NO 623
<211> LENGTH: 19
<212> TYPE: RNA
<213> ORGANISM: Hepatitis B virus

<400> SEQUENCE: 623
ccuagaaaau ugagagaag 19

<210> SEQ ID NO 624
<211> LENGTH: 19
<212> TYPE: RNA
<213> ORGANISM: Hepatitis B virus

<400> SEQUENCE: 624
cccuagaaaa uugagagaa 19

<210> SEQ ID NO 625
<211> LENGTH: 19
<212> TYPE: RNA
<213> ORGANISM: Hepatitis B virus

<400> SEQUENCE: 625
ccccuagaaa auugagaga 19

<210> SEQ ID NO 626
<211> LENGTH: 19
<212> TYPE: RNA
<213> ORGANISM: Hepatitis B virus

<400> SEQUENCE: 626
ggaguuccgc aguauggau 19

<210> SEQ ID NO 627
<211> LENGTH: 19
<212> TYPE: RNA
<213> ORGANISM: Hepatitis B virus

<400> SEQUENCE: 627
aggaguuccg caguaugga 19

<210> SEQ ID NO 628
<211> LENGTH: 19
<212> TYPE: RNA

<213> ORGANISM: Hepatitis B virus

<400> SEQUENCE: 628
ggcgagggag uucuucuuc 19

<210> SEQ ID NO 629
<211> LENGTH: 19
<212> TYPE: RNA
<213> ORGANISM: Hepatitis B virus

<400> SEQUENCE: 629
aggcgaggga guucuucuu 19

<210> SEQ ID NO 630
<211> LENGTH: 19
<212> TYPE: RNA
<213> ORGANISM: Hepatitis B virus

<400> SEQUENCE: 630
gaggcgaggg aguucuucu 19

<210> SEQ ID NO 631
<211> LENGTH: 19
<212> TYPE: RNA
<213> ORGANISM: Hepatitis B virus

<400> SEQUENCE: 631
cgaggcgagg gaguucuuc 19

<210> SEQ ID NO 632
<211> LENGTH: 19
<212> TYPE: RNA
<213> ORGANISM: Hepatitis B virus

<400> SEQUENCE: 632
gcgaggcgag ggaguucuu 19

<210> SEQ ID NO 633
<211> LENGTH: 19
<212> TYPE: RNA
<213> ORGANISM: Hepatitis B virus

<400> SEQUENCE: 633
ugcgaggcga gggaguucu 19

<210> SEQ ID NO 634
<211> LENGTH: 19
<212> TYPE: RNA
<213> ORGANISM: Hepatitis B virus

<400> SEQUENCE: 634
caccacgagu cuagacucu 19

<210> SEQ ID NO 635
<211> LENGTH: 19
<212> TYPE: RNA
<213> ORGANISM: Hepatitis B virus

<400> SEQUENCE: 635
agaaaauuga gagaagucc 19

<210> SEQ ID NO 636
<211> LENGTH: 19

-continued

<212> TYPE: RNA
<213> ORGANISM: Hepatitis B virus

<400> SEQUENCE: 636
gaguuccgca guauggauc 19

<210> SEQ ID NO 637
<211> LENGTH: 19
<212> TYPE: RNA
<213> ORGANISM: Hepatitis B virus

<400> SEQUENCE: 637
cagaggugaa aaaguugca 19

<210> SEQ ID NO 638
<211> LENGTH: 19
<212> TYPE: RNA
<213> ORGANISM: Hepatitis B virus

<400> SEQUENCE: 638
gcagagguga aaaaguugc 19

<210> SEQ ID NO 639
<211> LENGTH: 19
<212> TYPE: RNA
<213> ORGANISM: Hepatitis B virus

<400> SEQUENCE: 639
ggcagaggug aaaaaguug 19

<210> SEQ ID NO 640
<211> LENGTH: 19
<212> TYPE: RNA
<213> ORGANISM: Hepatitis B virus

<400> SEQUENCE: 640
ggacugcgaa uuuuggcca 19

<210> SEQ ID NO 641
<211> LENGTH: 19
<212> TYPE: RNA
<213> ORGANISM: Hepatitis B virus

<400> SEQUENCE: 641
gggacugcga auuuuggcc 19

<210> SEQ ID NO 642
<211> LENGTH: 19
<212> TYPE: RNA
<213> ORGANISM: Hepatitis B virus

<400> SEQUENCE: 642
guuccgcagu auggaucgg 19

<210> SEQ ID NO 643
<211> LENGTH: 19
<212> TYPE: RNA
<213> ORGANISM: Hepatitis B virus

<400> SEQUENCE: 643
aguuccgcag uauggaucg 19

<210> SEQ ID NO 644

-continued

<211> LENGTH: 19
<212> TYPE: RNA
<213> ORGANISM: Hepatitis B virus

<400> SEQUENCE: 644
uuaggcagag gugaaaaag 19

<210> SEQ ID NO 645
<211> LENGTH: 19
<212> TYPE: RNA
<213> ORGANISM: Hepatitis B virus

<400> SEQUENCE: 645
auuaggcaga ggugaaaaa 19

<210> SEQ ID NO 646
<211> LENGTH: 19
<212> TYPE: RNA
<213> ORGANISM: Hepatitis B virus

<400> SEQUENCE: 646
gauuaggcag aggugaaaa 19

<210> SEQ ID NO 647
<211> LENGTH: 19
<212> TYPE: RNA
<213> ORGANISM: Hepatitis B virus

<400> SEQUENCE: 647
ugauuaggca gaggugaaa 19

<210> SEQ ID NO 648
<211> LENGTH: 19
<212> TYPE: RNA
<213> ORGANISM: Hepatitis B virus

<400> SEQUENCE: 648
gccacccaag gcacagcuu 19

<210> SEQ ID NO 649
<211> LENGTH: 19
<212> TYPE: RNA
<213> ORGANISM: Hepatitis B virus

<400> SEQUENCE: 649
agccacccaa ggcacagcu 19

<210> SEQ ID NO 650
<211> LENGTH: 19
<212> TYPE: RNA
<213> ORGANISM: Hepatitis B virus

<400> SEQUENCE: 650
aagccaccca aggcacagc 19

<210> SEQ ID NO 651
<211> LENGTH: 19
<212> TYPE: RNA
<213> ORGANISM: Hepatitis B virus

<400> SEQUENCE: 651
aaagccaccc aaggcacag 19

-continued

<210> SEQ ID NO 652
<211> LENGTH: 19
<212> TYPE: RNA
<213> ORGANISM: Hepatitis B virus

<400> SEQUENCE: 652
gagugcgaau ccacacucc 19

<210> SEQ ID NO 653
<211> LENGTH: 19
<212> TYPE: RNA
<213> ORGANISM: Hepatitis B virus

<400> SEQUENCE: 653
ggagugcgaa uccacacuc 19

<210> SEQ ID NO 654
<211> LENGTH: 19
<212> TYPE: RNA
<213> ORGANISM: Hepatitis B virus

<400> SEQUENCE: 654
accacgaguc uagacucug 19

<210> SEQ ID NO 655
<211> LENGTH: 19
<212> TYPE: RNA
<213> ORGANISM: Hepatitis B virus

<400> SEQUENCE: 655
aguccaagag uccucuuau 19

<210> SEQ ID NO 656
<211> LENGTH: 19
<212> TYPE: RNA
<213> ORGANISM: Hepatitis B virus

<400> SEQUENCE: 656
uuaugccuac agccuccua 19

<210> SEQ ID NO 657
<211> LENGTH: 19
<212> TYPE: RNA
<213> ORGANISM: Hepatitis B virus

<400> SEQUENCE: 657
uuuaugccua cagccuccu 19

<210> SEQ ID NO 658
<211> LENGTH: 19
<212> TYPE: RNA
<213> ORGANISM: Hepatitis B virus

<400> SEQUENCE: 658
gaggugaaaa aguugcaug 19

<210> SEQ ID NO 659
<211> LENGTH: 19
<212> TYPE: RNA
<213> ORGANISM: Hepatitis B virus

<400> SEQUENCE: 659
agaggugaaa aaguugcau 19

<210> SEQ ID NO 660
<211> LENGTH: 19
<212> TYPE: RNA
<213> ORGANISM: Hepatitis B virus

<400> SEQUENCE: 660
augauuaggc agaggugaa 19

<210> SEQ ID NO 661
<211> LENGTH: 19
<212> TYPE: RNA
<213> ORGANISM: Hepatitis B virus

<400> SEQUENCE: 661
gaugauuagg cagagguga 19

<210> SEQ ID NO 662
<211> LENGTH: 19
<212> TYPE: RNA
<213> ORGANISM: Hepatitis B virus

<400> SEQUENCE: 662
agaugauuag gcagaggug 19

<210> SEQ ID NO 663
<211> LENGTH: 19
<212> TYPE: RNA
<213> ORGANISM: Hepatitis B virus

<400> SEQUENCE: 663
cccaaggcac agcuuggag 19

<210> SEQ ID NO 664
<211> LENGTH: 19
<212> TYPE: RNA
<213> ORGANISM: Hepatitis B virus

<400> SEQUENCE: 664
acccaaggca cagcuugga 19

<210> SEQ ID NO 665
<211> LENGTH: 19
<212> TYPE: RNA
<213> ORGANISM: Hepatitis B virus

<400> SEQUENCE: 665
cacccaaggc acagcuugg 19

<210> SEQ ID NO 666
<211> LENGTH: 19
<212> TYPE: RNA
<213> ORGANISM: Hepatitis B virus

<400> SEQUENCE: 666
ccacccaagg cacagcuug 19

<210> SEQ ID NO 667
<211> LENGTH: 19
<212> TYPE: RNA
<213> ORGANISM: Hepatitis B virus

<400> SEQUENCE: 667
gagggaguuc uucuucuag 19

<210> SEQ ID NO 668
<211> LENGTH: 19
<212> TYPE: RNA
<213> ORGANISM: Hepatitis B virus

<400> SEQUENCE: 668
cgagggaguu cuucuucua 19

<210> SEQ ID NO 669
<211> LENGTH: 19
<212> TYPE: RNA
<213> ORGANISM: Hepatitis B virus

<400> SEQUENCE: 669
gcgagggagu ucuucuucu 19

<210> SEQ ID NO 670
<211> LENGTH: 19
<212> TYPE: RNA
<213> ORGANISM: Hepatitis B virus

<400> SEQUENCE: 670
acagcuugga ggcuugaac 19

<210> SEQ ID NO 671
<211> LENGTH: 19
<212> TYPE: RNA
<213> ORGANISM: Hepatitis B virus

<400> SEQUENCE: 671
uaggggcauu uggugggucu 19

<210> SEQ ID NO 672
<211> LENGTH: 19
<212> TYPE: RNA
<213> ORGANISM: Hepatitis B virus

<400> SEQUENCE: 672
auaggggcau uuggugguc 19

<210> SEQ ID NO 673
<211> LENGTH: 19
<212> TYPE: RNA
<213> ORGANISM: Hepatitis B virus

<400> SEQUENCE: 673
gauaggggca uuugguggu 19

<210> SEQ ID NO 674
<211> LENGTH: 19
<212> TYPE: RNA
<213> ORGANISM: Hepatitis B virus

<400> SEQUENCE: 674
augaugggau gggaauaca 19

<210> SEQ ID NO 675
<211> LENGTH: 19
<212> TYPE: RNA
<213> ORGANISM: Hepatitis B virus

<400> SEQUENCE: 675

-continued

| | |
|---|---|
| gaugauggga ugggaauac | 19 |

<210> SEQ ID NO 676
<211> LENGTH: 19
<212> TYPE: RNA
<213> ORGANISM: Hepatitis B virus

<400> SEQUENCE: 676

| | |
|---|---|
| agugggggaa agcccuacg | 19 |

<210> SEQ ID NO 677
<211> LENGTH: 19
<212> TYPE: RNA
<213> ORGANISM: Hepatitis B virus

<400> SEQUENCE: 677

| | |
|---|---|
| caguggggga aagcccuac | 19 |

<210> SEQ ID NO 678
<211> LENGTH: 19
<212> TYPE: RNA
<213> ORGANISM: Hepatitis B virus

<400> SEQUENCE: 678

| | |
|---|---|
| acaguggggg aaagcccua | 19 |

<210> SEQ ID NO 679
<211> LENGTH: 19
<212> TYPE: RNA
<213> ORGANISM: Hepatitis B virus

<400> SEQUENCE: 679

| | |
|---|---|
| uccgcaguau ggaucggca | 19 |

<210> SEQ ID NO 680
<211> LENGTH: 19
<212> TYPE: RNA
<213> ORGANISM: Hepatitis B virus

<400> SEQUENCE: 680

| | |
|---|---|
| uuccgcagua uggaucggc | 19 |

<210> SEQ ID NO 681
<211> LENGTH: 19
<212> TYPE: RNA
<213> ORGANISM: Hepatitis B virus

<400> SEQUENCE: 681

| | |
|---|---|
| aagagaggug cgccccgug | 19 |

<210> SEQ ID NO 682
<211> LENGTH: 19
<212> TYPE: RNA
<213> ORGANISM: Hepatitis B virus

<400> SEQUENCE: 682

| | |
|---|---|
| aaagagaggu gcgccccgu | 19 |

<210> SEQ ID NO 683
<211> LENGTH: 19
<212> TYPE: RNA
<213> ORGANISM: Hepatitis B virus

<400> SEQUENCE: 683
uaaagagagg ugcgccccg 19

<210> SEQ ID NO 684
<211> LENGTH: 19
<212> TYPE: RNA
<213> ORGANISM: Hepatitis B virus

<400> SEQUENCE: 684
guaaagagag gugcgcccc 19

<210> SEQ ID NO 685
<211> LENGTH: 19
<212> TYPE: RNA
<213> ORGANISM: Hepatitis B virus

<400> SEQUENCE: 685
cguaaagaga ggugcgccc 19

<210> SEQ ID NO 686
<211> LENGTH: 19
<212> TYPE: RNA
<213> ORGANISM: Hepatitis B virus

<400> SEQUENCE: 686
gcguaaagag aggugcgcc 19

<210> SEQ ID NO 687
<211> LENGTH: 19
<212> TYPE: RNA
<213> ORGANISM: Hepatitis B virus

<400> SEQUENCE: 687
cgcguaaaga gaggugcgc 19

<210> SEQ ID NO 688
<211> LENGTH: 19
<212> TYPE: RNA
<213> ORGANISM: Hepatitis B virus

<400> SEQUENCE: 688
gcuuggaggc uugaacagu 19

<210> SEQ ID NO 689
<211> LENGTH: 19
<212> TYPE: RNA
<213> ORGANISM: Hepatitis B virus

<400> SEQUENCE: 689
agcuuggagg cuugaacag 19

<210> SEQ ID NO 690
<211> LENGTH: 19
<212> TYPE: RNA
<213> ORGANISM: Hepatitis B virus

<400> SEQUENCE: 690
cagcuuggag gcuugaaca 19

<210> SEQ ID NO 691
<211> LENGTH: 19
<212> TYPE: RNA
<213> ORGANISM: Hepatitis B virus

<400> SEQUENCE: 691
ggacaaacgg gcaacauac 19

<210> SEQ ID NO 692
<211> LENGTH: 19
<212> TYPE: RNA
<213> ORGANISM: Hepatitis B virus

<400> SEQUENCE: 692
aggacaaacg ggcaacaua 19

<210> SEQ ID NO 693
<211> LENGTH: 19
<212> TYPE: RNA
<213> ORGANISM: Hepatitis B virus

<400> SEQUENCE: 693
agaggacaaa cgggcaaca 19

<210> SEQ ID NO 694
<211> LENGTH: 19
<212> TYPE: RNA
<213> ORGANISM: Hepatitis B virus

<400> SEQUENCE: 694
gcaacggggu aaagguuca 19

<210> SEQ ID NO 695
<211> LENGTH: 19
<212> TYPE: RNA
<213> ORGANISM: Hepatitis B virus

<400> SEQUENCE: 695
uaggaguucc gcaguaugg 19

<210> SEQ ID NO 696
<211> LENGTH: 19
<212> TYPE: RNA
<213> ORGANISM: Hepatitis B virus

<400> SEQUENCE: 696
cuaggaguuc cgcaguaug 19

<210> SEQ ID NO 697
<211> LENGTH: 19
<212> TYPE: RNA
<213> ORGANISM: Hepatitis B virus

<400> SEQUENCE: 697
gcuaggaguu ccgcaguau 19

<210> SEQ ID NO 698
<211> LENGTH: 19
<212> TYPE: RNA
<213> ORGANISM: Hepatitis B virus

<400> SEQUENCE: 698
agagaggugc gccccgugg 19

<210> SEQ ID NO 699
<211> LENGTH: 19
<212> TYPE: RNA
<213> ORGANISM: Hepatitis B virus

<400> SEQUENCE: 699
gggaguucuu cuucuaggg 19

<210> SEQ ID NO 700
<211> LENGTH: 19
<212> TYPE: RNA
<213> ORGANISM: Hepatitis B virus

<400> SEQUENCE: 700
agggaguucu ucuucuagg 19

<210> SEQ ID NO 701
<211> LENGTH: 19
<212> TYPE: RNA
<213> ORGANISM: Hepatitis B virus

<400> SEQUENCE: 701
ucgucugcga ggcgaggga 19

<210> SEQ ID NO 702
<211> LENGTH: 19
<212> TYPE: RNA
<213> ORGANISM: Hepatitis B virus

<400> SEQUENCE: 702
gcagcaggau gaagaggaa 19

<210> SEQ ID NO 703
<211> LENGTH: 19
<212> TYPE: RNA
<213> ORGANISM: Hepatitis B virus

<400> SEQUENCE: 703
agcagcagga ugaagagga 19

<210> SEQ ID NO 704
<211> LENGTH: 19
<212> TYPE: RNA
<213> ORGANISM: Hepatitis B virus

<400> SEQUENCE: 704
uagcagcagg augaagagg 19

<210> SEQ ID NO 705
<211> LENGTH: 19
<212> TYPE: RNA
<213> ORGANISM: Hepatitis B virus

<400> SEQUENCE: 705
auagcagcag gaugaagag 19

<210> SEQ ID NO 706
<211> LENGTH: 19
<212> TYPE: RNA
<213> ORGANISM: Hepatitis B virus

<400> SEQUENCE: 706
cauagcagca ggaugaaga 19

<210> SEQ ID NO 707
<211> LENGTH: 19
<212> TYPE: RNA

<213> ORGANISM: Hepatitis B virus

<400> SEQUENCE: 707
gcauagcagc aggaugaag 19

<210> SEQ ID NO 708
<211> LENGTH: 19
<212> TYPE: RNA
<213> ORGANISM: Hepatitis B virus

<400> SEQUENCE: 708
ggcauagcag caggaugaa 19

<210> SEQ ID NO 709
<211> LENGTH: 19
<212> TYPE: RNA
<213> ORGANISM: Hepatitis B virus

<400> SEQUENCE: 709
aggcauagca gcaggauga 19

<210> SEQ ID NO 710
<211> LENGTH: 19
<212> TYPE: RNA
<213> ORGANISM: Hepatitis B virus

<400> SEQUENCE: 710
gacaaacggg caacauacc 19

<210> SEQ ID NO 711
<211> LENGTH: 19
<212> TYPE: RNA
<213> ORGANISM: Hepatitis B virus

<400> SEQUENCE: 711
gaggacaaac gggcaacau 19

<210> SEQ ID NO 712
<211> LENGTH: 19
<212> TYPE: RNA
<213> ORGANISM: Hepatitis B virus

<400> SEQUENCE: 712
ucagcgccga cgggacgua 19

<210> SEQ ID NO 713
<211> LENGTH: 19
<212> TYPE: RNA
<213> ORGANISM: Hepatitis B virus

<400> SEQUENCE: 713
uucagcgccg acgggacgu 19

<210> SEQ ID NO 714
<211> LENGTH: 19
<212> TYPE: RNA
<213> ORGANISM: Hepatitis B virus

<400> SEQUENCE: 714
auucagcgcc gacgggacg 19

<210> SEQ ID NO 715
<211> LENGTH: 19

<212> TYPE: RNA
<213> ORGANISM: Hepatitis B virus

<400> SEQUENCE: 715
gauucagcgc cgacgggac 19

<210> SEQ ID NO 716
<211> LENGTH: 19
<212> TYPE: RNA
<213> ORGANISM: Hepatitis B virus

<400> SEQUENCE: 716
ggauucagcg ccgacggga 19

<210> SEQ ID NO 717
<211> LENGTH: 19
<212> TYPE: RNA
<213> ORGANISM: Hepatitis B virus

<400> SEQUENCE: 717
aggagugcga auccacacu 19

<210> SEQ ID NO 718
<211> LENGTH: 19
<212> TYPE: RNA
<213> ORGANISM: Hepatitis B virus

<400> SEQUENCE: 718
ggaguucuuc uucuagggg 19

<210> SEQ ID NO 719
<211> LENGTH: 19
<212> TYPE: RNA
<213> ORGANISM: Hepatitis B virus

<400> SEQUENCE: 719
aaacgggcaa cauaccuug 19

<210> SEQ ID NO 720
<211> LENGTH: 19
<212> TYPE: RNA
<213> ORGANISM: Hepatitis B virus

<400> SEQUENCE: 720
caaacgggca acauaccuu 19

<210> SEQ ID NO 721
<211> LENGTH: 19
<212> TYPE: RNA
<213> ORGANISM: Hepatitis B virus

<400> SEQUENCE: 721
acaaacgggc aacauaccu 19

<210> SEQ ID NO 722
<211> LENGTH: 19
<212> TYPE: RNA
<213> ORGANISM: Hepatitis B virus

<400> SEQUENCE: 722
aggugcgccc cguggucgg 19

<210> SEQ ID NO 723

```
<211> LENGTH: 19
<212> TYPE: RNA
<213> ORGANISM: Hepatitis B virus

<400> SEQUENCE: 723

gaggugcgcc ccguggucg                                                   19

<210> SEQ ID NO 724
<211> LENGTH: 19
<212> TYPE: RNA
<213> ORGANISM: Hepatitis B virus

<400> SEQUENCE: 724

agaggugcgc cccgugguc                                                   19

<210> SEQ ID NO 725
<211> LENGTH: 19
<212> TYPE: RNA
<213> ORGANISM: Hepatitis B virus

<400> SEQUENCE: 725

gagaggugcg ccccguggu                                                   19

<210> SEQ ID NO 726
<211> LENGTH: 19
<212> TYPE: RNA
<213> ORGANISM: Hepatitis B virus

<400> SEQUENCE: 726

agaaggcaca gacggggag                                                   19

<210> SEQ ID NO 727
<211> LENGTH: 19
<212> TYPE: RNA
<213> ORGANISM: Hepatitis B virus

<400> SEQUENCE: 727

gagaaggcac agacgggga                                                   19

<210> SEQ ID NO 728
<211> LENGTH: 19
<212> TYPE: RNA
<213> ORGANISM: Hepatitis B virus

<400> SEQUENCE: 728

gagaucuucu gcgacgcgg                                                   19

<210> SEQ ID NO 729
<211> LENGTH: 19
<212> TYPE: RNA
<213> ORGANISM: Hepatitis B virus

<400> SEQUENCE: 729

ugagaucuuc ugcgacgcg                                                   19

<210> SEQ ID NO 730
<211> LENGTH: 19
<212> TYPE: RNA
<213> ORGANISM: Hepatitis B virus

<400> SEQUENCE: 730

uugagaucuu cugcgacgc                                                   19
```

```
<210> SEQ ID NO 731
<211> LENGTH: 19
<212> TYPE: RNA
<213> ORGANISM: Hepatitis B virus

<400> SEQUENCE: 731

auugagaucu ucugcgacg                                                  19

<210> SEQ ID NO 732
<211> LENGTH: 19
<212> TYPE: RNA
<213> ORGANISM: Hepatitis B virus

<400> SEQUENCE: 732

gauugagauc uucugcgac                                                  19

<210> SEQ ID NO 733
<211> LENGTH: 19
<212> TYPE: RNA
<213> ORGANISM: Hepatitis B virus

<400> SEQUENCE: 733

agauugagau cuucugcga                                                  19

<210> SEQ ID NO 734
<211> LENGTH: 19
<212> TYPE: RNA
<213> ORGANISM: Hepatitis B virus

<400> SEQUENCE: 734

uaacacgagc aggguccu                                                   19

<210> SEQ ID NO 735
<211> LENGTH: 19
<212> TYPE: RNA
<213> ORGANISM: Hepatitis B virus

<400> SEQUENCE: 735

guaacacgag caggggucc                                                  19

<210> SEQ ID NO 736
<211> LENGTH: 19
<212> TYPE: RNA
<213> ORGANISM: Hepatitis B virus

<400> SEQUENCE: 736

uguaacacga gcagggguc                                                  19

<210> SEQ ID NO 737
<211> LENGTH: 19
<212> TYPE: RNA
<213> ORGANISM: Hepatitis B virus

<400> SEQUENCE: 737

cuguaacacg agcaggggu                                                  19

<210> SEQ ID NO 738
<211> LENGTH: 19
<212> TYPE: RNA
<213> ORGANISM: Hepatitis B virus

<400> SEQUENCE: 738

ccuguaacac gagcagggg                                                  19
```

<210> SEQ ID NO 739
<211> LENGTH: 19
<212> TYPE: RNA
<213> ORGANISM: Hepatitis B virus

<400> SEQUENCE: 739
gcagacacau ccagcgaua 19

<210> SEQ ID NO 740
<211> LENGTH: 19
<212> TYPE: RNA
<213> ORGANISM: Hepatitis B virus

<400> SEQUENCE: 740
cgcagacaca uccagcgau 19

<210> SEQ ID NO 741
<211> LENGTH: 19
<212> TYPE: RNA
<213> ORGANISM: Hepatitis B virus

<400> SEQUENCE: 741
ccgcagacac auccagcga 19

<210> SEQ ID NO 742
<211> LENGTH: 19
<212> TYPE: RNA
<213> ORGANISM: Hepatitis B virus

<400> SEQUENCE: 742
gccgcagaca cauccagcg 19

<210> SEQ ID NO 743
<211> LENGTH: 19
<212> TYPE: RNA
<213> ORGANISM: Hepatitis B virus

<400> SEQUENCE: 743
cgccgcagac acauccagc 19

<210> SEQ ID NO 744
<211> LENGTH: 19
<212> TYPE: RNA
<213> ORGANISM: Hepatitis B virus

<400> SEQUENCE: 744
acgccgcaga cacauccag 19

<210> SEQ ID NO 745
<211> LENGTH: 19
<212> TYPE: RNA
<213> ORGANISM: Hepatitis B virus

<400> SEQUENCE: 745
uagaggacaa acgggcaac 19

<210> SEQ ID NO 746
<211> LENGTH: 19
<212> TYPE: RNA
<213> ORGANISM: Hepatitis B virus

<400> SEQUENCE: 746
cgaaccacug aacaaaugg 19

<210> SEQ ID NO 747
<211> LENGTH: 19
<212> TYPE: RNA
<213> ORGANISM: Hepatitis B virus

<400> SEQUENCE: 747
gacaaaagaa aauugguaa                                            19

<210> SEQ ID NO 748
<211> LENGTH: 19
<212> TYPE: RNA
<213> ORGANISM: Hepatitis B virus

<400> SEQUENCE: 748
gaaaggccuu guaaguugg                                            19

<210> SEQ ID NO 749
<211> LENGTH: 19
<212> TYPE: RNA
<213> ORGANISM: Hepatitis B virus

<400> SEQUENCE: 749
agaaaggccu uguaaguug                                            19

<210> SEQ ID NO 750
<211> LENGTH: 19
<212> TYPE: RNA
<213> ORGANISM: Hepatitis B virus

<400> SEQUENCE: 750
uggggguugc gucagcaaa                                            19

<210> SEQ ID NO 751
<211> LENGTH: 19
<212> TYPE: RNA
<213> ORGANISM: Hepatitis B virus

<400> SEQUENCE: 751 gugggguug cgucagcaa                                             19

<210> SEQ ID NO 752
<211> LENGTH: 19
<212> TYPE: RNA
<213> ORGANISM: Hepatitis B virus

<400> SEQUENCE: 752
aguggggguu gcgucagca                                            19

<210> SEQ ID NO 753
<211> LENGTH: 19
<212> TYPE: RNA
<213> ORGANISM: Hepatitis B virus

<400> SEQUENCE: 753 caguggggu ugcgucagc                                             19

<210> SEQ ID NO 754
<211> LENGTH: 19
<212> TYPE: RNA
<213> ORGANISM: Hepatitis B virus

<400> SEQUENCE: 754

-continued ccaguggggg uugcgucag 19

<210> SEQ ID NO 755
<211> LENGTH: 19
<212> TYPE: RNA
<213> ORGANISM: Hepatitis B virus

<400> SEQUENCE: 755
ggcagaugag aaggcacag 19

<210> SEQ ID NO 756
<211> LENGTH: 19
<212> TYPE: RNA
<213> ORGANISM: Hepatitis B virus

<400> SEQUENCE: 756
cggcagauga gaaggcaca 19

<210> SEQ ID NO 757
<211> LENGTH: 19
<212> TYPE: RNA
<213> ORGANISM: Hepatitis B virus

<400> SEQUENCE: 757
ccggcagaug agaaggcac 19

<210> SEQ ID NO 758
<211> LENGTH: 19
<212> TYPE: RNA
<213> ORGANISM: Hepatitis B virus

<400> SEQUENCE: 758
aaaguugcau ggugcuggu 19

<210> SEQ ID NO 759
<211> LENGTH: 19
<212> TYPE: RNA
<213> ORGANISM: Hepatitis B virus

<400> SEQUENCE: 759
aaaaguugca uggugcugg 19

<210> SEQ ID NO 760
<211> LENGTH: 19
<212> TYPE: RNA
<213> ORGANISM: Hepatitis B virus

<400> SEQUENCE: 760
aaaaaguugc auggugcug 19

<210> SEQ ID NO 761
<211> LENGTH: 19
<212> TYPE: RNA
<213> ORGANISM: Hepatitis B virus

<400> SEQUENCE: 761
gaaaaaguug cauggugcu 19

<210> SEQ ID NO 762
<211> LENGTH: 19
<212> TYPE: RNA
<213> ORGANISM: Hepatitis B virus

<400> SEQUENCE: 762
ugaaaaaguu gcauggugc 19

<210> SEQ ID NO 763
<211> LENGTH: 19
<212> TYPE: RNA
<213> ORGANISM: Hepatitis B virus

<400> SEQUENCE: 763
gugaaaaagu ugcauggug 19

<210> SEQ ID NO 764
<211> LENGTH: 19
<212> TYPE: RNA
<213> ORGANISM: Hepatitis B virus

<400> SEQUENCE: 764
ggugaaaaag uugcauggu 19

<210> SEQ ID NO 765
<211> LENGTH: 19
<212> TYPE: RNA
<213> ORGANISM: Hepatitis B virus

<400> SEQUENCE: 765
aggugaaaaa guugcaugg 19

<210> SEQ ID NO 766
<211> LENGTH: 19
<212> TYPE: RNA
<213> ORGANISM: Hepatitis B virus

<400> SEQUENCE: 766
gagauugaga ucuucugcg 19

<210> SEQ ID NO 767
<211> LENGTH: 19
<212> TYPE: RNA
<213> ORGANISM: Hepatitis B virus

<400> SEQUENCE: 767
acgagcaggg guccuagga 19

<210> SEQ ID NO 768
<211> LENGTH: 19
<212> TYPE: RNA
<213> ORGANISM: Hepatitis B virus

<400> SEQUENCE: 768
cacgagcagg gguccuagg 19

<210> SEQ ID NO 769
<211> LENGTH: 19
<212> TYPE: RNA
<213> ORGANISM: Hepatitis B virus

<400> SEQUENCE: 769
acacgagcag ggguccuag 19

<210> SEQ ID NO 770
<211> LENGTH: 19
<212> TYPE: RNA
<213> ORGANISM: Hepatitis B virus

<400> SEQUENCE: 770
aacacgagca gggguccua                                            19

<210> SEQ ID NO 771
<211> LENGTH: 19
<212> TYPE: RNA
<213> ORGANISM: Hepatitis B virus

<400> SEQUENCE: 771
gccuguaaca cgagcaggg                                            19

<210> SEQ ID NO 772
<211> LENGTH: 19
<212> TYPE: RNA
<213> ORGANISM: Hepatitis B virus

<400> SEQUENCE: 772
cgccuguaac acgagcagg                                            19

<210> SEQ ID NO 773
<211> LENGTH: 19
<212> TYPE: RNA
<213> ORGANISM: Hepatitis B virus

<400> SEQUENCE: 773
ccgccuguaa cacgagcag                                            19

<210> SEQ ID NO 774
<211> LENGTH: 19
<212> TYPE: RNA
<213> ORGANISM: Hepatitis B virus

<400> SEQUENCE: 774
gaaccacuga acaaauggc                                            19

<210> SEQ ID NO 775
<211> LENGTH: 19
<212> TYPE: RNA
<213> ORGANISM: Hepatitis B virus

<400> SEQUENCE: 775
aggccuugua aguuggcga                                            19

<210> SEQ ID NO 776
<211> LENGTH: 19
<212> TYPE: RNA
<213> ORGANISM: Hepatitis B virus

<400> SEQUENCE: 776
aaggccuugu aaguuggcg                                            19

<210> SEQ ID NO 777
<211> LENGTH: 19
<212> TYPE: RNA
<213> ORGANISM: Hepatitis B virus

<400> SEQUENCE: 777
aaaggccuug uaaguuggc                                            19

<210> SEQ ID NO 778
<211> LENGTH: 19
<212> TYPE: RNA
<213> ORGANISM: Hepatitis B virus

<400> SEQUENCE: 778
aaagguucca cgcaugcgc 19

<210> SEQ ID NO 779
<211> LENGTH: 19
<212> TYPE: RNA
<213> ORGANISM: Hepatitis B virus

<400> SEQUENCE: 779
ccgcaguaug gaucggcag 19

<210> SEQ ID NO 780
<211> LENGTH: 19
<212> TYPE: RNA
<213> ORGANISM: Hepatitis B virus

<400> SEQUENCE: 780
uucacggugg ucuccaugc 19

<210> SEQ ID NO 781
<211> LENGTH: 19
<212> TYPE: RNA
<213> ORGANISM: Hepatitis B virus

<400> SEQUENCE: 781
guucacggug gucuccaug 19

<210> SEQ ID NO 782
<211> LENGTH: 19
<212> TYPE: RNA
<213> ORGANISM: Hepatitis B virus

<400> SEQUENCE: 782
cguucacggu ggucuccau 19

<210> SEQ ID NO 783
<211> LENGTH: 19
<212> TYPE: RNA
<213> ORGANISM: Hepatitis B virus

<400> SEQUENCE: 783
gcguucacgg uggucucca 19

<210> SEQ ID NO 784
<211> LENGTH: 19
<212> TYPE: RNA
<213> ORGANISM: Hepatitis B virus

<400> SEQUENCE: 784
ggcguucacg guggucucc 19

<210> SEQ ID NO 785
<211> LENGTH: 19
<212> TYPE: RNA
<213> ORGANISM: Hepatitis B virus

<400> SEQUENCE: 785
gggcguucac gguggucuc 19

<210> SEQ ID NO 786
<211> LENGTH: 19
<212> TYPE: RNA

<213> ORGANISM: Hepatitis B virus

<400> SEQUENCE: 786
aaguugcaug gugcuggug 19

<210> SEQ ID NO 787
<211> LENGTH: 19
<212> TYPE: RNA
<213> ORGANISM: Hepatitis B virus

<400> SEQUENCE: 787
uucgucugcg aggcgaggg 19

<210> SEQ ID NO 788
<211> LENGTH: 19
<212> TYPE: RNA
<213> ORGANISM: Hepatitis B virus

<400> SEQUENCE: 788
gccugagggc uccacccca 19

<210> SEQ ID NO 789
<211> LENGTH: 19
<212> TYPE: RNA
<213> ORGANISM: Hepatitis B virus

<400> SEQUENCE: 789
ggggacugcg aauuuuggc 19

<210> SEQ ID NO 790
<211> LENGTH: 19
<212> TYPE: RNA
<213> ORGANISM: Hepatitis B virus

<400> SEQUENCE: 790
uggggacugc gaauuuugg 19

<210> SEQ ID NO 791
<211> LENGTH: 19
<212> TYPE: RNA
<213> ORGANISM: Hepatitis B virus

<400> SEQUENCE: 791
uuggggacug cgaauuuug 19

<210> SEQ ID NO 792
<211> LENGTH: 19
<212> TYPE: RNA
<213> ORGANISM: Hepatitis B virus

<400> SEQUENCE: 792
agacaaaaga aaauuggua 19

<210> SEQ ID NO 793
<211> LENGTH: 19
<212> TYPE: RNA
<213> ORGANISM: Hepatitis B virus

<400> SEQUENCE: 793
cgucagcaaa cacuuggca 19

<210> SEQ ID NO 794
<211> LENGTH: 19

<212> TYPE: RNA
<213> ORGANISM: Hepatitis B virus

<400> SEQUENCE: 794
gcgucagcaa acacuuggc 19

<210> SEQ ID NO 795
<211> LENGTH: 19
<212> TYPE: RNA
<213> ORGANISM: Hepatitis B virus

<400> SEQUENCE: 795
ugcgucagca aacacuugg 19

<210> SEQ ID NO 796
<211> LENGTH: 19
<212> TYPE: RNA
<213> ORGANISM: Hepatitis B virus

<400> SEQUENCE: 796
cuucgucugc gaggcgagg 19

<210> SEQ ID NO 797
<211> LENGTH: 19
<212> TYPE: RNA
<213> ORGANISM: Hepatitis B virus

<400> SEQUENCE: 797
ugcgacgcgg cgauugaga 19

<210> SEQ ID NO 798
<211> LENGTH: 19
<212> TYPE: RNA
<213> ORGANISM: Hepatitis B virus

<400> SEQUENCE: 798
cugcgacgcg gcgauugag 19

<210> SEQ ID NO 799
<211> LENGTH: 19
<212> TYPE: RNA
<213> ORGANISM: Hepatitis B virus

<400> SEQUENCE: 799
ucugcgacgc ggcgauuga 19

<210> SEQ ID NO 800
<211> LENGTH: 19
<212> TYPE: RNA
<213> ORGANISM: Hepatitis B virus

<400> SEQUENCE: 800
ccaccuuaug aguccaagg 19

<210> SEQ ID NO 801
<211> LENGTH: 19
<212> TYPE: RNA
<213> ORGANISM: Hepatitis B virus

<400> SEQUENCE: 801
cccaccuuau gaguccaag 19

<210> SEQ ID NO 802

<211> LENGTH: 19
<212> TYPE: RNA
<213> ORGANISM: Hepatitis B virus

<400> SEQUENCE: 802
acuggagcca ccagcagga 19

<210> SEQ ID NO 803
<211> LENGTH: 19
<212> TYPE: RNA
<213> ORGANISM: Hepatitis B virus

<400> SEQUENCE: 803
gcacuaguaa acugagcca 19

<210> SEQ ID NO 804
<211> LENGTH: 19
<212> TYPE: RNA
<213> ORGANISM: Hepatitis B virus

<400> SEQUENCE: 804
ugggggaaag cccuacgaa 19

<210> SEQ ID NO 805
<211> LENGTH: 19
<212> TYPE: RNA
<213> ORGANISM: Hepatitis B virus

<400> SEQUENCE: 805
uugcgucagc aaacacuug 19

<210> SEQ ID NO 806
<211> LENGTH: 19
<212> TYPE: RNA
<213> ORGANISM: Hepatitis B virus

<400> SEQUENCE: 806
guugcgucag caaacacuu 19

<210> SEQ ID NO 807
<211> LENGTH: 19
<212> TYPE: RNA
<213> ORGANISM: Hepatitis B virus

<400> SEQUENCE: 807
gguugcguca gcaaacacu 19

<210> SEQ ID NO 808
<211> LENGTH: 19
<212> TYPE: RNA
<213> ORGANISM: Hepatitis B virus

<400> SEQUENCE: 808
ggguugcguc agcaaacac 19

<210> SEQ ID NO 809
<211> LENGTH: 19
<212> TYPE: RNA
<213> ORGANISM: Hepatitis B virus

<400> SEQUENCE: 809
gggguugcgu cagcaaaca 19

```
<210> SEQ ID NO 810
<211> LENGTH: 19
<212> TYPE: RNA
<213> ORGANISM: Hepatitis B virus

<400> SEQUENCE: 810

ggggguugcg ucagcaaac                                                  19

<210> SEQ ID NO 811
<211> LENGTH: 19
<212> TYPE: RNA
<213> ORGANISM: Hepatitis B virus

<400> SEQUENCE: 811

caaggucggu cguugacau                                                  19

<210> SEQ ID NO 812
<211> LENGTH: 19
<212> TYPE: RNA
<213> ORGANISM: Hepatitis B virus

<400> SEQUENCE: 812

ucaaggucgg ucguugaca                                                  19

<210> SEQ ID NO 813
<211> LENGTH: 19
<212> TYPE: RNA
<213> ORGANISM: Hepatitis B virus

<400> SEQUENCE: 813

cucaaggucg gucguugac                                                  19

<210> SEQ ID NO 814
<211> LENGTH: 19
<212> TYPE: RNA
<213> ORGANISM: Hepatitis B virus

<400> SEQUENCE: 814

ccucaagguc ggucguuga                                                  19

<210> SEQ ID NO 815
<211> LENGTH: 19
<212> TYPE: RNA
<213> ORGANISM: Hepatitis B virus

<400> SEQUENCE: 815

gccucaaggu cggucguug                                                  19

<210> SEQ ID NO 816
<211> LENGTH: 19
<212> TYPE: RNA
<213> ORGANISM: Hepatitis B virus

<400> SEQUENCE: 816

uucugcgacg cggcgauug                                                  19

<210> SEQ ID NO 817
<211> LENGTH: 19
<212> TYPE: RNA
<213> ORGANISM: Hepatitis B virus

<400> SEQUENCE: 817

cuucugcgac gcggcgauu                                                  19
```

<210> SEQ ID NO 818
<211> LENGTH: 19
<212> TYPE: RNA
<213> ORGANISM: Hepatitis B virus

<400> SEQUENCE: 818
ucuucugcga cgcggcgau 19

<210> SEQ ID NO 819
<211> LENGTH: 19
<212> TYPE: RNA
<213> ORGANISM: Hepatitis B virus

<400> SEQUENCE: 819
aucuucugcg acgcggcga 19

<210> SEQ ID NO 820
<211> LENGTH: 19
<212> TYPE: RNA
<213> ORGANISM: Hepatitis B virus

<400> SEQUENCE: 820
gaucuucugc gacgcggcg 19

<210> SEQ ID NO 821
<211> LENGTH: 19
<212> TYPE: RNA
<213> ORGANISM: Hepatitis B virus

<400> SEQUENCE: 821
agaucuucug cgacgcggc 19

<210> SEQ ID NO 822
<211> LENGTH: 19
<212> TYPE: RNA
<213> ORGANISM: Hepatitis B virus

<400> SEQUENCE: 822
cuggagccac cagcaggaa 19

<210> SEQ ID NO 823
<211> LENGTH: 19
<212> TYPE: RNA
<213> ORGANISM: Hepatitis B virus

<400> SEQUENCE: 823
gggggaaagc ccuacgaac 19

<210> SEQ ID NO 824
<211> LENGTH: 19
<212> TYPE: RNA
<213> ORGANISM: Hepatitis B virus

<400> SEQUENCE: 824
gugggggaaa gcccuacga 19

<210> SEQ ID NO 825
<211> LENGTH: 19
<212> TYPE: RNA
<213> ORGANISM: Hepatitis B virus

<400> SEQUENCE: 825
guauggaucg gcagaggag 19

<210> SEQ ID NO 826
<211> LENGTH: 19
<212> TYPE: RNA
<213> ORGANISM: Hepatitis B virus

<400> SEQUENCE: 826
aguauggauc ggcagagga 19

<210> SEQ ID NO 827
<211> LENGTH: 19
<212> TYPE: RNA
<213> ORGANISM: Hepatitis B virus

<400> SEQUENCE: 827
caguauggau cggcagagg 19

<210> SEQ ID NO 828
<211> LENGTH: 19
<212> TYPE: RNA
<213> ORGANISM: Hepatitis B virus

<400> SEQUENCE: 828
ucguccgcgg gauucagcg 19

<210> SEQ ID NO 829
<211> LENGTH: 19
<212> TYPE: RNA
<213> ORGANISM: Hepatitis B virus

<400> SEQUENCE: 829
ugagaaggca cagacgggg 19

<210> SEQ ID NO 830
<211> LENGTH: 19
<212> TYPE: RNA
<213> ORGANISM: Hepatitis B virus

<400> SEQUENCE: 830
augagaaggc acagacggg 19

<210> SEQ ID NO 831
<211> LENGTH: 19
<212> TYPE: RNA
<213> ORGANISM: Hepatitis B virus

<400> SEQUENCE: 831
gaugagaagg cacagacgg 19

<210> SEQ ID NO 832
<211> LENGTH: 19
<212> TYPE: RNA
<213> ORGANISM: Hepatitis B virus

<400> SEQUENCE: 832
agaugagaag gcacagacg 19

<210> SEQ ID NO 833
<211> LENGTH: 19
<212> TYPE: RNA
<213> ORGANISM: Hepatitis B virus

<400> SEQUENCE: 833
guccaagagu ccucuuaug 19

<210> SEQ ID NO 834
<211> LENGTH: 19
<212> TYPE: RNA
<213> ORGANISM: Hepatitis B virus

<400> SEQUENCE: 834
caaauucuuu auaaggguc 19

<210> SEQ ID NO 835
<211> LENGTH: 19
<212> TYPE: RNA
<213> ORGANISM: Hepatitis B virus

<400> SEQUENCE: 835
gaggagugcg aauccacac 19

<210> SEQ ID NO 836
<211> LENGTH: 19
<212> TYPE: RNA
<213> ORGANISM: Hepatitis B virus

<400> SEQUENCE: 836
cuucuagggg accugccuc 19

<210> SEQ ID NO 837
<211> LENGTH: 19
<212> TYPE: RNA
<213> ORGANISM: Hepatitis B virus

<400> SEQUENCE: 837
ucuucuaggg gaccugccu 19

<210> SEQ ID NO 838
<211> LENGTH: 19
<212> TYPE: RNA
<213> ORGANISM: Hepatitis B virus

<400> SEQUENCE: 838
gugauuggag guuggggac 19

<210> SEQ ID NO 839
<211> LENGTH: 19
<212> TYPE: RNA
<213> ORGANISM: Hepatitis B virus

<400> SEQUENCE: 839
agugauugga gguugggga 19

<210> SEQ ID NO 840
<211> LENGTH: 19
<212> TYPE: RNA
<213> ORGANISM: Hepatitis B virus

<400> SEQUENCE: 840
cgggcaacau accuugaua 19

<210> SEQ ID NO 841
<211> LENGTH: 19
<212> TYPE: RNA
<213> ORGANISM: Hepatitis B virus

<400> SEQUENCE: 841
acgggcaaca uaccuugau 19

<210> SEQ ID NO 842
<211> LENGTH: 19
<212> TYPE: RNA
<213> ORGANISM: Hepatitis B virus

<400> SEQUENCE: 842
acgaaccacu gaacaaaug 19

<210> SEQ ID NO 843
<211> LENGTH: 19
<212> TYPE: RNA
<213> ORGANISM: Hepatitis B virus

<400> SEQUENCE: 843
cuacgaacca cugaacaaa 19

<210> SEQ ID NO 844
<211> LENGTH: 19
<212> TYPE: RNA
<213> ORGANISM: Hepatitis B virus

<400> SEQUENCE: 844
ccuacgaacc acugaacaa 19

<210> SEQ ID NO 845
<211> LENGTH: 19
<212> TYPE: RNA
<213> ORGANISM: Hepatitis B virus

<400> SEQUENCE: 845
cccuacgaac cacugaaca 19

<210> SEQ ID NO 846
<211> LENGTH: 19
<212> TYPE: RNA
<213> ORGANISM: Hepatitis B virus

<400> SEQUENCE: 846
gcccuacgaa ccacugaac 19

<210> SEQ ID NO 847
<211> LENGTH: 19
<212> TYPE: RNA
<213> ORGANISM: Hepatitis B virus

<400> SEQUENCE: 847
agcccuacga accacugaa 19

<210> SEQ ID NO 848
<211> LENGTH: 19
<212> TYPE: RNA
<213> ORGANISM: Hepatitis B virus

<400> SEQUENCE: 848
aagcccuacg aaccacuga 19

<210> SEQ ID NO 849
<211> LENGTH: 19
<212> TYPE: RNA
<213> ORGANISM: Hepatitis B virus

<400> SEQUENCE: 849
aaagcccuac gaaccacug 19

<210> SEQ ID NO 850
<211> LENGTH: 19
<212> TYPE: RNA
<213> ORGANISM: Hepatitis B virus

<400> SEQUENCE: 850
gaaagcccua cgaaccacu 19

<210> SEQ ID NO 851
<211> LENGTH: 19
<212> TYPE: RNA
<213> ORGANISM: Hepatitis B virus

<400> SEQUENCE: 851
ggaaagcccu acgaaccac 19

<210> SEQ ID NO 852
<211> LENGTH: 19
<212> TYPE: RNA
<213> ORGANISM: Hepatitis B virus

<400> SEQUENCE: 852
gggaaagccc uacgaacca 19

<210> SEQ ID NO 853
<211> LENGTH: 19
<212> TYPE: RNA
<213> ORGANISM: Hepatitis B virus

<400> SEQUENCE: 853
ggggaaagcc cuacgaacc 19

<210> SEQ ID NO 854
<211> LENGTH: 19
<212> TYPE: RNA
<213> ORGANISM: Hepatitis B virus

<400> SEQUENCE: 854
agguuccacg caugcgcug 19

<210> SEQ ID NO 855
<211> LENGTH: 19
<212> TYPE: RNA
<213> ORGANISM: Hepatitis B virus

<400> SEQUENCE: 855
aagguuccac gcaugcgcu 19

<210> SEQ ID NO 856
<211> LENGTH: 19
<212> TYPE: RNA
<213> ORGANISM: Hepatitis B virus

<400> SEQUENCE: 856
caaagguucc acgcaugcg 19

<210> SEQ ID NO 857
<211> LENGTH: 19
<212> TYPE: RNA
<213> ORGANISM: Hepatitis B virus

<400> SEQUENCE: 857
gcaguaugga ucggcagag                                                19

<210> SEQ ID NO 858
<211> LENGTH: 19
<212> TYPE: RNA
<213> ORGANISM: Hepatitis B virus

<400> SEQUENCE: 858
cgcaguaugg aucggcaga                                                19

<210> SEQ ID NO 859
<211> LENGTH: 19
<212> TYPE: RNA
<213> ORGANISM: Hepatitis B virus

<400> SEQUENCE: 859
cguccgcggg auucagcgc                                                19

<210> SEQ ID NO 860
<211> LENGTH: 19
<212> TYPE: RNA
<213> ORGANISM: Hepatitis B virus

<400> SEQUENCE: 860
gagaugauua ggcagaggu                                                19

<210> SEQ ID NO 861
<211> LENGTH: 19
<212> TYPE: RNA
<213> ORGANISM: Hepatitis B virus

<400> SEQUENCE: 861
cgcaccucuc uuuacgcgg                                                19

<210> SEQ ID NO 862
<211> LENGTH: 19
<212> TYPE: RNA
<213> ORGANISM: Hepatitis B virus

<400> SEQUENCE: 862
gacucguggu ggacuucuc                                                19

<210> SEQ ID NO 863
<211> LENGTH: 19
<212> TYPE: RNA
<213> ORGANISM: Hepatitis B virus

<400> SEQUENCE: 863
ucguggugga cuucucuca                                                19

<210> SEQ ID NO 864
<211> LENGTH: 19
<212> TYPE: RNA
<213> ORGANISM: Hepatitis B virus

<400> SEQUENCE: 864
uggauguguc ugcggcguu                                                19

<210> SEQ ID NO 865
<211> LENGTH: 19
<212> TYPE: RNA

<213> ORGANISM: Hepatitis B virus

<400> SEQUENCE: 865
ccgugugcac uucgcuuca 19

<210> SEQ ID NO 866
<211> LENGTH: 19
<212> TYPE: RNA
<213> ORGANISM: Hepatitis B virus

<400> SEQUENCE: 866
gugugcacuu cgcuucacc 19

<210> SEQ ID NO 867
<211> LENGTH: 19
<212> TYPE: RNA
<213> ORGANISM: Hepatitis B virus

<400> SEQUENCE: 867
ugugcacuuc gcuucaccu 19

<210> SEQ ID NO 868
<211> LENGTH: 19
<212> TYPE: RNA
<213> ORGANISM: Hepatitis B virus

<400> SEQUENCE: 868
gugcacuucg cuucaccuc 19

<210> SEQ ID NO 869
<211> LENGTH: 19
<212> TYPE: RNA
<213> ORGANISM: Hepatitis B virus

<400> SEQUENCE: 869
gcacuucgcu ucaccucug 19

<210> SEQ ID NO 870
<211> LENGTH: 19
<212> TYPE: RNA
<213> ORGANISM: Hepatitis B virus

<400> SEQUENCE: 870
ucuagacucg ugguggacu 19

<210> SEQ ID NO 871
<211> LENGTH: 19
<212> TYPE: RNA
<213> ORGANISM: Hepatitis B virus

<400> SEQUENCE: 871
cuagacucgu gguggacuu 19

<210> SEQ ID NO 872
<211> LENGTH: 19
<212> TYPE: RNA
<213> ORGANISM: Hepatitis B virus

<400> SEQUENCE: 872
uagacucgug guggacuuc 19

<210> SEQ ID NO 873
<211> LENGTH: 19

<212> TYPE: RNA
<213> ORGANISM: Hepatitis B virus

<400> SEQUENCE: 873
agacucgugg uggacuucu 19

<210> SEQ ID NO 874
<211> LENGTH: 19
<212> TYPE: RNA
<213> ORGANISM: Hepatitis B virus

<400> SEQUENCE: 874
ggaggcugua ggcauaaau 19

<210> SEQ ID NO 875
<211> LENGTH: 19
<212> TYPE: RNA
<213> ORGANISM: Hepatitis B virus

<400> SEQUENCE: 875
gaggcuguag gcauaaauu 19

<210> SEQ ID NO 876
<211> LENGTH: 19
<212> TYPE: RNA
<213> ORGANISM: Hepatitis B virus

<400> SEQUENCE: 876
ggcuguaggc auaaauugg 19

<210> SEQ ID NO 877
<211> LENGTH: 19
<212> TYPE: RNA
<213> ORGANISM: Hepatitis B virus

<400> SEQUENCE: 877
gcuguaggca uaaauuggu 19

<210> SEQ ID NO 878
<211> LENGTH: 19
<212> TYPE: RNA
<213> ORGANISM: Hepatitis B virus

<400> SEQUENCE: 878
cuguaggcau aaauugguc 19

<210> SEQ ID NO 879
<211> LENGTH: 19
<212> TYPE: RNA
<213> ORGANISM: Hepatitis B virus

<400> SEQUENCE: 879
uguaggcaua aauuggucu 19

<210> SEQ ID NO 880
<211> LENGTH: 19
<212> TYPE: RNA
<213> ORGANISM: Hepatitis B virus

<400> SEQUENCE: 880
gugguggacu ucucucaau 19

<210> SEQ ID NO 881

<211> LENGTH: 19
<212> TYPE: RNA
<213> ORGANISM: Hepatitis B virus

<400> SEQUENCE: 881
uucaagccuc caagcugug 19

<210> SEQ ID NO 882
<211> LENGTH: 19
<212> TYPE: RNA
<213> ORGANISM: Hepatitis B virus

<400> SEQUENCE: 882
ucaagccucc aagcugugc 19

<210> SEQ ID NO 883
<211> LENGTH: 19
<212> TYPE: RNA
<213> ORGANISM: Hepatitis B virus

<400> SEQUENCE: 883
caagccucca agcugugcc 19

<210> SEQ ID NO 884
<211> LENGTH: 19
<212> TYPE: RNA
<213> ORGANISM: Hepatitis B virus

<400> SEQUENCE: 884
aagccuccaa gcugugccu 19

<210> SEQ ID NO 885
<211> LENGTH: 19
<212> TYPE: RNA
<213> ORGANISM: Hepatitis B virus

<400> SEQUENCE: 885
gaugugucug cggcguuuu 19

<210> SEQ ID NO 886
<211> LENGTH: 19
<212> TYPE: RNA
<213> ORGANISM: Hepatitis B virus

<400> SEQUENCE: 886
ugugucugcg gcguuuuau 19

<210> SEQ ID NO 887
<211> LENGTH: 19
<212> TYPE: RNA
<213> ORGANISM: Hepatitis B virus

<400> SEQUENCE: 887
ugucugcggc guuuuauca 19

<210> SEQ ID NO 888
<211> LENGTH: 19
<212> TYPE: RNA
<213> ORGANISM: Hepatitis B virus

<400> SEQUENCE: 888
aacuuuuuca ccucugccu 19

```
<210> SEQ ID NO 889
<211> LENGTH: 19
<212> TYPE: RNA
<213> ORGANISM: Hepatitis B virus

<400> SEQUENCE: 889

gagucuagac ucguggugg                                                   19

<210> SEQ ID NO 890
<211> LENGTH: 19
<212> TYPE: RNA
<213> ORGANISM: Hepatitis B virus

<400> SEQUENCE: 890

agucuagacu cguggugga                                                   19

<210> SEQ ID NO 891
<211> LENGTH: 19
<212> TYPE: RNA
<213> ORGANISM: Hepatitis B virus

<400> SEQUENCE: 891

gucuagacuc gugguggac                                                   19

<210> SEQ ID NO 892
<211> LENGTH: 19
<212> TYPE: RNA
<213> ORGANISM: Hepatitis B virus

<400> SEQUENCE: 892

cauccugcug cuaugccuc                                                   19

<210> SEQ ID NO 893
<211> LENGTH: 19
<212> TYPE: RNA
<213> ORGANISM: Hepatitis B virus

<400> SEQUENCE: 893

uccugcugcu augccucau                                                   19

<210> SEQ ID NO 894
<211> LENGTH: 19
<212> TYPE: RNA
<213> ORGANISM: Hepatitis B virus

<400> SEQUENCE: 894

ccugcugcua ugccucauc                                                   19

<210> SEQ ID NO 895
<211> LENGTH: 19
<212> TYPE: RNA
<213> ORGANISM: Hepatitis B virus

<400> SEQUENCE: 895

cugcugcuau gccucaucu                                                   19

<210> SEQ ID NO 896
<211> LENGTH: 19
<212> TYPE: RNA
<213> ORGANISM: Hepatitis B virus

<400> SEQUENCE: 896

ugcugcuaug ccucaucuu                                                   19
```

```
<210> SEQ ID NO 897
<211> LENGTH: 19
<212> TYPE: RNA
<213> ORGANISM: Hepatitis B virus

<400> SEQUENCE: 897

acucguggug gacuucucu                                            19

<210> SEQ ID NO 898
<211> LENGTH: 19
<212> TYPE: RNA
<213> ORGANISM: Hepatitis B virus

<400> SEQUENCE: 898

cucguggugg acuucucuc                                            19

<210> SEQ ID NO 899
<211> LENGTH: 19
<212> TYPE: RNA
<213> ORGANISM: Hepatitis B virus

<400> SEQUENCE: 899

cgugugcacu ucgcuucac                                            19

<210> SEQ ID NO 900
<211> LENGTH: 19
<212> TYPE: RNA
<213> ORGANISM: Hepatitis B virus

<400> SEQUENCE: 900

ugcacuucgc uucaccucu                                            19

<210> SEQ ID NO 901
<211> LENGTH: 19
<212> TYPE: RNA
<213> ORGANISM: Hepatitis B virus

<400> SEQUENCE: 901

cacuucgcuu caccucugc                                            19

<210> SEQ ID NO 902
<211> LENGTH: 19
<212> TYPE: RNA
<213> ORGANISM: Hepatitis B virus

<400> SEQUENCE: 902

ccgcguaaag agaggugcg                                            19

<210> SEQ ID NO 903
<211> LENGTH: 19
<212> TYPE: RNA
<213> ORGANISM: Hepatitis B virus

<400> SEQUENCE: 903

gagaagucca ccacgaguc                                            19

<210> SEQ ID NO 904
<211> LENGTH: 19
<212> TYPE: RNA
<213> ORGANISM: Hepatitis B virus

<400> SEQUENCE: 904

ugagagaagu ccaccacga                                            19
```

<210> SEQ ID NO 905
<211> LENGTH: 19
<212> TYPE: RNA
<213> ORGANISM: Hepatitis B virus

<400> SEQUENCE: 905
aacgccgcag acacaucca 19

<210> SEQ ID NO 906
<211> LENGTH: 19
<212> TYPE: RNA
<213> ORGANISM: Hepatitis B virus

<400> SEQUENCE: 906
ugaagcgaag ugcacacgg 19

<210> SEQ ID NO 907
<211> LENGTH: 19
<212> TYPE: RNA
<213> ORGANISM: Hepatitis B virus

<400> SEQUENCE: 907
ggugaagcga agugcacac 19

<210> SEQ ID NO 908
<211> LENGTH: 19
<212> TYPE: RNA
<213> ORGANISM: Hepatitis B virus

<400> SEQUENCE: 908
aggugaagcg aagugcaca 19

<210> SEQ ID NO 909
<211> LENGTH: 19
<212> TYPE: RNA
<213> ORGANISM: Hepatitis B virus

<400> SEQUENCE: 909
gaggugaagc gaagugcac 19

<210> SEQ ID NO 910
<211> LENGTH: 19
<212> TYPE: RNA
<213> ORGANISM: Hepatitis B virus

<400> SEQUENCE: 910
cagaggugaa gcgaagugc 19

<210> SEQ ID NO 911
<211> LENGTH: 19
<212> TYPE: RNA
<213> ORGANISM: Hepatitis B virus

<400> SEQUENCE: 911
aguccaccac gagucuaga 19

<210> SEQ ID NO 912
<211> LENGTH: 19
<212> TYPE: RNA
<213> ORGANISM: Hepatitis B virus

<400> SEQUENCE: 912
aaguccacca cgagucuag 19

<210> SEQ ID NO 913
<211> LENGTH: 19
<212> TYPE: RNA
<213> ORGANISM: Hepatitis B virus

<400> SEQUENCE: 913
gaaguccacc acgagucua 19

<210> SEQ ID NO 914
<211> LENGTH: 19
<212> TYPE: RNA
<213> ORGANISM: Hepatitis B virus

<400> SEQUENCE: 914
agaaguccac cacgagucu 19

<210> SEQ ID NO 915
<211> LENGTH: 19
<212> TYPE: RNA
<213> ORGANISM: Hepatitis B virus

<400> SEQUENCE: 915
auuuaugccu acagccucc 19

<210> SEQ ID NO 916
<211> LENGTH: 19
<212> TYPE: RNA
<213> ORGANISM: Hepatitis B virus

<400> SEQUENCE: 916
aauuuaugcc uacagccuc 19

<210> SEQ ID NO 917
<211> LENGTH: 19
<212> TYPE: RNA
<213> ORGANISM: Hepatitis B virus

<400> SEQUENCE: 917
ccaauuuaug ccuacagcc 19

<210> SEQ ID NO 918
<211> LENGTH: 19
<212> TYPE: RNA
<213> ORGANISM: Hepatitis B virus

<400> SEQUENCE: 918
accaauuuau gccuacagc 19

<210> SEQ ID NO 919
<211> LENGTH: 19
<212> TYPE: RNA
<213> ORGANISM: Hepatitis B virus

<400> SEQUENCE: 919
gaccaauuua ugccuacag 19

<210> SEQ ID NO 920
<211> LENGTH: 19
<212> TYPE: RNA
<213> ORGANISM: Hepatitis B virus

<400> SEQUENCE: 920
agaccaauuu augccuaca 19

<210> SEQ ID NO 921
<211> LENGTH: 19
<212> TYPE: RNA
<213> ORGANISM: Hepatitis B virus

<400> SEQUENCE: 921
auugagagaa guccaccac 19

<210> SEQ ID NO 922
<211> LENGTH: 19
<212> TYPE: RNA
<213> ORGANISM: Hepatitis B virus

<400> SEQUENCE: 922
cacagcuugg aggcuugaa 19

<210> SEQ ID NO 923
<211> LENGTH: 19
<212> TYPE: RNA
<213> ORGANISM: Hepatitis B virus

<400> SEQUENCE: 923
gcacagcuug gaggcuuga 19

<210> SEQ ID NO 924
<211> LENGTH: 19
<212> TYPE: RNA
<213> ORGANISM: Hepatitis B virus

<400> SEQUENCE: 924
ggcacagcuu ggaggcuug 19

<210> SEQ ID NO 925
<211> LENGTH: 19
<212> TYPE: RNA
<213> ORGANISM: Hepatitis B virus

<400> SEQUENCE: 925
aggcacagcu uggaggcuu 19

<210> SEQ ID NO 926
<211> LENGTH: 19
<212> TYPE: RNA
<213> ORGANISM: Hepatitis B virus

<400> SEQUENCE: 926
aaaacgccgc agacacauc 19

<210> SEQ ID NO 927
<211> LENGTH: 19
<212> TYPE: RNA
<213> ORGANISM: Hepatitis B virus

<400> SEQUENCE: 927
auaaaacgcc gcagacaca 19

<210> SEQ ID NO 928
<211> LENGTH: 19
<212> TYPE: RNA
<213> ORGANISM: Hepatitis B virus

<400> SEQUENCE: 928
ugauaaaacg ccgcagaca 19

<210> SEQ ID NO 929
<211> LENGTH: 19
<212> TYPE: RNA
<213> ORGANISM: Hepatitis B virus

<400> SEQUENCE: 929
aggcagaggu gaaaaaguu 19

<210> SEQ ID NO 930
<211> LENGTH: 19
<212> TYPE: RNA
<213> ORGANISM: Hepatitis B virus

<400> SEQUENCE: 930
ccaccacgag ucuagacuc 19

<210> SEQ ID NO 931
<211> LENGTH: 19
<212> TYPE: RNA
<213> ORGANISM: Hepatitis B virus

<400> SEQUENCE: 931
uccaccacga gucuagacu 19

<210> SEQ ID NO 932
<211> LENGTH: 19
<212> TYPE: RNA
<213> ORGANISM: Hepatitis B virus

<400> SEQUENCE: 932
guccaccacg agucuagac 19

<210> SEQ ID NO 933
<211> LENGTH: 19
<212> TYPE: RNA
<213> ORGANISM: Hepatitis B virus

<400> SEQUENCE: 933
gaggcauagc agcaggaug 19

<210> SEQ ID NO 934
<211> LENGTH: 19
<212> TYPE: RNA
<213> ORGANISM: Hepatitis B virus

<400> SEQUENCE: 934
augaggcaua gcagcagga 19

<210> SEQ ID NO 935
<211> LENGTH: 19
<212> TYPE: RNA
<213> ORGANISM: Hepatitis B virus

<400> SEQUENCE: 935
gaugaggcau agcagcagg 19

<210> SEQ ID NO 936
<211> LENGTH: 19
<212> TYPE: RNA
<213> ORGANISM: Hepatitis B virus

<400> SEQUENCE: 936
agaugaggca uagcagcag 19

<210> SEQ ID NO 937
<211> LENGTH: 19
<212> TYPE: RNA
<213> ORGANISM: Hepatitis B virus

<400> SEQUENCE: 937
aagaugaggc auagcagca 19

<210> SEQ ID NO 938
<211> LENGTH: 19
<212> TYPE: RNA
<213> ORGANISM: Hepatitis B virus

<400> SEQUENCE: 938
agagaagucc accacgagu 19

<210> SEQ ID NO 939
<211> LENGTH: 19
<212> TYPE: RNA
<213> ORGANISM: Hepatitis B virus

<400> SEQUENCE: 939
gagagaaguc caccacgag 19

<210> SEQ ID NO 940
<211> LENGTH: 19
<212> TYPE: RNA
<213> ORGANISM: Hepatitis B virus

<400> SEQUENCE: 940
gugaagcgaa gugcacacg 19

<210> SEQ ID NO 941
<211> LENGTH: 19
<212> TYPE: RNA
<213> ORGANISM: Hepatitis B virus

<400> SEQUENCE: 941
agaggugaag cgaagugca 19

<210> SEQ ID NO 942
<211> LENGTH: 19
<212> TYPE: RNA
<213> ORGANISM: Hepatitis B virus

<400> SEQUENCE: 942
gcagagguga agcgaagug 19

<210> SEQ ID NO 943
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 943
gagucuagac ucgugguggu u 21

<210> SEQ ID NO 944
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 944
ccaccacgag ucuagacucu u 21

<210> SEQ ID NO 945
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 945
agucuagacu cgugguggau u 21

<210> SEQ ID NO 946
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 946
uccaccacga gucuagacuu u 21

<210> SEQ ID NO 947
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 947
gucuagacuc gugguggacu u 21

<210> SEQ ID NO 948
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 948
guccaccacg agucuagacu u 21

<210> SEQ ID NO 949
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 949
ucuagacucg ugguggacuu u 21

<210> SEQ ID NO 950

<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 950
aguccaccac gagucuagau u 21

<210> SEQ ID NO 951
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 951
cuagacucgu gguggacuuu u 21

<210> SEQ ID NO 952
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 952
aaguccacca cgagucuagu u 21

<210> SEQ ID NO 953
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 953
uagacucgug guggacuucu u 21

<210> SEQ ID NO 954
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 954
gaaguccacc acgagucuau u 21

<210> SEQ ID NO 955
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 955
agacucgugg uggacuucuu u 21

<210> SEQ ID NO 956
<211> LENGTH: 21

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 956
agaaguccac cacgagucuu u 21

<210> SEQ ID NO 957
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 957
gacucguggu ggacuucucu u 21

<210> SEQ ID NO 958
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 958
gagaagucca ccacgagucu u 21

<210> SEQ ID NO 959
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 959
acucguggug gacuucucuu u 21

<210> SEQ ID NO 960
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 960
agagaagucc accacgaguu u 21

<210> SEQ ID NO 961
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 961
cucguggugg acuucucucu u 21

<210> SEQ ID NO 962
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 962
gagagaaguc caccacgagu u 21

<210> SEQ ID NO 963
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 963
ucguggugga cuucucucau u 21

<210> SEQ ID NO 964
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 964
ugagagaagu ccaccacgau u 21

<210> SEQ ID NO 965
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 965
gugguggacu ucucucaauu u 21

<210> SEQ ID NO 966
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 966
auugagagaa guccaccacu u 21

<210> SEQ ID NO 967
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 967
uggauguguc ugcggcguuu u 21

<210> SEQ ID NO 968
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 968
aacgccgcag acacauccau u 21

<210> SEQ ID NO 969
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 969
gaugugucug cggcguuuuu u 21

<210> SEQ ID NO 970
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 970
aaaacgccgc agacacaucu u 21

<210> SEQ ID NO 971
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 971
ugugucugcg gcguuuuauu u 21

<210> SEQ ID NO 972
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 972
auaaaacgcc gcagacacau u 21

<210> SEQ ID NO 973
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 973
ugucugcggc guuuuaucau u 21

<210> SEQ ID NO 974
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 974
ugauaaaacg ccgcagacau u 21

<210> SEQ ID NO 975
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 975
cauccugcug cuaugccucu u 21

<210> SEQ ID NO 976
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 976
gaggcauagc agcaggaugu u 21

<210> SEQ ID NO 977
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 977
uccugcugcu augccucauu u 21

<210> SEQ ID NO 978
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 978
augaggcaua gcagcaggau u 21

<210> SEQ ID NO 979
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 979
ccugcugcua ugccucaucu u 21

<210> SEQ ID NO 980
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 980
gaugaggcau agcagcaggu u 21

<210> SEQ ID NO 981
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 981
cugcugcuau gccucaucuu u 21

<210> SEQ ID NO 982
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 982
agaugaggca uagcagcagu u 21

<210> SEQ ID NO 983
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 983
ugcugcuaug ccucaucuuu u 21

<210> SEQ ID NO 984
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 984
aagaugaggc auagcagcau u 21

<210> SEQ ID NO 985
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 985
cgcaccucuc uuuacgcggu u 21

<210> SEQ ID NO 986
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 986
ccgcguaaag agaggugcgu u 21

<210> SEQ ID NO 987
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 987
ccgugugcac uucgcuucau u 21

<210> SEQ ID NO 988
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 988
ugaagcgaag ugcacacggu u 21

<210> SEQ ID NO 989
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 989
cgugugcacu ucgcuucacu u 21

<210> SEQ ID NO 990
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 990
gugaagcgaa gugcacacgu u 21

<210> SEQ ID NO 991
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 991
gugugcacuu cgcuucaccu u 21

<210> SEQ ID NO 992
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 992
ggugaagcga agugcacacu u 21

<210> SEQ ID NO 993
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 993
ugugcacuuc gcuucaccuu u 21

<210> SEQ ID NO 994
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 994
aggugaagcg aagugcacau u 21

<210> SEQ ID NO 995
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 995
gugcacuucg cuucaccucu u 21

<210> SEQ ID NO 996
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 996
gaggugaagc gaagugcacu u 21

<210> SEQ ID NO 997
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 997
ugcacuucgc uucaccucuu u 21

<210> SEQ ID NO 998
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 998
agaggugaag cgaagugcau u 21

<210> SEQ ID NO 999
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 999
gcacuucgcu ucaccucugu u 21

<210> SEQ ID NO 1000
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1000
cagaggugaa gcgaagugcu u 21

<210> SEQ ID NO 1001
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1001
cacuucgcuu caccucugcu u 21

<210> SEQ ID NO 1002
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1002
gcagagguga agcgaagugu u 21

<210> SEQ ID NO 1003
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1003
ggaggcugua ggcauaaauu u 21

<210> SEQ ID NO 1004
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1004
auuuaugccu acagccuccu u 21

<210> SEQ ID NO 1005
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1005
gaggcuguag gcauaaauuu u 21

<210> SEQ ID NO 1006
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1006
aauuuaugcc uacagccucu u 21

<210> SEQ ID NO 1007
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1007
ggcuguaggc auaaauuggu u 21

<210> SEQ ID NO 1008
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1008
ccaauuuaug ccuacagccu u 21

<210> SEQ ID NO 1009
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1009
gcuguaggca uaaauugguu u 21

<210> SEQ ID NO 1010
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1010
accaauuuau gccuacagcu u 21

<210> SEQ ID NO 1011
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1011
cuguaggcau aaauuggucu u 21

<210> SEQ ID NO 1012
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1012
gaccaauuua ugccuacagu u 21

<210> SEQ ID NO 1013
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1013
uguaggcaua aauuggucuu u 21

<210> SEQ ID NO 1014
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1014
agaccaauuu augccuacau u 21

<210> SEQ ID NO 1015
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1015
aacuuuuuca ccucugccuu u 21

<210> SEQ ID NO 1016
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1016
aggcagaggu gaaaaaguuu u 21

<210> SEQ ID NO 1017
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1017
uucaagccuc caagcugugu u 21

<210> SEQ ID NO 1018
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1018
cacagcuugg aggcuugaau u 21

<210> SEQ ID NO 1019
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1019
ucaagccucc aagcugugcu u 21

<210> SEQ ID NO 1020
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1020
gcacagcuug gaggcuugau u 21

<210> SEQ ID NO 1021
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1021
caagccucca agcugugccu u 21

<210> SEQ ID NO 1022
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1022
ggcacagcuu ggaggcuugu u 21

<210> SEQ ID NO 1023
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1023
aagccuccaa gcugugccuu u 21

<210> SEQ ID NO 1024
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1024
aggcacagcu uggaggcuuu u 21

<210> SEQ ID NO 1025
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1025
cgugugcacu ucgcuucacu u 21

<210> SEQ ID NO 1026
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1026
gugaagcgaa gugcacacgu u 21

<210> SEQ ID NO 1027
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1027
cgugugcacu ucgcuucacu u 21

<210> SEQ ID NO 1028
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1028
gugaagcgaa gugcacacgu u 21

<210> SEQ ID NO 1029

<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1029
cgugugcacu ucgcuucacu u 21

<210> SEQ ID NO 1030
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1030
gugaagcgaa gugcacacgu u 21

<210> SEQ ID NO 1031
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1031
cgugugcacu ucgcuucacu u 21

<210> SEQ ID NO 1032
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1032
gugaagcgaa gugcacacgu u 21

<210> SEQ ID NO 1033
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1033
cgugugcacu ucgcuucacu u 21

<210> SEQ ID NO 1034
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1034
gugaagcgaa gugcacacgu u 21

<210> SEQ ID NO 1035
<211> LENGTH: 21

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1035
cgugugcacu ucgcuucacu u 21

<210> SEQ ID NO 1036
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1036
gugaagcgaa gugcacacgu u 21

<210> SEQ ID NO 1037
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1037
cgugugcacu ucgcuucacu u 21

<210> SEQ ID NO 1038
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1038
gugaagcgaa gugcacacgu u 21

<210> SEQ ID NO 1039
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1039
cgugugcacu ucgcuucacu u 21

<210> SEQ ID NO 1040
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1040
gugaagcgaa gugcacacgu u 21

<210> SEQ ID NO 1041
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1041
ccgugugcac uucgcuucau u 21

<210> SEQ ID NO 1042
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1042
ugaagcgaag ugcacacggu u 21

<210> SEQ ID NO 1043
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1043
ccgugugcac uucgcuucau u 21

<210> SEQ ID NO 1044
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1044
ugaagcgaag ugcacacggu u 21

<210> SEQ ID NO 1045
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1045
ccgugugcac uucgcuucau u 21

<210> SEQ ID NO 1046
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1046
ugaagcgaag ugcacacggu u 21

<210> SEQ ID NO 1047
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1047
ugugcacuuc gcuucaccuu u 21

<210> SEQ ID NO 1048
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1048
aggugaagcg aagugcacau u 21

<210> SEQ ID NO 1049
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1049
ugugcacuuc gcuucaccuu u 21

<210> SEQ ID NO 1050
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1050
aggugaagcg aagugcacau u 21

<210> SEQ ID NO 1051
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1051
ugugcacuuc gcuucaccuu u 21

<210> SEQ ID NO 1052
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1052
aggugaagcg aagugcacau u 21

<210> SEQ ID NO 1053
<211> LENGTH: 21
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 1053
aacuuuuuca ccucugccuu u 21

<210> SEQ ID NO 1054
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1054
aggcagaggu gaaaaaguuu u 21

<210> SEQ ID NO 1055
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1055
aacuuuuuca ccucugccuu u 21

<210> SEQ ID NO 1056
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1056
aggcagaggu gaaaaaguuu u 21

<210> SEQ ID NO 1057
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1057
aacuuuuuca ccucugccuu u 21

<210> SEQ ID NO 1058
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1058
aggcagaggu gaaaaaguuu u 21

<210> SEQ ID NO 1059
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1059
agucuagacu cgugguggau u 21

<210> SEQ ID NO 1060
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1060
uccaccacga gucuagacuu u 21

<210> SEQ ID NO 1061
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1061
ugcacuucgc uucaccucuu u 21

<210> SEQ ID NO 1062
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1062
agaggugaag cgaagugcau u 21

<210> SEQ ID NO 1063
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1063
ugcacuucgc uucaccucuu u 21

<210> SEQ ID NO 1064
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1064
agaggugaag cgaagugcau u 21

<210> SEQ ID NO 1065
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1065
ugcacuucgc uucaccucuu u 21

<210> SEQ ID NO 1066
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1066
agaggugaag cgaagugcau u 21

<210> SEQ ID NO 1067
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1067
ugcacuucgc uucaccucuu u 21

<210> SEQ ID NO 1068
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1068
agaggugaag cgaagugcau u 21

<210> SEQ ID NO 1069
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1069
ugugcacuuc gcuucaccuu u 21

<210> SEQ ID NO 1070
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1070
aggugaagcg aagugcacau u 21

<210> SEQ ID NO 1071
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1071
ugugcacuuc gcuucaccuu u 21

<210> SEQ ID NO 1072
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1072
aggugaagcg aagugcacau u 21

<210> SEQ ID NO 1073
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1073
ugugcacuuc gcuucaccuu u 21

<210> SEQ ID NO 1074
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1074
aggugaagcg aagugcacau u 21

<210> SEQ ID NO 1075
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1075
ugugcacuuc gcuucaccuu u 21

<210> SEQ ID NO 1076
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1076
aggugaagcg aagugcacau u 21

<210> SEQ ID NO 1077
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1077
ugugcacuuc gcuucaccuu u 21

<210> SEQ ID NO 1078
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1078
aggugaagcg aagugcacau u 21

<210> SEQ ID NO 1079
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1079
ugugcacuuc gcuucaccuu u 21

<210> SEQ ID NO 1080
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1080
aggugaagcg aagugcacau u 21

<210> SEQ ID NO 1081
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1081
ugugcacuuc gcuucaccuu u 21

<210> SEQ ID NO 1082
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1082
aggugaagcg aagugcacau u 21

<210> SEQ ID NO 1083
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1083
ugugcacuuc gcuucaccuu u 21

<210> SEQ ID NO 1084
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1084
aggugaagcg aagugcacau u 21

<210> SEQ ID NO 1085
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1085
ugugcacuuc gcuucaccuu u 21

<210> SEQ ID NO 1086
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1086
aggugaagcg aagugcacau u 21

<210> SEQ ID NO 1087
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1087
ugugcacuuc gcuucaccuu u 21

<210> SEQ ID NO 1088
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1088
aggugaagcg aagugcacau u 21

<210> SEQ ID NO 1089
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1089
ugugcacuuc gcuucaccuu u 21

<210> SEQ ID NO 1090
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1090
aggugaagcg aagugcacau u 21

<210> SEQ ID NO 1091
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1091
ugugcacuuc gcuucaccuu u 21

<210> SEQ ID NO 1092
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1092
aggugaagcg aagugcacau u 21

<210> SEQ ID NO 1093
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1093
ugugcacuuc gcuucaccuu u 21

<210> SEQ ID NO 1094
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1094
aggugaagcg aagugcacau u 21

<210> SEQ ID NO 1095
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1095
ugugcacuuc gcuucaccuu u 21

<210> SEQ ID NO 1096
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1096
aggugaagcg aagugcacau u 21

<210> SEQ ID NO 1097
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1097
ugugcacuuc gcuucaccuu u 21

<210> SEQ ID NO 1098
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1098
aggugaagcg aagugcacau u 21

<210> SEQ ID NO 1099
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1099
ugugcacuuc gcuucaccuu u 21

<210> SEQ ID NO 1100
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1100
aggugaagcg aagugcacau u 21

<210> SEQ ID NO 1101
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1101
gaggcuguag gcauaaauuu u 21

-continued

<210> SEQ ID NO 1102
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1102
aauuuaugcc uacagccucu u 21

<210> SEQ ID NO 1103
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1103
gaggcuguag gcauaaauuu u 21

<210> SEQ ID NO 1104
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1104
aauuuaugcc uacagccucu u 21

<210> SEQ ID NO 1105
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1105
gaggcuguag gcauaaauuu u 21

<210> SEQ ID NO 1106
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1106
aauuuaugcc uacagccucu u 21

<210> SEQ ID NO 1107
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1107
ugucugcggc guuuuaucau u 21

<210> SEQ ID NO 1108

<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1108
ugauaaaacg ccgcagacau u 21

<210> SEQ ID NO 1109
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1109
ugucugcggc guuuuaucau u 21

<210> SEQ ID NO 1110
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1110
ugauaaaacg ccgcagacau u 21

<210> SEQ ID NO 1111
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1111
ugucugcggc guuuuaucau u 21

<210> SEQ ID NO 1112
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1112
ugauaaaacg ccgcagacau u 21

<210> SEQ ID NO 1113
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1113
ugucugcggc guuuuaucau u 21

<210> SEQ ID NO 1114
<211> LENGTH: 21

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1114
ugauaaaacg ccgcagacau u 21

<210> SEQ ID NO 1115
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1115
cgugugcacu ucgcuucacu u 21

<210> SEQ ID NO 1116
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1116
gugaagcgaa gugcacacgu u 21

<210> SEQ ID NO 1117
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1117
ccgugugcac uucgcuucau u 21

<210> SEQ ID NO 1118
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1118
ugaagcgaag ugcacacggu u 21

<210> SEQ ID NO 1119
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1119
ugcacuucgc uucaccucuu u 21

<210> SEQ ID NO 1120
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1120
agaggugaag cgaagugcau u 21

<210> SEQ ID NO 1121
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1121
ugugcacuuc gcuucaccuu t 21

<210> SEQ ID NO 1122
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1122
aggugaagcg aagugcacau t 21

<210> SEQ ID NO 1123
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1123
ugugcacuuc gcuucaccuu t 21

<210> SEQ ID NO 1124
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1124
aggugaagcg aagugcacau t 21

<210> SEQ ID NO 1125
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1125
ugugcacuuc gcuucaccuu t 21

<210> SEQ ID NO 1126
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1126
aggugaagcg aagugcacau t 21

<210> SEQ ID NO 1127
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1127
ugugcacuuc gcuucaccuu t 21

<210> SEQ ID NO 1128
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1128
aggugaagcg aagugcacau t 21

<210> SEQ ID NO 1129
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1129
gaggcuguag gcauaaauuu t 21

<210> SEQ ID NO 1130
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1130
gaggcuguag gcauaaauuu t 21

<210> SEQ ID NO 1131
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1131
gaggcuguag gcauaaauuu t 21

<210> SEQ ID NO 1132
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1132
aauuuaugcc uacagccucu t 21

<210> SEQ ID NO 1133
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1133
gaggcuguag gcauaaauuu t 21

<210> SEQ ID NO 1134
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1134
aauuuaugcc uacagccucu t 21

<210> SEQ ID NO 1135
<211> LENGTH: 21
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1135
gaggcuguag gcauaaauuu t                                               21

<210> SEQ ID NO 1136
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1136
gaggcuguag gcauaaauuu t                                               21

<210> SEQ ID NO 1137
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1137
gaggcuguag gcauaaauuu t                                               21

<210> SEQ ID NO 1138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1138
ugauaaaacg ccgcagacau u                                               21

<210> SEQ ID NO 1139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1139
ugucugcggc guuuuaucau u                                               21

<210> SEQ ID NO 1140
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1140
ugauaaaacg ccgcagacau u 21

<210> SEQ ID NO 1141
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1141
ugucugcggc guuuuaucau u 21

<210> SEQ ID NO 1142
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1142
ugauaaaacg ccgcagacau u 21

<210> SEQ ID NO 1143
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1143
ugucugcggc guuuuaucau u 21

<210> SEQ ID NO 1144
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1144
ugucugcggc guuuuaucau u 21

<210> SEQ ID NO 1145
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1145
ccgugugcac uucgcuucau t 21

<210> SEQ ID NO 1146
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 1146
ugaagcgaag ugcacacggu t 21

<210> SEQ ID NO 1147
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1147
cgugugcacu ucgcuucacu t 21

<210> SEQ ID NO 1148
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1148
gugaagcgaa gugcacacgu t 21

<210> SEQ ID NO 1149
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1149
gcacuucgcu ucaccucugu t 21

<210> SEQ ID NO 1150
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1150
cagaggugaa gcgaagugcu t 21

<210> SEQ ID NO 1151
<211> LENGTH: 21
<212> TYPE: DNA
<213> ORGANISM: Artificial Sequence
<220> FEATURE:

<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1151
ugcacuucgc uucaccucuu t 21

<210> SEQ ID NO 1152
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1152
agaggugaag cgaagugcau t 21

<210> SEQ ID NO 1153
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1153
gaugugucug cggcguuuuu t 21

<210> SEQ ID NO 1154
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1154
aaaacgccgc agacacaucu t 21

<210> SEQ ID NO 1155
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1155
ugugucugcg gcguuuuauu t 21

<210> SEQ ID NO 1156
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1156
auaaaacgcc gcagacacau t 21

<210> SEQ ID NO 1157
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1157
ugucugcggc guuuuaucau t 21

<210> SEQ ID NO 1158
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1158
ugauaaaacg ccgcagacau t 21

<210> SEQ ID NO 1159
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1159
cugcugcuau gccucaucuu t 21

<210> SEQ ID NO 1160
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1160
agaugaggca uagcagcagu t 21

<210> SEQ ID NO 1161
<211> LENGTH: 21
<212> TYPE: DNA

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1161
uccugcugcu augccucauu t 21

<210> SEQ ID NO 1162
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1162
augaggcaua gcagcaggau t 21

<210> SEQ ID NO 1163
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1163
gaggcuguag gcauaaauuu t 21

<210> SEQ ID NO 1164
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1164
aauuuaugcc uacagccucu t 21

<210> SEQ ID NO 1165
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1165
gcuguaggca uaaauugguu t 21

<210> SEQ ID NO 1166
<211> LENGTH: 21

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1166
accaauuuau gccuacagcu t 21

<210> SEQ ID NO 1167
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1167
cuguaggcau aaauuggucu t 21

<210> SEQ ID NO 1168
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1168
gaccaauuua ugccuacagu t 21

<210> SEQ ID NO 1169
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1169
uguaggcaua aauuggucuu t 21

<210> SEQ ID NO 1170
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1170
agaccaauuu augccuacau t 21

<210> SEQ ID NO 1171

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1171

ugugcacuuc gcuucaccuu t                                              21


<210> SEQ ID NO 1172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1172

aggugaagcg aagugcacau t                                              21


<210> SEQ ID NO 1173
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1173

ugucugcggc guuuuaucau u                                              21


<210> SEQ ID NO 1174
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1174

ugauaaaacg ccgcagacau u                                              21


<210> SEQ ID NO 1175
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1175

ugugcacuuc gcuucaccuu t                                              21


<210> SEQ ID NO 1176
<211> LENGTH: 21
<212> TYPE: DNA
<213> ORGANISM: Artificial Sequence
<220> FEATURE:
<223> OTHER INFORMATION: Description of Artificial Sequence: Synthetic
```

oligonucleotide
<220> FEATURE:
<223> OTHER INFORMATION: Description of Combined DNA/RNA Molecule:
Synthetic oligonucleotide

<400> SEQUENCE: 1176
aggugaagcg aagugcacau t 21

<210> SEQ ID NO 1177
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1177
ugucugcggc guuuuaucau t 21

<210> SEQ ID NO 1178
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1178
ugauaaaacg ccgcagacau t 21

<210> SEQ ID NO 1179
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1179
gaggcuguag gcauaaauuu t 21

<210> SEQ ID NO 1180
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1180
aauuuaugcc uacagccucu t 21

<210> SEQ ID NO 1181
<211> LENGTH: 3221
<212> TYPE: DNA
<213> ORGANISM: Hepatitis B virus

<400> SEQUENCE: 1181

```
ttccactgcc ttccaccaag ctctgcagga tcccagagtc aggggtctgt attttcctgc     60
tggtggctcc agttcaggaa cagtaaaccc tgctccgaat attgcctctc acatctcgtc    120
aatctccgcg aggactgggg accctgtgac gaacatggag aacatcacat caggattcct    180
aggacccctg ctcgtgttac aggcggggtt tttcttgttg acaagaatcc tcacaatacc    240
gcagagtcta gactcgtggt ggacttctct caattttcta gggggatcac ccgtgtgtct    300
tggccaaaat tcgcagtccc caacctccaa tcactcacca acctcctgtc ctccaatttg    360
tcctggttat cgctggatgt gtctgcggcg ttttatcata ttcctcttca tcctgctgct    420
atgcctcatc ttcttattgg ttcttctgga ttatcaaggt atgttgcccg tttgtcctct    480
aattccagga tcaacaacaa ccagtacggg accatgcaaa acctgcacga ctcctgctca    540
aggcaactct atgtttccct catgttgctg tacaaaacct acggatggaa attgcacctg    600
tattcccatc ccatcgtcct gggctttcgc aaaataccta tgggagtggg cctcagtccg    660
tttctcttgg ctcagtttac tagtgccatt tgttcagtgg ttcgtagggc tttcccccac    720
tgtttggctt tcagctatat ggatgatgtg gtattggggg ccaagtctgt acagcatcgt    780
gagtcccttt ataccgctgt taccaatttt cttttgtctc tgggtataca tttaaaccct    840
aacaaaacaa aaagatgggg ttattcccta aacttcatgg gttacataat tggaagttgg    900
ggaactttgc cacaggatca tattgtacaa aagatcaaac actgttttag aaaacttcct    960
gttaacaggc ctattgattg gaaagtatgt caaagaattg tgggtctttt gggctttgct   1020
gctccattta cacaatgtgg atatcctgcc ttaatgcctt tgtatgcatg tatacaagct   1080
aaacaggctt tcactttctc gccaacttac aaggcctttc taagtaaaca gtacatgaac   1140
ctttaccccg ttgctcggca acggcctggt ctgtgccaag tgtttgctga cgcaaccccc   1200
actggctggg gcttggccat aggccatcag cgcatgcgtg gaacctttgt ggctcctctg   1260
ccgatccata ctgcggaact cctagccgct tgttttgctc gcagccggtc tggagcaaag   1320
ctcatcggaa ctgacaattc tgtcgtcctc tcgcggaaat atacatcgtt tccatggctg   1380
ctaggctgta ctgccaactg gatccttcgc gggacgtcct ttgtttacgt cccgtcggcg   1440
ctgaatcccg cggacgaccc ctctcggggc cgcttgggac tctctcgtcc ccttctccgt   1500
ctgccgttcc agccgaccac ggggcgcacc tctctttacg cggtctcccc gtctgtgcct   1560
tctcatctgc cggtccgtgt gcacttcgct tcacctctgc acgttgcatg gagaccaccg   1620
tgaacgccca tcagatcctg cccaaggtct tacataagag gactcttgga ctcccagcaa   1680
tgtcaacgac cgaccttgag gcctacttca aagactgtgt gtttaaagac tgggaggagc   1740
tgggggagga gattaggtta aaggtctttg tattaggagg ctgtaggcat aaattggtct   1800
gcgcaccagc accatgcaac tttttcacct ctgcctaatc atctcttgta catgtcccac   1860
tgttcaagcc tccaagctgt gccttgggtg gctttggggc atggacattg acccttataa   1920
agaatttgga gctactgtgg agttactctc gtttttgcct tctgacttct ttccttccgt   1980
cagagatctc ctagacaccg cctcagctct gtatcgagaa gccttagaat ctcctgagca   2040
ttgctcacct caccatactg cactcaggca agccattctc tgctgggggg aattgatgac   2100
tctagctacc tgggtgggta ataatttgga agatccagca tccagggatc tagtagtcaa   2160
ttatgttaat actaacatgg gtttaaagat caggcaacta ttgtggtttc atatatcttg   2220
ccttactttt ggaagagaga ctgtacttga atatttggtc tctttcggag tgtggattcg   2280
cactcctcca gcctatagac caccaaatgc ccctatctta tcaacacttc cggaaactac   2340
```

tgttgttaga cgacgggacc gaggcaggtc ccctagaaga agaactccct cgcctcgcag 2400
acgcagatct caatcgccgc gtcgcagaag atctcaatct cgggaatctc aatgttagta 2460
ttccttggac tcataaggtg ggaaacttta cggggcttta ttcctctaca gtacctatct 2520
ttaatcctga atggcaaact ccttcctttc ctaagattca tttacaagag gacattatta 2580
ataggtgtca acaatttgtg ggccctctca ctgtaaatga aaagagaaga ttgaaattaa 2640
ttatgcctgc tagattctat cctactcaca ctaaatattt gcccttagac aaaggaatta 2700
aaccttatta tccagatcag gtagttaatc attacttcca aaccagacat tatttacata 2760
ctctttggaa ggctggtatt ctatataaga gggaaaccac acgtagcgca tcattttgtg 2820
ggtcaccata ttcttgggaa caagagctac agcatgggag gttggtcatc aaaacctcgc 2880
aaaggcatgg ggacgaatct ttctgttccc aaccctctgg gattctttcc cgatcatcag 2940
ttggaccctg cattcggagc caactcaaac aatccagatt gggacttcaa ccccatcaag 3000
gaccactggc cagcagccaa ccaggtagga gcgggagcat tcgggccagg gctcacccct 3060
ccacacggcg gtattctggg gtggagccct caggctcagg gcatattgac cacagtgtca 3120
acaattcctc ctcctgcctc caccaatcgg cagtcaggaa ggcagcctac tcccatctct 3180
ccacctctaa gagacagtca tcctcaggcc atgcagtgga a 3221

<210> SEQ ID NO 1182
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1182
gaggcuguag gcauaaauuu t 21

<210> SEQ ID NO 1183
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1183
aauuuaugcc uacagccucu t 21

<210> SEQ ID NO 1184
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1184
gaggcuguag gcauaaauuu t 21

<210> SEQ ID NO 1185
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1185
aauuuaugcc uacagccucu t 21

<210> SEQ ID NO 1186
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1186
gaggcuguag gcauaaauuu t 21

<210> SEQ ID NO 1187
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1187
aauuuaugcc uacagccucu t 21

<210> SEQ ID NO 1188
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1188
gaggcuguag gcauaaauuu t 21

<210> SEQ ID NO 1189
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1189
aauuuaugcc uacagccucu t 21

<210> SEQ ID NO 1190
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1190
gaggcuguag gcauaaauuu t 21

<210> SEQ ID NO 1191
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1191
aauuuaugcc uacagccuau t 21

<210> SEQ ID NO 1192
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1192
gaggcuguag gcauaaauuu t 21

<210> SEQ ID NO 1193
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1193
aauuuaugcc uacagccucu t 21

<210> SEQ ID NO 1194
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1194
gaggcuguag gcauaaauuu t 21

<210> SEQ ID NO 1195
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1195
aauuuaugcc uacagccucu t 21

<210> SEQ ID NO 1196
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1196
gaggcuguag gcauaaauuu t 21

<210> SEQ ID NO 1197
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1197
aauuuaugcc uacagccucu t 21

<210> SEQ ID NO 1198
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1198
gaggcuguag gcauaaauuu t 21

<210> SEQ ID NO 1199
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1199
aauuuaugcc uacagccucu t 21

<210> SEQ ID NO 1200
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1200
ugucugcggc guuuuaucau t 21

<210> SEQ ID NO 1201
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1201
ugauaaaacg ccgcagacau t 21

<210> SEQ ID NO 1202
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1202
ugucugcggc guuuuaucau t 21

<210> SEQ ID NO 1203
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1203
ugauaaaacg ccgcagacau t 21

<210> SEQ ID NO 1204
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1204
ugucugcggc guuuuaucau t 21

<210> SEQ ID NO 1205
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1205
ugauaaaacg ccgcagacau t 21

<210> SEQ ID NO 1206
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1206
ugucugcggc guuuuaucau t 21

<210> SEQ ID NO 1207
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1207
ugauaaaacg ccgcagacau t 21

<210> SEQ ID NO 1208
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1208
ugucugcggc guuuuaucau t 21

<210> SEQ ID NO 1209
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1209
ugauaaaacg ccgcagaccu t 21

<210> SEQ ID NO 1210
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1210
ugucugcggc guuuuaucau t 21

<210> SEQ ID NO 1211
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1211
ugauaaaacg ccgcagacau t 21

<210> SEQ ID NO 1212
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1212
ugucugcggc guuuuaucau t 21

<210> SEQ ID NO 1213
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1213
ugauaaaacg ccgcagacau t 21

<210> SEQ ID NO 1214
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 1214
ugucugcggc guuuuaucau t 21

<210> SEQ ID NO 1215
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1215
ugauaaaacg ccgcagacau t 21

<210> SEQ ID NO 1216
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1216
ugucugcggc guuuuaucau t 21

<210> SEQ ID NO 1217
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1217
ugauaaaacg ccgcagacau t 21

<210> SEQ ID NO 1218
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1218
ccgugugcac uucgcuucau t 21

<210> SEQ ID NO 1219
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule: Synthetic oligonucleotide

<400> SEQUENCE: 1219
ugaagcgaag ugcacacggu t 21

<210> SEQ ID NO 1220
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1220
ccgugugcac uucgcuucau t 21

<210> SEQ ID NO 1221
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1221
ugaagcgaag ugcacacggu t 21

<210> SEQ ID NO 1222
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1222
ccgugugcac uucgcuucau t 21

<210> SEQ ID NO 1223
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1223
ugaagcgaag ugcacacggu t 21

<210> SEQ ID NO 1224
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 1224
ccgugugcac uucgcuucau t 21

<210> SEQ ID NO 1225
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1225
ugaagcgaag ugcacacggu t 21

<210> SEQ ID NO 1226
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1226
ccgugugcac uucgcuucau t 21

<210> SEQ ID NO 1227
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1227
ugaagcgaag ugcacacgau t 21

<210> SEQ ID NO 1228
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1228
ccgugugcac uucgcuucau t 21

<210> SEQ ID NO 1229
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1229
ugaagcgaag ugcacacggu t 21

<210> SEQ ID NO 1230
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1230
ccgugugcac uucgcuucau t 21

<210> SEQ ID NO 1231
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1231
ugaagcgaag ugcacacggu t 21

<210> SEQ ID NO 1232
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1232
ccgugugcac uucgcuucau t 21

<210> SEQ ID NO 1233
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1233
ugaagcgaag ugcacacggu t 21

<210> SEQ ID NO 1234
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1234
ccgugugcac uucgcuucau t 21

<210> SEQ ID NO 1235
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1235
ugaagcgaag ugcacacggu t 21

<210> SEQ ID NO 1236
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1236
ugugcacuuc gcuucaccuu t 21

<210> SEQ ID NO 1237
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1237
aggugaagcg aagugcacau t 21

<210> SEQ ID NO 1238
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1238
ugugcacuuc gcuucaccuu t 21

<210> SEQ ID NO 1239
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1239
aggugaagcg aagugcacau t 21

<210> SEQ ID NO 1240
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1240
ugugcacuuc gcuucaccuu t 21

<210> SEQ ID NO 1241
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1241
aggugaagcg aagugcacau t 21

<210> SEQ ID NO 1242
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1242
ugugcacuuc gcuucaccuu t 21

<210> SEQ ID NO 1243
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1243
aggugaagcg aagugcacau t 21

<210> SEQ ID NO 1244
<211> LENGTH: 21
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1244
ugugcacuuc gcuucaccuu t 21

<210> SEQ ID NO 1245
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1245
aggugaagcg aagugcacau t 21

<210> SEQ ID NO 1246
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1246
ugugcacuuc gcuucaccuu t 21

<210> SEQ ID NO 1247
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1247
aggugaagcg aagugcaccu t 21

<210> SEQ ID NO 1248
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1248
ugugcacuuc gcuucaccuu t 21

<210> SEQ ID NO 1249
<211> LENGTH: 21

<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1249
aggugaagcg aagugcacau t 21

<210> SEQ ID NO 1250
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1250
ugugcacuuc gcuucaccuu t 21

<210> SEQ ID NO 1251
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1251
aggugaagcg aagugcacau t 21

<210> SEQ ID NO 1252
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1252
ugugcacuuc gcuucaccuu t 21

<210> SEQ ID NO 1253
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1253
aggugaagcg aagugcacau t 21

<210> SEQ ID NO 1254

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1254
ugugcacuuc gcuucaccuu t 21

<210> SEQ ID NO 1255
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1255
aggugaagcg aagugcacau t 21

<210> SEQ ID NO 1256
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1256
cgugugcacu ucgcuucacu t 21

<210> SEQ ID NO 1257
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1257
gugaagcgaa gugcacacgu t 21

<210> SEQ ID NO 1258
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1258
cgugugcacu ucgcuucacu t 21

<210> SEQ ID NO 1259
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1259
gugaagcgaa gugcacacgu t 21

<210> SEQ ID NO 1260
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1260
cgugugcacu ucgcuucacu t 21

<210> SEQ ID NO 1261
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1261
gugaagcgaa gugcacacgu t 21

<210> SEQ ID NO 1262
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1262
cgugugcacu ucgcuucacu t 21

<210> SEQ ID NO 1263
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1263
gugaagcgaa gugcacacgu t 21

<210> SEQ ID NO 1264
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1264
cgugugcacu ucgcuucacu t 21

<210> SEQ ID NO 1265
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1265
gugaagcgaa gugcacacau t 21

<210> SEQ ID NO 1266
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1266
cgugugcacu ucgcuucacu t 21

<210> SEQ ID NO 1267
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1267
gugaagcgaa gugcacacgu t 21

<210> SEQ ID NO 1268
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1268
cgugugcacu ucgcuucacu t 21

<210> SEQ ID NO 1269
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1269
gugaagcgaa gugcacacgu t 21

<210> SEQ ID NO 1270
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1270
cgugugcacu ucgcuucacu t 21

<210> SEQ ID NO 1271
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1271
gugaagcgaa gugcacacgu t 21

<210> SEQ ID NO 1272
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1272
cgugugcacu ucgcuucacu t 21

<210> SEQ ID NO 1273
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1273
gugaagcgaa gugcacacgu t 21

<210> SEQ ID NO 1274
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1274
ugugcacuuc gcuucaccuu u 21

<210> SEQ ID NO 1275
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1275
aggugaagcg aagugcacau u 21

<210> SEQ ID NO 1276
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1276
ugugcacuuc gcuucaccuu u 21

<210> SEQ ID NO 1277
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1277
aggugaagcg aagugcacau u 21

<210> SEQ ID NO 1278
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1278
gaggcuguag gcauaaauuu u 21

<210> SEQ ID NO 1279
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1279
aauuuaugcc uacagccucu u 21

<210> SEQ ID NO 1280
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1280
gaggcuguag gcauaaauuu u 21

<210> SEQ ID NO 1281
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1281
aauuuaugcc uacagccucu u 21

<210> SEQ ID NO 1282
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1282
ugucugcggc guuuuaucau u 21

<210> SEQ ID NO 1283
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1283
ugauaaaacg ccgcagacau u 21

<210> SEQ ID NO 1284
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1284
ugucugcggc guuuuaucau u 21

<210> SEQ ID NO 1285
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1285
ugauaaaacg ccgcagacau u 21